US008012984B2

(12) United States Patent
Stein et al.

(10) Patent No.: US 8,012,984 B2
(45) Date of Patent: Sep. 6, 2011

(54) SUBSTITUTED PYRAZINONE MELANIN CONCENTRATING HORMONE RECEPTOR-1 ANTAGONISTS AND METHODS

(75) Inventors: Philip D. Stein, Pennington, NJ (US); Sharon N. Bisaha, Lambertville, NJ (US); Saleem Ahmad, Wall, NJ (US); Khehyong Ngu, Pennington, NJ (US); William N. Washburn, Titusville, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 12/881,234

(22) Filed: Sep. 14, 2010

(65) Prior Publication Data
US 2011/0003759 A1    Jan. 6, 2011

Related U.S. Application Data

(63) Continuation of application No. 12/141,228, filed on Jun. 18, 2008, now abandoned.

(60) Provisional application No. 60/948,213, filed on Jul. 6, 2007.

(51) Int. Cl.
A61K 31/4965 (2006.01)

(52) U.S. Cl. ........... 514/255.06; 544/405; 546/268.1; 548/179; 548/306.1; 549/471

(58) Field of Classification Search .......... 544/405; 546/268.1; 548/179, 306.1; 549/471; 514/255.06
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau et al. |
| 5,612,359 A | 3/1997 | Murugesan |
| 5,691,322 A | 11/1997 | Robl |
| 5,698,527 A | 12/1997 | Kim |
| 5,712,396 A | 1/1998 | Magnin et al. |
| 5,753,675 A | 5/1998 | Wattanasin |
| 5,770,615 A | 6/1998 | Cheng et al. |
| 5,776,983 A | 7/1998 | Washburn et al. |
| 6,043,265 A | 3/2000 | Murugesan et al. |
| 6,414,002 B1 | 7/2002 | Cheng et al. |

FOREIGN PATENT DOCUMENTS
EP        0 221 025        5/1987
(Continued)

OTHER PUBLICATIONS

Borowsky, B. et al. "Antidepressant, anxiolytic and anorectic effects of a melanin-concentrating hormone-1 receptor antagonist", Nature Medicine vol. 8, No. 8:825-830, (2002).

(Continued)

Primary Examiner — James O Wilson
Assistant Examiner — Douglas M Willis
(74) Attorney, Agent, or Firm — John Levis; Maureen Gibbons; Jing G. Sun

(57) ABSTRACT

The present application provides compounds, including all stereoisomers, solvates, prodrugs and pharmaceutically acceptable forms thereof according to Formula I

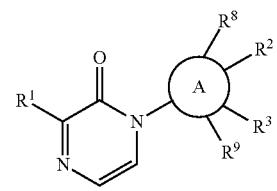

wherein

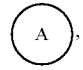

$R^1$, $R^2$, $R^3$, $R^8$, and $R^9$ are defined herein.
Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

24 Claims, No Drawings

FOREIGN PATENT DOCUMENTS

| | | |
|---|---|---|
| EP | 0 142 146 | 8/1988 |
| EP | 0 675 714 | 1/1999 |
| EP | 0 818 448 | 11/2003 |
| EP | 1 022 272 | 5/2004 |
| EP | 0 992 496 | 8/2005 |
| FR | 2 596 393 | 4/1986 |
| GB | 2 205 837 | 12/1988 |
| GB | 2 304 106 | 8/1996 |
| WO | WO 86/03488 | 6/1986 |
| WO | WO 86/07054 | 12/1986 |
| WO | WO 97/46226 | 5/1997 |
| WO | WO 97/21993 | 6/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 2007/071646 | 6/2007 |

OTHER PUBLICATIONS

Biller et al., "Isoprenoid (Phosphinylmethyl)phosphonates as Inhibitor of Squalene Synthetase", J. Med. Chem., vol. 31, No. 10, pp. 1869-1871 (1988).
Biller et al., "Squalene Synthetase Inhibitors", Curr. Pharm. Des, 2, pp. 1-40 (1996).
Capson, T.L., "Synthesis and Evaluation of Ammonium Analogs of Carbocationic intermediates in Squalene Biosynthesis", Dept. Med. Chem. U of Utah, Table of Contents pp. 16, 17, 40-43, 48-51, Summary, (1987).
Corey, E. J. et al, "Application of Unreactive Analogs of Terpenoid Pyrophosphates of Studies of Multistep Biosynthesis. Demonstration That 'Presqualene Pyrophosphate' is Essential Intermediate on the Path to Squalene", J. Amer. Chem. Soc. 98, pp. 1291-1293 (1976).
Ghiselli, G., "The pharmacological profile of FCE 27677: a novel ACAT inhibitor with potent hypolipdemic activity mediated by selective suppression of the hepatic secretion of ApoB100-containing lipoprotein", Cardiovasc. Drug Rev. 16(1)16-30(1998).
Hara, S., "Ileal Na+/bile acid Contransporter Inhibitors", Drugs of the Future, 24(4), pp. 425-430 (1999).
Kowalski, T. et al., "Melanin-concentrating hormone-1 receptor antagonism decreases feeding by reducing meal size", European Journal of Pharmacology 497:41-47 (2004).
Kowalski, T. et al., "Therapeutic potential of melanin-concentrating hormone-1 receptor antagonists for the treatment of obesity", Expert Opin. Investing. Drugs 13(9):1113-1122 (2004).
Krause, B.R. et al. "ACAT Inhibitors: Physiologic Mechanisms for Hypolipidemic and Anti-Atherosclerotic Activities in Experimental Animals", Inflammation: Mediators and Pathways, CRC Press Inc, publ., Ruffolo, Jr., R.R. et al., eds., pp. 173-198 (1995).
Ljung, B. et al., "AZ 242, a novel PPARα/γ agonist with beneficial effects on insulin resistance and carbohydrate and lipid metabolism in ob/ob mice and obese Zucker rats", Journal of Lipid Research vol. 43:1855-1863 (2002).
McClard, R.W. et al., "Novel Phosphonylphosphinyl (P-C-P-C) Analogues of Biochemically Interesting Diphosphates. Syntheses and Properties of P-C-P-C Analogues of Isopentenyl Diphosphate and Dimethylallyl Diphosphate", J. Am. Chem. Soc. 109, pp. 5544-5545 (1987).
Nicolosi et al., "The ACAT inhibitor, C1-1011 is effective in the prevention and regression of aortic fatty streak area in hamsters", Atherosclerosis 137(1):77-85 (1998).
Ortiz de Montellano, P. et al., "Inhibition of Squalene Synthetase by Farnesyl Pyrophosphate Analogues", J. Med. Chem., 20:243-249 (1977).
Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem. 41, pp. 973-980 (1998).
Salisbury, B.G. et al., "Hypocholesterolemic activity of a novel inhibitor of cholesterol absorption, SCH 48461", Atherosclerosis, vol. 115, pp. 45-63 (1995).
Sliskovic, D.R. et al., "ACAT Inhibitors: Potential Anti-atherosclerotic Agents", Current Medicinal Chemistry, vol. 1, No. 3, pp. 204-225 (1994).
Smith, C. et al., "RP 73163: A Bioavailable Alkylsulphinyl-diphenylimidazole ACAT Inhibitor", Bioorganic & Med. Chem. Lett., vol. 6, No. 1, pp. 47-50, (1996).
Stout, et al., "Inhibitors of acyl-CoA:cholesterol O-acyl transferase (ACAT) as hypocholeserolemic agents. 6 . . . " Chemtracts: Org. Chem., 8(6):359-362 (1995).
Sorbera, L.A. et al., "Treatment of Lipoprotein Disorders ACAT Inhibitor", Drugs of the Future, 24(1), pp. 9-15 (1999).
Takekawa, S. et al., "T226296: a novel, orally active and selective melanin-concentrating hormone receptor antagonist", European Journal of Pharmacology 438, pp. 129-135 (2002).
Ulven, T. et al., "6-Acylamino-2-aminoquinolines as potent melanin-concentrating hormone 1 receptor antagonists. Identification, structure-activity relationship, and investigation of binding mode", J. Med. Chem. 48:5684-5697 (2005).
Yajima, K. et al., "Combination Therapy with PPARγ and PPARα agonists increases glucose-stimulate insulin secretion in db/db mice", Am. J. Physiol. Endocrinol. Metab. 284:E966-E971 (2003).
Database Registry [Online] Chemical Abstracts Service, Columbus, Ohio, US; Jul. 17, 2006, XP002512332 retrieved from STN see CAS Registry Nos. 893789-93-0; 893789-91-8 abstract.
Database Registry [Online] Chemical Abstracts Service, Columbus, Ohio, US; Jul. 23, 2006, XP002512333 retrieved from STN see CAS Registry Nos. 895110-1301; 895108-64-2; 895108-47-1; 895107-87-6; 895107-51-4; 895107-45-6; 985107-39-8; 895107-33-2; 895107-27-4; 985107-21-8; 895106-79-3 abstract.
Database Registry [Online] Chemical Abstracts Service, Columbus, Ohio, US; Aug. 8, 2006, XP002512334 retrieved from STN see CAS Registry No.: 899759-27-4; abstract.
Database Registry [Online] Chemical Abstracts Service, Columbus, Ohio, US; Aug. 9, 2006, XP002512335 retrieved from STN see CAS Registry No. 899944-25-3; abstract.
Database Registry [Online] Chemical Abstracts Service, Columbus, Ohio, US; Feb. 28, 2007, XP002512336 retrieved from STN see CAS Registry No. 023679-96-3; abstract.
Database Registry [Online] Chemical Abstracts Service, Columbus, Ohio, US; Apr. 24, 2007, XP002512337 retrieved from STN see CAS Registry Nos. 932301-72-9; 932301-63-8 abstract.
Database Registry [Online] Chemical Abstracts Service, Columbus, Ohio, US; Apr. 24, 2007, XP002512338 retrieved from STN see CAS Registry Nos. 932489-83-3; 932489-73-1; 932489-63-9; 932351-53-6; 932351-50-3 abstract.
Database Registry [Online] Chemical Abstracts Service, Columbus, Ohio, US; Apr. 26, 2007, XP002512339 retrieved from STN see CAS Registry Nos. 932540-40-4; 932540-33-5; 932540-27-7; 932540-15-3; 932540-03-9 abstract.
Database Registry [Online] Chemical Abstracts Service, Columbus, Ohio, US; Sep. 7, 2007, XP002512340 retrieved from STN see CAS Registry Nos. 946270-19-5; 946238-65-9; 946218-30-0; 946215-02-7; 946215-98-8 abstract.

SUBSTITUTED PYRAZINONE MELANIN CONCENTRATING HORMONE RECEPTOR-1 ANTAGONISTS AND METHODS

CROSS-REFERENCE TO RELATED APPLICATIONS

This application is a continuation of U.S. Ser. No. 12/141,228 filed Jun. 18, 2008 now abandoned which claims the benefit of U.S. Provisional Application Ser. No. 60/948,213 filed Jul. 6, 2007.

FIELD OF THE INVENTION

The present invention relates to non-basic melanin concentrating hormone receptor-1 (MCHR1) antagonists, pharmaceutical compositions containing MCHR1 antagonists and methods of treating diabetes, obesity and related diseases employing such MCHR1 antagonists.

BACKGROUND OF THE INVENTION

Several lines of pharmacological and genetic evidence support the role of Melanin Concentrating Hormone Receptor-1 (hereafter "MCHR1") as a modulator of food intake and body weight. Central administration of melanin concentrating hormone (MCH) increases food intake and body weight both in rats and in mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J. Pharmacol.*, 438:129-135 (2002), *Nat. Med.*, 8:825-830 (2002), *Eur. J. Pharmacol.*, 497:41-47 (2004).

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached." (Kowalski, T. J. et al., *Expert Opin. Investig. Drugs*, 13:1113-1122 (2004)). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (Ulven, T., *J. Med. Chem.*, 48:5684-5697 (2005)) However, incorporation of this basic amine in a MCHR1 antagonist increases substantially the probability of binding to off-target ion-channels and biogenic amine receptors.

In accordance with the present invention, there is provided a series of novel high affinity selective MCHR1 antagonists for which binding affinity is not dependent upon inclusion of a basic amine functionality that is common to most of the disclosed MCHR antagonists. As a consequence, the absence of the basic center greatly reduces the probability of off-target interactions such as binding to other biogenic amine receptors as well as binding to ion channels such as the HERG receptor in the heart. The reduction/abolition of affinity for the HERG receptor is especially important since ligand occupancy is associated with initiation of fatal arrhythmias.

SUMMARY OF THE INVENTION

In one embodiment of the present invention, a compound of the Formula I or a pharmaceutically acceptable salt thereof is provided

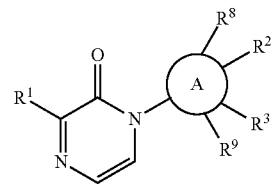

I wherein

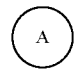

is a phenylene ring or a heteroaryl ring which is a monocyclic ring or a bicyclic ring which contains one or two nitrogen atoms or one oxygen atom;

$R^1$ is Z—Y—X—, wherein
X is O, S,

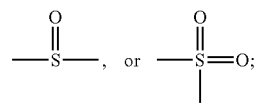

Y is a bond, a 3- to 6-membered cycloalkyl, or an alkyl chain; and
Z is aryl such as phenyl and naphthyl, or heteroaryl such as pyridinyl, pyridimidinyl, pyrazinyl, benzimidazolyl, benzothiazolyl, benzoxazolyl, or other "heteroaryl";
$R^2$ is -E-G-$(J)_m$, with m being an integer from 1 to 3;
E is O, S, or a bond;
G is lower alkyl, phenylalkyl, cycloalkyl, cycloalkylalkyl, alkylcycloalkyl, cycloalkoxy, alkylcycloalkoxy, or cycloalkoxyalkyl;
each J is independently hydrogen, hydroxyl, CN, —$SO_2R^7$, —$SR^7$, —$SOR^7$, lower alkyl, lower alkoxy, $CF_3$, $CF_3O$—, —$COOR^5$ (wherein $R^5$ is H, $C_{1-3}$ alkyl, or cycloalkyl), or —CO—$NR^{5a}R^6$ wherein $R^{5a}$ and $R^6$ are each independently selected from H, $C_{1-3}$ alkyl, or cycloalkyl, or $R^{5a}$ and $R^6$ taken together can be propanediyl, butanediyl or pentanediyl to form with the N atom to which they are attached a 4-, 5- or 6-membered cyclic amine, such as azetidinyl, pyrrolidinyl, piperidinyl, morpholinyl, or piperazinyl, optionally substituted with substituents as set out for "heterocyclo";

$R^7$ is lower alkyl;

$R^3$ is $C_{1-6}$ alkyl, cycloalkyl, $C_{1-6}$ alkoxy, halogen, hydrogen, —S—$C_{1-6}$ alkyl, CN, $CF_3O$, or $CF_3$;

and wherein $R^2$ and $R^3$ can be taken together to form a 5- to 7-membered ring which is saturated, unsaturated, or partially unsaturated and may include an E heteroatom, which is O, or 0, 1 or 2 N atoms, which ring is substituted with one or two of —O-G-$(J)_m$ groups, wherein at least one J is OH, and optionally other substituents as set out for "alkyl", "aryl", or "heteroaryl", such as alkyl and/or OH;

with the proviso that where

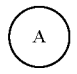

is a phenylene ring, E-G and $R^3$ are not identical unsubstituted lower alkoxy groups, and when G is lower alkyl and J is H, $R^3$ is not hydrogen; and $R^8$ and $R^9$ are each independently hydrogen, halogen, or lower alkyl;

including esters thereof, prodrugs thereof, solvates thereof, and all stereoisomers thereof.

Any of the foregoing Z moieties may either be unsubstituted or substituted with 1, 2 or 3 of amino, halo, $C_{1-6}$ alkyl, $C_{1-3}$ alkylamino, di-$C_{1-3}$ alkylamino, $C_{1-3}$ alkoxy, $C_{1-3}$ thioalkyl, $C_{1-3}$ trifluoroalkoxy, trifluoromethyl, cycloalkyl, cycloalkoxy, or heteroaryl such as pyridyl or substituted with any of the substituents as set out for "aryl", "heteroaryl", or "alkyl".

Examples of substituents for the J group in the form of a cyclic amine include but are not limited to lower alkyl, lower alkoxy, OH, $CF_3$, or $CF_3O$, or other substituents as set out for "alkyl" and "heteroaryl".

In a further aspect of the invention, there is provided a pharmaceutical composition which contains a therapeutically effective amount of the compound of the invention Formula I as defined above, in association with a pharmaceutically acceptable carrier or diluent.

There is also provided a method for the treatment of diabetes, obesity and other related conditions involving the MCHR1 in a mammal (such as a human, dog or cat) in need thereof, which includes the steps of administering to the mammal a therapeutically effective amount of the compound of Formula I of the invention as defined above.

The invention also sets forth one or more methods for making the compound of Formula I of the invention. In one embodiment, there is provided a process for the preparation of the compound of Formula I of the invention, wherein the compound a

is reacted with the alkali metal salt of Z—Y—$X^1$H (b) ($X^1$=O or S), preferably Z—$(CH_2)_n$—$X^1$H (n=0, 1, 2 or 3).

In another embodiment of the invention, there is provided a process for the preparation of the compound of Formula I of the invention, wherein the compound c

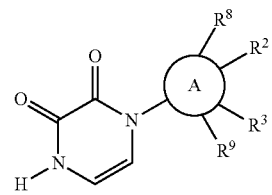

is reacted with Z—Y—$X^1$H (b), preferably Z—$(CH_2)_n$—$X^1$H (n=0, 1, 2 or 3), and preferably in the presence of an activating agent.

The present invention is directed to these, as well as other important ends, hereinafter described.

DETAILED DESCRIPTION OF THE INVENTION

The present application provides compounds, including all stereoisomers, solvates, prodrugs and pharmaceutically acceptable forms thereof according to Formula I. Additionally, the present application provides pharmaceutical compositions containing at least one compound according to Formula I of the invention alone and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I of the invention as defined above.

DEFINITIONS

Unless otherwise indicated, the term "lower alkyl" as may be employed herein alone or as part of another group includes both straight and branched chain hydrocarbons containing 1 to 8 carbons, and the terms "alkyl", "alk", "alkyl chain", "alkylene", or "alkylene chain" as may be employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 2 free bonds and thus are linking groups, namely "alkylene", as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" or "lower cycloalkyl" as may be employed herein alone or as part of another group includes saturated or partially unsaturated (containing 1 or 2 double bonds) cyclic hydrocarbon groups containing 1 to 3 rings, any one of which may optionally be a spiro substituted cycloalkyl, including monocycloalkyl, bicycloalkyl and tricycloalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

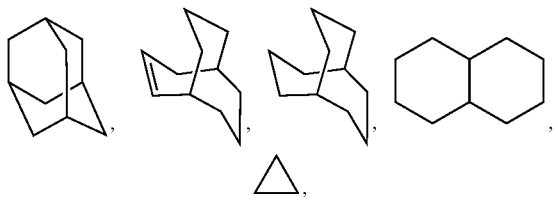

as well as such groups including 2 free bonds and thus are linking groups, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the substituents set for "alkyl".

Unless otherwise indicated, the term "cycloalkoxy" or "lower cycloalkoxy" as employed herein alone or as part of another group, represents a 4-, 5- or 6-membered saturated ring containing an oxygen in the ring and includes

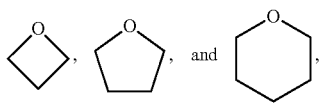

as well as such groups including 2 free bonds and thus are linking groups, and which may be optionally substituted with 1 or two of any of the substituents as set out for cycloalkyl.

The term "heterocyclo", "heterocycle", "heterocyclyl", "heterocyclic" or "cycloheteroalkyl" ring, as may be used herein, represents an unsubstituted or substituted stable 4- to 7-membered monocyclic ring system which may be saturated or unsaturated, preferably saturated or partially unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized, and including any bicyclic group in which the heterocyclic ring is fused to a benzene ring. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl,

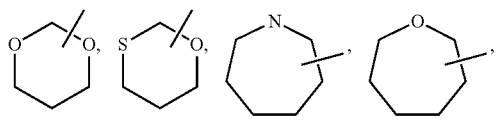

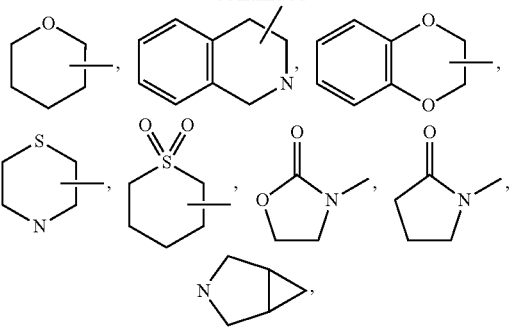

and other heterocycles described in Katritzky, A. R. et al., eds., *Comprehensive Heterocyclic Chemistry: The Structure, Reactions, Synthesis and Uses of Heterocyclic Compounds*, Pergamon Press, New York, N.Y., publ. (1984); and Katritzky, A. R. et al., eds., *Comprehensive Heterocyclic Chemistry II: A Review of the Literature 1982-1995*, Elsevier Science, Inc., Tarrytown, N.Y., publ. (1996); and references therein, as well as such groups including 2 free bonds and thus are linking groups, as well as such groups optionally substituted with 1 to 3 of F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl, and/or alkylthio.

The term "alkanoyl" as may be used herein alone or as part of another group refers to alkyl linked to a carbonyl group.

The term "halogen" or "halo" as may be used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as may be employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings), for example

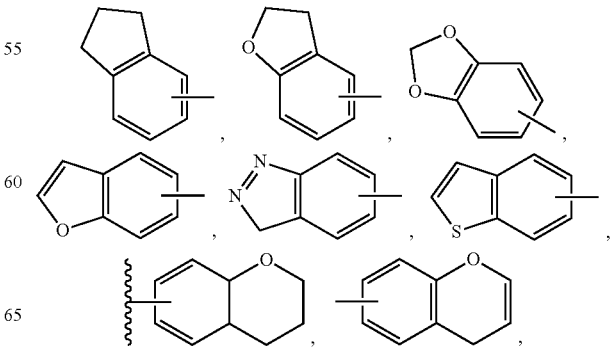

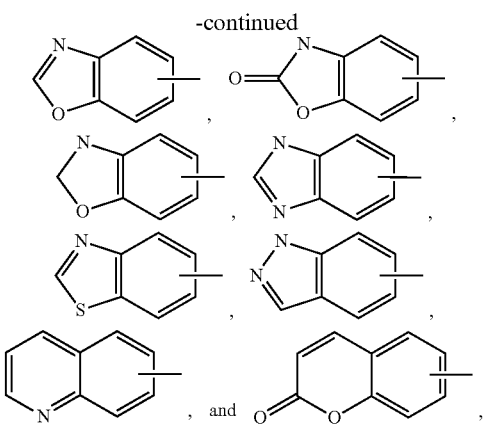

and as well as such groups including 2 free bonds and thus are linking groups, and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the substituents for "alkyl" set out herein.

Unless otherwise indicated, the term "heteroaryl" as may be used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds., *Comprehensive Heterocyclic Chemistry: The Structure, Reactions, Synthesis and Uses of Heterocyclic Compounds*, Pergamon Press, New York, N.Y., publ. (1984); and Katritzky, A. R. et al., eds., *Comprehensive Heterocyclic Chemistry II: A Review of the Literature* 1982-1995, Elsevier Science, Inc., Tarrytown, N.Y., publ. (1996); and references therein as well as such groups including 2 free bonds and thus are linking groups. Further, "heteroaryl", as defined herein, may optionally be substituted with one or more substituents such as the substituents included above for "alkyl" and/or "aryl". Examples of heteroaryl groups include the following:

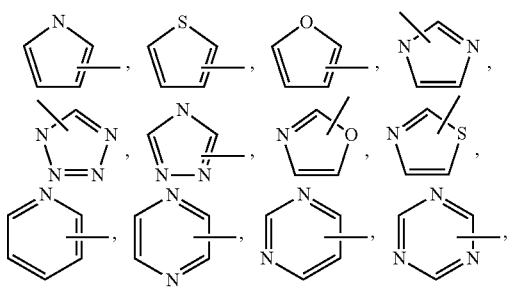

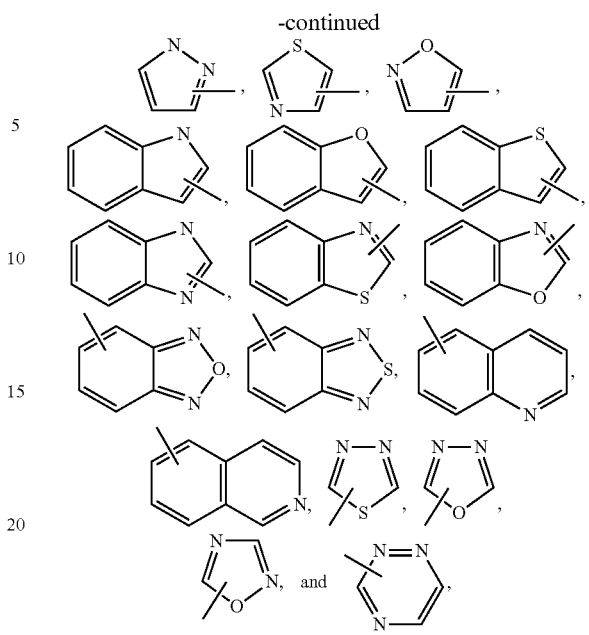

and the like.

Unless otherwise indicated, the term "lower alkoxy", "alkoxy", "aryloxy" or "aralkoxy" as may be employed herein alone or as part of another group includes any of the above alkyl, aralkyl or aryl groups linked to an oxygen atom.

Unless otherwise indicated, the term "lower alkylthio", alkylthio", "arylthio" or "aralkylthio" as may be employed herein alone or as part of another group includes any of the above alkyl, aralkyl or aryl groups linked to a sulfur atom.

The term "polyhaloalkyl" as may be used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as may be used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

Unless otherwise indicated, the term "alkenyl" as used herein alone or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally, said alkenyl group may be substituted with one or substituents, such as those substituents disclosed for alkyl.

Unless otherwise indicated, the term "alkynyl" as used herein alone or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Optionally, said alkynyl group may be substituted with one or substituents, such as those substituents disclosed for alkyl.

The term "cycloalkenyl" as employed herein alone or as part of another group refers to partially unsaturated cyclic hydrocarbons containing 3 to 12 carbons, preferably 5 to 10 carbons and 1 or 2 double bonds. Exemplary cycloalkenyl groups include cyclobutenyl, cyclopentenyl, cyclohexenyl, cycloheptenyl, cyclooctenyl, cyclohexadienyl, and cycloheptadienyl. Optionally, said cycloalkenyl group may be substituted with one or substituents, such as those substituents disclosed for alkyl.

The term "bicycloalkyl" as employed herein alone or as part of another group includes saturated bicyclic ring groups such as, without limitation, [3.3.0]bicyclooctane, [4.3.0]bicyclononane, [4.4.0]bicyclodecane (decalin), [2.2.2]bicyclooctane, and so forth.

The term "polycycloalkyl" as employed herein alone or as part of another group includes two or more cycloalkyl ring systems, as defined herein, wherein at least one carbon atom is a part of at least two separately identifiable ring systems. The polycycloalkyl group may contain bridging between two carbon atoms, for example, bicyclo[1.1.0]butyl, bicyclo[3.2.1]octyl, bicyclo[5.2.0]nonyl, tricycl[2.2.1.0.sup.1]heptyl, norbornyl and pinanyl. The polycycloalkyl group may contain one or more fused ring systems, for example, decalinyl (radical from decalin) and perhydroanthracenyl. The polycycloalkyl group may contain a spiro union, in which a single atom is the only common member of two rings, for example, spiro[3.4]octyl, spiro[3.3]heptyl and spiro[4.5]decyl.

The term "acyl" as employed herein by itself or part of another group, as defined herein, refers to an organic radical linked to a carbonyl $$\left( \underset{C}{\overset{O}{\|}} \right)$$

group; examples of acyl groups include a substituent group attached to a carbonyl, such as alkanoyl, alkenoyl, aroyl, aralkanoyl, heteroaryl, cycloalkanoyl, cycloheteroalkanoyl and the like.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Substituted," as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a $CH_2$ is substituted by a keto substituent (=O), then 2 hydrogens on the atom are replaced. Combinations of substituents and/or variables are permissible only if such combinations result in stable compounds. Further, when more than one position in a given structure may be substituted with a substituent selected from a specified group, the substituents may be either the same or different at every position.

The designation "  " or " $\xi$— " attached to a ring or other group refers to a free bond or linking group.

SPECIFIC EMBODIMENTS

The

group may be phenylene or a heteroaryl which is monocyclic or bicyclic and includes rings such as

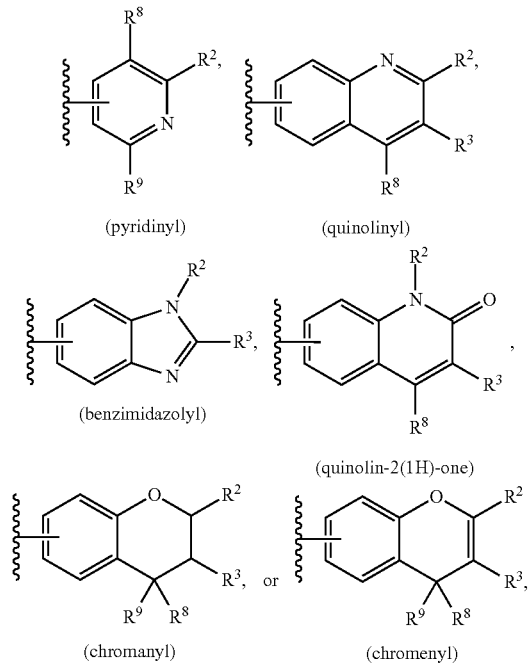

with phenylene and pyridinyl being preferred.

The Formula I compound of the invention may have the structure

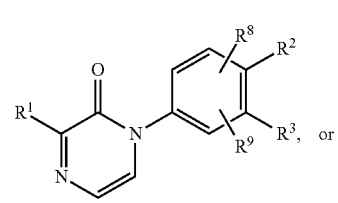

IA

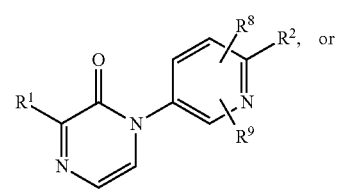

IB

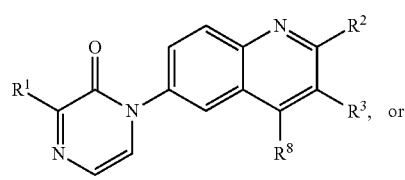

IC

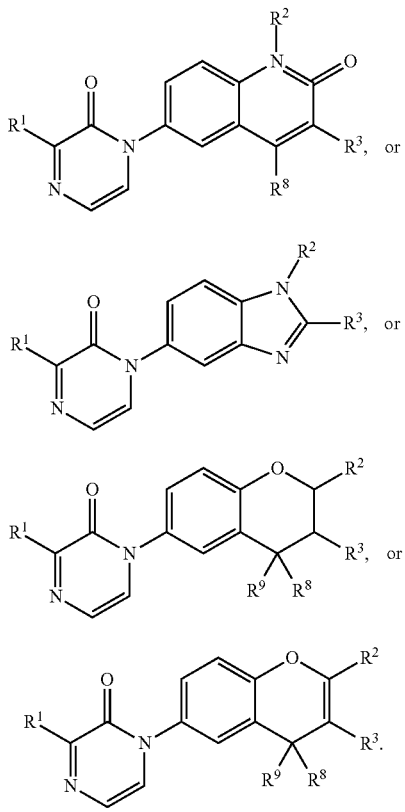

In the compound of Formula I of the invention, it is desired that

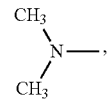

is phenylene or pyridinyl;

X is O or S; and/or

Y is a bond or an alkylene chain of 1, 2 or 3 atoms; and/or

Z is phenyl; or

Z is a heteroaryl such as pyridinyl or benzothiazole; and/or $R^2$ is E-G-J; and/or E is O or S; and/or G is a lower alkyl or alkylcycloalkyl; and/or J is H, OH, $SO_2R^7$, lower alkyl, lower alkoxy, or $CF_3$, more preferably OH; and/or $R^3$ is $C_{1-6}$ alkyl, $C_{1-6}$ alkoxy, H, or halo; and/or $R^8$ and $R^9$ are independently H or $CH_3$; and/or wherein $R^2$ and $R^3$ can be taken together to form a 5- to 7-membered ring which is saturated, unsaturated, or partially unsaturated and may include an E heteroatom, which is O, or 0, 1 or 2 N atoms, which ring is substituted with one or two of —O-G-(J)$_m$ groups, wherein at least one J is OH and optionally other substituents as set out for "alkyl", "aryl", or "heteroaryl", such as alkyl and/or OH.

The above groups may be substituted as indicated herein.

Examples of the various groups of the compounds of Formula I of the invention are set out below:

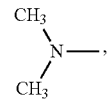

is phenylene or pyridinyl;

Z is (1) aryl, such as phenyl or naphthyl, each of which is optionally substituted with:
  a) halogen such as Cl, Br or F,
  b) alkyl such as $CH_3$, $C_2H_5$ or i-$C_3H_7$,
  c) alkoxy such as $CH_3O$,
  d) polyhaloalkyl such as $CF_3$,
  e) polyhaloalkoxy such as $CF_3O$,
  f) amino, alkylamino or dialkylamino such as $$\begin{array}{c} CH_3 \\ \diagdown \\ N— \\ \diagup \\ CH_3 \end{array},$$

g) alkylthio such as $CH_3S$,
  h) OH,
  i) esters such as —$COOCH_3$, or
  j) aryl such as phenyl, (2) monocyclic heteroaryl such as
  a) pyridinyl,
  b) pyrazinyl, or
  c) pyrimidinyl, each of a), b) or c) being optionally substituted with alkyl such as methyl, polyhaloalkyl such as trifluoromethyl, halogen such as Cl or F, or alkoxy such as $CH_3O$;

(3) benzothiazole optionally substituted with halo such as F, Cl, alkoxy such as $CH_3O$, (4) benzoxazole optionally substituted with halo such as Cl, (5) benzimidazole, (6) thiazole optionally substituted with aryl such as phenyl, and alkyl such as t-$C_4H_9$, (7) indanyl, (8) quinolinyl optionally substituted with $CF_3$, or (9) imidazolidinyl; and/or Y is a bond or alkylene such as methylene, or ethylene or propylene; and/or X is S, O, SO, or $SO_2$; and/or J is (1) H, (2) —CO—$NR^{5a}R^6$ where $R^{5a}$ and $R^6$ together with the N to which they are attached form a pyrrolidinyl ring, (3) OH, (4) COOH, (5) COOalkyl such as $COOCH_3$, (6) $SO_2R^7$ such as $SO_2C_2H_5$, or (7) prodrug esters such as glycine

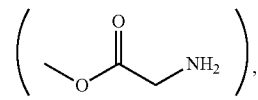

phosphate

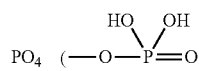

and the corresponding Na salt thereof), and valine

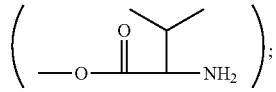

and/or
  m is 1 or 2; and/or
  G is $CH_2$, $(CH_2)_2$, $(CH_2)_3$,

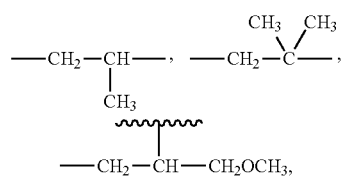

cycloalkyl such as

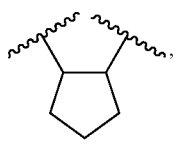

cycloalkoxy such as

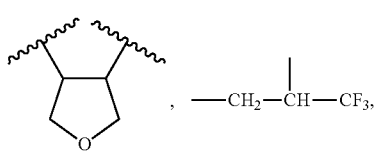

or alkylcycloalkyl such as

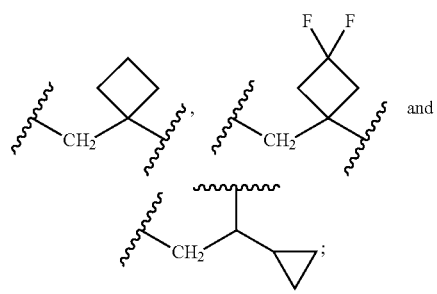

and/or
  E is O; and/or
  $R^3$ is H, alkoxy such as $CH_3O$, hydroxyalkyl such as $HOCH_2CH_2$—, alkyl such as $CH_3$ or $C_2H_5$, halo such as F or Cl, CN, or hydroxyalkoxy such as $HOCH_2CH_2O$—; and/or $R^2$ and $R^3$ can be optionally taken together to form a 5- or 6-membered unsaturated or aromatic ring containing one or two N atoms, which ring is optionally substituted with hydroxyalkyl such as

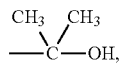

for example

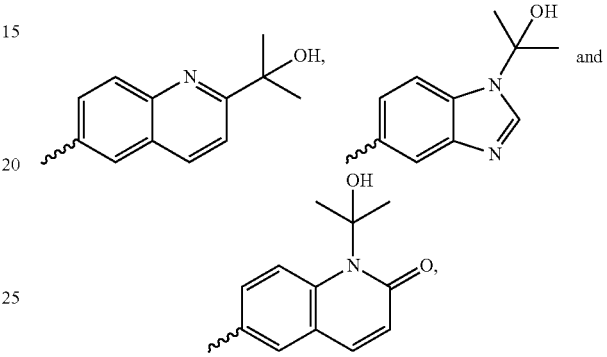

or where $R^2$ and $R^3$ can be optionally taken together to form a 6-membered saturated, unsaturated or partially unsaturated O-containing ring, which ring is optionally substituted with hydroxyalkyl such as alkyl such as

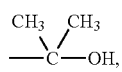

$CH_3$ and OH, for example

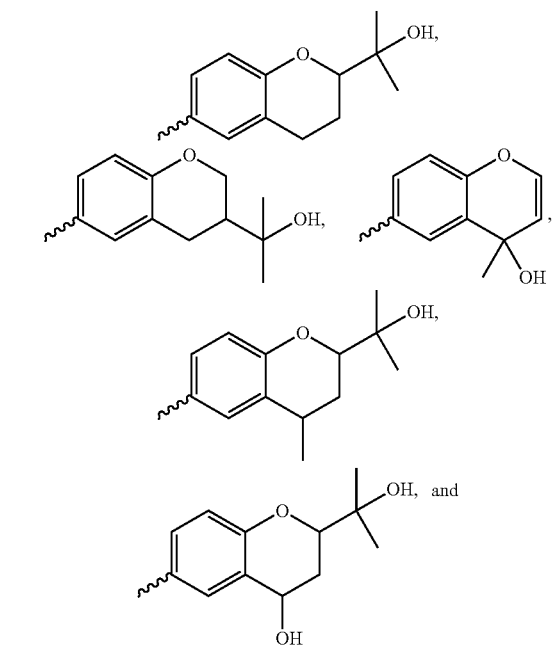

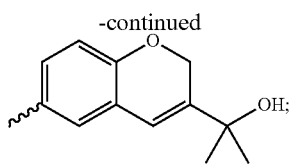

and/or $R^8$ is H, halo such as F and Cl, or alkyl such as methyl; and/or $R^9$ is H.

In a further embodiment of the compound of Formula I of the invention, X=O and

is phenylene or pyridinyl. In another embodiment, X=S and

is phenylene.

In a further embodiment in Formula I of the invention, Y is a bond. Also in a further embodiment, Y is methylene, ethylene or propylene. In addition, the alkyl chain or alkyl moiety in Y may be attached to the ortho-position of Z to generate a bicyclic moiety. In this embodiment, the bicyclic moiety is preferably 1-indanyl or 2-indanyl when Z is phenyl.

In a further embodiment, Z is selected from phenyl, naphthyl, pyridinyl, pyrazinyl, benzimidazolyl, benzothiazolyl, and benzoxazolyl, preferably phenyl and pyridinyl.

Furthermore, in the embodiment wherein $R^5$ and $R^6$ taken together form a 4-, 5- or 6-membered cyclic amine, it is preferred that this component be selected from the group consisting of azetidinyl, pyrrolidinyl, piperidinyl, morpholinyl, and piperazinyl.

Also preferred is the embodiment wherein $R^3$ is $C_1$-$C_6$ alkoxy. Especially preferred is the embodiment wherein $R^3$ is $C_1$-$C_3$ alkoxy or $C_1$-$C_3$ alkyl. Even more preferably, $R^3$ is methoxy or methyl.

In one embodiment of the invention, $R^1$ may be selected from the group consisting of:

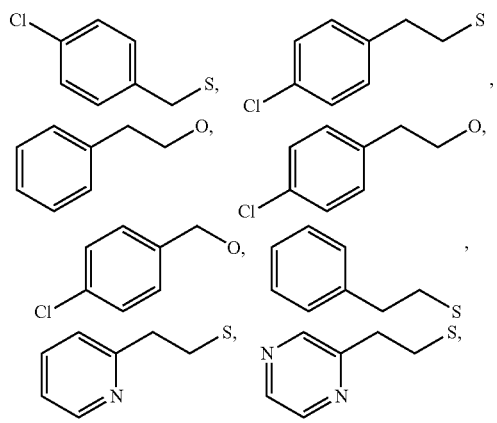

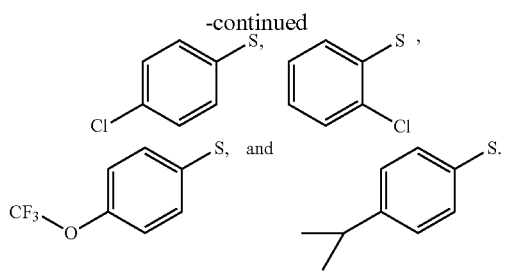

It is also desirable that in Formula I, $R^2$ is —O—2-hydroxy-propane, $R^3$ is methoxy, and $R^1$ is selected from the group consisting of:

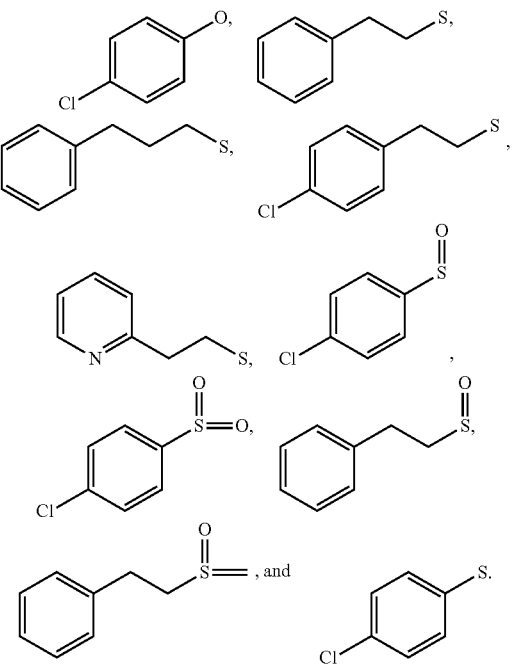

In another embodiment of the invention, it is desirable that

is phenylene;

$R^2$ is

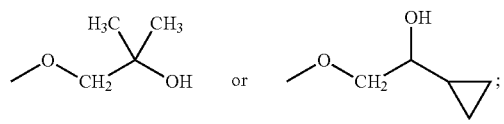

or $R^2$ and $R^3$ can be optionally taken together to form a 5- or 6-membered unsaturated or aromatic ring containing one or two N atoms, which ring is optionally substituted with hydroxyalkyl such as

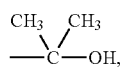
for example
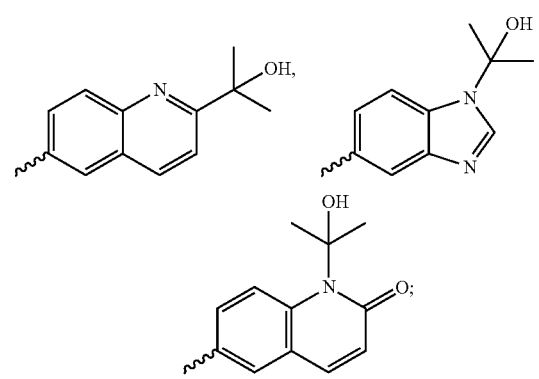
and
R³ is methoxy or methyl, and R¹ is selected from the group consisting of:
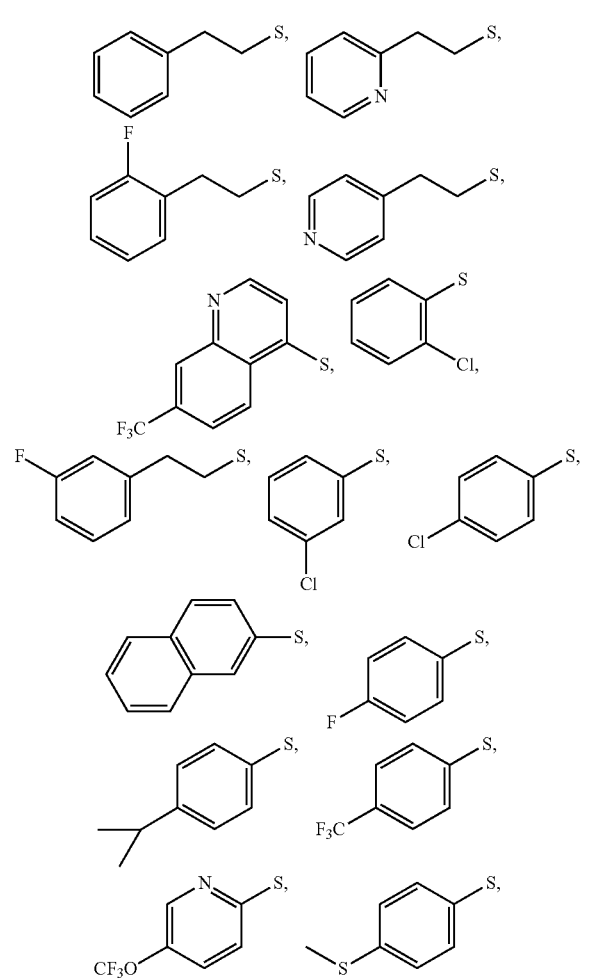
-continued
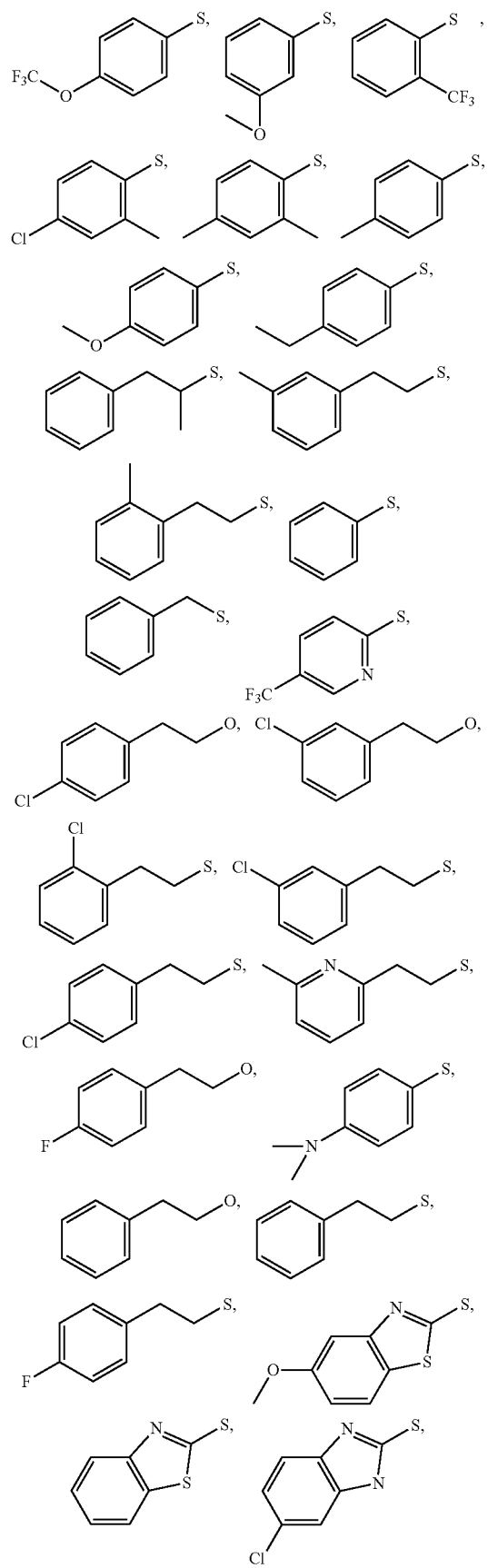

-continued

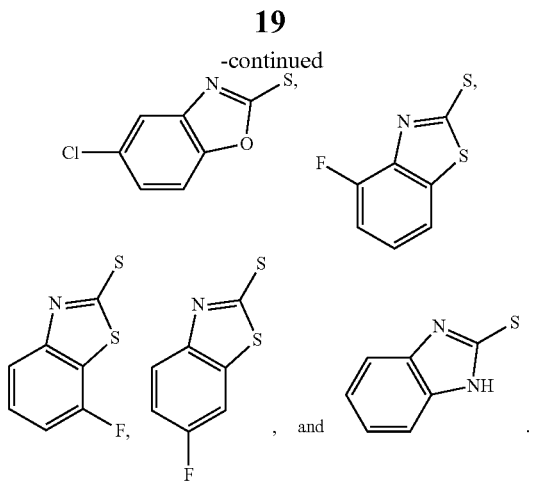

Also desired is the prodrug embodiment, hereinafter described, wherein in Formula I, $R^2$ is E-G-hydroxyl-$^{Pro-Drug}$ or more preferably

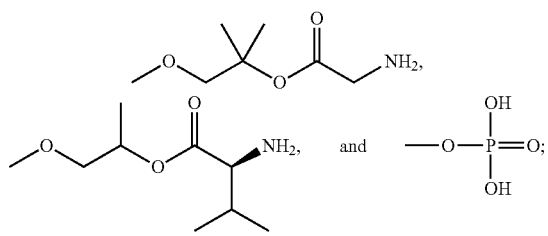

$R^3$ is methoxy; and
$R^1$ is selected from

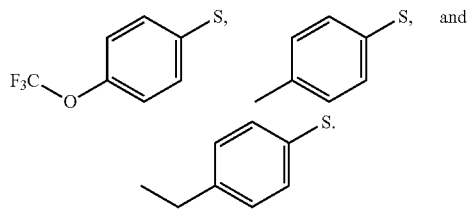

Also desired are compounds of Formula I wherein

is phenylene;
$R^1$ is Z—Y—X— wherein
X is S,
Y is an alkyl chain of 1 to 3 carbons or a bond,
Z is heteroaryl or phenyl,
each of which Z is optionally substituted with $CF_3$, $CF_3O$, or halo;
$R^2$ is -E-G-J wherein
E is O,
G is lower alkyl such as

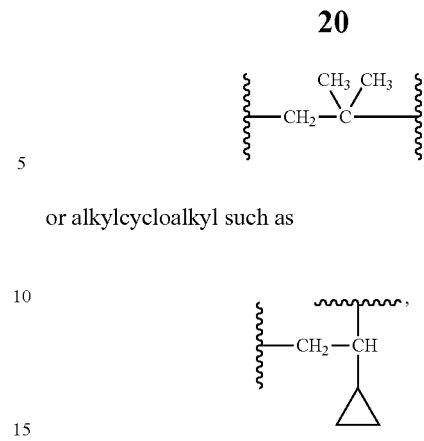

or alkylcycloalkyl such as

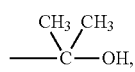

and
J is OH;
$R^3$ is H, alkoxy such as $CH_3O$, or alkyl such as $CH_3$;
$R^8$ and $R^9$ are independently H or $CH_3$; and
$R^2$ and $R^3$ can be optionally taken together to form a 5- or 6-membered unsaturated or aromatic ring containing one or two N atoms, which ring is optionally substituted with hydroxyalkyl such as

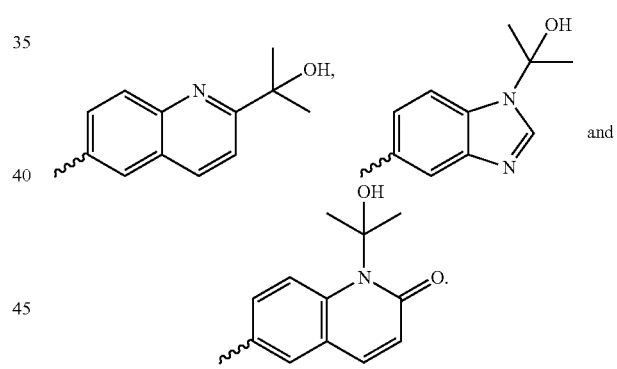

for example

In still more preferred compounds of Formula I,

is phenylene;
X is S;
Y is a bond or $(CH_2)_2$;

Z is 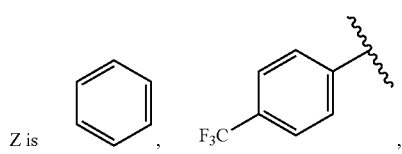

-continued

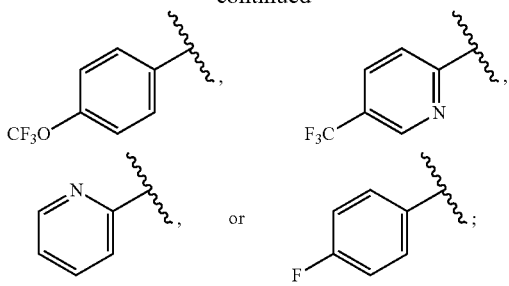

E-G-J is

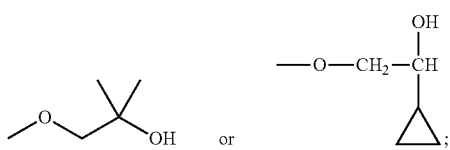

R³ is CH₃O or CH₃;

R⁸ and R⁹ are each H; and

R² and R³ can be optionally taken together to form a 5- or 6-membered unsaturated or aromatic ring containing one or two N atoms, which ring is optionally substituted with hydroxyalkyl such as

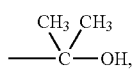

for example

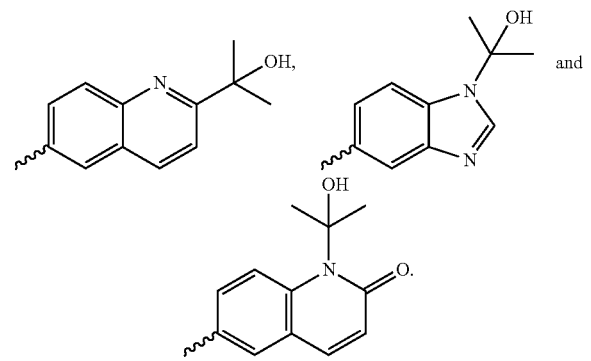

Some preferred compounds of the invention include the following:

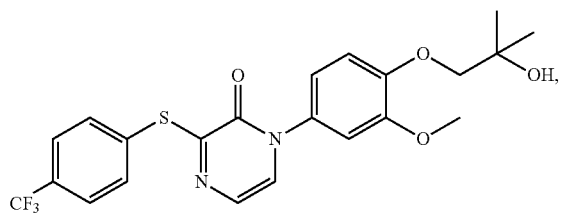

-continued

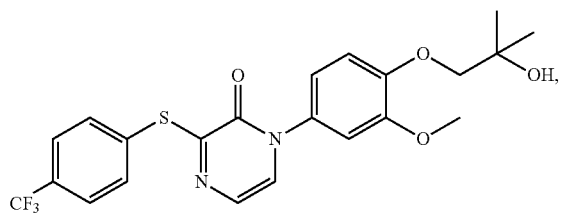

Also desired are compounds of Formula I wherein

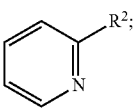

is

R¹ is Z—Y—X— wherein
X is S,
Y is an alkyl chain of 1 to 3 carbons such as $(CH_2)_2$ or a bond,
Z is heteroaryl such as 2-pyridyl or phenyl, each of which Z is optionally substituted with $CF_3$, $CF_3O$, or halo such as F, so that $R^1$ can be selected from:

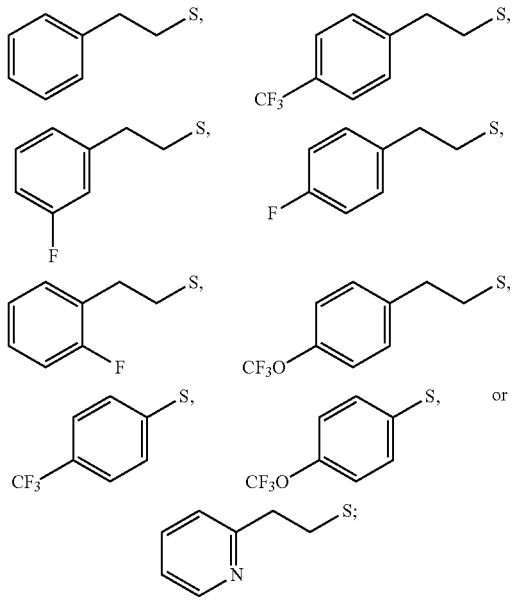

$R^2$ is -E-G-J wherein

E is O,

G is lower alkyl or alkylcycloalkyl, and

J is OH, for example, $R^2$ is

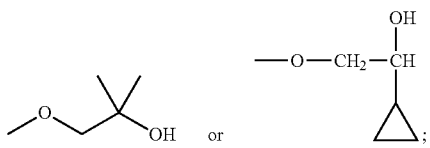

$R^3$ is alkoxy such as $CH_3O$, alkyl such as $CH_3$, or halo such as Cl; and $R^8$ and $R^9$ are independently H or $CH_3$.

In still more desired compounds of Formula I,

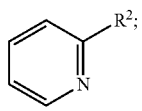

is

X is S;

Y is a bond or $(CH_2)_2$;

Z is

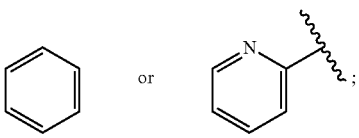

E-G-J is

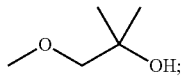

and $R^3$ is $CH_3$, H or Cl.

Methods of Preparation

The compounds of Formula I according to the various embodiments herein described can be prepared as shown in the following non-limiting reaction schemes and description thereof, as well as relevant published literature procedures that may be used by one skilled in the art.

Scheme 1 below portrays a generalized reaction sequence for the synthesis of compounds of Formula I.

Compounds of Formula I, for which $R^1$ is Z—Y—O or Z—Y—S and $R^2$ does not contain a tertiary alcohol, can be prepared by condensation of compounds of Formula II in a solvent such as THF with alkali metal salts such as $Na^+$ or $K^+$ of compounds of Formula III. The alkali salts of compounds of Formula III had been previously prepared by addition of compounds of Formula III to a stirred dispersion of NaH or KH in a solvent such as THF under an inert atmosphere of $N_2$ or Ar. Compounds of Formula II can be prepared by treatment of compounds of Formula IV with thionyl chloride in a solvent such as DMF. Compounds of Formula III are commercially available or may be readily prepared by one skilled in the arts.

Alternatively, a general synthesis of compounds of Formula I, for which $R^1$ is Z—Y—O, Z—Y—S or Z—Y—$NR^4H$, entails condensation of compounds of Formula IV with compounds of Formula III by stirring these components in a solvent such as DMF containing benzotriazo-1-yl-oxy-trispyrrolidinophosphonium hexafluoroborate (PyBOP) as an activating agent, DMAP and a hindered amine such as $Et(iPr)_2N$. Other activating agents may be utilized by the skilled artisan.

Compounds of Formula IV can be prepared by heating compounds of Formula V to 120-150° C. in microwave in a 1:1.1 mixture of HOAc/TFA. Compounds of Formula V can be prepared by stirring compounds of Formula VI with 2,2-dimethoxyethylamine in a solvent such as EtOAc. Compounds of Formula VI can be prepared by treatment of compounds of Formula VII with ethyl oxalyl chloride in a mixture of EtOAC and water containing a weak base such as potassium carbonate. Compounds of Formula VII are either commercially available or can be prepared as described in U.S. Ser. No. 11/586,255.

Compounds of Formula I for which $R^1$ is Z—Y—SO or Z—Y—$SO_2$ can be prepared by treatment of compounds of Formula I where $R^1$ is Z—Y—S with one or two equivalents of an oxidant such as m-chloroperbenzoic acid in a solvent such as $CH_2Cl_2$.

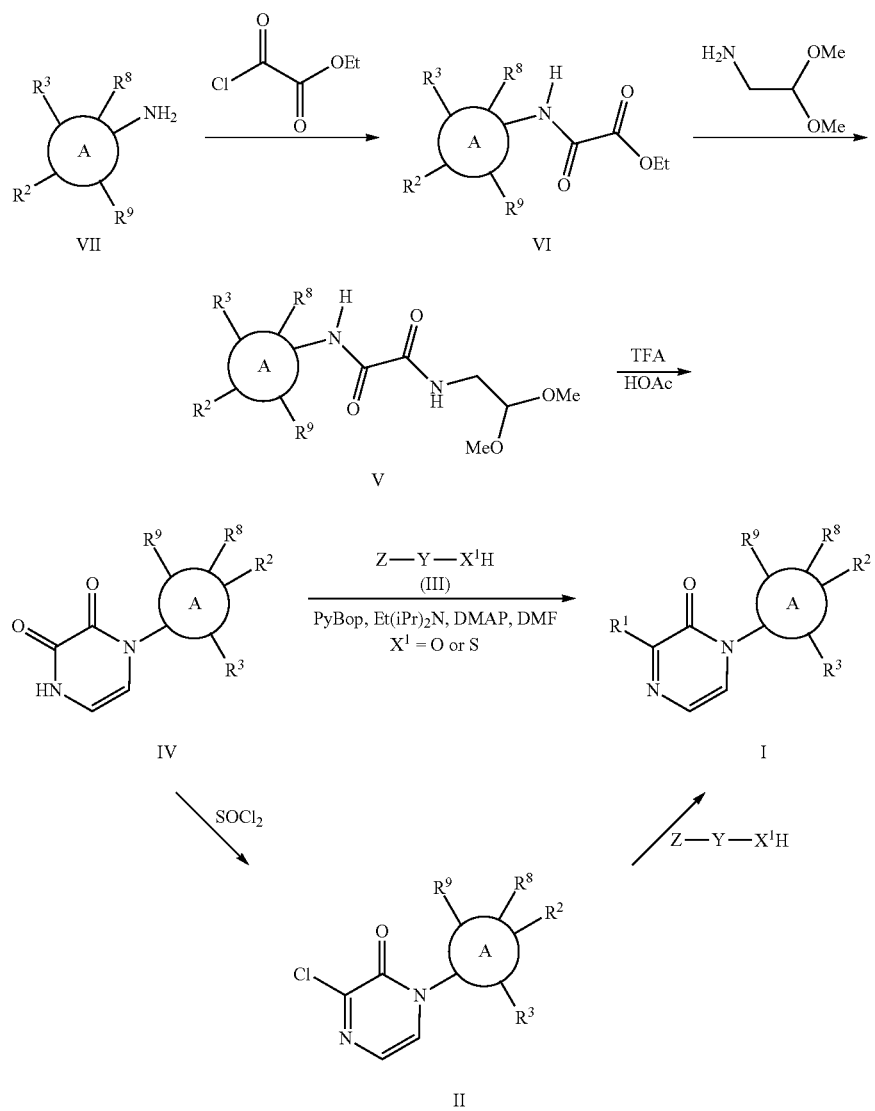

Alternatively compounds of formula I can be prepared as outlined in Scheme 2. by Cu catalyzed arylation of compounds of formula X by heating X with aryl halides or iodides of formula XI in a solvent such as dioxane containing a cuprous salt such as cuprous iodide along with potassium tribasic phosphate and a chelating agent such as N-methyl, N'-methyl ethylene diamine Compounds of formula X can be prepared by heating compounds of formula IX in TFA. Compounds of formula IX can be prepared by condensation of compound of Formula VIII with compounds of Formula III by stirring these components in a solvent such as DMF containing benzotriazo-1-yl-oxy-trispyrrolidinophosphonium hexafluoroborate (PyBOP) as an activating agent, DMAP and a hindered amine such as Et(iPr)$_2$N. Compound of formula VIII is readily obtained from p-methoxybenzyl amine utilizing the chemistry described in Scheme 1. Aryl halides of formula XI are readily prepared by one skilled in the arts by alkylation of the corresponding commercially available halogenated phenol.

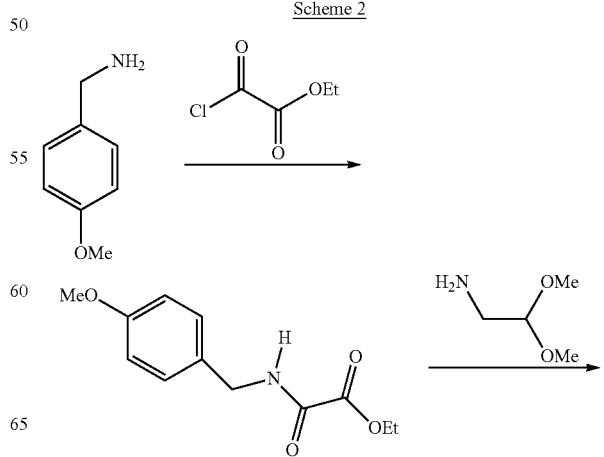

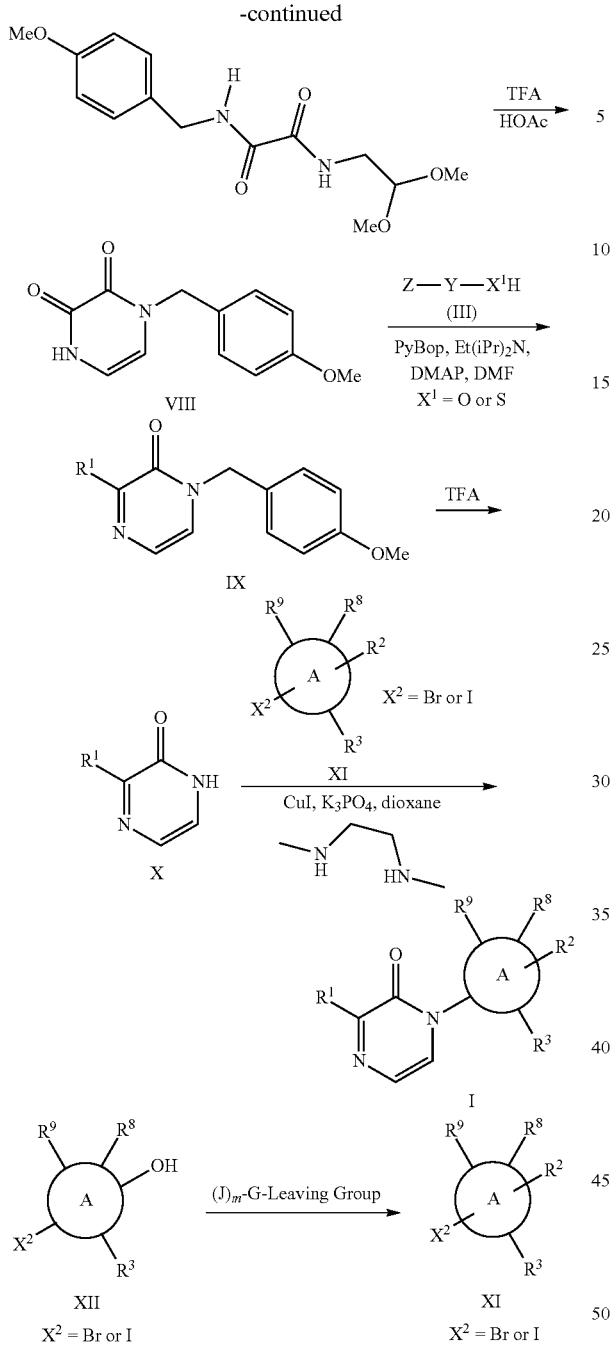

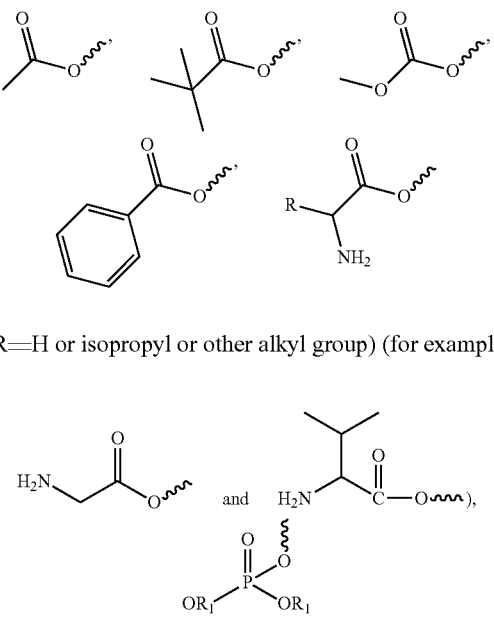

Examples of such prodrug esters include (R=H or isopropyl or other alkyl group) (for example,

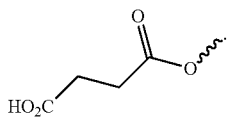

(where $R_1$ is H or an alkali metal such as Na), that is

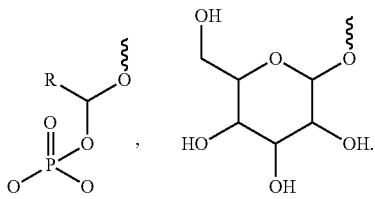

The term "prodrug ethers" include both phosphate acetals and O-glucosides. Representative examples of such prodrug ethers include Other methods of preparing the compounds of Formula I are within the scope of the invention as well.

Prodrugs, Salts, Esters and Stereoisomers

The compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

The compounds of Formula I can also be present as salts, which are further within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid (phosphate ester) or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic acid, glutamic acid, glycine, valine, lysine, or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines All stereoisomers of the compounds of the invention are contemplated, either in admixture or in pure or substantially pure form. The compounds of the present application can have asymmetric centers at any of the carbon atoms including any one of the R substituents. Consequently, compounds of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Utility

The compounds of the present application can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease.

The compounds described in the present application could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

Pharmaceutical Combinations

The present application includes within its scope pharmaceutical compositions comprising, as an active ingredient, a therapeutically effective amount of at least one of the compounds of Formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the melanin-concentrating hormone receptor (MCHR) antagonists in accordance with the application.

Examples of suitable anti-obesity agents for use in combination with the compounds of the present application include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Preproglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present application include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors including saxagliptin, SGLT2 inhibitors including dapagliflozin and serglifozin, glycogen phosphorylase inhibitors, and/or meglitinides, as well as insulin, and/or glucagon-like peptide-1 (GLP-1), GLP-1 agonist, incretin modulators, AMP kinase activators, glucocortical antagonists, fructose b is 1,6-phosphatase inhibitors, glucokinase inhibitors and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present application may also be employed with a PPARα/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T. L., Ph.D., dissertation, June, 1987, Dept. Med. Chem., U. of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24:9-15 (1999), (Avasimibe); Nicolosi et al., "The ACAT inhibitor, Cl-1011 is effective in the prevention and regression of aortic fatty streak area in hamsters", *Atherosclerosis* (Shannon, Irel.), 137(1):77-85

(1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.*, 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid co-transporter inhibitor such as disclosed in *Drugs of the Future*, 24:425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may also be employed in combination with anti-hypertensive agents. Examples of suitable anti-hypertensive agents for use in combination with the compounds of the present application include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could also be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Dosage Forms

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and Eudragit (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the compound of Formula I of the invention for a human adult can be selected from the clinical oral dose range of 0.01 to 30 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight) or 1 to 1000 mg/day. The other active component or components having different modes of action for use in combination can also be used in dose ranges selected by referring to the respective recommended clinical dose ranges. Administration is generally carried out in a single dose/day or in divided doses, for example, 2 to 4 times a day.

Abbreviations

The following abbreviations may be employed herein:
Ph=phenyl
Bn=benzyl
t-Bu=tertiary butyl
Me=methyl
Et=ethyl
TMS=trimethylsilyl
TBS=tert-butyldimethylsilyl
$Et_2O$=diethyl ether
EtOAc=ethyl acetate
MeOH=methanol
EtOH=ethanol
i-PrOH=isopropanol
HOAc or AcOH=acetic acid
i-$Pr_2$NEt=diisopropylethylamine
$Et_3$N=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

EXAMPLES

The following examples are provided to illustrate various preferred embodiments of the invention, and should not be construed as limiting the scope thereof.
General Experimental Information Section
In the following examples, nomenclature conforms to either IUPAC or CAS guidelines; was generated using (or is consistent with) the Autonom® module (version 2.1) distributed with ChemDraw Ultra 6.0®; or are taken from vendor literature.
brine=saturated aqueous sodium chloride
DIC=diisopropylcarbodiimide
DMF=N,N-dimethylformamide
HOBT=Hydroxybenzotriazole
PyBOP=benzotriazo-1-yl-oxy-trispyrrolidinophosphonium hexafluoroborate
TFA=trifluoroacetic acid
THF=tetrahydrofuranyl
WSC=1-[3-(dimethylamino)propyl]-3-ethylcarbodiimide hydrochloride
Analytical Chromatography Methods
  HPLC: column:
    Method 1: Phenom-Luna (ODS) S-5, 4.6 mm×50 mm; flow-5.0 mL/min.; detection at 220 nm; solvent-A=10% methanol/water+0.2% phosphoric acid, B=90% methanol/water+0.2% phosphoric acid; gradient-linear, 0% B to 100% B over 4 min and 100% B for 1 min.
    Method 2: YMC Combiscreen S-5, 4.6 mm×50 mm; flow-4.0 mL/min.; detection at 220 nm; solvent-A=10% methanol/water+0.2% phosphoric acid, B=90% methanol/water+0.2% phosphoric acid; gradient-linear, 0% B to 100% B over 4 min and 100% B for 1 min.
    LC MS: column-Phen-Luna (S5 ODS column) 4.6 mm×30 mm; detection at 220 nm; flow-4 mL/min; solvent-A=10% methanol/water+0.1% TFA, B=90% methanol/water+0.1% TFA; linear gradient, 0% B to 100% B over 2 min and 100% B for 1 min.
Preparative HPLC Chromatography Method
  Phenomenex Luna C18, S5, 21×100 mm; flow-20 mL/min, detection at 220 nm; solvent-A=10% methanol/water+0.1% TFA, B=90% methanol/water+0.1% TFA; gradient-linear, 10% B to 90% B over 20 min.

General Experimental Procedures for Preparation of 3-(Arylthio)-1-(aryl)pyrazin-2(1H)-one Preparation of 1-Aryl pyrazine-2,3(1H,4H)-dione Part A

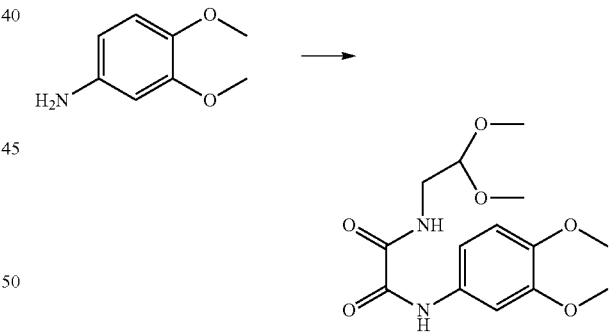

Ethyl oxalyl chloride (7.8 g, 6.8 mL, 57 mmol) was added to a mixture of 3,4-dimethoxyaniline (4.4 g, 29 mmol) and $K_2CO_3$ (14 g, 140 mmol) in EtOAc (44 mL) and water (12 mL) at 0° C. After stirring at 0° C. for 10 min, water (18 mL) was added; whereupon the mixture was transferred to a separatory funnel and extracted with EtOAc (2×40 mL). The combined EtOAc were filtered through $Na_2SO_4$ and evaporated to about 30 mL. After addition of 2,2-dimethoxyethylamine (3.8 g, 3.9 mL, 36 mmol), the reaction was stirred at ambient temperature overnight. The resultant white solid was filtered and then washed with hexane to afford N1-(2,2-dimethoxyethyl)-N2-(3,4-dimethoxyphenyl)oxalamide as a light purple-grey solid (6.3 g, 71% yield). HPLC 33% 2.47 min and 63% at 2.79 min. LC MS 1.37 min (M+1=281 and 335). H-NMR (CDCl₃) 9.15 (broad s, 1H), 7.76 (broad s, 1H), 7.41 (d, J=2.4 Hz, 1H), 7.06 (dd, J=2.4, 8.7 Hz, 1H), 6.85 (d, J=8.7 Hz, 1H), 4.45 (t, J=5.5 Hz, 1H), 3.90 (s, 3H), 3.88 (s, 3H), 3.52 (t, J=5.5 Hz, 2H), 3.42 (s, 6H).

Part B

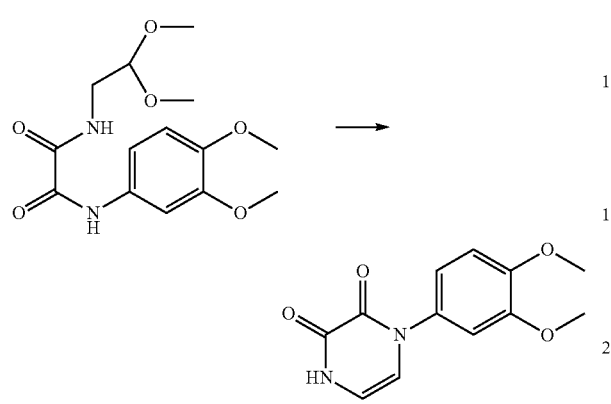

After addition of trifluoroacetic acid (0.12 mL, 1.7 mmol) to a mixture of the aryl oxalamide prepared in Part A (0.50 g, 1.6 mmol) in acetic acid (1.0 mL), the resulting solution was heated to 125° C. for 20 min using a microwave. Following evaporation of the solvent, the residue was triturated with EtOAc to afford 1-(3,4-dimethoxyphenyl)pyrazine-2,3(1H, 4H)-dione as a white solid (1.1 g, 92% yield). HPLC 1.83 min. LC MS 1.20 min (M+1=249). H-NMR (CD₃OD) 7.06 (m, 2H), 6.97 (m, 1H), 6.56 (d, J=5.7 Hz, 1H), 6.45 (d, J=5.7 Hz, 1H), 3.89 (s, 3H), 3.85 (s, 3H).

Preparation of Desired Substituted 3-thio-1-aryl-pyrazin-2(1H)-one

Method 1

Part C

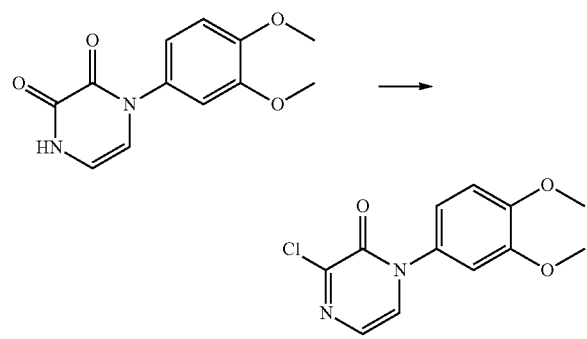

Thionyl chloride (0.28 g, 0.17 mL, 2.4 mmol) was slowly added to a stirred solution of the 1-aryl pyrazine-2,3(1H,4H)-dione prepared in Part B (0.54 g, 2.2 mmol) in EtOAc (0.88 mL) and DMF (0.44 mL) at 45° C. After stirring at 55 to 60° C. for 2 h, the reaction was transferred to a separatory funnel, diluted with EtOAc and 2N KHCO₃ and extracted with EtOAc (2×). The combined organic layers were washed with 2N KHCO₃ and water; whereupon, the combined aqueous layers were extracted with CH₂Cl₂. All of the organic layers were combined prior to drying over MgSO₄ to afford 3-chloro-1-(3,4-dimethoxyphenyl)pyrazin-2(1H)-one (0.34 g, 59% yield). HPLC 2.33 min. LC MS 1.00 min (M+1=267/269). The chloropyrazinone was used in the subsequent steps without further purification.

Part D

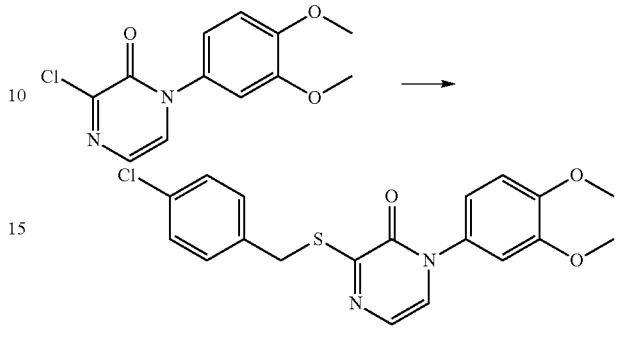

4-Chlorobenzylmercaptan (71 mg, 0.059 mL, 0.45 mmol) was added to a stirred THF (1.0 mL) suspension of sodium hydride (60% oil dispersion, 18 mg, 0.45 mmol), that had been previously washed with hexane 3×. The reaction was stirred at ambient temperature for 20 min until it became a solid mass; whereupon, the chloropyrazinone prepared in Part C (100 mg, 0.38 mmol) in THF (5 mL) was added resulting in gas evolution. After stirring at ambient temperature for 40 min, the reaction was diluted with CH₂Cl₂/H₂O, extracted with CH₂Cl₂ (2×) and dried over MgSO₄ to afford 220 mg of crude product after evaporation of the solvent. The desired was purified by chromatography on silica gel (12 g) employing gradient elution (0-100% EtOAc/hexane over 12 min) to elute the desired 3-(4-chlorobenzylthio)-1-(3,4-dimethoxyphenyl)pyrazin-2(1H)-one (130 mg, 89% yield).

Method 2

A solution of the 1-aryl pyrazine-2,3(1H,4H)-dione prepared in Part B (67 mg, 0.27 mmol), diisopropylethyl amine (0.15 mL, 0.81 mmol), pyBOP (0.23 g, 0.46 mmol), and dimethylaminopyridine (13 mg) in DMF (1.2 mL) was stirred at ambient temperature for 15 min. After addition of 2-pyridylethyl mercaptan (28 mg, 0.40 mmol), the reaction was stirred at ambient temperature for 2.5 h prior to quenching by addition of H₂O and extraction with EtOAc. The EtOAc extracts were washed with water (2×), brine, dried over MgSO₄ and concentrated to yield 204 mg of crude product. Chromatography on silica employing a gradient elution with hexane/EtOAc afforded the desired product 1-(3,4-dimethoxyphenyl)-3-(2-(pyrazin-2-yl)ethylthio)pyrazin-2(1H)-one (17 mg, 17% yield).

Method 2a

The same procedure was employed as that described in Method 2 except that the reaction was run for 18 hr.

Method 3

Following preparation of the oxalamide as described in Part A, ring closure can be effected by prolonged thermal heating in TFA/HOAc at 78° C. for 1d. In the case of 3-methoxy-4-(2-(pyrrolidin-1-yl)ethoxy)aniline which contained a basic amine, the reaction was brought to pH 6 to 7 with saturated NaHCO₃ and then evaporated in vacuo. The residue was absorbed on silica gel and purified by flash chromatography (5 to 15% 2N NH₃ in MeOH/CH₂Cl₂) to afford the desired 1-aryl pyrazine-2,3(1H,4H)-dione in 36% yield. This material was subsequently converted to final product following the procedure described in Method 2.

Method 4

If the oxalamide as described in Part A contained a primary or secondary alcohol, prolonged thermal heating in TFA/HOAc at 78° C. for 1 day not only effected ring closure but also converted the alcohol moiety to an acetate. The resulting 1-aryl pyrazine-2,3(1H,4H)-dione was converted to the desired 3-thio substituted-1-arylpyrazin-2-one employing Method 1. Following workup and purification as described in Method 1, the acetylated product was converted to the desired 3-thio substituted-1-arylpyrazin-2-one (19 mg, 0.041 mmol) bearing a free hydroxyl by dissolution in MeOH (1.0 mL) and H₂O (0.1 mL) and stirring at ambient temperature for 1 h after addition of potassium carbonate (30 mg). The reaction was then diluted with CH₂Cl₂/H₂O prior to extraction with CH₂Cl₂ (2×). After drying the combined organic layers over MgSO₄, concentration afforded the desired final product (16 mg, 93% yield).

Method 5

For weakly nucleophilic thiols more forcing conditions were required effect PyBOP mediated conversion of the 1-aryl pyrazine-2,3(1H,4H)-dione to a 3-thio substituted-1-arylpyrazin-2-ones. Accordingly, a DMF solution (0.4 mL) containing the 1-aryl pyrazine-2,3(1H,4H)-dione prepared in Part B (92 mg, 0.30 mmol), PyBOP (0.27 g, 0.53 mmol) and diisopropylethylamine (0.16 mL, 0.9 mmol) was stirred for 3 h before addition of a DMF solution prepared by stirring 5-methoxybenzo[d]thiazole-2-thiol (296 mg, 1.502 mmol) with NaH (60.1 mg, 1.502 mmol, rinsed with hexane 2×) in DMF (0.2 mL) at ambient temperature for 10 min. After stirring at ambient temperature for 7 days, the reaction mixture was diluted with EtOAc and washed sequentially with water (2×) and brine prior to drying over MgSO₄. After evaporation of the solvent, CH₂Cl₂ (10 mL) was added to the 0.30 g of crude product. Filtration to remove any residual solids followed by evaporation of the filtrate afforded 0.10 g crude product. Final purification required flash chromatography on 12 g silica gel using gradient elution (0 to 100% EtOAc/CH₂Cl₂) followed by preparatory HPLC (YMC S5 ODS 20×100 mm, 20 mL/min, 30 to 100% B in A over 10 min. Solvent A=10% MeOH/H₂O-0.1% TFA, Solvent B=90% MeOH/H₂O-0.1% TFA) to afford pure desired product (6.3 mg, 4% yield).

Method 6

General Experimental Procedures for Preparation of 1-(4-(2-Hydroxy-2-methylpropoxy)-3-methylphenyl)-3-(4-(trifluoromethoxy)phenylthio)pyrazin-2(1H)-one

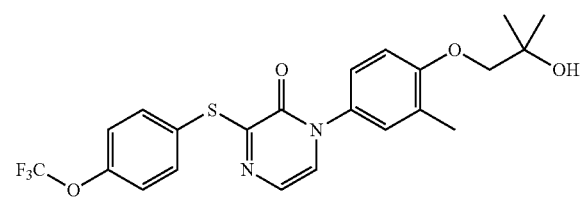

Part A. N1-(2,2-Dimethoxyethyl)-N2-(4-methoxybenzyl)oxalamide

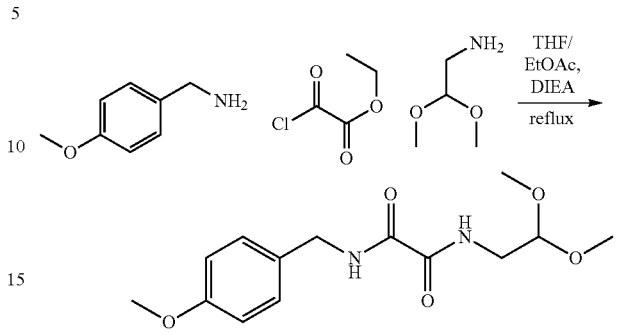

To a mixture of (4-methoxyphenyl)methanamine (9.90 g, 72.2 mmol) in THF (40 mL) was slowly added ethyl 2-chloro-2-oxoacetate (10.84 g, 79 mmol). After stirring the reaction at RT for 15 min, a solution of 2,2-dimethoxyethanamine (9.10 g, 87 mmol) and N,N-diisopropylethylamine (37.8 mL, 217 mmol) in EtOAc (40.0 mL) was added. The reaction was heated at reflux for 18 hours; whereupon, after cooling to RT, saturated NaHCO₃ (50 ml) was added and the mixture extracted with EtOAc (50 ml). The EtOAc layer was dried over Na₂SO₄ and concentrated. The crude product was purified by silica gel chromatography employing a solvent gradient (CH₂Cl₂ to 5% MeOH/CH₂Cl₂) to elute N1-(2,2-dimethoxyethyl)-N2-(4-methoxybenzyl)oxalamide (7.50 g, 25.3 mmol, 35.1% yield) as white solid. 1H NMR (400 MHz, chloroform-d) δ ppm 9.07 (1H, s), 7.69 (1H, t, J=5.65 Hz), 7.59 (1H, d, J=8.78 Hz), 6.74 (1H, d, J=8.78 Hz), 4.46 (1H, t, J=5.40 Hz), 3.79 (2H, s), 3.53 (2H, t), 3.44 (6H, s), 2.23 (6H, d, J=5.27 Hz), 1.37 (6H, s).

Part B.
3-Hydroxy-1-(4-methoxybenzyl)pyrazin-2(1H)-one

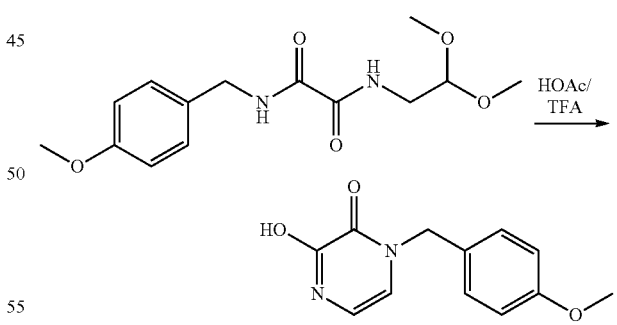

A solution of N1-(2,2-dimethoxyethyl)-N2-(4-methoxybenzyl)oxalamide (7.5 g, 25.3 mmol) and TFA (2.340 mL, 30.4 mmol) in AcOH (160 mL) was stirred at 135° C. in a seal tube for 1.5 hours. After cooling to RT and removal of the volatiles under vacuum, ethyl ether (150 ml) and sat. aq. NaHCO₃ solution (150 ml) were added. The resulting precipitate was collected by filtration, washed with H₂O (50 ml) and ether (50 ml) prior to drying under high vacuum to yield 3-hydroxy-1-(4-methoxybenzyl)pyrazin-2(1H)-one (5.30 g, 21.68 mmol, 86% yield) as brown solid. 1H NMR (400 MHz, DMSO-$d_6$) δ ppm 11.17 (1H, br. s.), 7.18 (2H, d), 6.81 (2H, d), 6.46 (1H, d, J=5.77 Hz), 6.23 (1H, br. s.), 4.74 (2H, s), 3.24 (1H, s).

Part C. 1-(4-Methoxybenzyl)-3-(4-(trifluoromethoxy)phenylthio)pyrazin-2(1H)-one

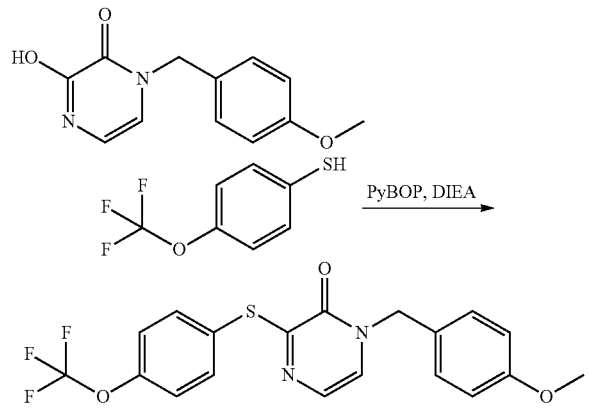

A mixture of 3-hydroxy-1-(4-methoxybenzyl)pyrazin-2(1H)-one (2.0 g, 8.61 mmol), PyBOP (7.84 g, 15.07 mmol) and N,N-diisopropylethylamine (4.51 mL, 8 mmol) in DMF (40 mL) was stirred at RT under $N_2$ for 3 hours whereupon 4-(trifluoromethoxy)benzenethiol (2.007 g, 10.33 mmol) was added. After having stirred for 18 additional hours, the reaction was diluted with saturated aq. $NaHCO_3$ (65 ml) and was then extracted with EtOAc (60 ml). The EtOAc layer was dried over $Na_2SO_4$ and concentrated. The crude product was purified by silica gel chromatography employing a solvent gradient (hexane to 75% EtOAc/hexane) to elute 1-(4-methoxybenzyl)-3-(4-(trifluoromethoxy)phenylthio)pyrazin-2(1H)-one (2.76 g, 6.42 mmol, 74.6% yield) as white solid. 1H NMR (400 MHz, chloroform-d) δ ppm 7.58 (2H, d, J=8.78 Hz), 7.21-7.35 (4H, m), 7.02 (1H, d, J=4.52 Hz), 6.90 (2H, d, J=8.78 Hz), 6.85 (1H, d, J=4.27 Hz), 5.03 (2H, s), 3.81 (3H, s).

Part D. 3-(4-(Trifluoromethoxy)phenylthio)pyrazin-2(1H)-one

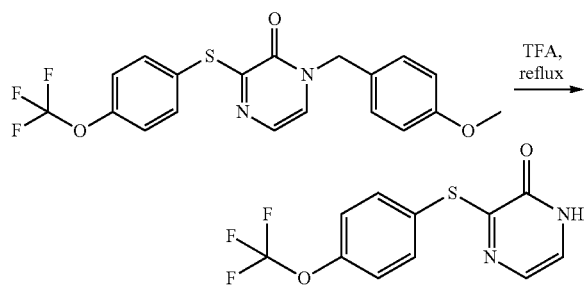

A solution of 1-(4-methoxybenzyl)-3-(4-(trifluoromethoxy)phenylthio)-pyrazin-2(1H)-one (2.76 g, 6.76 mmol) in TFA (25 mL) was stirred at reflux for 2 days. Since LC-MS analysis revealed that 28% SM remained, the reaction was stirred for 7 days. After removal of the TFA under vacuum, the crude product was purified by silica gel chromatography employing a solvent gradient (hexane to 100% EtOAc to elute 3-(4-(trifluoromethoxy)phenylthio)pyrazin-2(1H)-one (1.60 g, 5.27 mmol, 78% yield) as off-white solid. 1H NMR (400 MHz, chloroform-d) δ ppm 7.61 (2H, d, J=9.03 Hz), 7.29 (2H, d, J=7.78 Hz), 7.24 (1H, d, J=4.02 Hz), 7.07 (1H, d).

Part E. 1-(4-(2-Hydroxy-2-methylpropoxy)-3-methylphenyl)-3-(4-(trifluoromethoxy)phenylthio)pyrazin-2(1H)-one

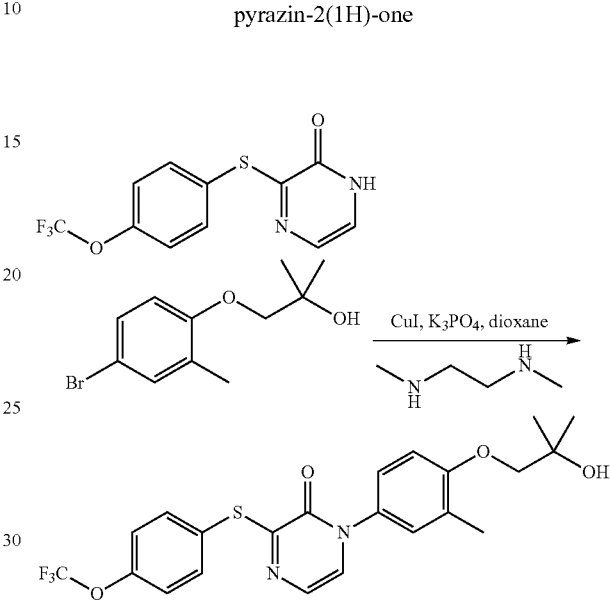

A mixture of 3-(4-(trifluoromethoxy)phenylthio)pyrazin-2(1H)-one (100 mg, 0.347 mmol), 1-(4-bromo-2-methylphenoxy)-2-methylpropan-2-ol (90 mg, 0.347 mmol), N1,N2-dimethylethane-1,2-diamine (92 mg, 1.041 mmol), copper(I) iodide (19.82 mg, 0.104 mmol) and $K_3PO_4$ (221 mg, 1.041 mmol) in dioxane (1.0 mL) was stirred at 115° C. in a sealed tube for 2 hours. After removal of the precipitate by filtration, the filtrate was concentrated. The crude product was purified by silica gel chromatography employing a solvent gradient (hexane to 100% EtOAc) to elute 1-(4-(2-hydroxy-2-methylpropoxy)-3-methylphenyl)-3-(4-(trifluoromethoxy)phenylthio)-pyrazin-2(1H)-one (18.65 mg, 0.040 mmol, 11.52% yield) as off-white solid. 1H NMR (500 MHz, methanol-$d_3$) δ ppm 7.62-7.68 (2H, m), 7.37 (2H, d, J=7.97 Hz), 7.21-7.28 (3H, m), 7.16 (1H, d, J=4.40 Hz), 7.02 (1H, d, J=8.25 Hz), 3.84 (2H, s), 2.31 (3H, s), 1.36 (6H, s).

Method 7

General Experimental Procedures for Preparation of 3-(4-Chlorophenethoxy)-1-(4-(2-hydroxy-2-methylpropoxy)phenyl)pyrazin-2(1H)-one

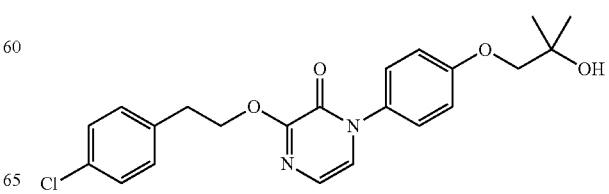

Part A. 2-(4-Chlorophenethoxy)-3-methoxypyrazine

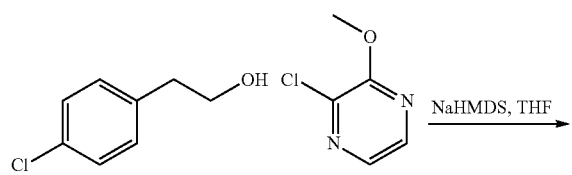

To a mixture of 2-(4-chlorophenyl)ethanol (1.246 g, 7.96 mmol) in THF was added 1.0 M sodium bis(trimethylsilyl) amide in THF (6.92 mL, 6.92 mmol). After stirring at RT under nitrogen for 18 hours, the reaction was diluted with a solution of saturated NaHCO$_3$ (65 ml) and extracted with EtOAc 720 ml). The ethyl acetate layer was dried over Na$_2$SO$_4$ and concentrated. The crude product was purified by silica gel chromatography employing a solvent gradient (hexane to 30% ethyl acetate) to elute 2-(4-chlorophenethoxy)-3-methoxypyrazine (1.25 g, 4.72 mmol, 68.3% yield) as clear oil. 1H NMR (500 MHz, CDCl$_3$) δ ppm 7.61-7.64 (1H, m), 7.59-7.61 (1H, m), 7.26-7.30 (2H, m), 7.20-7.24 (2H, m), 7.15 (1H, d, J=8.52 Hz), 4.49-4.63 (2H, m), 4.02 (3H, s), 3.12 (2H, t, J=7.29 Hz).

Part B. 3-(4-Chlorophenethoxy)pyrazin-2(1H)-one

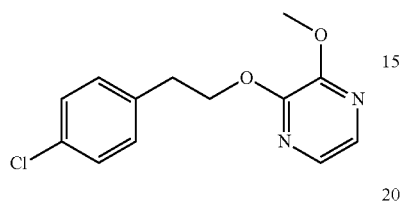

A mixture of benzo[d]thiazole-2-thiol (1.264 g, 7.56 mmol), 2-(4-chlorophenethoxy)-3-methoxypyrazine (1.00 g, 3.78 mmol) and NaHCO$_3$ (1.587 g, 18.89 mmol) in DMA (10 mL) was stirred at 135° C. for 6 hours. After cooling to RT, the mixture was diluted with a solution of saturated NaHCO$_3$ (55 ml) and was then extracted with EtOAc (60 ml). The EtOAc layer was dried over Na$_2$SO$_4$ and concentrated. The crude product was purified by silica gel chromatography employing a solvent gradient (hexane to 100% EtOAc) to elute 3-(4-chlorophenethoxy)pyrazin-2(1H)-one (477 mg, 1.808 mmol, 47.9% yield) as off-white solid. 1H NMR (400 MHz, chloroform-d) δ ppm 7.27-7.31 (2H, m), 7.19-7.25 (2H, m), 6.95 (1H, d, J=4.27 Hz), 6.89 (1H, d, J=4.52 Hz), 4.54 (2H, t, J=7.53 Hz), 3.14 (2H, t, J=7.40 Hz).

Part C. 3-(4-Chlorophenethoxy)-1-(4-(2-hydroxy-2-methylpropoxy)phenyl)pyrazin-2(1H)-one

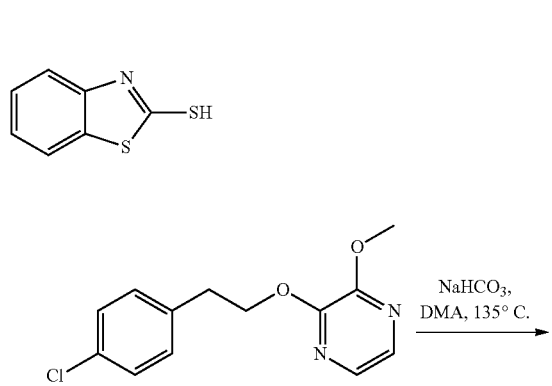

A mixture of 3-(4-chlorophenethoxy)pyrazin-2(1H)-one (25 mg, 0.100 mmol), K$_3$PO$_4$ (63.5 mg, 0.299 mmol), copper (1) iodide (18.99 mg, 0.100 mmol), 1-(4-bromophenoxy)-2-methylpropan-2-ol and N,N'-dimethylethylenediamine (0.032 mL, 0.299 mmol) in dioxane (1.0 mL) was stirred at 110° C. for 60 min. After removal of the precipitate by filtration, the filtrate was concentrated. The crude product was purified by silica gel chromatography employing a solvent gradient (CH$_2$Cl$_2$ to 10% MeOH/CH$_2$Cl$_2$) to elute 3-(4-chlorophenethoxy)-1-(4-(2-hydroxy-2-methylpropoxy)phenyl) pyrazin-2(1H)-one (31.82 mg, 0.073 mmol, 73.1% yield) as white solid. 1H NMR (500 MHz, chloroform-d) δ ppm 7.32 (2H, d), 7.23-7.29 (4 H, m), 7.02 (2H, d), 6.84 (2H, s), 4.51 (2H, t, J=7.29 Hz), 3.83 (2H, s), 3.13 (2H, t, J=7.15 Hz), 1.36 (6H, s).

TABLE 1

3-Thio substituted-1-arylpyrazin-2(1H)-ones

| Ex. No. | Structure | Aniline/Bromide Component |
|---|---|---|
| 1 | 3-(4-chlorobenzylthiol)-1-(3,4-dimethoxyphenyl)pyrazin-2(1H)-one | 3,4-dimethoxyaniline |
| 2 | 1-(4-(benzyloxy)phenyl)-3-(4-chlorobenzylthio)pyrazin-2(1H)-one | 4-(benzyloxy)aniline |
| 3 | 3-(4-chlorophenethylthio)-1-(3,4-dimethoxyphenyl)pyrazin-2(1H)-one | 3,4-dimethoxyaniline |
| 4 | 1-(3,4-dimethoxyphenyl)-3-(phenethylthio)pyrazin-2(1H)-one | 3,4-dimethoxyaniline |
| 5 | 1-(3,4-dimethoxyphenyl)-3-(2-(pyridin-2-yl)ethylthio)pyrazin-2(1H)-one | 3,4-dimethoxyaniline |

TABLE 1-continued
3-Thio substituted-1-arylpyrazin-2(1H)-ones
6 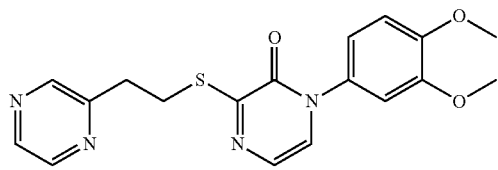 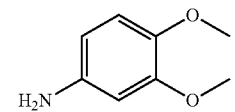
1-(3,4-dimethoxyphenyl)-3-(2-
(pyrazin-2-yl)ethylthio)pyrazin-2(1H)-one
7 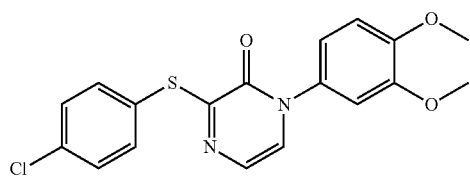 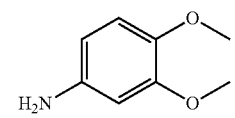
3-(4-chlorophenylthio)-1-
(3,4-dimethoxyphenyl)pyrazin-2(1H)-one
8 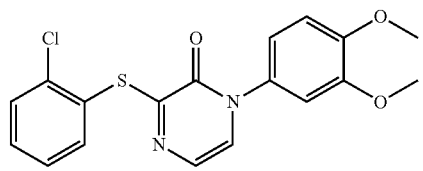 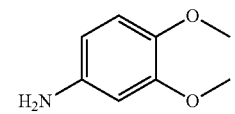
3-(2-chlorophenylthio)-1-
(3,4-dimethoxyphenyl)pyrazin-2(1H)-one
9 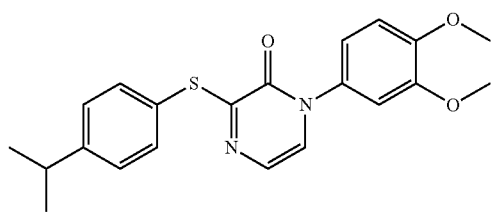 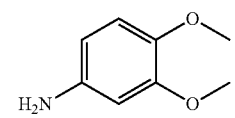
1-(3,4-dimethoxyphenyl)-3-
(4-isopropylphenylthio)-pyrazin-2(1H)-one
10 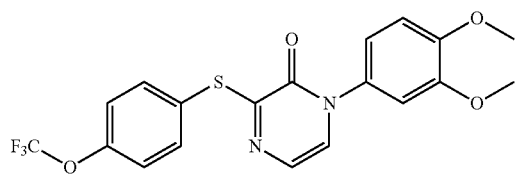 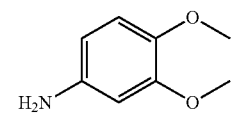
1-(3,4-dimethoxyphenyl)-3-(4-(trifluoro-
methoxyphenylthio)-pyrazin-2(1H)-one TABLE 1-continued 3-Thio substituted-1-arylpyrazin-2(1H)-ones 11 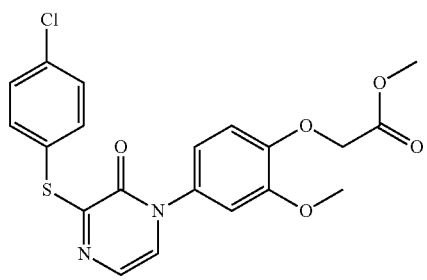 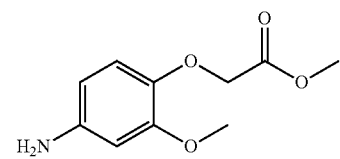

methyl 2-(4-(3-(4-chlorophenylthio)-2-oxopyrazin-1(2H)-yl)-2-methoxyphenoxy)acetate 12 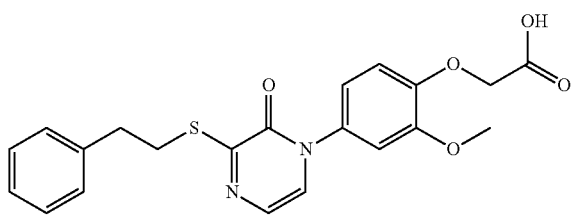 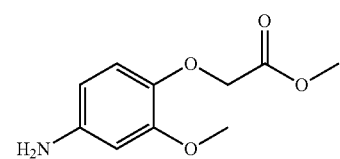

2-(2-methoxy-4-(2-oxo-3-(phenethylthio)pyrazin-1(2H)-yl)phenoxy)acetic acid

13 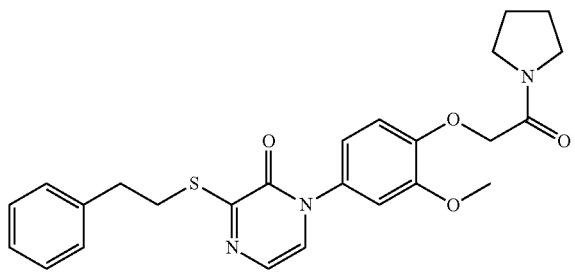 

1-(3-methoxy-4-(2-oxo-2-(pyrrolidin-1-yl)ethoxy)-phenyl)-3-(phenethylthio)pyrazin-2(1H)-one 14 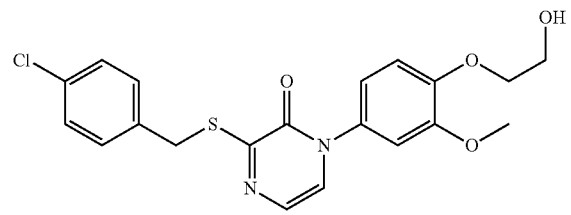 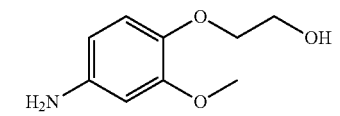

3-(4-chlorobenzylthio)-1-(4-(2-hydroxyethoxy)-3-methoxyphenyl)pyrazin-2(1H)-one

15 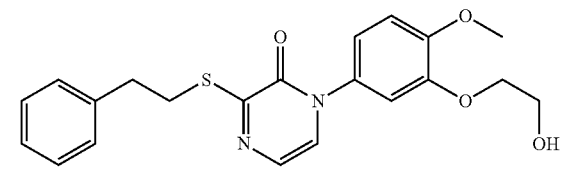 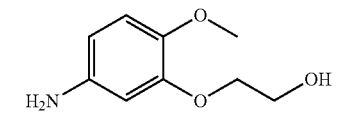

1-(3-(2-hydroxyethoxy)-4-methoxyphenyl)-3-(phenethylthio)pyrazin-2(1H)-one

TABLE 1-continued

3-Thio substituted-1-arylpyrazin-2(1H)-ones

16
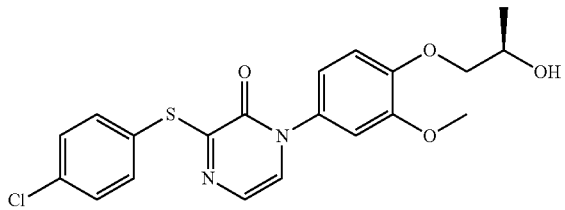
(R)-3-(4-chlorophenylthio)-1-(4-(2-hydroxypropoxy)-3-
methoxyphenyl)pyrazin-2(1H)-one
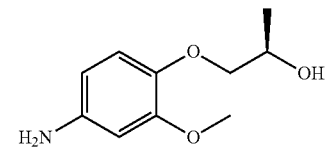

17
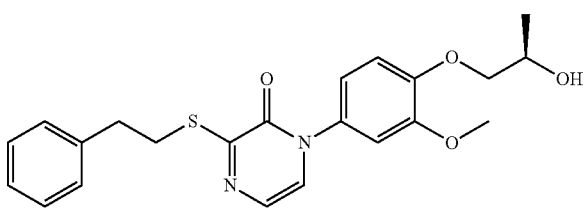
(R)-1-(4-(2-hydroxypropoxy)-3-methoxyphenyl)-3-
(phenethylthio)pyrazin-2(1H)-one
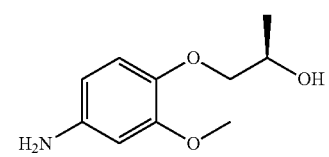

18
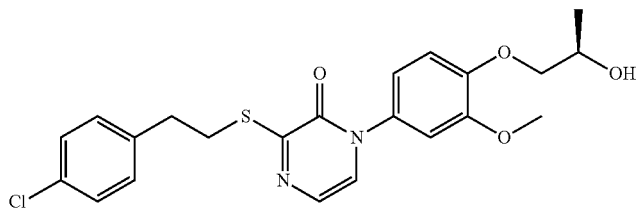
(R)-3-(4-chlorophenethylthio)-1-(4-(2-hydroxypropoxy)-3-
methoxyphenyl)pyrazin-2(1H)-one
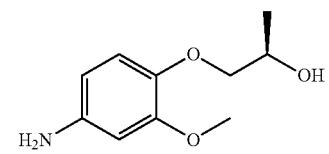

19
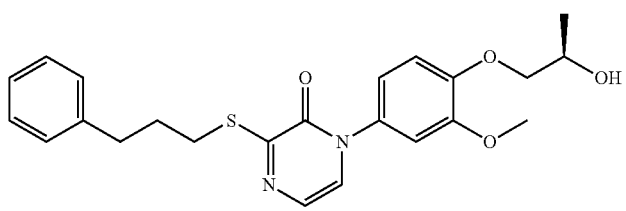
(R)-1-(4-(2-hydroxypropoxy)-3-methoxyphenyl)-3-(3-
phenylpropylthio)pyrazin-2(1H)-one
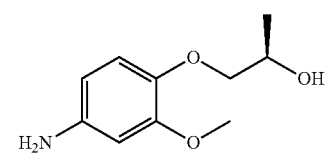

20
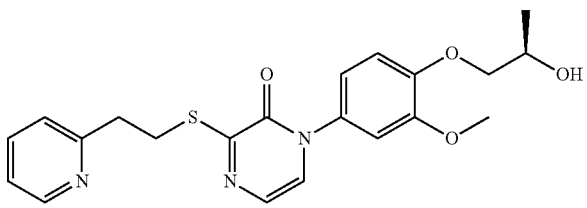
(R)-1-(4-(2-hydroxypropoxy)-3-methoxyphenyl)-3-(2-(pyridin-2-
yl)ethylthio)pyrazin-2(1H)-one
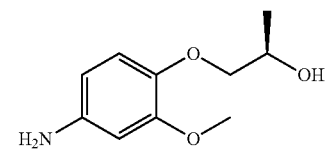

TABLE 1-continued

3-Thio substituted-1-arylpyrazin-2(1H)-ones

21 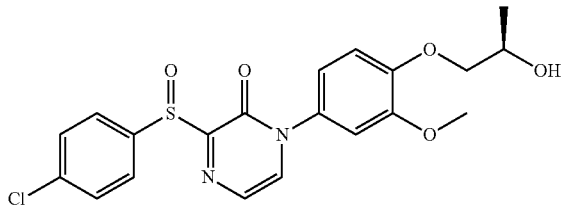

3-(4-chlorophenylsulfinyl)-1-(4-((R)-2-hydroxypropoxy)-3-
methoxyphenyl)pyrazin-2(1H)-one 22 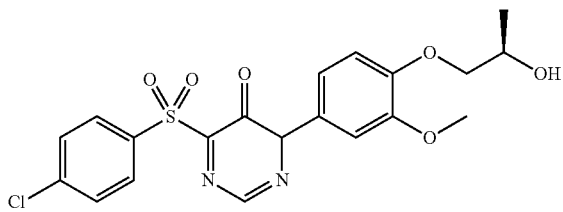

(R)-3-(4-chlorophenylsulfonyl)-1-(4-(2-hydroxy-
propoxy)-3-methoxyphenyl)pyrazin-2(1H)-one 23 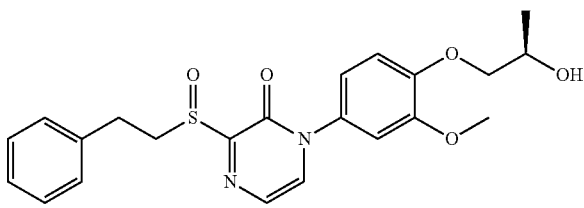

1-(4-((R)-2-hydroxypropoxy)-3-methoxyphenyl)-3-
(phenethylsulfinyl)pyrazin-2(1H)-one 24 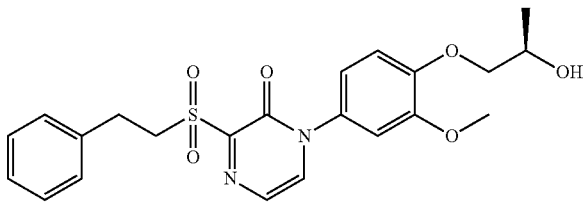

(R)-1-(4-(2-hydroxypropoxy)-3-methoxyphenyl)-3-
(phenethylsulfinyl)pyrazin-2(1H)-one 25 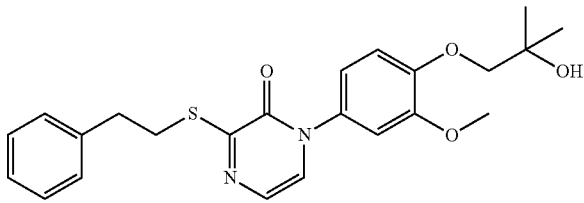 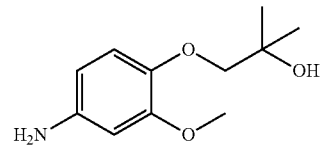

1-(4-(2-hydroxy-2-methylpropoxy)-3-methoxyphenyl)-3-
(phenethylthio)pyrazin-2(1H)-one TABLE 1-continued 3-Thio substituted-1-arylpyrazin-2(1H)-ones 26 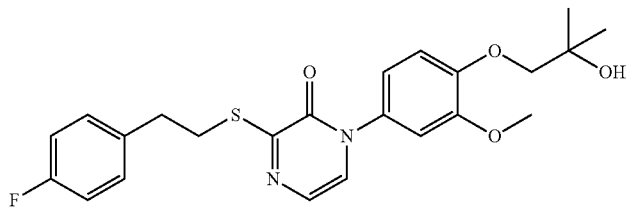 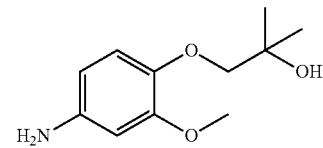

3-(4-fluorophenethylthio)-1-(4-(2-hydroxy-2-
methylpropoxy)-3-methoxyphenyl)pyrazin-2(1H)-one 27 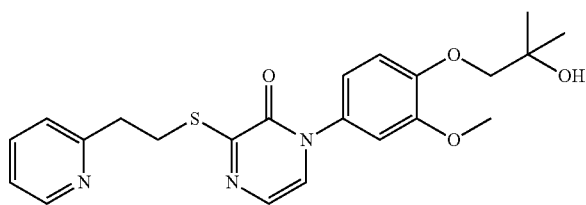 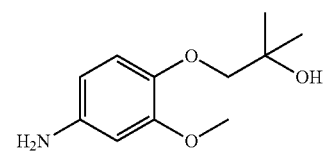

1-(4-(2-hydroxy-2-methylpropoxy)-3-methoxyphenyl)-3-(2-
(pyridin-2-yl)ethylthio)pyrazin-2(1H)-one 28 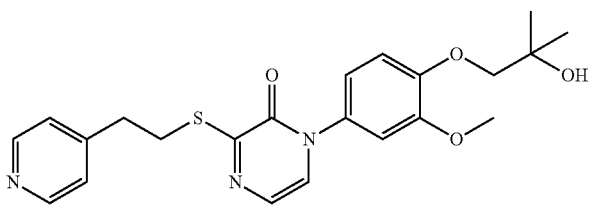 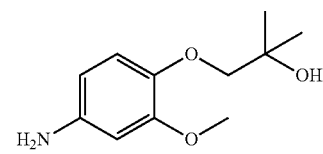

1-(4-(2-hydroxy-2-methylpropoxy)-3-methoxyphenyl)-3-(2-
(pyridin-4-yl)ethylthio)pyrazin-2(1H)-one 29 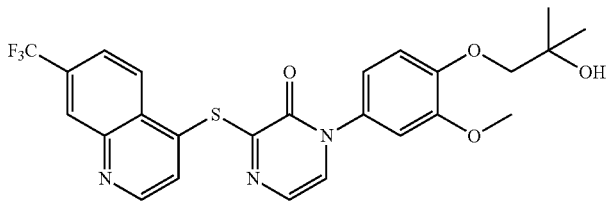 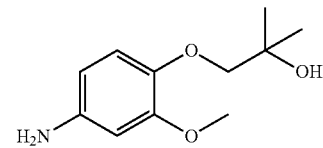

1-(4-(2-hydroxy-2-methylpropoxy)-3-methoxyphenyl)-3-(7-
(trifluoromethyl)quinolin-4-ylthio)pyrazin-2(1H)-one 30 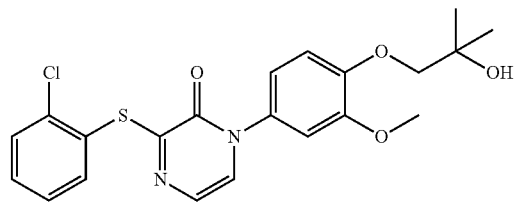 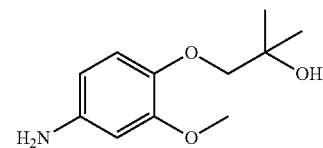

3-(2-chlorophenylthio)-1-(4-(2-hydroxy-2-methylpropoxy)-3-
methoxyphenyl)pyrazin-2(1H)-one TABLE 1-continued 3-Thio substituted-1-arylpyrazin-2(1H)-ones 31 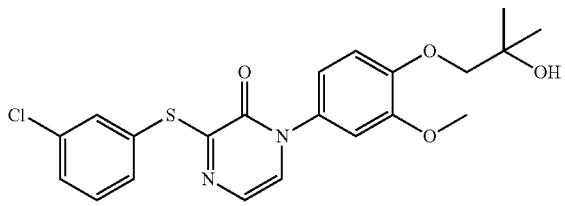 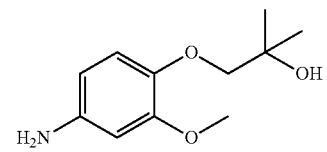

3-(3-chlorophenylthio)-1-(4-(2-hydroxy-2-methylpropoxy)-3-
methoxyphenyl)pyrazin-2(1H)-one 32 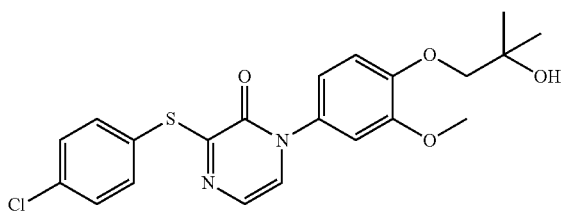 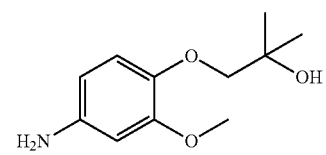

3-(4-chlorophenylthio)-1-(4-(2-hydroxy-2-methylpropoxy)-3-
methoxyphenyl)pyrazin-2(1H)-one 33 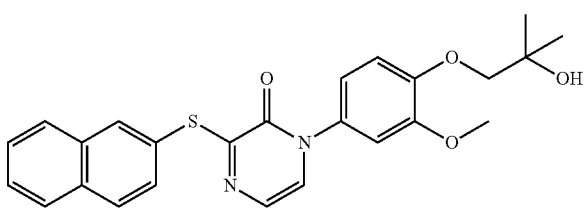 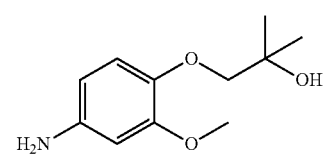

1-(4-(2-hydroxy-2-methylpropoxy)-3-methoxyphenyl)-3-
(naphthalen-2-ylthio)pyrazin-2(1H)-one 34 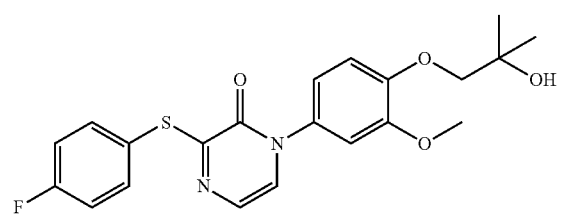 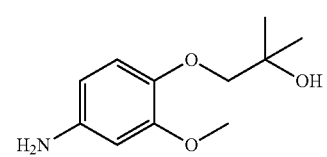

3-(4-fluorophenylthio)-1-(4-(2-hydroxy-2-methylpropoxy)-3-
methoxyphenyl)pyrazin-2(1H)-one 35 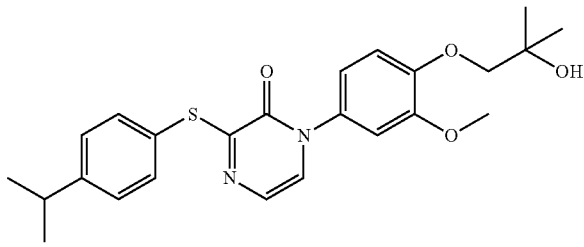 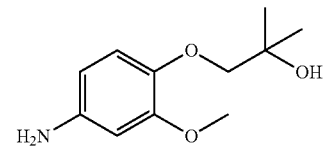

1-(4-(2-hydroxy-2-methylpropoxy)-3-methoxyphenyl)-3-(4-
isopropylphenylthio)pyrazin-2(1H)-one TABLE 1-continued 3-Thio substituted-1-arylpyrazin-2(1H)-ones 36 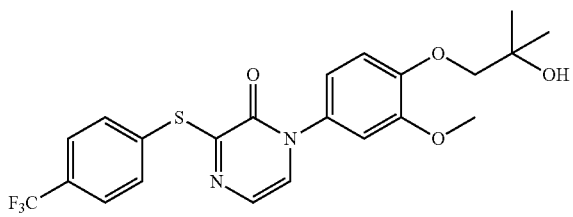 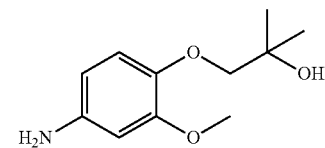

1-(4-(2-hydroxy-2-methylpropoxy)-3-methoxyphenyl)-3-(4-
(trifluoromethyl)phenylthio)pyrazin-2(1H)-one 37 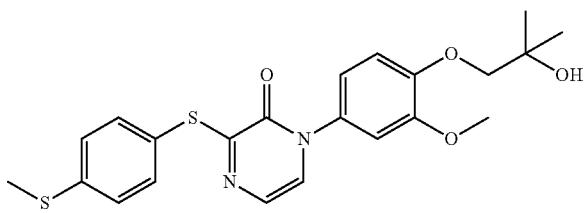 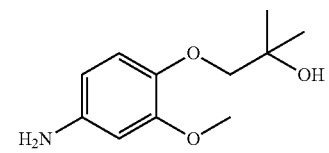

1-(4-(2-hydroxy-2-methylpropoxy)-3-methoxyphenyl)-3-(4-
(methylthio)phenylthio)pyrazin-2(1H)-one 38 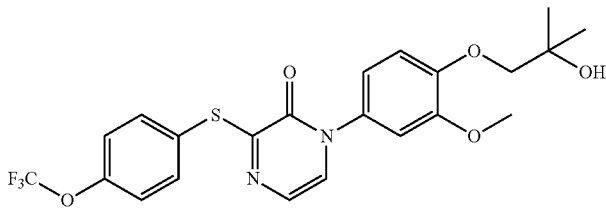 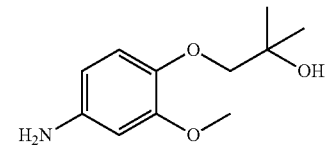

1-(4-(2-hydroxy-2-methylpropoxy)-3-methoxyphenyl)-3-(4-
(trifluoromethoxy)phenylthio)pyrazin-2(1H)-one 39 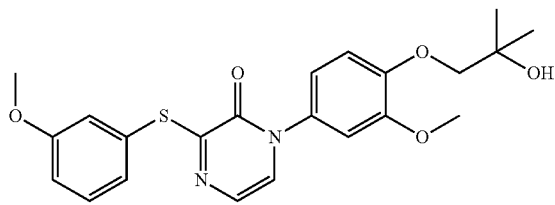 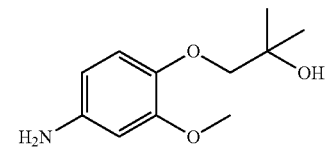

1-(4-(2-hydroxy-2-methylpropoxy)-3-methoxyphenyl)-3-(3-
methoxyphenylthio)pyrazin-2(1H)-one 40 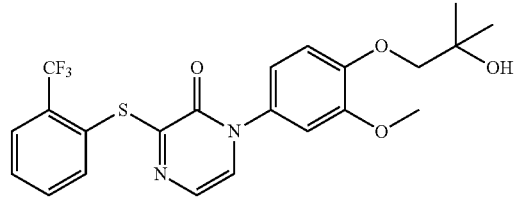 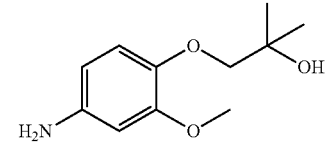

1-(4-(2-hydroxy-2-methylpropoxy)-3-methoxyphenyl)-3-(2-
(trifluoromethyl)phenylthio)pyrazin-2(1H)-one TABLE 1-continued 3-Thio substituted-1-arylpyrazin-2(1H)-ones 41 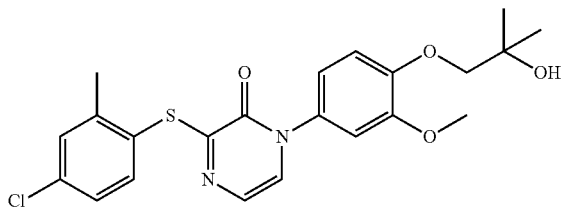 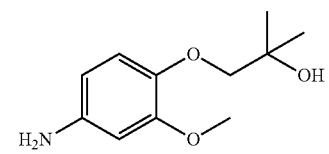

3-(4-chloro-2-methylphenylthio)-1-(4-(2-hydroxy-2-methylpropoxy)-
3-methoxyphenyl)pyrazin-2(1H)-one 42 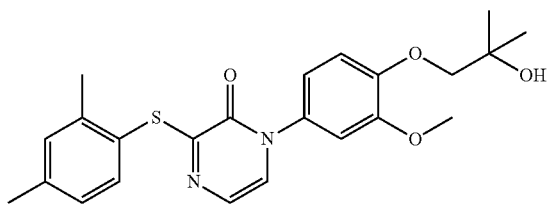 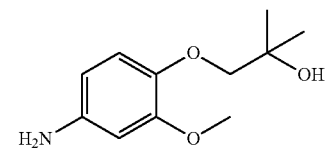

3-(2,4-dimethylphenylthio)-1-(4-(2-hydroxy-2-methylpropoxy)-3-
methoxyphenyl)pyrazin-2(1H)-one 43 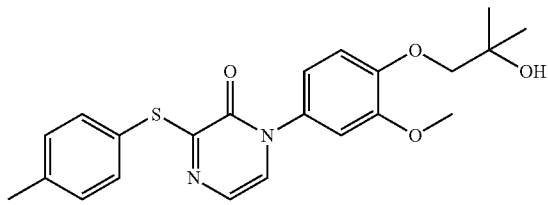 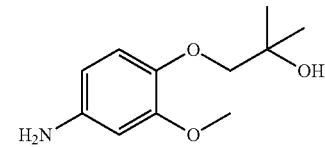

1-(4-(2-hydroxy-2-methylpropoxy)-3-methoxyphenyl)-3-(p-
tolylthio)pyrazin-2(1H)-one 44 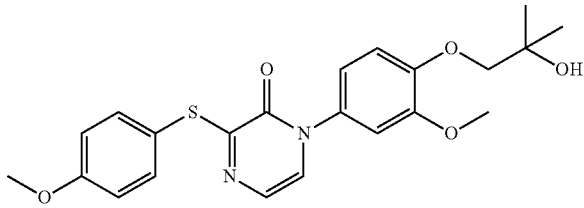 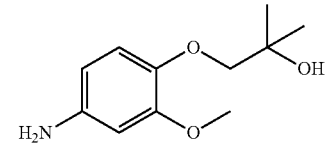

1-(4-(2-hydroxy-2-methylpropoxy)-3-methoxyphenyl)-3-(4-
methoxyphenylthio)pyrazin-2(1H)-one 45 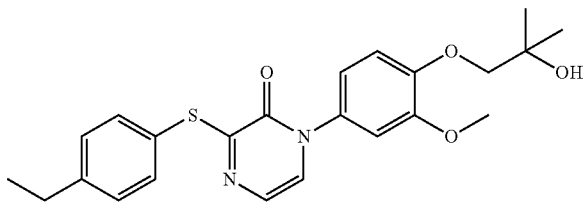 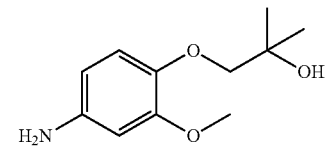

3-(4-ethylphenylthio)-1-(4-(2-hydroxy-2-methylpropoxy)-3-
methoxyphenyl)pyrazin-2(1H)-one TABLE 1-continued 3-Thio substituted-1-arylpyrazin-2(1H)-ones 46 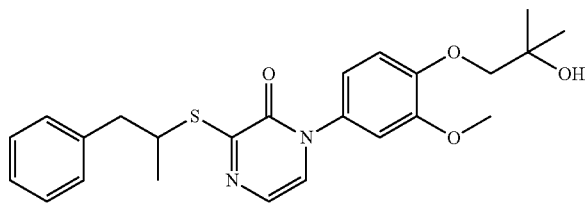 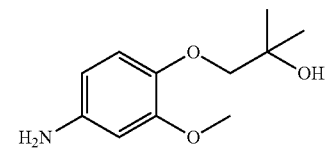

1-(4-(2-hydroxy-2-methylpropoxy)-3-methoxyphenyl)-3-(1-phenylpropan-2-ylthio)pyrazin-2(1H)-one 47 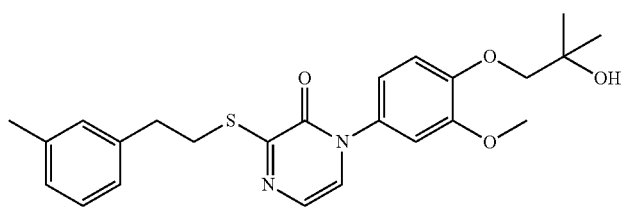 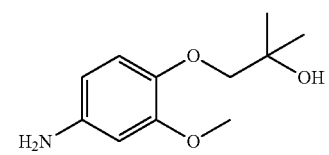

1-(4-(2-hydroxy-2-methylpropoxy)-3-methoxyphenyl)-3-(3-methylphenethylthio)pyrazin-2(1H)-one 48 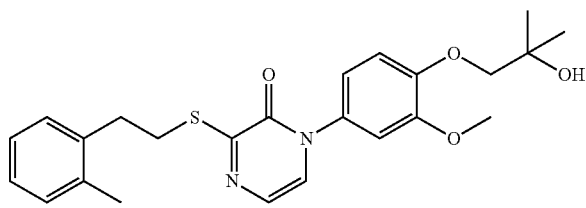 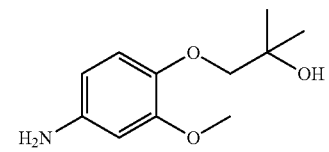

1-(4-(2-hydroxy-2-methylpropoxy)-3-methoxyphenyl)-3-(2-methylphenethylthio)pyrazin-2(1H)-one 49 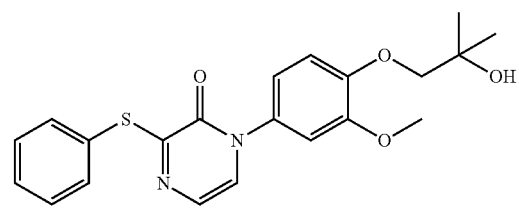 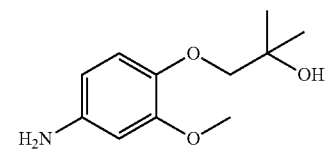

1-(4-(2-hydroxy-2-methylpropoxy)-3-methoxyphenyl)-3-(phenylthio)pyrazin-2(1H)-one 50 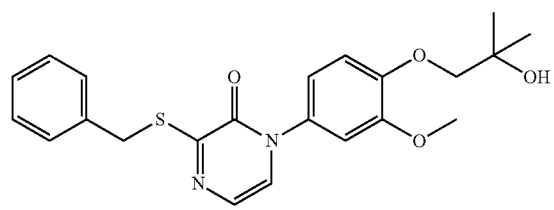 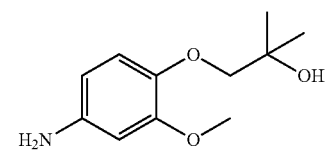

3-(benzylthio)-1-(4-(2-hydroxy-2-methylpropoxy)-3-methoxyphenyl)pyrazin-2(1H)-one TABLE 1-continued 3-Thio substituted-1-arylpyrazin-2(1H)-ones 51 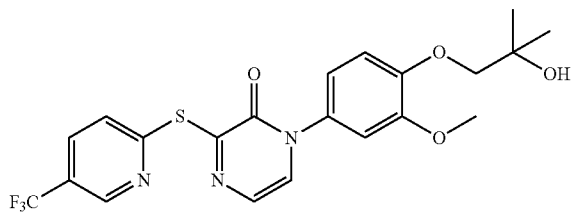 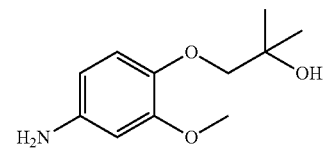

1-(4-(2-hydroxy-2-methylpropoxy)-3-methoxyphenyl)-3-(5-
(trifluoromethyl)pyridin-2-ylthio)pyrazin-2(1H)-one 52 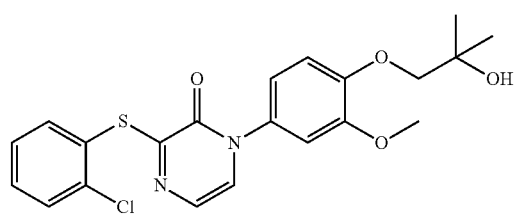 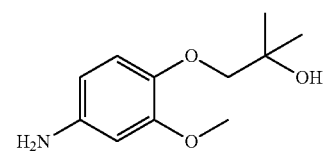

3-(2-chlorophenylthio)-1-(4-(2-hydroxy-2-
methylpropoxy)-3-methoxyphenyl)pyrazin-2(1H)-one 53 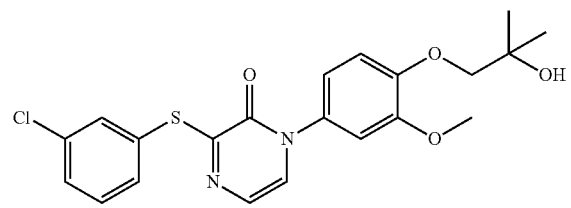 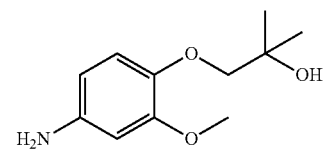

3-(3-chlorophenylthio)-1-(4-(2-hydroxy-2-
methylpropoxy)-3-methoxyphenyl)pyrazin-2(1H)-one 54 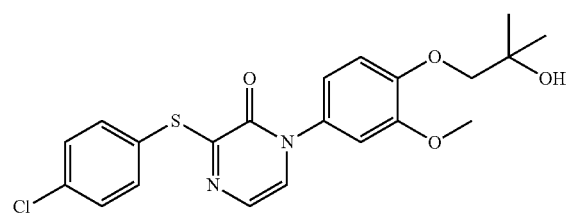 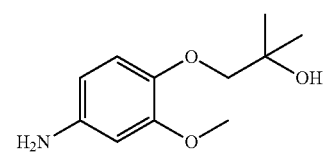

3-(4-chlorophenylthio)-1-(4-(2-hydroxy-2-
methylpropoxy)-3-methoxyphenyl)pyrazin-2(1H)-one 55 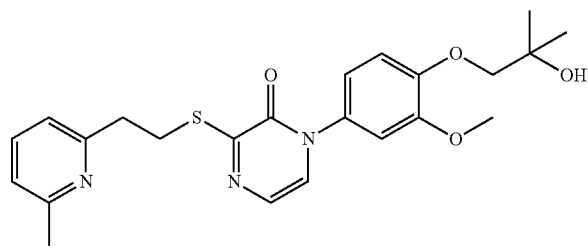 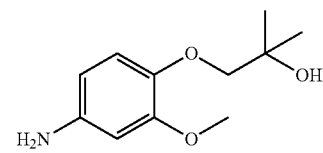

1-(4-(2-hydroxy-2-methylpropoxy)-3-methoxyphenyl)-3-(2-(6-
methylpyridin-2-yl)ethylthio)pyrazin-2(1H)-one TABLE 1-continued 3-Thio substituted-1-arylpyrazin-2(1H)-ones 56 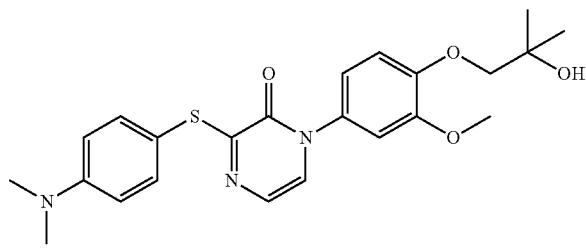 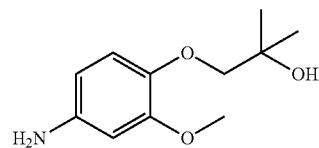

3-(4-(dimethylamino)phenylthio)-1-(4-(2-hydroxy-2-methylpropoxy)-3-methoxyphenyl)pyrazin-2(1H)-one 57 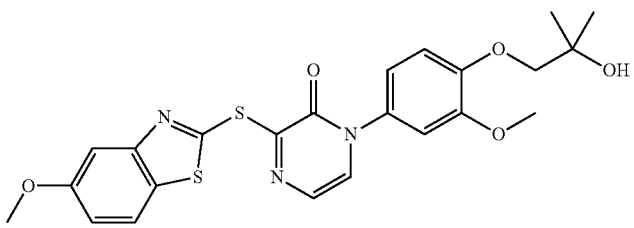 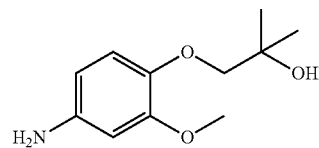

1-(4-(2-hydroxy-2-methylpropoxy)-3-methoxyphenyl)-3-(5-methoxybenzo[d]thiazol-2-ylthio)pyrazin-2(1H)-one 58 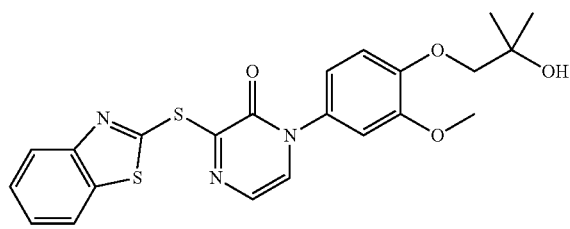 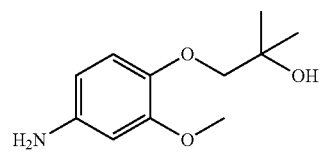

3-(benzo[d]thiazol-2-ylthio)-1-(4-(2-hydroxy-2-methylpropoxy)-3-methoxyphenyl)pyrazin-2(1H)-one 59 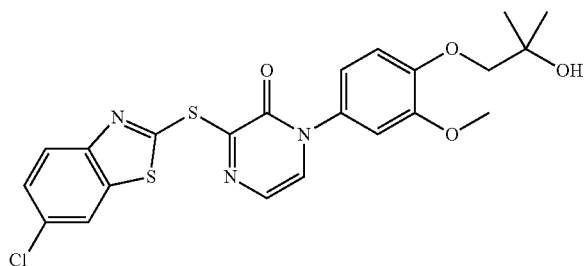 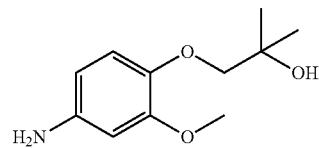

3-(6-chlorobenzo[d]thiazol-2-ylthio)-1-(4-(2-hydroxy-2-methylpropoxy)-3-methoxyphenyl)pyrazin-2(1H)-one 60 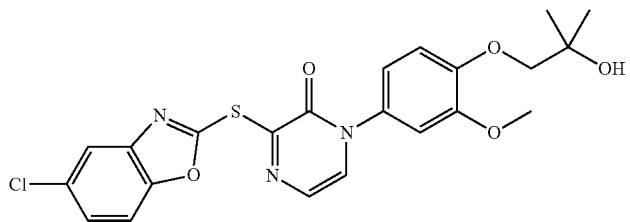 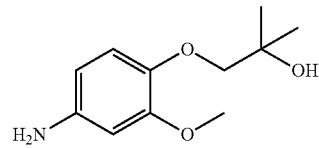

3-(5-chlorobenzo[d]oxazol-2-ylthio)-1-(4-(2-hydroxy-2-methylpropoxy)-3-methoxyphenyl)pyrazin-2(1H)-one TABLE 1-continued 3-Thio substituted-1-arylpyrazin-2(1H)-ones 61 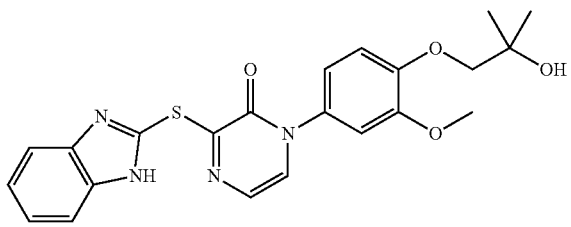 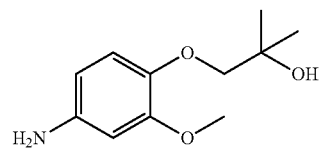

3-(1H-benzo[d]imidazol-2-ylthio)-1-(4-(2-hydroxy-2-
methylpropoxy)-3-methoxyphenyl)pyrazin-2(1H)-one 62 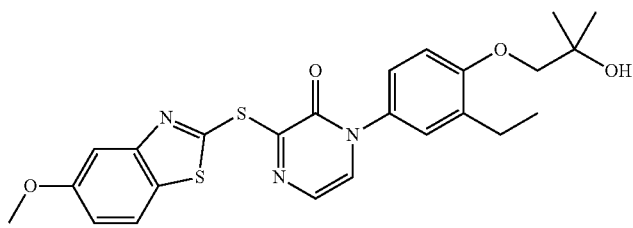 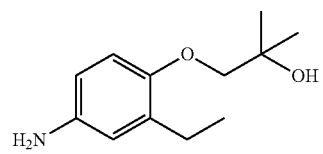

1-(3-ethyl-4-(2-hydroxy-2-methylpropoxy)phenyl)-3-(5-
methoxybenzo[d]thiazol-2-ylthio)pyrazin-2(1H)-one 63 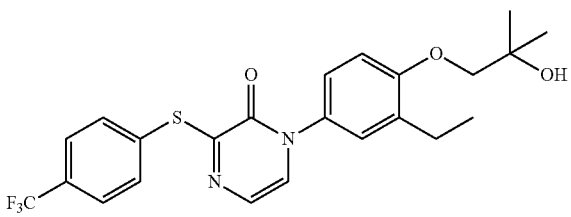 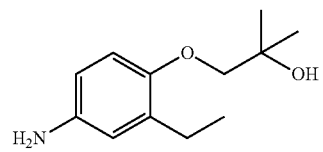

1-(3-ethyl-4-(2-hydroxy-2-methylpropoxy)phenyl)-3-(4-
(trifluoromethyl)phenylthio)pyrazin-2(1H)-one 64 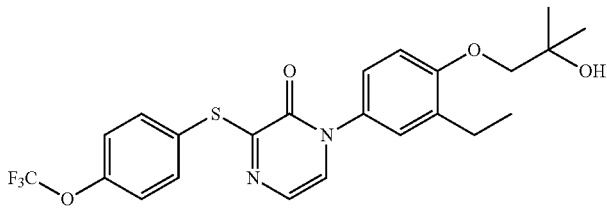 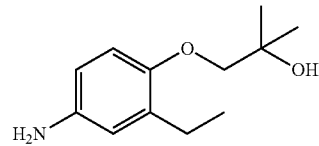

1-(3-ethyl-4-(2-hydroxy-2-methylpropoxy)phenyl)-3-(4-
(trifluoromethoxy)phenylthio)pyrazin-2(1H)-one 65 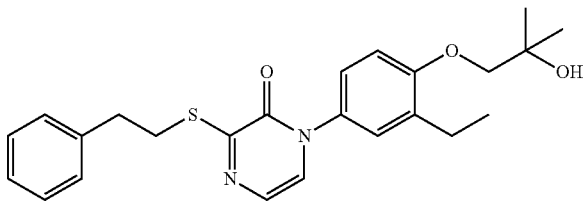 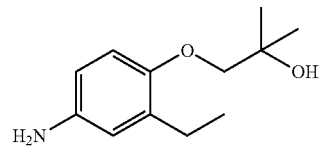

1-(3-ethyl-4-(2-hydroxy-2-methylpropoxy)phenyl)-3-
(phenethylthio)pyrazin-2(1H)-one TABLE 1-continued 3-Thio substituted-1-arylpyrazin-2(1H)-ones 66
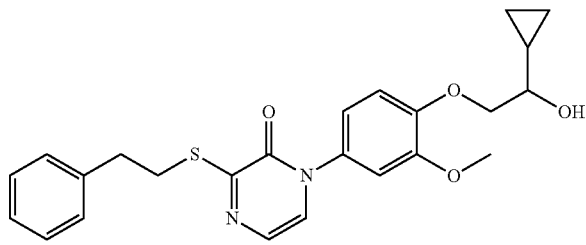
1-(4-(2-cyclopropyl-2-hydroxyethoxy)-3-methoxyphenyl)-3-
(phenethylthio)pyrazin-2(1H)-one
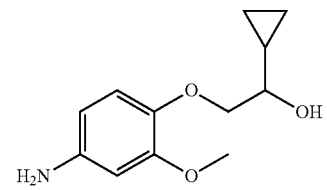

67
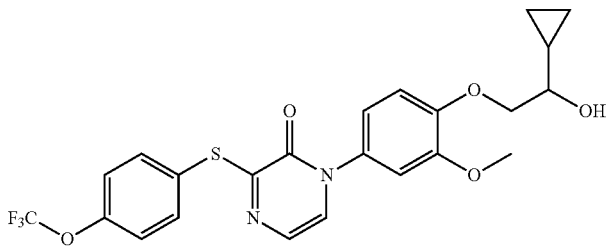
1-(4-(2-cyclopropyl-2-hydroxyethoxy)-3-methoxyphenyl)-3-(4-
(trifluoromethoxy)phenylthio)pyrazin-2(1H)-one
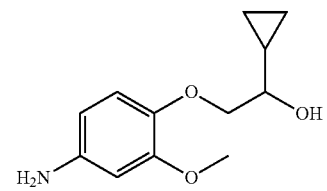

68
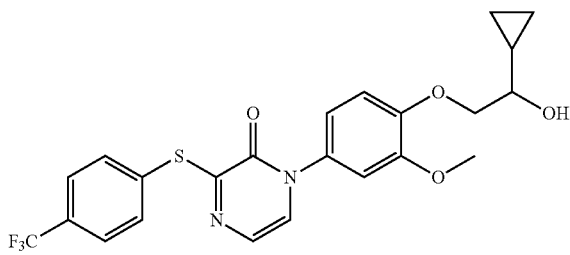
1-(4-(2-cyclopropyl-2-hydroxyethoxy)-3-methoxyphenyl)-3-(4-
(trifluoromethyl)phenylthio)pyrazin-2(1H)-one
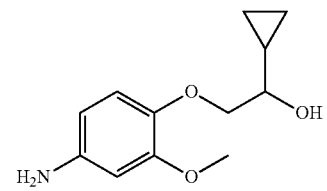

69
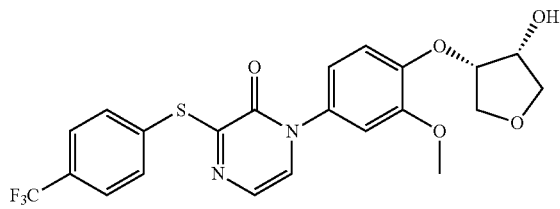
1-(4-((3S,4R)-4-hydroxytetrahydrofuran-3-yloxy)-3-methoxyphenyl)-3-
(4-(trifluoromethyl)phenylthio)pyrazin-2(1H)-one
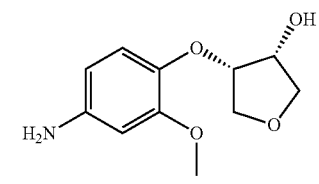

70
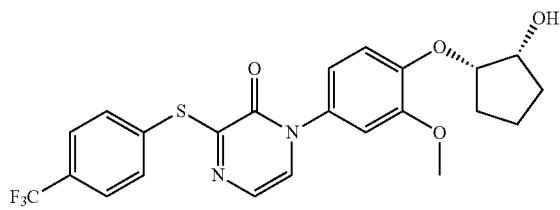
1-(4-((1S,2R)-2-hydroxycyclopentyloxy)-3-methoxyphenyl)-3-(4-
(trifluoromethyl)phenylthio)pyrazin-2(1H)-one
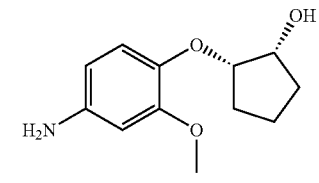

TABLE 1-continued

3-Thio substituted-1-arylpyrazin-2(1H)-ones

71 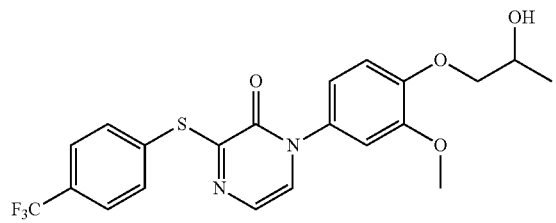 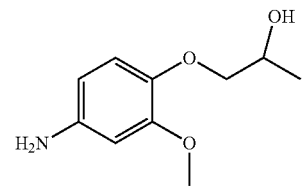

1-(4-(2-hydroxypropoxy)-3-methoxyphenyl)-3-(4-
(trifluoromethyl)phenylthio)pyrazin-2(1H)-one 72 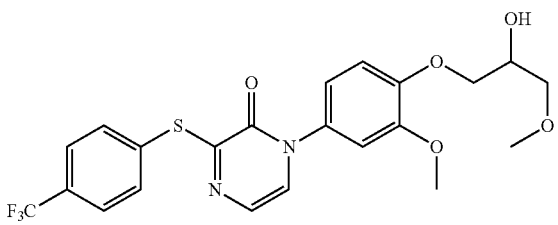 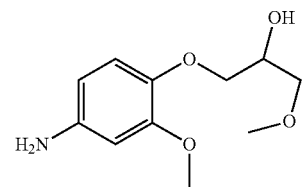

1-(4-(2-hydroxy-3-methoxypropoxy)-3-methoxyphenyl)-
3-(4-(trifluoromethyl)phenylthio)pyrazin-2(1H)-one 73 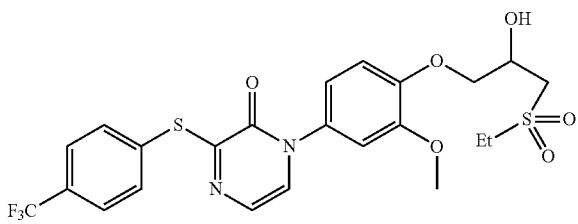 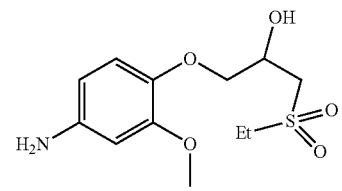

1-(4-(3-(ethylsulfonyl)-2-hydroxypropoxy)-3-methoxyphenyl)-3-
(4-(trifluoromethyl)phenylthio)pyrazin-2(1H)-one 74 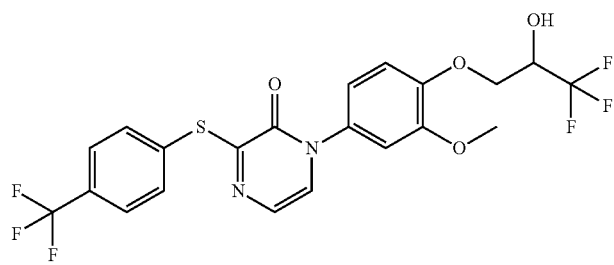 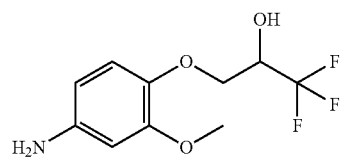

1-(3-methoxy-4-(3,3,3-trifluoro-2-hydroxypropoxy)phenyl)-3-(4-
(trifluoromethyl)phenylthio)pyrazin-2(1H)-one TABLE 1-continued 3-Thio substituted-1-arylpyrazin-2(1H)-ones 75 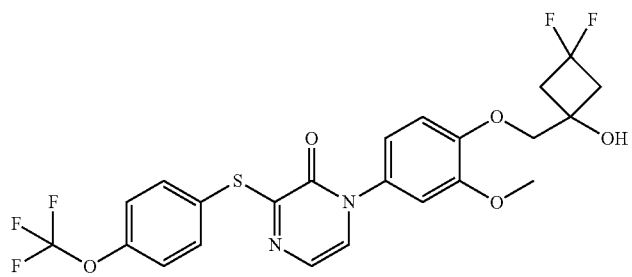 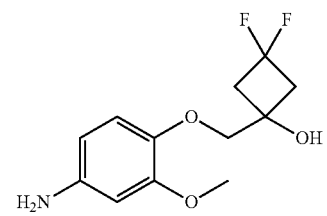

1-(4-((3,3-difluoro-1-hydroxycyclobutyl)methoxy)-3-methoxyphenyl)-3-(4-
(trifluoromethoxy)phenylthio)pyrazin-2(1H)-one 76 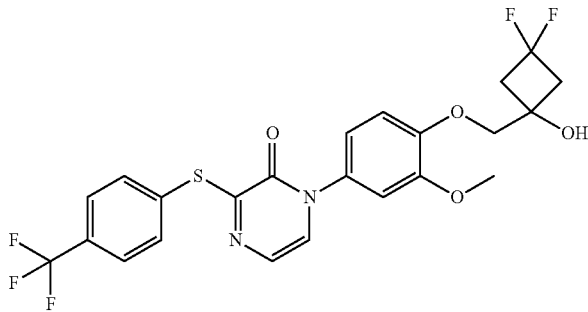 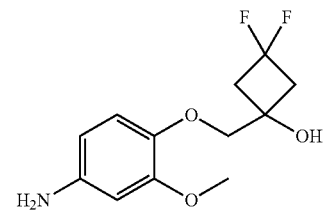

1-(4-((3,3-difluoro-1-hydroxycyclobutyl)methoxy)-3-methoxyphenyl)-3-(4-
(trifluoromethyl)phenylthio)pyrazin-2(1H)-one 77 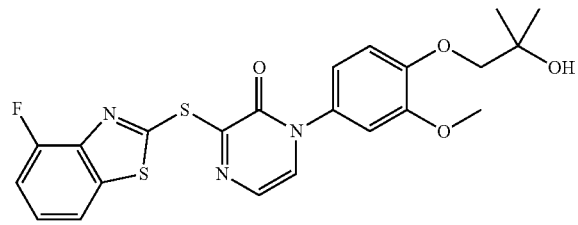 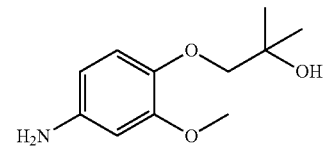

3-(4-fluorobenzo[d]thiazol-2-ylthio)-1-(4-(2-hydroxy-2-
methylpropoxy)-3-methoxyphenyl)pyrazin-2(1H)-one 78 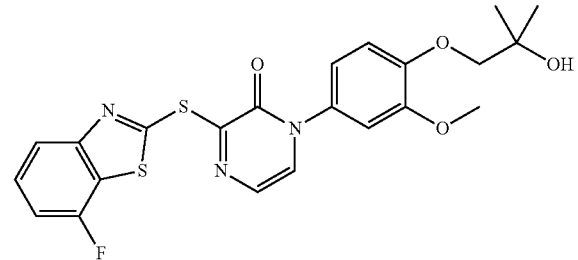 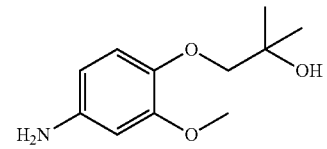

3-(7-fluorobenzo[d]thiazol-2-ylthio)-1-(4-(2-hydroxy-2-
methylpropoxy)-3-methoxyphenyl)pyrazin-2(1H)-one TABLE 1-continued 3-Thio substituted-1-arylpyrazin-2(1H)-ones 79 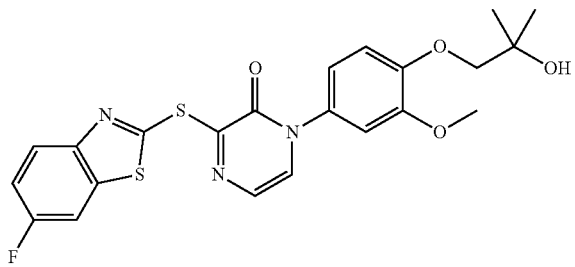 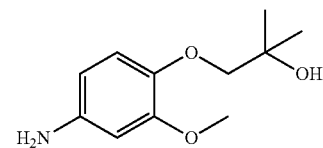

3-(6-fluorobenzo[d]thiazol-2-ylthio)-1-(4-(2-hydroxy-2-methylpropoxy)-3-methoxyphenyl)pyrazin-2(1H)-one 80 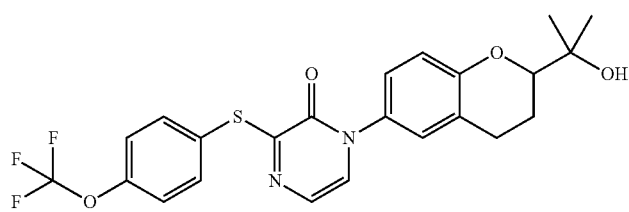 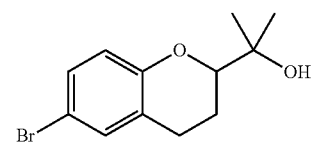

1-(2-(2-hydroxypropan-2-yl)chroman-6-yl)-3-(4-(trifluoromethoxy)phenylthio)pyrazin-2(1H)-one 81 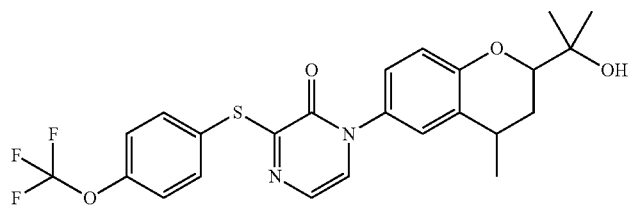 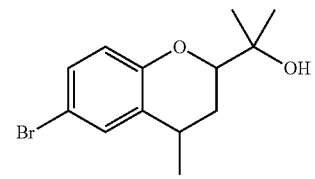

1-(2-(2-hydroxypropan-2-yl)-4-methylchroman-6-yl)-3-(4-(trifluoromethoxy)phenylthio)pyrazin-2(1H)-one 82 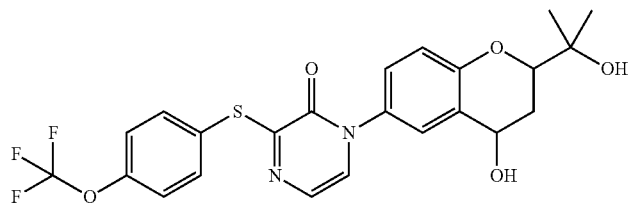 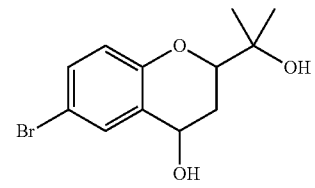

1-(4-hydroxy-2-(2-hydroxypropan-2-yl)chroman-6-yl)-3-(4-(trifluoromethoxy)phenylthio)pyrazin-2(1H)-one 83 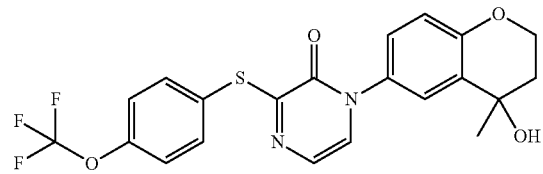 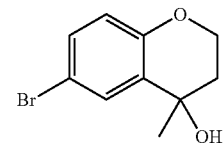

1-(4-hydroxy-4-methylchroman-6-yl)-3-(4-(trifluoromethoxy)phenylthio)pyrazin-2(1H)-one TABLE 1-continued 3-Thio substituted-1-arylpyrazin-2(1H)-ones 84 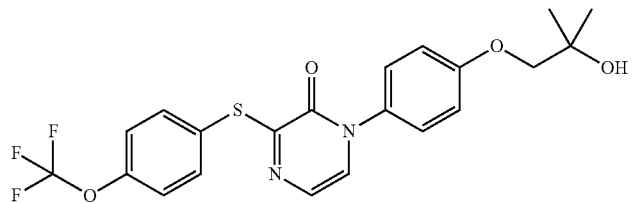 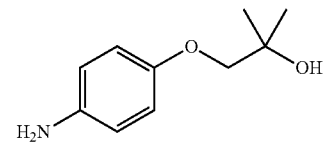

1-(4-(2-hydroxy-2-methylpropoxy)phenyl)-3-
(4-(trifluoromethoxy)phenylthio)pyrazin-2(1H)-one 85 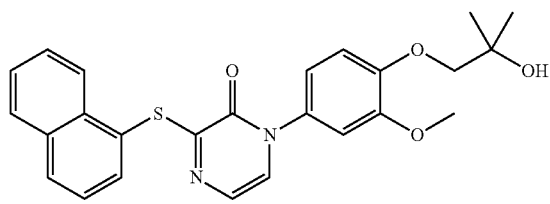 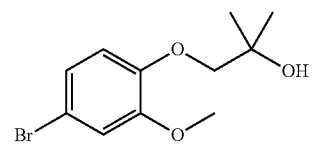

1-(4-(2-hydroxy-2-methylpropoxy)-3-methoxyphenyl)-
3-(naphthalen-1-ylthio)pyrazin-2(1H)-one 86 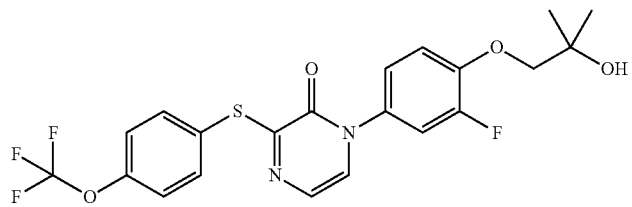 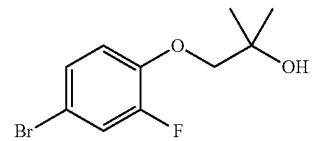

1-(3-fluoro-4-(2-hydroxy-2-methylpropoxy)phenyl)-
3-(4-(trifluoromethoxy)phenylthio)pyrazin-2(1H)-one 87 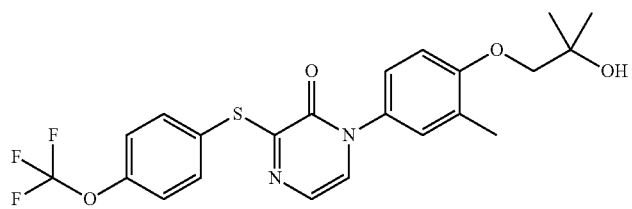 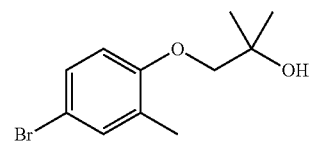

1-(4-(2-hydroxy-2-methylpropoxy)-3-methylphenyl)-
3-(4-(trifluoromethoxy)phenylthio)pyrazin-2(1H)-one 88 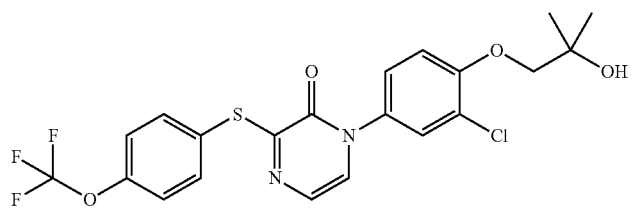 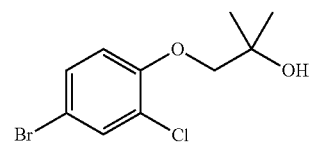

1-(3-chloro-4-(2-hydroxy-2-methylpropoxy)phenyl)-
3-(4-(trifluoromethoxy)phenylthio)pyrazin-2(1H)-one TABLE 1-continued 3-Thio substituted-1-arylpyrazin-2(1H)-ones

89

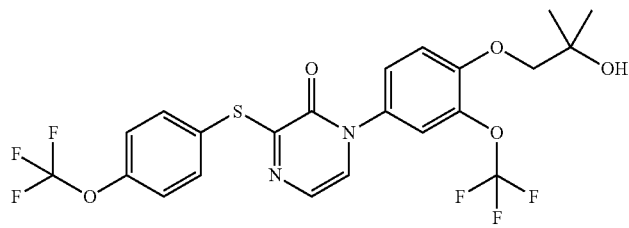 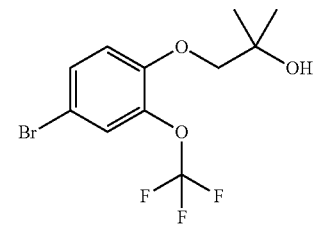

1-(4-(2-hydroxy-2-methylpropoxy)-3-(trifluoromethoxy)phenyl)-
3-(4-(trifluoromethoxy)phenylthio)pyridin-2(1H)-one

90

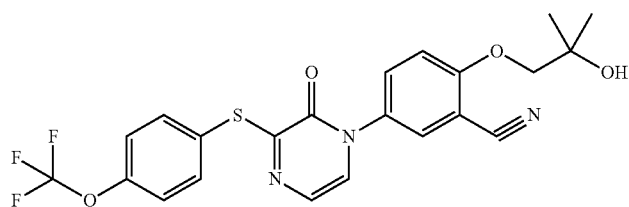 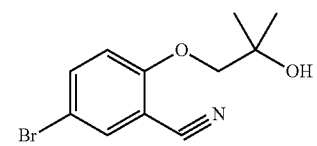

2-(2-hydroxy-2-methylpropoxy)-5-(2-oxo-3-
(4-(trifluoromethoxy)phenylthio)pyrazin-1(2H)-yl)benzonitrile

91

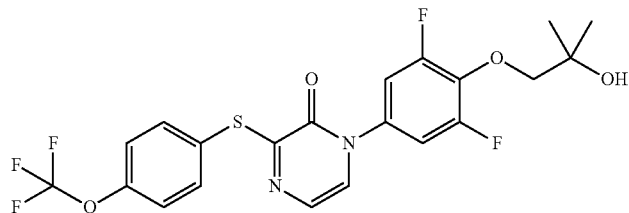 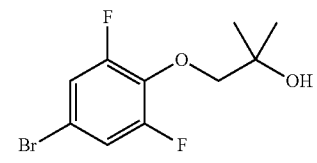

1-(3,5-difluoro-4-(2-hydroxy-2-methylpropoxy)phenyl)-3-(4-
(trifluoromethoxy)phenylthio)pyrazin-2(1H)-one

92

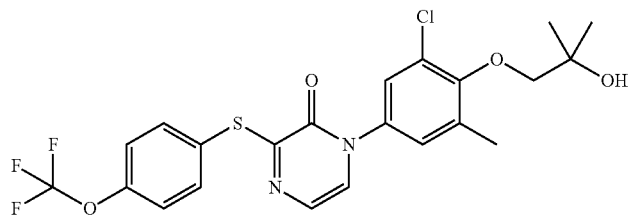 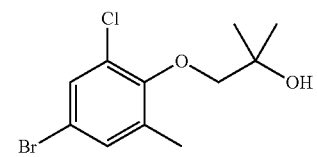

1-(3-chloro-4-(2-hydroxy-2-methylpropoxy)-5-methylphenyl)-
3-(4-trifluoromethoxy)phenylthio)pyrazin-2(1H)-one

93

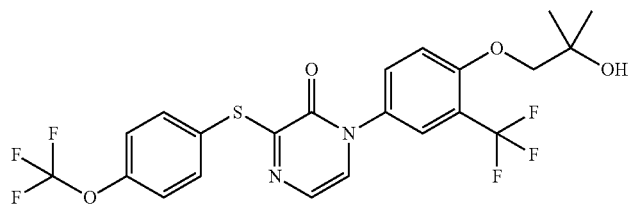 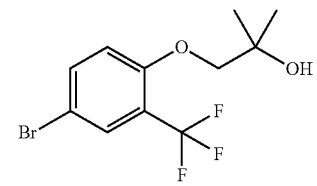

1-(4-(2-hydroxy-2-methylpropoxy)-3-(trifluoromethylphenyl)-
3-(4-(trifluoromethoxy)phenylthio)pyrazin-2(1H)-one TABLE 1-continued 3-Thio substituted-1-arylpyrazin-2(1H)-ones 94 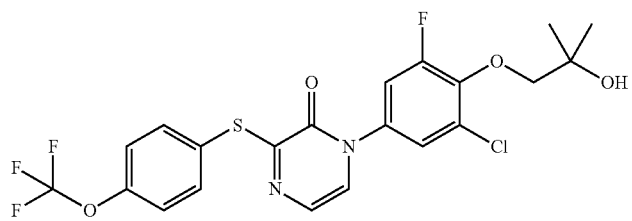

1-(3-chloro-5-fluoro-4-(2-hydroxy-2-methylpropoxy)phenyl)-
3-(4-(trifluoromethyl)phenylthio)pyrazin-2(1H)-one 95 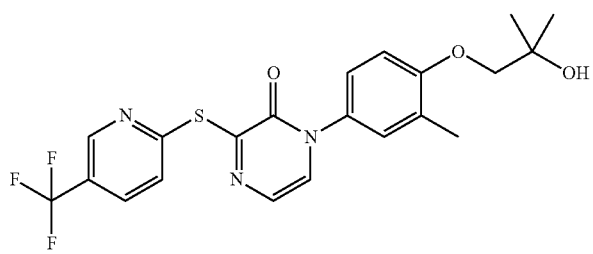

1-(4-(2-hydroxy-2-methylpropoxy)-3-methylphenyl)-
3-(5-(trifluoromethoxy)pyridin-2-ylthio)pyrazin-2(1H)-one 96 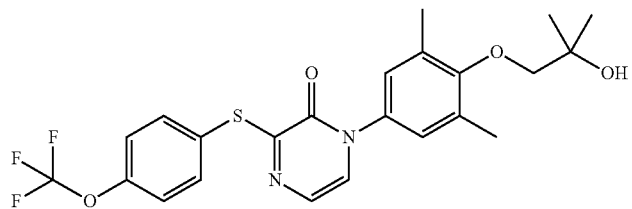

1-(4-(2-hydroxy-2-methylpropoxy)-3,5-dimethylphenyl)-
3-(4-(trifluoromethoxy)phenylthio)pyrazin-2(1H)-one 97 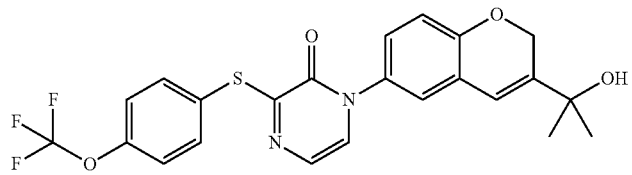

1-(3-(2-hydroxypropan-2-yl)-2H-chromen-6-yl)-3-
(4-(trifluoromethoxy)phenylthio)pyrazin-2(1H)-one 98 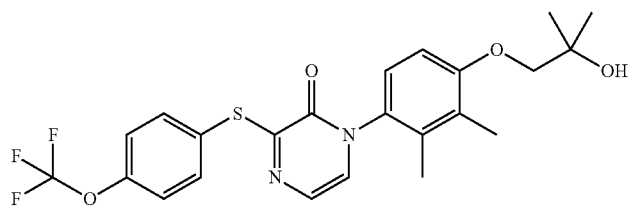

1-(4-(2-hydroxy-2-methylpropoxy)-2,3-dimethylphenyl)-3-(4-
(trifluoromethoxy)phenylthio)pyrazin-2(1H)-one TABLE 1-continued 3-Thio substituted-1-arylpyrazin-2(1H)-ones 99 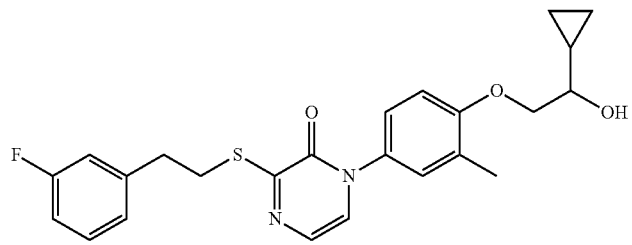 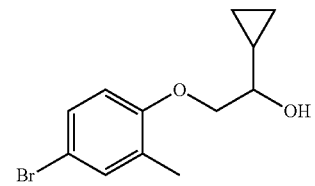

1-(4-(2-cyclopropyl-2-hydroxyethoxy)-3-methylphenyl)-
3-(3-fluorophenylethylthio)pyrazin-2(1H)-one 100 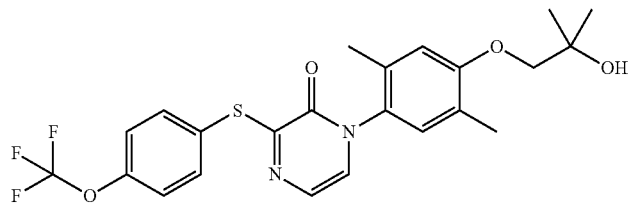 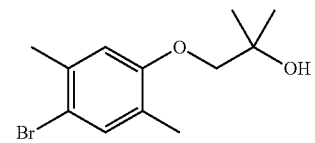

1-(4-(2-hydroxy-2-methylpropoxy)-2,5-dimethylphenyl)-3-(4-
(trifluoromethoxy)phenylthio)pyrazin-2(1H)-one 101 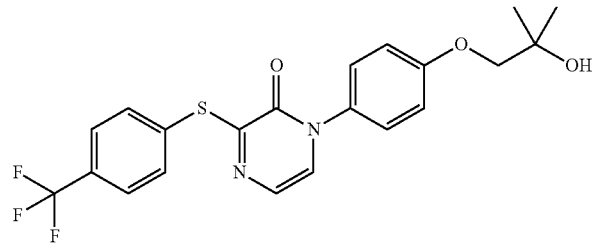 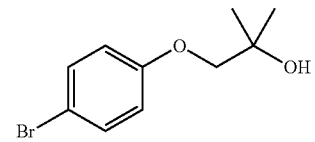

1-(4-(2-hydroxy-2-methylpropoxy)phenyl)-3-
(4-(trifluoromethyl)phenylthio)pyrazin-2(1H)-one 102 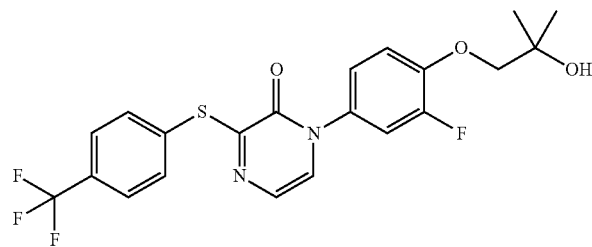 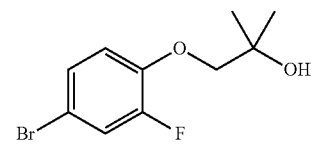

1-(3-fluoro-4-(2-hydroxy-2-methylpropoxy)phenyl)-3-
(4-(trifluoromethyl)phenylthio)pyrazin-2(1H)-one TABLE 1-continued 3-Thio substituted-1-arylpyrazin-2(1H)-ones 103 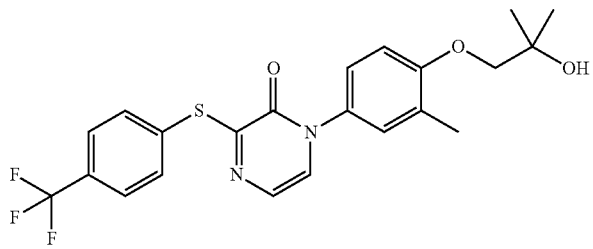 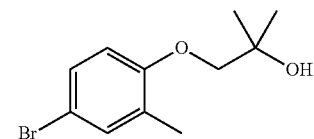

1-(4-(2-hydroxy-2-methylpropoxy)-3-methylphenyl)-
3-(4-(trifluoromethyl)phenylthio)pyrazin-2(1H)-one 104 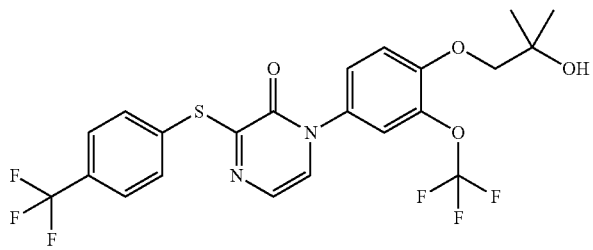 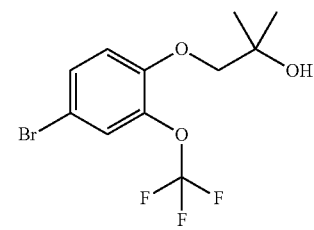

1-(4-(2-hydroxy-2-methylpropoxy)-3-(trifluoromethoxy)phenyl)-
3-(4-trifluoromethyl)phenylthio)pyrazin-2(1H)-one 105 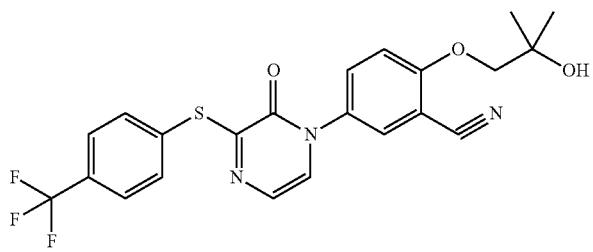 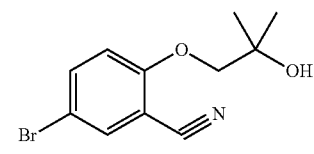

2-(2-hydroxy-2-methylpropoxy)-5-(2-oxo-3-(4-
(trifluoromethyl)phenylthio)pyrazin-1(2H)-yl)benzonitrile 106 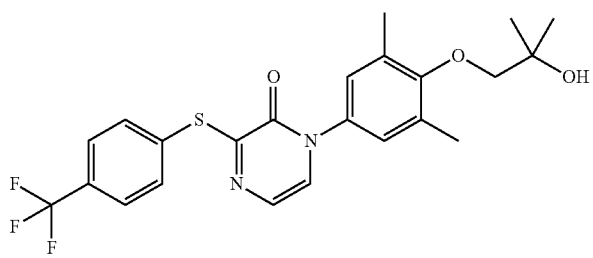 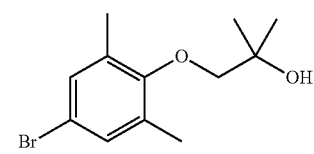

1-(4-(2-hydroxy-2-methylpropoxy)-3,5-dimethylphenyl)-
3-(4-(trifluoromethyl)phenylthio)pyrazin-2(1H)-one TABLE 1-continued 3-Thio substituted-1-arylpyrazin-2(1H)-ones 107 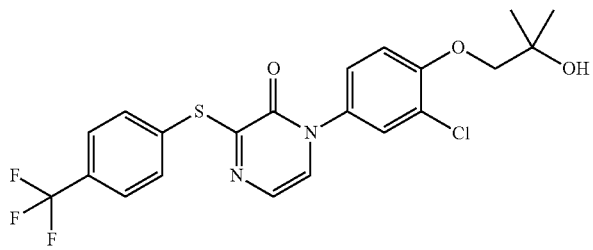 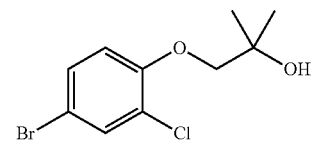

1-(3-chloro-4-(2-hydroxy-2-methylpropoxy)phenyl)-
3-(4-(trifluoromethyl)phenylthio)pyrazin-2(1H)-one 108 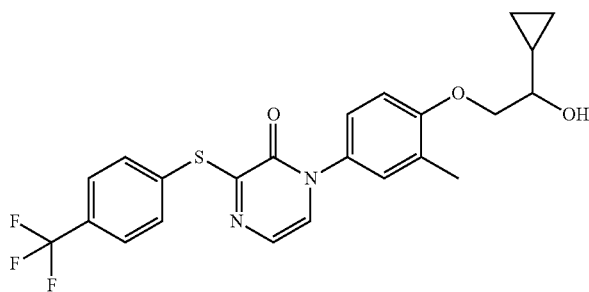 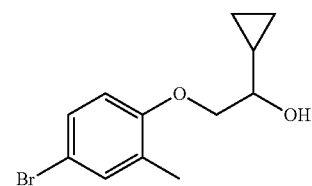

1-(4-(2-cyclopropyl-2-hydroxyethoxy)-3-methylphenyl)-
3-(4-(trifluoromethyl)phenylthio)pyrazin-2(1H)-one 109 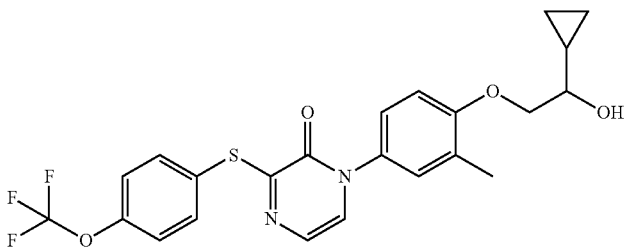 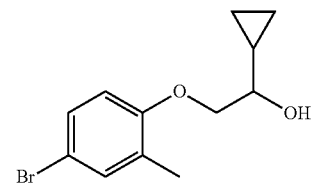

1-(4-(2-cyclopropyl-2-hydroxyethoxy)-3-methylphenyl)-
3-(4-(trifluoromethoxy)phenylthio)pyrazin-2(1H)-one 110 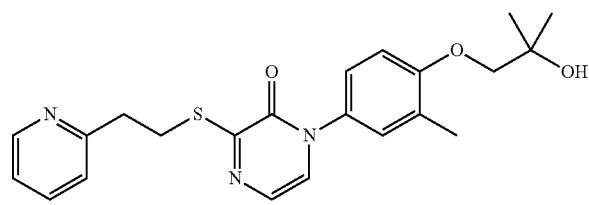 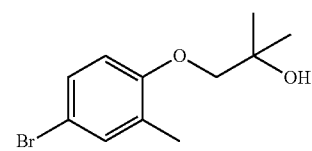

1-(4-(2-hydroxy-2-methylpropoxy)-3-methylphenyl)-
3-(2-(pyridin-2-yl)methylthio)pyrazin-2(1H)-one

US 8,012,984 B2

TABLE 1-continued

3-Thio substituted-1-arylpyrazin-2(1H)-ones

111 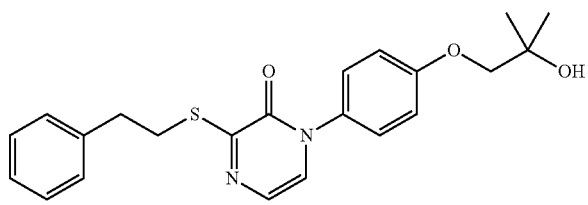 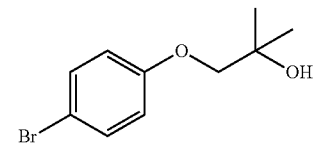

1-(4-(2-hydroxy-2-methylpropoxy)phenyl)-
3-(phenethylthio)pyrazin-2(1H)-one

112 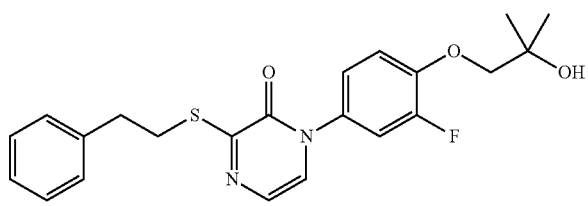 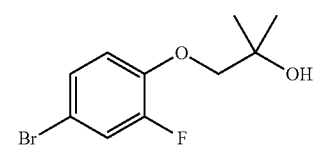

1-(3-fluoro-4-(2-hydroxy-2-methylpropoxy)
phenyl)-3-(phenethylthio)pyrazin-2(1H)-one 113 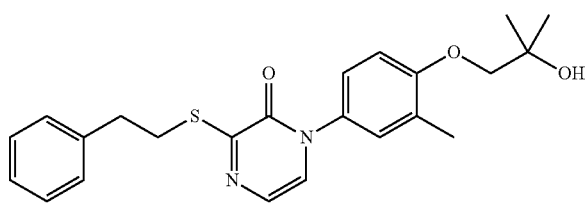 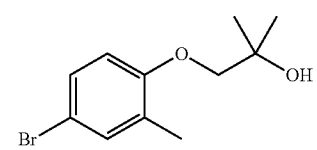

1-(4-(2-hydroxy-2-methylpropoxy)-3-methylphenyl)-
3-(phenethylthio)pyrazin-2(1H)-one 114 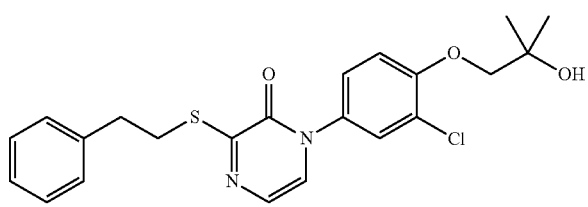 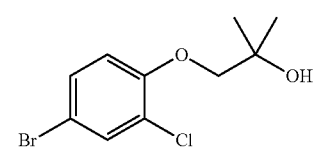

1-(3-chloro-4-(2-hydroxy-2-methylpropoxy)
phenyl)-3-(phenethylthio)pyrazin-2(1H)-one 115 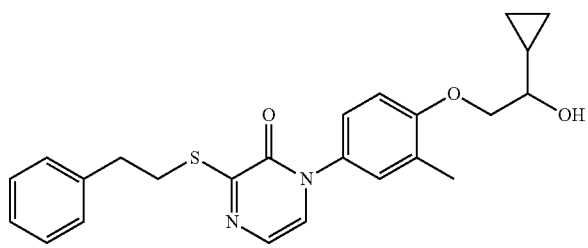 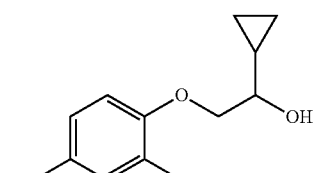

1-(4-(2-cyclopropyl-2-hydroxyethoxy)-3-methylphenyl)-
3-(phenethylthio)pyrazin-2(1H)-one TABLE 1-continued 3-Thio substituted-1-arylpyrazin-2(1H)-ones 116 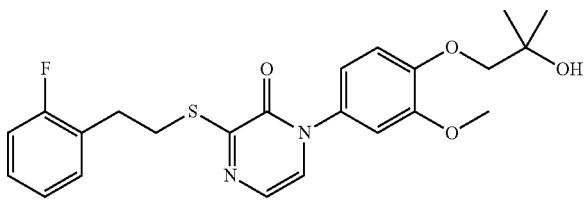 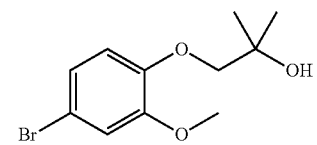

3-(2-fluorophenethylthio)-1-(4-(2-hydroxy-2-methylpropoxy)-
3-methoxyphenyl)pyrazin-2(1H)-one 117 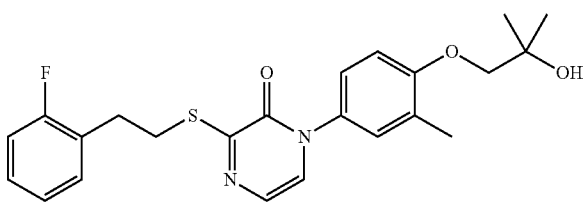 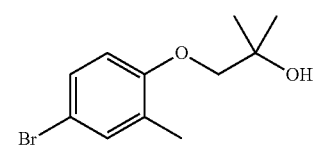

3-(2-fluorophenethylthio)-1-(4-(2-hydroxy-2-methyl
propoxy)-3-methylphenyl)pyrazin-2(1H)-one 118 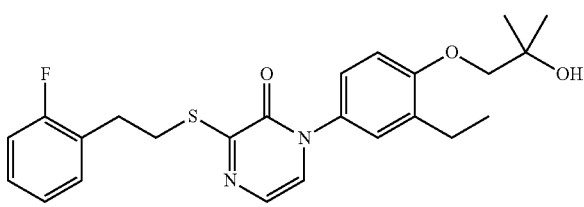 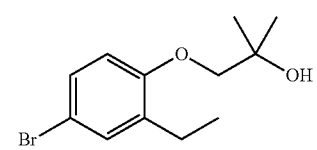

1-(3-ethyl-4-(2-hydroxy-2-methylpropoxy)phenyl)-
3-(2-fluorophenethylthio)pyrazin-2(1H)-one 119 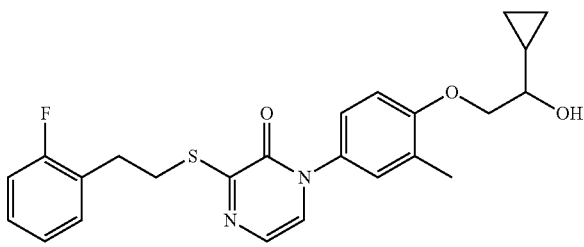 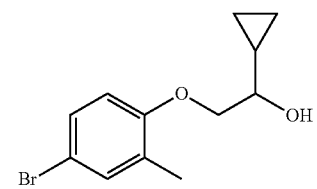

1-(4-(2-cyclopropyl-2-hydroxyethoxy)-3-methylphenyl)-
3-(2-fluorophenylethylthio)pyrazin-2(1H)-one 120 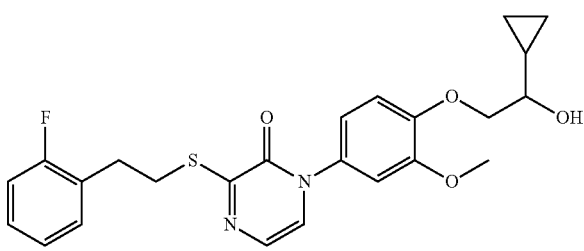 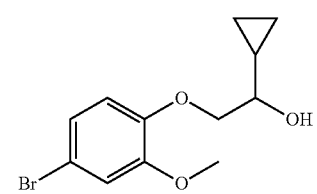

1-(4-(2-cyclopropyl-2-hydroxyethoxy)-3-methoxyphenyl)-
3-(2-fluorophenethylthio)pyrazin-2(1H)-one TABLE 1-continued 3-Thio substituted-1-arylpyrazin-2(1H)-ones 121
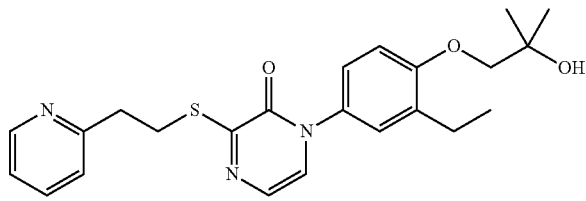
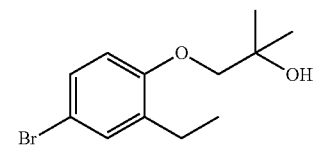

1-(3-ethyl-4-(2-hydroxy-2-methylpropoxy)phenyl)-
3-(2-(pyridin-2-yl)ethylthio)pyrazin-2(1H)-one 122
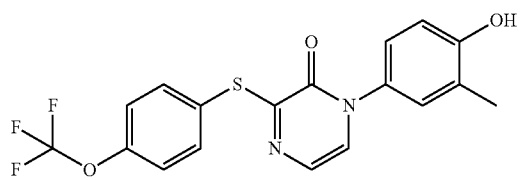
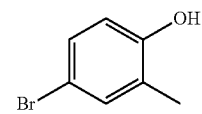

1-(4-hydroxy-3-methylphenyl)-3-(4-
(trifluoromethoxy)phenylthio)pyrazin-2(1H)-one 123
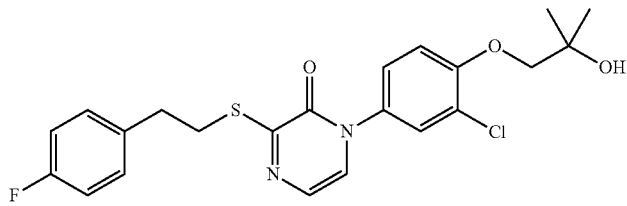
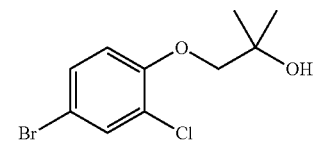

1-(3-chloro-4-(2-hydroxy-2-methylpropoxy)phenyl)-
3-(4-fluorophenethylthio)pyrazin-2(1H)-one 124
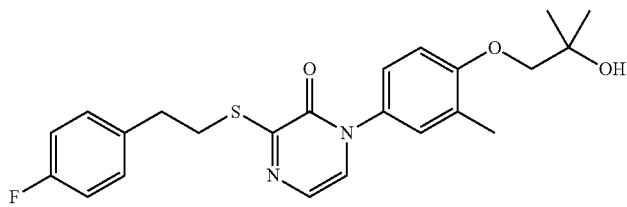
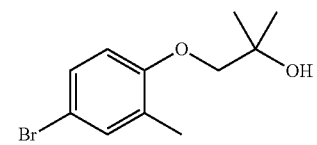

3-(4-fluorophenethylthio)-1-(4-(2-hydroxy-2-methyl
propoxy)-3-methylphenyl)pyrazin-2(1H)-one 125
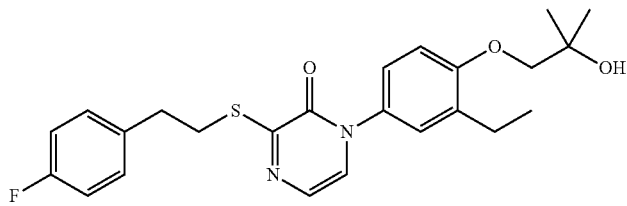
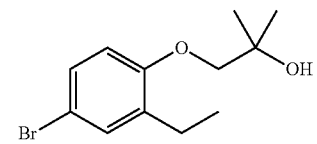

1-(3-ethyl-4-(2-hydroxy-2-methylpropoxy)
phenyl)-3-(4-fluorophenethylthio)pyrazin-2(1H)-one TABLE 1-continued 3-Thio substituted-1-arylpyrazin-2(1H)-ones

126

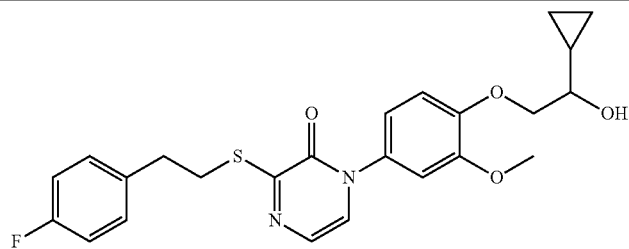

1-(4-(2-cyclopropyl-2-hydroxyethoxy)-3-methoxyphenyl)-
3-(4-fluorophenethylthio)pyrazin-2(1H)-one

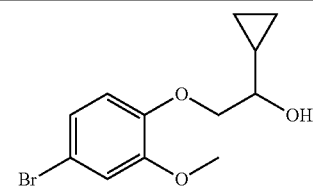

127

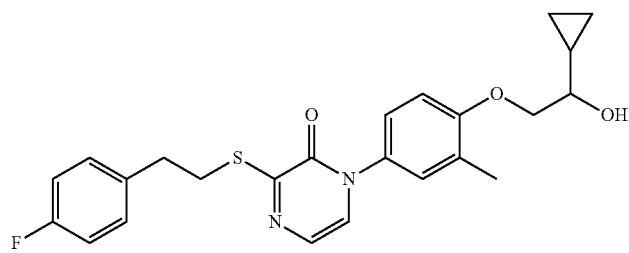

1-(4-(2-cyclopropyl-2-hydroxyethoxy)-3-methylphenyl)-
3-(4-fluorophenethylthio)pyrazin-2(1H)-one

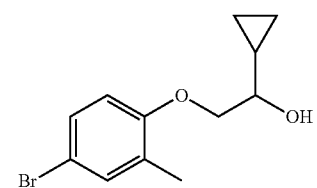

128

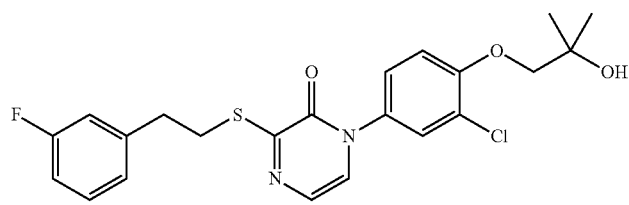

1-(3-chloro-4-(2-hydroxy-2-methylpropoxy)
phenyl)-3-(3-fluorophenethylthio)pyrazin-2(1H)-one

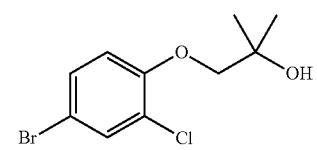

129

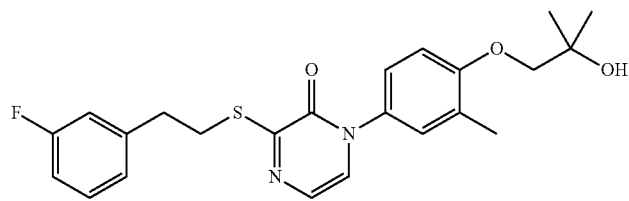

3-(3-fluorophenethylthio)-1-(4-(2-hydroxy-2-methyl
propoxy)-3-methylphenyl)pyrazin-2(1H)-one

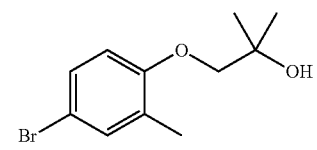

130

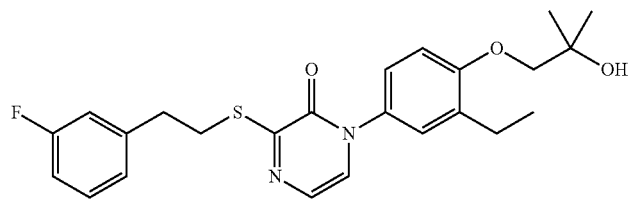

1-(3-ethyl-4-(2-hydroxy-2-methylpropoxy)
phenyl)-3-(3-fluorophenethylthio)pyrazin-2(1H)-one

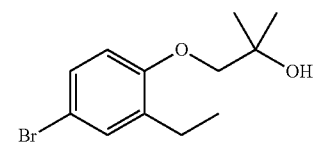

TABLE 1-continued

3-Thio substituted-1-arylpyrazin-2(1H)-ones

131

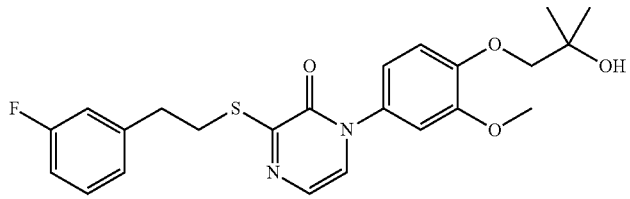 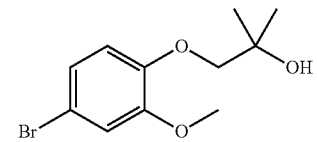

3-(3-fluorophenethylthio)-1-(4-(2-hydroxy-2-methyl
propoxy)-3-methoxyphenyl)pyrazin-2(1H)-one

132

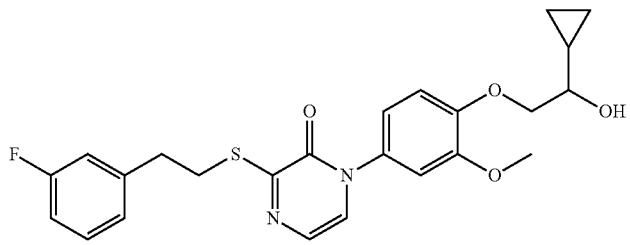 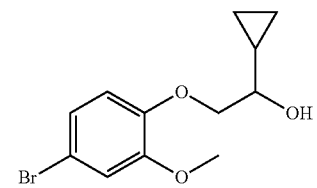

1-(4-(2-cyclopropyl-2-hydroxyethoxy)-3-methoxyphenyl)-
3-(3-fluorophenethylthio)pyrazin-2(1H)-one

| Ex. No. | Thiol Component | Method | Yield (%) | HPLC (Min) Method 1 | LC-MS (M + H) | H-NMR Data (CDCl$_3$) |
|---|---|---|---|---|---|---|
| 1 | Cl–C$_6$H$_4$–CH$_2$–SH (4-Cl-benzyl) | 1 | 50 | 4.09 | 389/391 | 7.36(d, J = 8.4 Hz, 2H), 7.26(d, J = 8.4 Hz, 2H), 7.41(d, J = 2.4 Hz, 1H), 7.25(d, J = 4.6 Hz, 1H), 6.98(d, J = 4.6 Hz, 1H), 6.94(d, J = 2.2 Hz, 1H), 6.91(d, J = 8.5 Hz, 1H), 6.88(dd, J = 2.2 and 8.5 Hz, 1H), 4.28(s, 2H), 3.91(s, 3H), 3.87(s, 3H). |
| 2 | Cl–C$_6$H$_4$–CH$_2$–SH | 1 | | 4.60 | 435/437 | 7.44-7.24(m, 12H), 7.05(d, J = 8.9 Hz, 2H), 6.96(d, J = 4.5 Hz, 1H), 5.09(s, 2H), 4.27(s, 2H). |
| 3 | 4-Cl-C$_6$H$_4$–CH$_2$CH$_2$–SH | 1 | 9 | 4.23 | 403/405 | 7.27(m, 6H), 6.93(m, 3H), 3.92(s, 3H), 3.89(s, 3H), 3.30(t, J = 7.3 Hz, 2H), 2.98(t, J = 7.3 Hz, 2H) |
| 4 | C$_6$H$_5$–CH$_2$CH$_2$–SH | 1 | 68 | 4.01 | 369 | 7.28(m, 6H), 6.92(m, 4H), 3.91(s, 3H), 3.88(s, 3H), 3.32(dd, J = 2.2 and 7.5 Hz, 2H), 3.02(dd, J = 2.2 and 7.5 Hz, 2H) |
| 5 | 2-pyridyl–CH$_2$CH$_2$–SH | 2 | 11 | 2.36 | 370 | CD$_3$OD) 8.35(dd, J = 1.0 and 4.5 Hz, 1H), 7.65(m, 1H), 7.27(d, J = 7.8 Hz, 1H), 7.23(d, J = 4.3 Hz, 1H), 7.16(m, 1H), 7.11(d, J = 4.3 Hz, 1H), 6.93(d, J = 2.3 Hz, 1H), 6.92(d, J = 8.5 Hz, 1H), 6.82(dd, J = 2.3 and 8.5 Hz, 1H), 3.74(s, 3H), 3.69(s, 3H), 3.33(t, J = 7.1 Hz, 2H), 3.06(t, J = 7.1 Hz, 2H). |

TABLE 1-continued

3-Thio substituted-1-arylpyrazin-2(1H)-ones

| # | Structure | | | | NMR |
|---|---|---|---|---|---|
| 6 | pyrazin-2-yl-ethanethiol | 2 | 37 | 3.01 | 371 | 8.45(s, 1H), 8.44(d, J = 3.0 Hz, 1H), 8.33(d, J = 3.0 Hz, 1H), 7.22(d, J = 4.5 Hz, 1H), 7.12(d, J = 4.5 Hz, 1H), 6.94(d, J = 2.4 Hz, 1H), 6.93(d, J = 8.5 Hz, 1H), 6.83(dd, J = 2.4 and 8.5 Hz, 1H), 374(s, 3H), 3.71(s, 3H), 3.39(t, J = 7.2 Hz, 2H), 3.13(t, J = 7.2 Hz, 2H) |
| 7 | 4-chlorobenzenethiol | 2 | 9 | 3.87 | 375/377 | 7.52(d, J = 8.5 Hz, 2H), 7.42(d, J = 8.5 Hz, 2H), 7.13(d, J = 4.5 Hz, 1H), 6.97(d, J = 4.5 Hz, 1H), 6.95(m, 1H), 6.92(m, 2H), 3.93(s, 3H), 3.89(s, 3H). |
| 8 | 2-chlorobenzenethiol | 2 | 23 | 3.59 | 375/377 | 7.67(dd, J = 1.7 and 7.6 Hz, 1H), 7.57(dd, J = 1.3 and 8.0 Hz, 1H), 7.43(dd, J = 1.7 and 7.6 Hz, 1H), 7.35 Hz(dd, J = 1.3 and 7.5 Hz, 1H), 7.12(d, J = 4.4 Hz, 1H), 7.00(d, J = 1.6 Hz, 1H), 6.98(d, J = 4.4 Hz, 1H), 6.95(m, 2H), 3.93(s, 3H), 3.91(s, 3H). |
| 9 | 4-isopropylbenzenethiol | 2 | 70 | 4.13 | 383 | 7.51(d, J = 8.2 Hz, 2H), 7.32(d, J = 8.2 Hz, 2H), 7.13(d, J = 4.5 Hz, 1H), 6.99(m, 1H), 6.96(d, J = 4.5 Hz, 1H), 6.91(m, 2H), 3.92(s, 3H), 3.90(s, 3H), 2.96(sept, J = 7.7 Hz, 1H), 1.28(d, J = 7.7 Hz, 6H). |
| 10 | 4-(trifluoromethoxy)benzenethiol | 2 | 60 | 4.02 | 425 | 7.61(d, J = 8.5 Hz, 2H), 7.29(d, J = 8.5 Hz, 2H), 7.13(d, J = 4.4 Hz, 1H), 7.00(d, J = 4.4 Hz, 1H), 6.96(m, 1H), 6.92(m, 2H), 3.93(s, 3H), 3.90(s, 3H) |
| 11 | 4-chlorobenzyl thiol | 1 | 2.5 | 3.94 | 433/435 | 7.36(m, 2H), 7.28(m, 3H), 6.96(m, 3H), 6.87(m, 1H), 4.72(s, 3H), 4.28(s, 2H), 2.87(s, 3H). |
| 12 | phenethylthiol | 1 | 8 | | 413 | 9.45(broad s, 1H), 7.39(m, 1H), 7.28(m, 5H), 6.98(m, 2H), 6.87(m, 2H), 4.73(s, 2H), 3.85(s, 3H), 3.34(t, J = 8.2 Hz, 2H), 3.01(t, J = 8.2 Hz, 2H) |
| 13 | | WSC, HOBT mediated coupling of Ex 15 | 27 | 3.95 | 466 | 7.30(m, 6H), 7.05(d, J = 7.5 Hz, 1H), 7.01(d, J = 1.6 Hz, 1H), 6.96(d, J = 6.6 Hz, 1H), 6.84(dd, J = 1.6 and 7.5 Hz, 1H), 4.72(s, 2H), 3.87(s, 3H), 3.55(m, 4H), 3.32(t, J = 7.4 Hz, 2H), 3.02(t, J = 7.4 Hz, 2H), 1.97(m, 2H), 1.86(m, 2H). |
| 14 | 4-chlorobenzyl thiol | 4 | 3.9 | 3.96 | 419/421 | 7.36(m, 2H), 7.26(m, 3H), 6.97(m, 3H), 6.87(m, 1H), 4.28(s, 2H), 4.15(t, J = 4.2 Hz, 2H), 3.98(t, J = 4.2 Hz, 2H), 3.85(s, 3H). |
| 15 | phenethylthiol | 2 Method 4 for ester hydrolysis | 2 | 3.86 | 399 | (CD$_3$OD) 7.41(d, J = 4.3 Hz, 1H), 7.31(m, 4H), 7.26(d, J = 4.3 Hz, 1H), 7.20(m, 1H), 7.10(d, J = 8.6 Hz, 1H), 7.12(d, J = 2.4 Hz, 1H), 7.00(dd, J = 2.4 and 8.6 Hz, 1H), 4.09(t, J = 4.7 Hz, 2H), 3.92(s, 3H), 3.90(t, J = 4.7 Hz, 2H), 3.33(dd, J = 6.0 and 8.0 Hz, 2H), 3.00(dd, J = 6.0 and 8.0 Hz, 2H). |

TABLE 1-continued

3-Thio substituted-1-arylpyrazin-2(1H)-ones

| # | Structure | Method | Yield | Time | MS | NMR |
|---|---|---|---|---|---|---|
| 16 | 4-Cl-C6H4-SH | 4 | 12 | 3.93 | 419/421 | 7.51(d, J = 8.5 Hz, 2H), 7.42(d, J = 8.5 Hz, 2H), 7.13(d, J = 4.5 Hz, 1H), 6.99(m, 3H), 6.90(dd, J = 1.8 and 5.9 Hz, 1H), 4.22(m, 1H), 4.04(dd, J = 3.0 and 9.5 Hz, 1H), 3.87(s, 3H), 3.84(dd, J = 1.2 and 9.5 Hz, 1H), 2.77(broad s, 1H), 1.28(d, J = 6.4 Hz, 3H). |
| 17 | PhCH2CH2-SH | 4 |  | 4.06 | 413 | 7.27(m, 6H), 6.97(m, 3H), 6.89(dd, J = 2.2 and 8.4 Hz, 1H), 4.23(m, 1H), 4.03(dd, J = 3.0 and 9.6 Hz, 1H), 3.86(s, 3H), 3.84(dd, J = 1.0 and 9.6 Hz, 1H), 3.32(t, J = 5.4 Hz, 2H), 3.02(t, J = 5.4 Hz, 2H), 2.83(broad s, 1H), 1.27(d, J = 6.4 Hz, 3H). |
| 18 | 4-Cl-C6H4-CH2CH2-SH | 4 |  | 4.20 | 447/449 | 7.27(m, 5H), 6.98(m, 3H), 6.89(dd, J = 2.4 and 8.5 Hz, 1H), 4.23(m, 1H), 4.02(dd, J = 3.0 and 9.6 Hz, 1H), 3.86(s, 3H), 3.83(dd, J = 1.0 and 9.6 Hz, 1H), 3.30(t, J = 7.3 Hz, 2H), 2.98(t, J = 7.3 Hz, 2H), 2.81(broad s, 1H), 1.27(d, J = 6.3 Hz, 3H). |
| 19 | Ph-CH2CH2CH2-SH | 4 |  | 4.13 | 427 | 7.23(m, 6H), 6.98(m, 2H), 6.97(d, J = 4.6 Hz, 1H), 6.95(dd, J = 2.2 and 8.4 Hz, 1H), 4.23(m, 1H), 4.07(dd, J = 3.0 and 9.6 Hz, 1H), 3.87(s, 3H), 3.84(dd, J = 1.0 and 9.6 Hz, 1H), 3.12(m, 2H), 2.81(m, 2H), 2.67(broad s, 1H), 2.07(m, 2H), 1.27(d, J = 6.5 Hz, 3H). |
| 20 | 2-pyridyl-CH2CH2-SH | 4 |  | 2.45 | 414 | 8.57(d, J = 4.4 Hz, 1H), 7.62(dd, J = 1.6 and 6.5 Hz, 1H), 7.27(m, 2H), 7.15(dd, J = 1.2 and 5.5 Hz, 1H), 6.96(m, 3H), 6.88(dd, J = 2.4 and 8.5 Hz, 1H), 4.22(m, 1H), 4.02(dd, J = 3.0 and 9.5 Hz, 1H), 3.85(s, 3H), 3.86(dd, J = 1.0 and 9.6 Hz, 1H), 3.50(t, J = 6.8 Hz, 2H), 3.22(t, J = 6.8 Hz, 2H), 2.98(broad s, 1H), 1.27(d, J = 8.6 Hz, 3H). |
| 21 |  | MCPBA oxidation of Ex 19 | 57 | 3.18 | 435/437 | 7.90(d, J = 8.6 Hz, 2H), 7.65(d, J = 4.2 Hz, 1H), 7.44(d, J = 8.6 Hz, 2H), 7.35(d, J = 4.2 Hz, 1H), 6.97(d, J = 8.5 Hz, 1H), 6.87(d, J = 2.1 Hz, 1H), 6.84(dd, J = 2.1 and 8.5 Hz, 1H), 4.23(m, 1H), 4.01(dd, J = 2.9 and 9.4 Hz, 1H), 3.85(s, 3H), 3.83(dd, J = 1.1 and 9.4 Hz, 1H) 1.27(d, J = 6.4 Hz, 3H). |
| 22 |  | MCPBA oxidation of Ex 19 | 10 | 3.18 | 451/453 | 8.12(d, J = 8.6 Hz, 2H), 7.60(d, J = 6.1 Hz, 1H), 7.51(d, J = 6.1 Hz, 1H), 7.50(d, J = 8.6 Hz, 2H), 6.96(d, J = 8.6 Hz, 1H), 6.90(d, J = 2.4 Hz, 1H), 6.84(dd, J = 2.4 and 8.6 Hz, 1H), 4.23(m, 1H), 4.01(dd, J = 3.0 and 9.5 Hz, 1H), 3.86(s, 3H), 3.84(dd, J = 1.2 and 9.5 Hz, 1H) 1.28(d, J = 6.0 Hz, 3H). |
| 23 |  | MCPBA oxidation of Ex 20 | 17 | 2.96 | 445 | 7.52(d, J = 4.1 Hz, 1H), 7.40(d, J = 4.1 Hz, 1H), 7.20(m, 5H), 7.00(d, J = 8.6 Hz, 1H), 6.90(d, J = 2.5 Hz, 1H), 6.81(dd, J = 2.5 and 8.6 Hz, 1H), 4.25(m, 1H), 4.05(dd, J = 3.1 and 9.5 Hz, 1H), 3.88(s, 3H), 3.86(m, 3H), 3.20(t, H = 7.8 Hz, 2H), 1.29(d, J = 6.2 Hz, 3H). |

TABLE 1-continued

3-Thio substituted-1-arylpyrazin-2(1H)-ones

| # | Structure | Method | Yield | Rt | MS | NMR |
|---|---|---|---|---|---|---|
| 24 | | MCPBA oxidation of Ex 20 | 61 | 3.02 | 429 | 7.65(d, J = 6.2 Hz, 1H), 7.30 (d, J = 6.2 Hz, 1H), 7.20(m, 5H), 6.99(d, J = 8.4 Hz, 1H), 6.85(d, J = 1.0 Hz, 1H), 6.84(dd, J = 1.0 and 8.4 Hz, 1H) 4.25(m, 1H), 4.02(dd, J = 2.9 and 9.6 Hz, 1H), 3.87(s, 3H), 3.85(dd, J = 1.2 and 9.6 Hz, 1H), 3.61(m, 2H), 3.53(m, 1H), 3.17(m, 2H), 1.28(d, J = 6.8 Hz, 3H). |
| 25 | phenethyl-SH | 2a | 33 | 4.11 | 4.27 | 7.28(m, 2H), 6.97(d, J = 2.3 Hz, 1H), 6.97(d, J = 8.5 Hz, 1H), 6.88 (dd, J = 2.3, 8.5 Hz, 1H), 3.86(s, 5H), 3.33(dd, J = 7.6 and 8.8 Hz, 2H), 3.02(dd, J = 5.9 and 8.8 Hz, 2H), 1.36(s, 6H). |
| 26 | 4-F-phenethyl-SH | 2a | 10 | 3.8 | 445 | 7.25(d, J = 4.4 Hz, 1H), 7.17(m, 2H), 6.94(m, 5 H), 6.84(dd, J = 2.2 and 8.5 Hz, 1H), 3.82(s, 3H), 3.77(s, 2H), 3.23(t, J = 7.4 Hz, 2H), 2.91(t, J = 7.4 Hz, 2H), 1.27 (s, 6H) |
| 27 | 2-pyridyl-ethyl-SH | 2a | 29 | 2.67 | 428 | 8.57(d, J = 4.2 Hz, 1H), 7.62(dd, J = 5.9 and 7.6 Hz, 1H), 7.27(m, 2H), 7.15(m, 1H), 6.97(m, 3H), 6.88(dd, J = 2.3, 8.4 Hz, 1H), 3.85 (s, 5H), 3.50(t, J = 7.2 Hz, 2H), 3.22(t, J = 7.2 Hz, 2H), 1.36(s, 6H). |
| 28 | 4-pyridyl-ethyl-SH | 2a | 31 | 2.74 | 428 | 8.68(d, J = 6.1 Hz, 2H), 797(d, J = 6.1 Hz, 2H), 7.29(d, J = 5.4 Hz, 1H), 7.21(d, J = 5.4 Hz, 1H), 7.00 (d, J = 2.0 Hz, 1H), 6.98(d, J = 8.8 Hz, 1H), 6.86(dd, J = 2.0 and 8.8 Hz, 1H), 3.77(s, 3H), 3.75(s, 2H), 3.42(t, J = 7.2 Hz, 2H), 3.30(t, J = 7.2 Hz, 2H), 1.24(s, 6H). |
| 29 | 7-CF3-quinolin-4-SH | 2a | 12 | 4.02 | 518 | 8.94(d, J = 4.5 Hz, 1H), 8.36(d, J = 8.8 Hz, 1H), 8.32(s, 1H), 7.92 (d, J = 4.5 Hz, 1H), 7.74(dd, J = 1.5 and 8.9 Hz, 1H), 7.21(d, J = 4.4 Hz, 1H), 7.06(d, J = 2.3 Hz, 1H), 7.00(d, J = 8.6 Hz, 1H), 6.92 (dd, J = 2.3 and 8.6 Hz, 1H), 6.90 (d, J = 4.4 Hz, 1H), 3.79(s, 3H), 3.75(s, 2H), 1.24(s, 6H). |
| 30 | 2-Cl-phenyl-SH | 2a | 50 | 3.76 | 433/435 | 7.67(dd, J = 1.4 and 7.5 Hz, 1H), 7.56(dd, J = 1.2 and 8.0 Hz, 1H), 7.42(dt, J = 1.4 and 7.5 Hz, 1H), 7.36(dt, J = 1.2 and 7.5 Hz, 1H), 7.11(d, J = 4.5 Hz, 1H), 7.01(d, J = 2.3 Hz, 1H), 6.96(d, J = 8.4 Hz, 1H), 6.93(d, J = 4.5 Hz, 1H), 6.90 (dd, J = 2.3 and 8.4 Hz, 1H), 3.87 (s, 3H), 3.86(s, 2H), 2.72(broad s, 1H), 1.36(s, 6H). |
| 31 | 3-Cl-phenyl-SH | 2a | 62 | 3.98 | 433/435 | 7.59(d, J = 1.7 Hz, 1H), 7.48(m, 1H), 7.41(m, 2H), 7.14(d, J = 4.5 Hz, 1H), 7.00(m, 3H), 6.90(dd, J = 2.4 and 8.5 Hz, 1H), 3.87(s, 3H), 3.86(s, 2H), 2.71(broad s, 1H), 1.36(s, 6H). |

TABLE 1-continued

3-Thio substituted-1-arylpyrazin-2(1H)-ones

| | | | | | |
|---|---|---|---|---|---|
| 32 | 4-Cl-C6H4-SH | 2a | 58 | 4.00 | 433/435 | 7.52(dd, J = 1.9 and 6.7 Hz, 2H), 7.43(dd, J = 1.9 and 6.7 Hz, 2H), 7.13(d, J = 4.4 Hz, 1H), 6.99(d, J = 2.3 Hz, 1H), 6.98(d, J = 4.4 Hz, 1H), 6.96(d, J = 8.4 Hz, 1H), 6.90(dd, J = 2.3 and 8.4 Hz, 1H), 3.87(s, 3H), 3.86(s, 2H), 2.70(broad s, 1H), 1.36(s, 6H). |
| 33 | 2-naphthyl-SH | 2a | 70 | 4.11 | 449 | 8.12(s, 1H), 7.88(m, 3H), 7.61(dd, J = 1.4 and 8.6 Hz, 1H), 7.53(m, 2H), 7.09(d, J = 4.5 Hz, 1H), 7.02(d, J = 2.3 Hz, 1H), 6.98(d, J = 4.5 Hz, 1H), 6.96(d, J = 8.5 Hz, 1H), 6.91(dd, J = 2.3 and 8.5 Hz, 1H), 3.88(s, 3H), 3.87(s, 2H), 2.75(broad s, 1H), 1.37(s, 6H). |
| 34 | 4-F-C6H4-SH | 2a | 34 | 3.72 | 417 | 7.56(m, 2H), 7.12(m, 3H), 6.98(m, 3H), 6.89(m, 1H), 3.86(s, 5H), 1.36(s, 6H). |
| 35 | 4-iPr-C6H4-SH | 2a | 39 | 4.24 | 441 | 7.50(d, J = 8.2 Hz, 2H), 7.32(d, J = 8.2 Hz, 2H), 7.15(d, J = 4.5 Hz, 1H), 7.02(d, J = 2.3 Hz, 1H), 6.97(d, J = 4.5 Hz, 1H), 6.96(d, J = 8.5 Hz, 1H), 6.92(dd, J = 2.3 and 8.5 Hz, 1H), 3.90(s, 3H), 3.85(s, 2H), 2.98(m, 1H), 2.85(broad s, 1H), 1.35(s, 6H), 1.24(d, J = 6.8 Hz, 6H). |
| 36 | 4-CF3-C6H4-SH | 2a | 16 | 4.10 | 467 | 7.64(d, J = 9.0 Hz, 2H), 7.62(d, J = 9.0 Hz, 2H), 7.18(d, J = 4.5 Hz, 1H), 7.04(d, J = 4.5 Hz, 1H), 7.00(d, J = 2.2 Hz, 1H), 6.98(d, J = 8.5 Hz, 1H), 6.86(dd, J = 2.2 and 8.5 Hz, 1H), 3.75(s, 1H), 3.73(s, 2H), 1.22(s, 6H). |
| 37 | 4-MeS-C6H4-SH | 2a | 50 | 3.96 | 445 | 7.48(d, J = 8.4 Hz, 2H), 7.30(d, J = 8.4 Hz, 2H), 7.28(d, J = 4.5 Hz, 1H), 7.12(d, J = 4.5 Hz, 1H), 6.99(d, J = 8.5 Hz, 1H), 6.96(d, J = 2.4 Hz, 1H), 6.89(dd, J = 2.4 and 8.5 Hz, 1H), 3.86(s, 5H), 2.51(s, 3H), 1.35(s, 6H). |
| 38 | 4-CF3O-C6H4-SH | 2a | 52 | 415 | 483 | 7.62(d, J = 8.6 Hz, 2H), 7.30(d, J = 8.6 Hz, 2H), 7.16(d, J = 4.4 Hz, 1H), 7.06(d, J = 4.4 Hz, 1H), 7.00(d, J = 8.5 Hz, 1H), 6.98(d, J = 2.3 Hz, 1H), 6.95(dd, J = 2.3 and 8.5 Hz, 1H), 3.91(s, 3H), 3.86(s, 2H), 1.36(s, 6H). |
| 39 | 3-MeO-C6H4-SH | 2a | 60 | 3.72 | 429 | 7.37(t, J = 8.0 Hz, 1H), 7.18(d, J = 8.0 Hz, 1H), 7.14(m, 2H), 6.98(m, 4H), 6.90(m, 1H), 3.86(s, 5H), 3.77(s, 3H), 1.36(s, 6H). |

TABLE 1-continued

3-Thio substituted-1-arylpyrazin-2(1H)-ones

| 40 | (2-trifluoromethylphenyl-SH) | 2a | 49 | 3.88 | 467 | 7.84(d, J = 7.5 Hz, 1H), 7.71(d, J = 7.5 Hz, 1H), 7.62(t, J = 7.5 Hz, 1H), 7.60(t, J = 7.5 Hz, 1H), 7.05 (d, J = 4.4 Hz, 1H), 7.01(d, J = 2.4 Hz, 1H), 6.98(d, J = 8.5 Hz, 1H), 6.97(d, J = 4.4 Hz, 1H), 6.90(dd, J = 2.4 and 8.5 Hz, 1H), 3.88(s, 3H), 3.86(s, 2H), 1.36(s, 6H). |
|---|---|---|---|---|---|---|
| 41 | (4-chloro-2-methylphenyl-SH) | 2a | 50 | 4.20 | 447/449 | 7.48(d, J = 8.4 Hz, 1H), 7.36(d, J = 2.0 Hz, 1H), 7.24(dd, J = 2.0 and 8.4 Hz, 1H), 7.10(d, J = 4.5 Hz, 1H), 7.00(d, J = 2.4 Hz, 1H), 6.98(d, J = 8.5 Hz, 1H), 6.96(d, J = 4.5 Hz, 1H), 6.90(dd, J = 2.4 and 8.5 Hz, 1H), 3.88(s, 3H), 3.87(s, 2H), 2.40(s, 3H), 1.38(s, 6H). |
| 42 | (2,4-dimethylphenyl-SH) | 2a | 60 | 4.04 | 427 | 7.44(d, J = 7.9 Hz, 1H), 7.19(s, 1H), 7.11(d, J = 4.5 Hz, 1H), 7.08 (d, J = 7.9 Hz, 1H), 7.01(d, J = 2.3 Hz, 1H), 6.97(d, J = 8.6 Hz, 1H), 6.93(d, J = 4.5 Hz, 1H), 6.90(dd, J = 2.3 and 8.6 Hz, 1H), 3.87(s, 3H), 3.86(s, 2H), 2.39(s, 3H), 2.37(s, 3H), 1.36(s, 6H). |
| 43 | (4-methylphenyl-SH) | 2a | 60 | 3.87 | 413 | 7.46(d, J = 8.0 Hz, 2H), 7.27(d, J = 8.0 Hz, 2H), 7.15(d, J = 4.4 Hz, 1H), 7.01(d, J = 2.3 Hz, 1H), 6.97 (d, J = 8.5 Hz, 1H), 6.96(d, J = 4.4 Hz, 1H), 6.92(dd, J = 2.3 and 8.5 Hz, 1H), 3.91(s, 3H), 3.85(s, 2H), 2.40(s, 3H), 1.35(s, 6H). |
| 44 | (4-methoxyphenyl-SH) | 2a | 39 | 3.71 | 429 | 7.48(d, J = 8.7 Hz, 2H), 7.14(d, J = 4.5 Hz, 1H), 7.00(d, J = 2.3 Hz, 1H), 6.99(d, J = 8.0 Hz, 2H), 6.97 (d, J = 4.5 Hz, 1H), 6.97(d, J = 8.5 Hz, 1H), 6.92(dd, J = 2.3 and 8.5 Hz, 1), 3.89(s, 3H), 3.85(s, 5H), 1.35(s, 6H). |
| 45 | (4-ethylphenyl-SH) | 2a | 64 | 4.05 | 427 | 7.45(d, J = 8.3 Hz, 2H), 7.25(d, J = 8.3 Hz, 2H), 7.11(d, J = 3.9 Hz, 1H), 6.97(d, J = 2.2 Hz, 1H), 6.93 (d, J = 8.2 Hz, 1H), 6.92(d, J = 3.9 Hz, 1H), 6.87(dd, J = 2.2 and 8.2 Hz, 1H), 3.86(s, 3H), 3.81(s, 2H), 2.66(q, J = 5.5 Hz, 2H), 1.31(s, 6H), 1.22(t, J = 5.5 Hz, 3H). |
| 46 | (1-phenylpropan-2-SH) | 2a | 29 | 4.25 | 441 | 7.27(m, 5H), 7.20(m, 1H), 6.92 (m, 3H), 6.85(dd, J = 2.2, 8.0 Hz, 1H), 3.97(m, 1H), 3.84(s, 3H), 3.81(s, 2H), 3.16(dd, J = 2.0 and 8.0 Hz, 1H), 2.74(dd, J = 5.0 and 8.0 Hz, 1H), 1.33(s, 6H), 1.32(d, J = 9.3 Hz, 3H). |
| 47 | (2-(3-methylphenyl)ethyl-SH) | 2a | 59 | 4.31 | 441 | 7.30(m, 1H), 7.21(m, 1H), 7.11 (m, 1H), 7.05(m, 1H), 6.97(m, 4H), 6.89(m, 1H), 3.87(s, 3H), 3.84(s, 2H), 3.31(dd, J = 6.0 and 8.3 Hz, 2H), 2.98(t, J = 8.3 Hz, 2H), 2.35(s, 3H), 1.35(s, 6H) |

TABLE 1-continued

3-Thio substituted-1-arylpyrazin-2(1H)-ones

| | | | | | | |
|---|---|---|---|---|---|---|
| 48 | 2-methylphenethyl thiol | 2a | 88 | 4.30 | 441 | 7.26(d, J = 4.4 Hz, 1H), 7.39(d, J =7.2 Hz, 1H), 7.10(m, 3H), 6.95(m, 3H), 6.84(dd, J = 2.2 and 8.2 Hz, 1H), 3.83(s, 3H), 3.79(s, 2H), 3.22(dd, J = 5.7 and 8.5 Hz, 2H), 2.96(dd, J = 5.5 and 8.5 Hz, 2H), 2.34(s, 3H), 1.29(s, 6H). |
| 49 | thiophenol | 2a | 51 | 3.62 | 399 | 7.52(m, 2H), 7.39(m, 3H), 7.05 (d, J = 4.4 Hz, 1H), 6.92(d, J = 2.4 Hz, 1H), 6.90(d, J = 8.4 Hz, 1H), 6.89(d, J = 4.4 Hz, 1H), 6.83(dd, J = 2.4 and 8.4 Hz, 1H), 3.80(s, 3H), 3.79(s, 2H), 1.29(s, 6H). |
| 50 | benzyl thiol | 2a | 51 | 3.95 | 413 | 7.43(d, J = 7.1 Hz, 2H), 7.30(m, 4H), 6.96(m, 3H), 6.88(dd, J = 2.4 and 8.5 Hz, 1H), 4.33(s, 2H), 3.87(s, 3H), 3.84(s, 2H), 1.35(s, 6H). |
| 51 | 5-(trifluoromethyl)pyridine-2-thiol | 2a | 6 | 3.63 | 468 | 8.89(s, 1H), 8.17(d, J = 7.2 Hz, 1H), 8.10(d, J = 7.2 Hz, 1H), 7.45 (d, J = 4.4 Hz, 1H), 7.30(d, J = 4.4 Hz, 1H), 7.15(d, J = 2.4 Hz, 1H), 7.12(d, J = 8.6 Hz, 1H), 7.01(dd, J = 2.4 and 8.6 Hz, 1H), 3.91(s, 3H), 3.87(s, 2H), 1.35(s, 6H). |
| 52 | 2-chlorothiophenol | 2a | 50 | 4.02 | 433/435 | 7.67(dd, J = 1.4 and 7.5 Hz, 1H), 7.56(dd, J = 1.2 and 8.0 Hz, 1H), 7.42(dt, J = 1.4 and 7.5 Hz, 1H), 7.36(dt, J = 1.2 and 7.5 Hz, 1H), 7.11(d, J = 4.5 Hz, 1H), 7.01(d, J = 2.3 Hz, 1H), 6.96 (d, J = 8.4 Hz, 1H), 6.93(d, J = 4.5 Hz, 1H), 6.90 (dd, J = 2.3 and 8.5 Hz, 1H), 3.87 (s, 3H), 3.96(s, 2H), 2.72(broad s, 1H), 1.36(s, 6H). |
| 53 | 3-chlorothiophenol | 2a | 62 | 3.76 | 433/435 | 7.59(d, J = 1.7 Hz, 1H), 7.48(m, 1H), 7.41(m, 2H), 7.14(d, J = 4.5 Hz, 1H), 7.00(m, 3H), 6.90(dd, J = 2.4 and 8.5 Hz, 1H), 3.87(s, 3H), 3.86(s, 2H), 2.71(broad s, 1H), 1.36(s, 6H). |
| 54 | 4-chlorothiophenol | 2a | 58 | 3.98 | 433/435 | 7.52(dd, J = 1.9 and 6.7 Hz, 2H), 7.43(dd, J = 1.9 and 6.7 Hz, 2H), 7.13(d, J = 4.4 Hz, 1H), 6.99(d, J = 2.3 Hz, 1H), 6.98(d, J = 4.4 Hz, 1H), 6.96(d, J = 8.4 Hz, 1H), 6.90 (dd, J = 2.3 and 8.4 Hz, 1H), 3.87 (s, 3H), 3.86(s, 2H), 2.70(broad s, 1H), 1.36(s, 6H). |
| 55 | 2-(6-methylpyridin-2-yl)ethanethiol | 2a | 50% | 2.74 | 442 | 7.67(t, J = 7.7 Hz, 1H), 7.38(d, J = 4.4 Hz, 1H), 7.25(d, J = 4.4 Hz, 1H), 7.16(m, 2H), 7.10(d, J = 2.4 Hz, 1H), 7.08(d, J = 8.6 Hz, 1H), 6.95(dd, J = 2.4 and 8.6 Hz, 1H), 3.89(s, 3H), 3.86(s, 2H), 3.45(t, J = 7.1 Hz, 2H), 3.15(t, J = 7.1 Hz, 2H), 2.53(s, 3H), 1.34(s, 6H). |

TABLE 1-continued

3-Thio substituted-1-arylpyrazin-2(1H)-ones

| 56 | 4-(dimethylamino)phenyl-SH | 2a | 44% | 3.03 | 442 | 7.40(d, J = 8.9 Hz, 2H), 7.13(d, J = 4.8 Hz, 1H), 7.00(d, J = 2.3 Hz, 1H), 6.97(d, J = 8.5 Hz, 1H), 6.92(d, J = 4.8 Hz, 1H), 6.90(dd, J = 2.3 and 8.5 Hz, 1H), 6.76(d, J = 8.9 Hz, 2H), 3.87(s, 3H), 3.86(s, 2H), 3.01(s, 6H), 1.36(s, 6H). |
|---|---|---|---|---|---|---|
| 57 | 6-methoxybenzothiazol-2-SH | 5 | 3 | 3.68 | 486 | 7.77(d, J = 8.8 Hz, 1H), 7.57(d, J = 2.5 Hz, 1H), 7.37(d, J = 4.4 Hz, 1H), 7.14(d, J = 4.4 Hz, 1H), 7.08(dd, J = 2.5, 8.8 Hz, 1H), 7.02(m, 2H), 6.93(dd, J = 2.5, 8.5 Hz, 1H), 3.92(s, 3H), 3.90(s, 2H), 1.39(s, 6H). |
| 58 | 2-aminobenzothiazole | 5 | | 3.64 | 456 | 7.93(d, J = 8.3 Hz, 1H), 7.87(d, J = 8.1 Hz, 1H), 7.43(t, J = 8.2 Hz, 1H), 7.35(m, 3H), 7.07(d, J = 2.3 Hz, 1H), 7.01(d, J = 8.6 Hz, 1H), 6.93(dd, J = 2.3 and 8.5 Hz, 1H), 3.79(s, 3H), 3.76(s, 2H), 1.24(s, 6H). |
| 59 | 6-chlorobenzothiazol-2-SH | 5 | | 3.99 | 490/492 | 7.87(d, J = 8.6 Hz, 1H), 7.79(d, J = 2.0 Hz, 1H), 7.38(dd, J = 2.0 and 8.6 Hz, 1H), 7.30(d, J = 4.4 Hz, 1H), 7.08(d, J = 4.4 Hz, 1H), 6.92(d, J = 2.5 Hz, 1H), 6.91(d, J = 8.6 Hz, 1H), 6.85(dd, J = 2.5 and 8.6 Hz, 1H), 3.80(s, 5H), 1.30(s, 6H). |
| 60 | 5-chlorobenzothiazol-2-SH | 5 | | 3.67 | 474/476 | 7.71(d, J = 2.0, 1H), 7.45(d, J = 8.7 Hz, 1H), 7.32(dd, J = 2.0 and 8.7 Hz, 1H), 7.11(d, J = 4.4 Hz, 1H), 7.04(d, J = 4.4 Hz, 1H), 6.91(d, J = 8.6 Hz, 1H), 6.90(d, J = 2.4 Hz, 1H), 6.84(dd, J = 2.4 and 8.6 Hz, 1H), 3.81(s, 3H), 3.79(s, 2H), 1.29(s, 6H). |
| 61 | benzimidazol-2-SH | 5 | | 2.68 | 439 | 7.71(dd, J = 3.1 and 6.2 Hz, 2H), 7.49(dd, J = 3.1 and 6.2 Hz, 2H), 7.43(d, J = 4.4 Hz, 1H), 7.22(d, J = 4.4 Hz, 1H), 7.04(d, J = 2.5 Hz, 1H), 7.01(d, J = 8.5 Hz, 1H), 6.91(dd, J = 2.4 and 8.5 Hz, 1H), 3.79(s, 3H), 3.75(s, 2H), 1.24(s, 6H). |
| 62 | 6-methoxybenzothiazol-2-SH (ethyl) | 5 | | 4.11 | 484 | 7.68(d, J = 8.8 Hz, 1H), 7.46(d, J = 2.4 Hz, 1H), 7.27(d, J = 4.4 Hz, 1H), 7.16(m, 2H), 7.04(d, J = 4.4 Hz, 1H), 7.00(dd, J = 2.5 and 8.7 Hz, 1H), 6.85(d, J = 9.4 Hz, 1H), 3.82(s, 3H), 3.78(s, 2H), 2.65(q, J = 7.5 Hz, 2H), 1.32(s, 6H), 1.15(t, J = 7.5 Hz, 3H). |
| 63 | 4-(trifluoromethyl)phenyl-SH | 2a | | 4.05 | 465 | 7.64(d, J = 8.5 Hz, 2H), 7.62(d, J = 8.5 Hz, 2H), 7.15(m, 2H), 7.04(d, J = 4.4 Hz, 1H), 6.93(d, J = 4.4 Hz, 1H), 6.84(d, J = 9.2 Hz, 1H), 3.77(s, 2H), 2.63(q, J = 7.5 Hz, 2H), 1.30(s, 6H), 1.17(t, J = 7.5 Hz, 3H) |

TABLE 1-continued

3-Thio substituted-1-arylpyrazin-2(1H)-ones

| # | Structure | | | |
|---|---|---|---|---|
| 64 | F₃C–O–C₆H₄–SH | 2a | 4.15 | 481 | 7.43(d, J = 8.8 Hz, 2H), 7.31(d, J = 8.8 Hz, 2H), 7.24(d, J = 2.4 Hz, 1H), 7.22(d, J = 8.5 Hz, 1H), 7.14(d, J = 4.4 Hz, 1H), 7.00(d, J = 4.4 Hz, 1H), 6.94(dd, J = 2.4, 8.5 Hz, 1H), 3.86(s, 2H), 2.74(q, J = 7.5 Hz, 2H), 1.41(s, 6H), 1.26(t, J = 7.5 Hz, 3H). |
| 65 | PhCH₂CH₂–SH | 2a | 4.08 Method 2 | 425 | 7.10(m, 8H), 6.84(d, J = 4.4 Hz, 1H), 6.76(d, J = 8.5 Hz, 1H), 3.70 (s, 2H), 3.21(m, 2H), 2.90(m, 2H), 2.59(q, J = 7.4 Hz, 2H), 1.26 (s, 6H), 1.12(t, J = 7.4 Hz, 3H) |
| 66 | PhCH₂CH₂–SH | 2a | 3.81 | 439 | 7.23(m, 5H), 7.14(m, 1H), 6.92 (m, 3H), 6.83(dd, J = 2.4, 8.6 Hz), 4.08(dd, J = 2.6, 9.7 Hz, 1H), 3.93(t, J = 8.2 Hz, 1H), 3.80(s, 3H), 3.25(m, 3H), 2.94(m, 2H), 0.88 (m, 1H), 0.57(m, 1H), 0.51(m, 1H), 0.36(m, 1H), 0.22(m, 1H) |
| 67 | F₃C–O–C₆H₄–SH | 2a | 3.87 | 495 | 7.54(d, J = 8.8 Hz, 2H), 7.21(d, J = 8.8 Hz, 2H), 7.05(d, J = 4.4 Hz, 1H), 6.93(d, J = 8.5 Hz, 1H), 6.92 (d, J = 2.4 Hz, 1H), 6.91(d, J = 4.4 Hz, 1H), 6.84(dd, J = 2.4, 8.5 Hz, 1H), 4.13(dd, J = 2.8, 9.7 Hz, 1H), 3.96(dd, J = 1.3, 8.2 Hz, 1H), 3.79(s, 3H), 3.29(dt, J = 2.5, 9.8 Hz, 1H), 0.93(m, 1H), 0.57(m, 1H), 0.51(m, 1H), 0.41(m, 1H), 0.25(m, 1H) |
| 68 | F₃C–C₆H₄–SH | 2a | 3.74 Method 2 | 479 | 7.66(d, J = 8.5 Hz, 2H), 7.64(d, J = 8.5 Hz, 2H), 7.51(d, J = 4.4 Hz, 1H), 7.09(d, J = 4.4 Hz, 1H), 7.00(d, J = 8.2 Hz, 1H), 6.98(d, J = 2.2 Hz, 1H), 6.89(dd, J = 2.2, 8.2 Hz,1H), 4.22(dd, J = 2.2, 9.3 Hz, 1H), 3.96(dd, J = 1.1, 9.4 Hz, 1H), 3.84(s, 3H), 3.27(dt, J = 2.5, 9.8 Hz, 1H), 0.93(m, 1H), 0.57(m, 1H), 0.51(m, 1H), 0.41(m, 1H), 0.25 (m, 1H) |
| 69 | F₃C–C₆H₄–SH | 2a | 3.59 Method 2 | 481 | 7.64(m, 4H), 7.06(d, J = 4.4 Hz, 1H), 6.98(d, J = 2.8 Hz, 1H), 6.95 (d, J = 9.7 Hz, 1H), 6.93(d, J = 4.4 Hz, 1H), 6.86(dd, J = 2.8 and 9.7 Hz, 1H), 4.63(m, 1H), 4.34(m, 1H), 4.09(m, 1H), 3.97(m, 2H), 3.83(s, 3H), 3.78(m, 1H), 3.07(d, J = 6.4 Hz, 1H). |
| 70 | F₃C–C₆H₄–SH | 2a | 3.87 Method 2 | 479 | 7.62(m, 4 H), 7.05(d, J = 4.5 Hz, 1H), 6.95(d, J = 8.5 Hz, 1H), 6.93 (d, J = 4.5 Hz, 1H), 6.92(d, J = 2.4 Hz, 1H), 6.83(dd, J = 2.4 and 8.5 Hz, 1H), 4.42(m, 1H), 4.13(m, 1H), 3.75(s, 3H), 3.04(m, 1H), 1.99(m, 1H), 1.70 to 1.90(m, 4H), 1.52(m, 1H). |

TABLE 1-continued

3-Thio substituted-1-arylpyrazin-2(1H)-ones

| # | Structure | Method | Time | MW | ¹H NMR |
|---|---|---|---|---|---|
| 71 | 4-CF₃-C₆H₄-SH | 2a | 3.74 Method 2 | 453 | 7.85(d, J = 8.4 Hz, 2H), 7.80(d, J = 8.4 Hz, 2H), 7.48(d, J = 4.4 Hz, 1H), 7.16(d, J = 4.4 Hz, 1H), 7.15(d, J = 2.4 Hz, 1H), 7.10(d, J = 8.6 Hz, 1H), 7.01(dd, J = 2.4, 8.6 Hz, 1H), 3.97(m, 1H), 3.90(m, 1H), 3.81(m, 1H), 3.78(s, 3H), 1.16(d, 3H) |
| 72 | 4-CF₃-C₆H₄-SH | 2a | 3.72 Method 2 | 483 | 7.64(m, 4H), 7.06(d, J = 4.5 Hz, 1H), 6.96(d, J = 8.5 Hz, 1H), 6.94(d, J = 4.5 Hz, 1H), 6.92(d, J = 2.5 Hz, 1H), 6.84(dd, J = 2.5, 8.5 Hz, 1H), 4.04(m, 2H), 3.81(s, 3H), 3.50(m, 2H), 3.36(s, 3H) |
| 73 | 4-CF₃-C₆H₄-SH | 2a | 3.62 Method 2 | 545 | 7.63(m, 4H), 7.06(d, J = 4.4 Hz, 2H), 6.94(d, J = 4.4 Hz, 1H), 6.92(d, J = 2.0 Hz, 1H), 6.90(d, J = 8.5 Hz, 1H), 6.83(dd, J = 2.0 and 8.5 Hz, 1H), 4.54(m, 1H), 4.02(d, J = 5.4 Hz, 2H), 3.78(s, 3H), 3.62(m, 1 H), 3.0 to 3.40(m, 3H), 1.86(m, 1 H), 1.38(t, J = 7.4 Hz, 3H). |
| 74 | 4-CF₃-C₆H₄-SH | 2a | | 507 | 3.90(s, 3H), 4.14-4.22(m, 1H), 4.32(dd, J = 10.45, 3.65 Hz, 1H), 4.36-4.47(m, 1H), 7.03(dd, J = 8.56, 2.27 Hz, 1H), 7.14-7.22(m, 3H), 7.34(d, J = 4.28 Hz, 1H), 7.74-7.83(m, 4H) |
| 75 | 4-OCF₃-C₆H₄-SH | 2a | | 531 | ¹H NMR (400 MHz, MeOD) δ ppm 7.69(d, 2H), 7.38(d, 2H), 7.33(d, 1H), 7.18(m, 3H), 7.03(d, 1H), 4.09(s, 2H), 3.91(s, 3H), 2.93(m, 2H), 2.66(m, 2H). |
| 76 | 4-CF₃-C₆H₄-SH | 2a | | 515 | ¹H NMR (400 MHz, MeOD) δ ppm 7.78(s, 4H), 7.34(s, 1H), 7.19(m, 3H), 7.03(d, 1H), 4.09(s, 2H), 3.90(s, 3H), 2.93_m, 2H), 2.66(m, 2H). |
| 77 | 4-F-benzothiazole-2-SH | 2a | | 474 | ¹H NMR (400 MHz, MeOD) δ ppm 7.78(d, 1H), 7.53(m, 3H), 7.30(m, 1H), 7.20(s, 1H), 7.12(m, 1H), 7.06(d, 1H), 3.91(s, 3H), 3.88(s, 2H), 1.36(s, 6H). |
| 78 | 7-F-benzothiazole-2-SH | 2a | | 474 | ¹H NMR (400 MHz, MeOD) δ ppm 7.85(d, 1H), 7.53(m, 3H), 7.21(m, 4H), 3.91(s, 3H), 3.88(s, 2H), 1.36(s, 6H). |
| 79 | 6-F-benzothiazole-2-SH | 2a | | 474 | ¹H NMR (400 MHz, MeOD) δ ppm 7.97(d, 1H), 7.85(d, 1H), 7.53(d, 2H), 7.35(t, 1H), 7.21(s, 1H), 7.16(m, 1H), 7.07(m, 1H), 3.91(s, 1H), 3.88(s, 2H), 1.36(s, 6H). |
| 80 | 4-OCF₃-C₆H₄-SH | 6 | | 479 | ¹H NMR (400 MHz, MeOD) δ ppm 7.68(d, 2H), 7.40(d, 2H), 7.28(s, 1H), 7.17(m, 1H), 6.97(d, 1H), 3.82(s, 1H), 2.96(m, 2H), 2.24(m, 1H), 2.81(m, 1H), 1.33(s, 6H). |

TABLE 1-continued

3-Thio substituted-1-arylpyrazin-2(1H)-ones

| # | Structure | R | MS | NMR |
|---|---|---|---|---|
| 81 | 4-(OCF3)C6H4-SH | 6 | 491 | $^1$H NMR (400 MHz, MeOD) δ ppm 7.69(d, 2H), 7.40(d, 2H), 7.28(m, 2H), 7.20(m, 2H), 6.91(d, 1H), 5.79(s, 1H), 4.70(s, 1H), 2.08(s, 2H), 1.31(d, 6H). |
| 82 | 4-(OCF3)C6H4-SH | 6 | 495 | $^1$H NMR (400 MHz, CDCl$_3$) δ ppm 7.61(d, 2H), 7.59(s, 1H), 7.28(m, 2H), 7.14(m, 2H), 6.99(s, 1H), 6.92(d, 1H), 4.87(t, 1H), 4.00(d, 1H), 2.36(m, 1H), 1.84(q, 1H), 1.38(d, 6H). |
| 83 | 4-(OCF3)C6H4-SH | 6 | 433 (M + H - H$_2$O) | $^1$H NMR (400 MHz, MeOD) δ ppm 7.70(d, 2H), 7.61(s, 1H), 7.43(d, 2H), 7.28(m, 2H), 7.20(s, 1H), 6.95(d, 1H), 4.35(m, 2H), 2.12(br-s, 2H), 1.62(s, 3H). |
| 84 | 4-(OCF3)C6H4-SH | 6 | 453 | 1H NMR (500 MHz, chloroform-d) δ ppm 7.62(2 H, d, J = 8.80 Hz), 7.36(2 H, d, J = 8.80 Hz), 7.29(2 H, d, J = 7.97 Hz), 7.13(1 H, d, J = 4.67 Hz), 7.04(2 H, d, J = 8.80 Hz), 6.98(1 H, d, J = 4.40 Hz), 3.84(2 H, s), 1.37(6 H, s). |
| 85 | naphthalen-1-yl-SH | 6 | 449 | 1H NMR (500 MHz, chloroform-d) δ ppm 8.31(1 H, dd, J = 6.19, 3.44 Hz), 8.00(1 H, d, J = 8.25 Hz), 7.85-7.95(2 H, m), 7.51-7.56(3 H, m), 7.04(1 H, d, J = 2.20 Hz), 6.97-7.02(1 H, m), 6.89-6.96(3 H, m), 3.90(3 H, s), 3.88(2 H, s), 1.37(6 H, s). |
| 86 | 4-(OCF3)C6H4-SH | 6 | 471 | 1H NMR (500 MHz, methanol-d$_3$) δ ppm 7.62-7.68(2 H, m), 7.34-7.39(3 H, m), 7.21-7.29(3 H, m), 7.15(1 H, d, J = 4.40 Hz), 3.91(2 H, s), 1.34(6 H, s). |
| 87 | 4-(OCF3)C6H4-SH | 6 | 467 | 1H NMR (500 MHz, methanol-d$_3$) δ ppm 7.62-7.69(2 H, m), 7.36(2 H, d, J = 7.97 Hz), 7.21-7.28(3 H, m), 7.15(1 H, d, J = 4.40 Hz), 7.02(1 H, d, J = 8.52 Hz), 3.84(2 H, s), 2.31(3 H, s), 1.36(6 H, s). |
| 88 | 4-(OCF3)C6H4-SH | 6 | 487 | 1H NMR (500 MHz, methanol-d$_3$) δ ppm 7.65(2 H, d, J = 8.80 Hz), 7.59(1 H, d, J = 2.75 Hz), 7.33-7.41(3 H, m), 7.27(1 H, d, J = 4.40 Hz), 7.22(1 H, d, J = 8.80 Hz), 7.15(1 H, d, J = 4.40 Hz), 3.91(2 H, s), 1.37(6 H, s) |
| 89 | 4-(OCF3)C6H4-SH | 6 | 537 | 1H NMR (500 MHz, methanol-d$_3$) δ ppm 7.66(2 H, d), 7.52-7.56(1H, m), 7.46(1 H, dd, J = 8.94, 2.61 Hz), 7.37(2 H, d, J = 7.97 Hz), 7.33 (1 H, d, J = 8.80 Hz), 7.29(1 H, d, J = 4.40 Hz), 7.16(1 H, d, J = 4.67 Hz), 3.91(2 H, s), 1.34(6 H, s). |

TABLE 1-continued

3-Thio substituted-1-arylpyrazin-2(1H)-ones

| 90 | 4-(trifluoromethoxy)benzenethiol | 6 | 478 | 1H NMR (500 MHz, methanol-d₃) δ ppm 7.85(1 H, d, J = 2.75 Hz), 7.74(1 H, dd, J = 8.94, 2.61 Hz), 7.65(2 H, d), 7.33-7.39(3 H, m), 7.29(1 H, d, J = 4.67 Hz), 7.16(1 H, d, J = 4.40 Hz), 4.01(2 H, s), 1.38(6 H, s). |
| --- | --- | --- | --- | --- |
| 91 | 4-(trifluoromethoxy)benzenethiol | 6 | 489 | 1H NMR (500 MHz, methanol-d₃) δ ppm 7.65(2 H, d, J = 8.80 Hz), 7.37 (2 H, d, J = 7.97 Hz), 7.24-7.32 (3 H, m), 7.15(1 H, d, J = 1.40 Hz), 4.00(2 H, s), 1.33(6 H, s). |
| 92 | 4-(trifluoromethoxy)benzenethiol | 6 | 501 | 1H NMR (500 MHz, methanol-d₃) δ ppm 7.65(2 H, d, J = 8.80 Hz), 7.45(1 H, d, J = 2.75 Hz), 7.37(2 H, d, J = 7.97 Hz), 7.30(1 H, d, J = 1.92 Hz), 7.27(1 H, d, J = 4.40 Hz), 7.15(1 H, d, J = 4.67 Hz), 3.78(2 H, s), 2.40(3 H, s), 1.39(6 H, s). |
| 93 | 4-(trifluoromethoxy)benzenethiol | 6 | 521 | 1H NMR (500 MHz, methanol-d₃) δ ppm 7.77 (1 H, d, J = 2.47 Hz), 7.62-7.71(3 H, m), 7.35(3 H, dd, J = 14.57, 8.52 Hz), 7.30(1 H, d, J = 4.40 Hz), 7.17(1 H, d, J = 4.40 Hz), 3.94(2 H, s), 1.35(6 H, s). |
| 94 | 4-(trifluoromethoxy)benzenethiol | 6 | 505 | 1H NMR (500 MHz, methanol-d₃) δ ppm 7.65(2 H, d), 7.46-7.51(1H, m), 7.42(1 H, dd, J = 11.27, 2.47 Hz), 7.37(2 H, d, J = 7.97 Hz), 7.28 (1 H, d, J = 4.40 Hz), 7.15(1 H, d, J = 4.40 Hz), 3.98(2 H, s), 1.37(6 H, s). |
| 95 | 4-(trifluoromethyl)benzenethiol | 6 | 452 | 1H NMR (500 MHz, chloroform-d) δ ppm 8.88(1 H, s), 7.89-7.99 (2 H, m), 7.16-7.24(3 H, m), 7.07(1 H, d, J = 4.40 Hz), 6.90(1 H, d, J = 8.52 Hz), 3.84(2 H, s), 2.30(3 H, s), 1.39(6 H, s). |
| 96 | 4-(trifluoromethoxy)benzenethiol | 6 | 481 | 1H NMR (500 MHz, chloroform-d) δ ppm 7.62(2 H, d, J = 8.78 Hz), 7.29(2 H, d, J = 8.03 Hz), 7.11(1 H, d, J = 4.52 Hz), 7.08(2 H, s), 6.96(1 H, d, J = 4.52 Hz), 3.64(2 H, s), 2.33(6 H, s), 1.39(6 H, s). |
| 97 | 4-(trifluoromethoxy)benzenethiol | 6 | 477 | 1H NMR (400 MHz, MeOD) δ ppm 7.68(d, 2H), 7.39(d, 2H), 7.28(d, 1H), 7.18(m, 3H), 6.93(d, 1H), 6.49(s, 1H), 1.42(s, 6H). |
| 98 | 4-(trifluoromethoxy)benzenethiol | 6 | 481 | 1H NMR (400 MHz, MeOD) δ ppm 7.69(2 H, d), 7.39(2 H, d, J = 8.03 Hz), 7.18(2 H, dd), 7.08 (1 H, d, J = 8.53 Hz), 6.93(1 H, d, J = 8.78 Hz), 3.84(2 H, s), 2.30(3 H, s), 2.02(3 H, s), 1.38(6 H, s). |

TABLE 1-continued

3-Thio substituted-1-arylpyrazin-2(1H)-ones

| # | Structure | | MW | 1H NMR |
|---|---|---|---|---|
| 99 | 3-fluorophenethyl thiol | 6 | 441 | 1H NMR (500 MHz, chloroform-d) δ ppm 7.23-7.31(2 H, m), 7.16-7.23(2 H, m), 7.07(1 H, d, J = 7.42 Hz), 6.98-7.04(1 H, m), 6.88-6.98(3 H, m), 4.14(1 H, dd, J = 9.35, 3.30 Hz), 4.04(1 H, dd, J = 9.35, 7.15 Hz), 3.26-3.40(3 H, m), 2.97-3.06(2 H, m), 2.27(3 H, s), 0.99-1.10(1 H, m), 0.55-0.68(2 H, m), 0.43-0.51(1 H, m), 0.30-0.38(1 H, m) |
| 100 | 4-(trifluoromethoxy)thiophenol | 6 | 481 | 1H NMR (400 MHz, chloroform-d) δ ppm 7.63(2 H, dd, J = 8.78, 2.26 Hz), 7.30(2 H, d, J = 7.78 Hz), 7.11(1 H, dd, J = 4.27, 2.26 Hz), 6.98(1 H, s), 6.84(1 H, dd, J = 4.52, 2.26 Hz), 6.76(1 H, s), 3.84(2 H, br. s.), 2.24(3 H, s), 2.14(3 H, s), 1.39(6 H, d, J = 2.26 Hz). |
| 101 | 4-(trifluoromethyl)thiophenol | 6 | 437 | 1H NMR (500 MHz, chloroform-d) δ ppm 7.71(4 H, m), 7.36(2 H, d, J = 8.80 Hz), 7.13(1 H, d, J = 4.40 Hz), 7.04(2 H, d, J = 9.35 Hz), 7.00(1 H, d, J = 4.40 Hz), 3.84(2 H, s), 1.37(6 H, s). |
| 102 | 4-(trifluoromethyl)thiophenol | 6 | 455 | 1H NMR (500 MHz, chloroform-d) δ ppm 7.71(4 H, m), 7.26(1 H, dd, J = 11.00, 2.75 Hz), 7.11-7.19(2 H, m), 7.05-7.11(1 H, m), 6.98(1 H, d, J = 4.95 Hz), 3.91(2 H, s), 1.38(6 H, s) |
| 103 | 4-(trifluoromethyl)thiophenol | 6 | 451 | 1H NMR (500 MHz, chloroform-d) δ ppm 7.67-7.75(4 H, m), 7.18-7.25(2 H, m), 7.12(1 H, d, J = 4.40 Hz), 6.99(1 H, d, J = 4.40 Hz), 6.91(1 H, d, J = 8.25 Hz), 3.85(2 H, s), 2.31(3 H, s), 1.39(6 H, s) |
| 104 | 4-(trifluoromethyl)thiophenol | 6 | 521 | 1H NMR (500 MHz, chloroform-d) δ ppm 7.66-7.78(4 H, m), 7.35-7.42(2 H, m), 7.08-7.17(2 H, m), 6.99(1 H, d, J = 4.40 Hz), 3.90(2 H, s), 1.38(6 H, s). |
| 105 | 4-(trifluoromethyl)thiophenol | 6 | 462 | 1H NMR (500 MHz, chloroform-d) δ ppm 7.60-7.78(6 H, m), 7.09-7.17(2 H, m), 6.95(1 H, d, J = 4.40 Hz), 3.97(2 H, s), 1.43(6 H, s) |
| 106 | 4-(trifluoromethyl)thiophenol | 6 | 465 | 1H NMR (500 MHz, chloroform-d) δ ppm 7.71(4 H, d, J = 6.05 Hz), 7.07-7.14(3 H, m), 6.98(1 H, d, J = 4.40 Hz), 3.64(2 H, s), 2.33(6 H, s), 1.40(6 H, s) |
| 107 | 4-(trifluoromethyl)thiophenol | 6 | 471 | 1H NMR (500 MHz, chloroform-d) δ ppm 7.67-7.74(4 H, m), 7.50(1 H, d, J = 2.47 Hz), 7.32(1 H, dd, J = 8.80, 2.47 Hz), 7.13(1 H, d, J = 4.67 Hz), 7.03(1 H, d, J = 8.80 Hz), 6.97(1 H, d, J = 4.40 Hz), 3.91(2 H, s), 1.40(6 H, s) |

TABLE 1-continued

3-Thio substituted-1-arylpyrazin-2(1H)-ones

| 108 | 4-(trifluoromethyl)benzenethiol | 6 | 463 | 1H NMR (500 MHz, chloroform-d) δ ppm 7.64-7.77(4 H, m), 7.19-7.24(2 H, m), 7.12(1 H, d, J = 4.40 Hz), 7.00(1 H, d, J = 4.40 Hz), 6.94(1 H, d, J = 8.80 Hz), 4.16 (1 H, dd, J = 9.35, 3.30 Hz), 4.06 (1 H, dd, J = 9.35, 7.15 Hz), 3.31-3.42(1 H, m), 2.29(3 H, s), 0.99-1.11(1 H, m), 0.55-0.71 (2 H, m), 0.43-0.52(1 H, m), 0.29-0.41(1 H, m) |
| --- | --- | --- | --- | --- |
| 109 | 4-(trifluoromethoxy)benzenethiol | 6 | 479 | 1H NMR (500 MHz, chloroform-d) δ ppm 7.61(2 H, d), 7.29(2 H, d, J = 7.97 Hz), 7.19-7.24(2 H, m), 7.11(1 H, d, J = 4.67 Hz), 6.98(1 H, d, J = 4.40 Hz), 6.94 (1 H, d, J = 8.52 Hz), 4.15(1 H, dd, J = 9.35, 3.30 Hz), 4.05(1 H, dd, J = 9.35, 7.15 Hz), 3.30-3.42(1 H, m), 2.28(3 H, s), 0.99-1.11(1 H, m), 0.55-0.70(2 H, m), 0.42-0.52(1 H, m), 0.30-0.39(1 H, m) |
| 110 | 2-(pyridin-2-yl)ethanethiol | 6 | 412 | 1H NMR (400 MHz, MeOD) δ ppm 8.67(1 H, d), 8.48(1 H, td, J = 7.91, 1.51 Hz), 8.02(1 H, d, J = 8.28 Hz), 7.81-7.95(1 H, m), 7.07-7.29(4 H, m), 6.93(1 H, d, J = 8.78 Hz), 3.76(2 H, s), 3.35-3.57(4 H, m), 2.22(3 H, s), 1.27 (6 H, s) |
| 111 | 2-phenylethanethiol | 6 | 397 | 1H NMR (500 MHz, methanol-d₃) δ ppm 7.32-7.40(3 H, m), 7.25-7.29(4 H, m), 7.16-7.23(2 H, m), 7.08(2 H, d, J = 8.80 Hz), 3.83 (2 H, s), 3.31(2 H, s), 2.89-3.03 (2 H, m), 1.32(6 H, s) |
| 112 | 2-phenylethanethiol | 6 | 415 | 1H NMR (500 MHz, methanol-d₃) δ ppm 7.12-7.46(10 H, m), 3.90(1 H, s), 3.21-3.42(2 H, m), 2.90-3.03(2 H, m), 1.33(6 H, s) |
| 113 | 2-phenylethanethiol | 6 | 411 | 1H NMR (500 MHz, methanol-d₃) δ ppm 7.38(1 H, d, J = 4.40 Hz), 7.25-7.32(4 H, m), 7.16-7.24(4 H, m), 7.00(1 H, d, J = 8.25 Hz), 3.83(1 H, s), 3.24-3.39(2 H, m), 2.90-3.05(2 H, m), 2.29(3 H, s), 1.35(6 H, s) |
| 114 | 2-phenylethanethiol | 6 | 431 | 1H NMR (500 MHz, methanol-d₃) δ ppm 7.56(1 H, d, J = 2.20 Hz), 7.33-7.42(2 H, m), 7.17-7.31(7 H, m), 3.90(2 H, s), 3.23-3.42(2 H, m), 2.89-3.08(2 H, m), 1.36 (6 H, s) |
| 115 | 2-phenylethanethiol | 6 | 423 | 1H NMR (500 MHz, methanol-d₃) δ ppm 7.37(1 H, d, J = 4.40 Hz), 7.25-7.32(4 H, m), 7.16-7.23(4 H, m), 7.03(1 H, d, J = 9.35 Hz), 3.99-4.17(2 H, m), 3.25-3.39(3 H, m), 2.91-3.04(2 H, m), 2.28 (3 H, s), 0.98-1.11(1 H, m), 0.51-0.61(2H, m), 0.29-0.47(2 H, m) |

TABLE 1-continued

3-Thio substituted-1-arylpyrazin-2(1H)-ones

| # | Structure | | | NMR |
|---|---|---|---|---|
| 116 | 2-F-C6H4-CH2CH2-SH | 6 | 445 | 1H NMR (500 MHz, methanol-d3) δ ppm 7.30-7.39(2 H, m), 7.20-7.27(2 H, m), 7.01-7.13(4 H, m), 6.95(1 H, dd, J = 8.52, 2.47 Hz), 3.86(2 H, s), 3.24-3.39(2 H, m), 2.97-3.11(2 H, m), 1.32 (6 H, s) |
| 117 | 2-F-C6H4-CH2CH2-SH | 6 | 429 | 1H NMR (500 MHz, methanol-d3) δ ppm 7.29-7.38(2 H, m), 7.17-7.26(4 H, m), 6.97-7.13(3 H, m), 3.83(2 H, s), 3.28-3.36(2 H, m), 3.04(2 H, t, J = 7.42 Hz), 2.29(3 H, s), 1.35(6 H, s) |
| 118 | 2-F-C6H4-CH2CH2-SH | 6 | 443 | 1H NMR (400 MHz, chloroform-d) δ ppm 7.16-7.35(5 H, m), 6.86-7.13(4 H, m), 3.84(2 H, s), 3.26-3.41(2 H, m), 3.07(2 H, t, J = 7.65 Hz), 2.71(2 H, q, J = 7.53 Hz), 1.32-1.47(6 H, m), 1.23(3 H, t, J = 7.65 Hz) |
| 119 | 2-F-C6H4-CH2CH2-SH | 6 | 441 | 1H NMR (500 MHz, methanol-d3) δ ppm 7.28-7.37(2 H, m), 7.16-7.26(4 H, m), 6.99-7.12(3 H, m), 3.95-4.18(2 H, m), 3.22-3.42(3 H, m), 3.04(2 H, t, J = 7.42 Hz), 2.27(3 H, s), 0.97-1.13(1 H, m), 0.46-0.63(2 H, m), 0.29-0.46(2 H, m) |
| 120 | 2-F-C6H4-CH2CH2-SH | 6 | 457 | 1H NMR (500 MHz, methanol-d3) δ ppm 7.20-7.30(2 H, m), 7.11-7.18(2 H, m), 6.92-7.04(4 H, m), 6.86(1 H, dd, J = 8.52, 2.47 Hz), 3.85-4.12(2 H, m), 3.76(3 H, s), 3.16-3.31(3 H, m), 2.87-3.03(2 H, m), 0.82-1.00(1 H, m), 0.38-0.54(2 H, m), 0.18 0.37(2 H, m) |
| 121 | pyridin-2-yl-CH2CH2-SH | 6 | 426 | 1H NMR (400 MHz, MeOD) δ ppm 8.29(1 H, d, J = 4.02 Hz), 7.60 (1 H, td, J = 7.65, 1.76 Hz), 7.16-7.26(2 H, m), 6.98-7.14(4 H, m), 6.85(1 H, d, J = 9.03 Hz), 3.66 (2 H, s), 3.29(2 H, t, J = 7.28 Hz), 3.02(2 H, t, J = 7.40 Hz), 2.56(2 H, q, J = 7.53 Hz), 1.18(6 H, s), 1.05(3 H, t, J = 7.53 Hz) |
| 122 | 4-(OCF3)-C6H4-SH | 6 | 395 | 1H NMR (400 MHz, chloroform-d) δ ppm 7.62(2 H, d, J = 8.78 Hz), 7.30(2 H, d, J = 8.03 Hz), 7.16(1 H, d, J = 4.52 Hz), 7.10(1 H, d, J = 2.01 Hz), 6.91-7.05(2 H, m), 6.70(1 H, d, J = 8.53 Hz), 6.22(1 H, s), 2.21(3 H, s) |
| 123 | 4-F-C6H4-CH2CH2-SH | 6 | 449 | 1H NMR (500 MHz, chloroform-d) δ ppm 7.47(1 H, d, J = 2.47 Hz), 7.21-7.32(4 H, m), 6.97-7.04 (3 H, m), 6.93(1 H, d, J = 4.67 Hz), 3.89(2 H, s), 3.30(2 H, t, J = 7.70 Hz), 2.98(2 H, t, J = 7.84 Hz), 1.40(6 H, s) |

TABLE 1-continued

3-Thio substituted-1-arylpyrazin-2(1H)-ones

| | | | | |
|---|---|---|---|---|
| 124 | 4-F-C6H4-CH2CH2-SH | 6 | 429 | 1H NMR (400 MHz, chloroform-d) δ ppm 7.22-7.29(3 H, m), 7.16-7.22(2 H, m), 6.99(2 H, t, J = 8.66 Hz), 6.95(1 H, d, J = 4.40 Hz), 6.88(1 H, d, J = 8.52 Hz), 3.84(2 H, s), 3.21-3.36(2 H, m), 2.90-3.08(2 H, m), 2.29(3 H, s), 1.38(6 H, s) |
| 125 | 4-F-C6H4-CH2CH2-SH | 6 | 443 | 1H NMR (500 MHz, chloroform-d) δ ppm 7.22-7.29(3 H, m), 7.17-7.22(2 H, m), 6.94-7.03(3 H, m), 6.90(1 H, d, J = 8.25 Hz), 3.84(2 H, s), 3.25-3.35(2 H, m), 2.92-3.05(2 H, m), 2.71(2 H, q), 1.39(6 H, s), 1.23(3 H, t, J = 7.56 Hz) |
| 126 | 4-F-C6H4-CH2CH2-SH | 6 | 457 | 1H NMR (500 MHz, chloroform-d) δ ppm 7.23-7.28(2 H, m), 6.95-7.03(6 H, m), 6.90(1 H, dd, J = 8.52, 2.20 Hz), 4.20(1 H, dd, J = 9.62, 2.75 Hz), 4.03(1 H, dd, J = 9.62, 8.25 Hz), 3.86(3 H, s), 3.26-3.40(3 H, m), 2.93-3.06(2 H, m), 0.89-1.04(1 H, m), 0.52-0.66(2 H, m), 0.41-0.49(1 H, m), 0.27-0.36(1 H, m) |
| 127 | 4-F-C6H4-CH2CH2-SH | 6 | 441 | 1H NMR (500 MHz, chloroform-d) δ ppm 7.22-7.28(3 H, m), 7.16-7.22(2 H, m), 6.90-7.03(4 H, m), 4.14(1 H, dd, J = 9.35, 3.30 Hz), 4.04(1 H, dd, J = 9.35, 7.15 Hz), 3.24-3.41(3 H, m), 2.93-3.05(2 H, m), 2.27(3 H, s), 0.99-1.09(1 H, m), 0.55-0.70(2 H, m), 0.43-0.51(1 H, m), 0.29-0.39(1 H, m) |
| 128 | 3-F-C6H4-CH2CH2-SH | 6 | 449 | 1H NMR (500 MHz, chloroform-d) δ ppm 7.47(1 H, d, J = 2.75 Hz), 7.21-7.34(3 H, m), 6.88-7.10(5 H, m), 3.89(2 H, s), 3.27-3.37(2 H, m), 2.97-3.06(2 H, m), 1.40(6 H, s) |
| 129 | 3-F-C6H4-CH2CH2-SH | 6 | 429 | 1H NMR (500 MHz, chloroform-d) δ ppm 7.23-7.31(3 H, m), 7.16-7.22(2 H, m), 6.88-7.09(4 H, m), 3.84(2 H, s), 3.27-3.35(2 H, m), 2.96-3.05(2 H, m), 2.29(3 H, s), 1.38(6 H, s) |
| 130 | 3-F-C6H4-CH2CH2-SH | 6 | 443 | 1H NMR (500 MHz, chloroform-d) δ ppm 7.24-7.30(2 H, m), 7.17-7.22(2 H, m), 6.86-7.11(5 H, m), 3.84(2 H, s), 3.24-3.38(2 H, m), 2.96-3.08(2 H, m), 2.71(2 H, q, J = 7.70 Hz), 1.38(6 H, s), 1.23(3 H, t, J = 7.56 Hz) |
| 131 | 3-F-C6H4-CH2CH2-SH | 6 | 445 | 1H NMR (500 MHz, chloroform-d) δ ppm 7.20-7.38(2 H, m), 6.83-7.14(7 H, m), 3.86(5 H, s), 3.23-3.40(2 H, m), 2.93-3.10(2 H, m), 1.36(6 H, s) |

TABLE 1-continued

3-Thio substituted-1-arylpyrazin-2(1H)-ones

| Ex. No. | Structure | | | NMR |
|---|---|---|---|---|
| 132 | 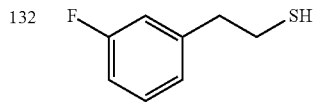 | SH | 6 | 457 | 1H NMR (500 MHz, chloroform-d) δ ppm 7.24-7.31(2 H, m), 7.07 (1 H, d, J = 7.42 Hz), 6.96-7.04(4 H, m), 6.87-6.96(2 H, m), 4.20 (1 H, dd, J = 9.62, 2.75 Hz, 4.03 (1 H, dd, J = 9.90, 8.25 Hz), 3.86(5 H, s), 3.26-3.43(3 H, m), 2.96-3.06 (2 H, m), 0.91-1.03(1H, m), 0.52-0.68(2 H, m), 0.41-0.50(1 H, m), 0.26-0.35(1 H, m) |

TABLE 2

3-Oxa substituted -1-arylpyrazin-2(1H)-ones

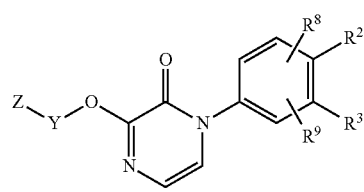

| Ex. No. | Structure | Aniline/Bromide Component |
|---|---|---|
| 133 | 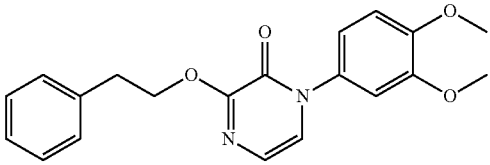<br>1-(3,4-dimethoxyphenyl)-3-phenethoxypyrazin-2(1H)-one | 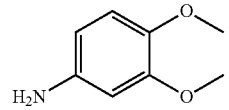 |
| 134 | 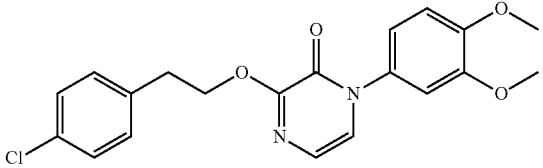<br>3-(4-chlorophenethoxy)-1-(3,4-dimethoxyphenyl)pyrazin-2(1H)-one | 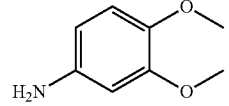 |
| 135 | 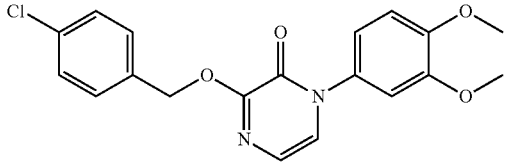<br>3-(4-chlorobenzyloxy)-1-(3,4-dimethoxyphenyl)pyrazin-2(1H)-one | 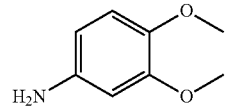 |

TABLE 2-continued

3-Oxa substituted -1-arylpyrazin-2(1H)-ones

136 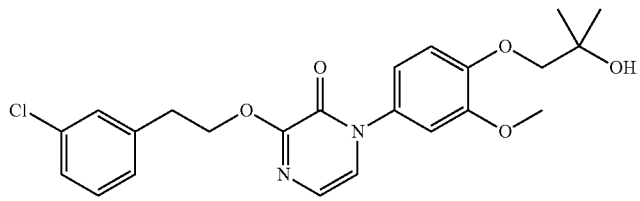 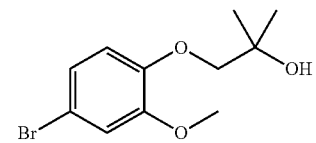

3-(3-chlorophenethoxy)-1-(4-(2-hydroxy-2-methyl
propoxy)-3-methoxyphenyl)pyrazin-2(1H)-one 137 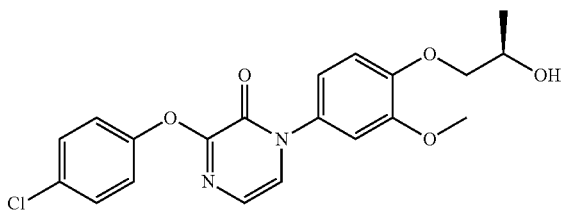 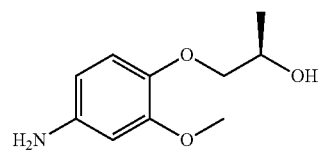

(R)-3-(4-chlorophenoxy)-1-(4-(2-hydroxypropoxy)-3-
methoxyphenyl)pyrazin-2(1H)-one 138 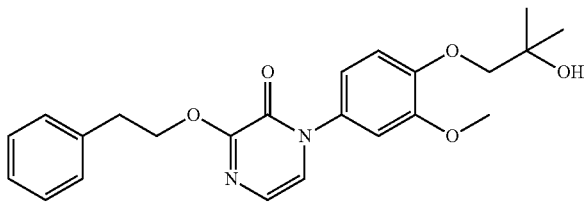 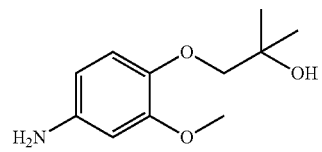

1-(4-(2-hydroxy-2-methylpropoxy)-3-methoxyphenyl)-3-
phenethoxypyrazin-2(1H)-one 139 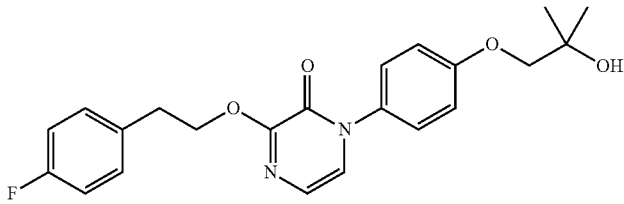 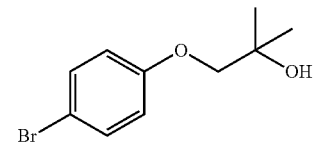

3-(4-fluorophenethoxy)-1-(4-(2-hydroxy-2-
methylpropoxy)phenyl)pyrazin-2(1H)-one 140 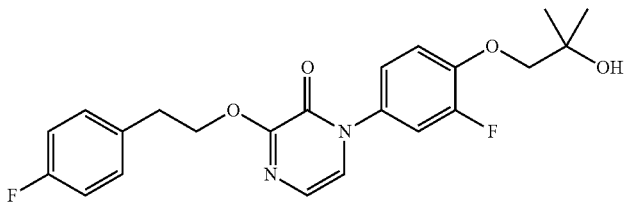 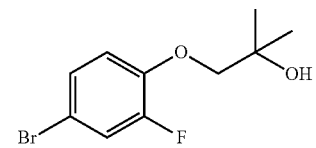

1-(3-fluoro-4-(2-hydroxy-2-methylpropoxy)phenyl)-
3-(4-fluorophenethoxy)pyrazin-2(1H)-one TABLE 2-continued 3-Oxa substituted -1-arylpyrazin-2(1H)-ones

141

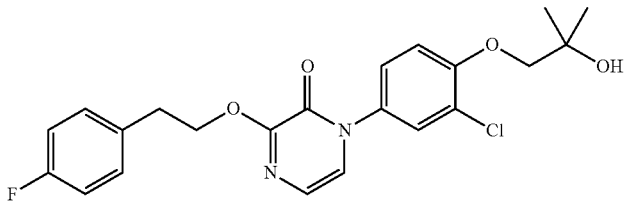

1-(3-chloro-4-(2-hydroxy-2-methylpropoxy)phenyl)-
3-(4-fluorophenethoxy)pyrazin-2(1H)-one

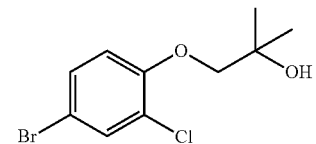

142

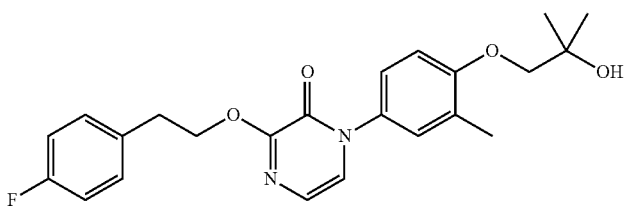

3-(4-fluorophenethoxy)-1-(4-(2-hydroxy-2-methyl
propoxy)-3-methylphenyl)pyrazin-2(1H)-one

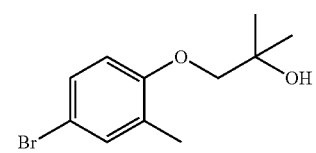

143

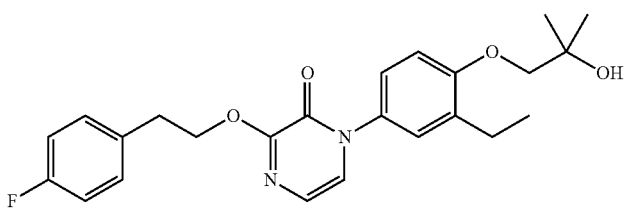

1-(3-ethyl-4-(2-hydroxy-2-methylpropoxy)
phenyl)-3-(4-fluorophenethoxy)pyrazin-2(1H)-one

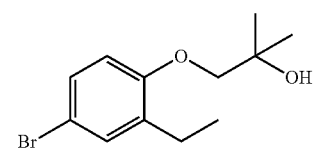

144

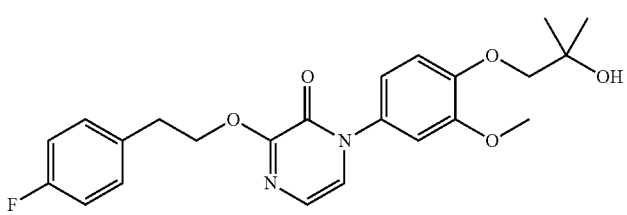

3-(4-fluorophenethoxy)-1-(4-(2-hydroxy-2-methyl
propoxy)-3-methoxy)phenyl)pyrazin-2(1H)-one

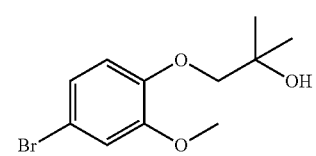

145

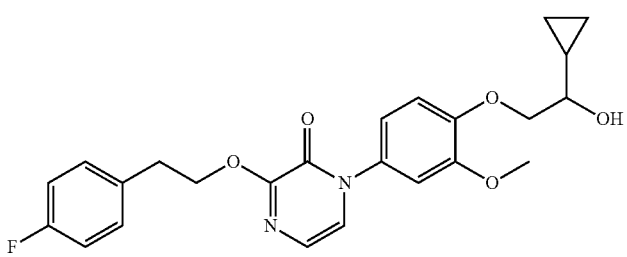

1-(4-(2-cyclopropyl-2-hydroxyethoxy)-3-methoxyphenyl)-
3-(4-fluorophenethoxy)pyrazin-2(1H)-one

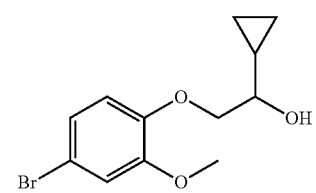

TABLE 2-continued

3-Oxa substituted -1-arylpyrazin-2(1H)-ones

146

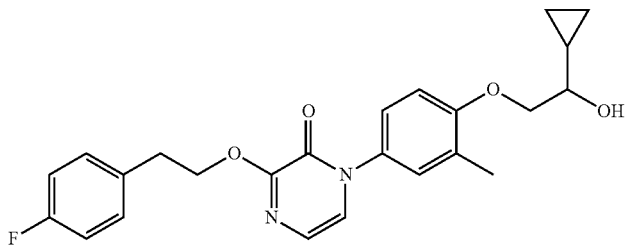 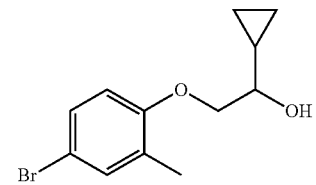

1-(4-(2-cyclopropyl-2-hydroxyethoxy)-3-methylphenyl)-
3-(4-fluorophenethoxy)pyrazin-2(1H)-one

147

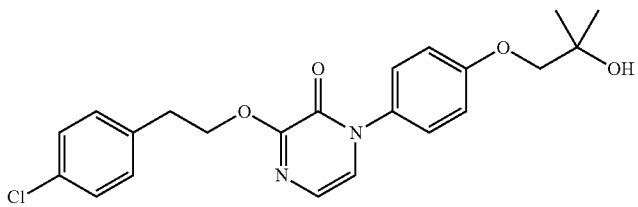 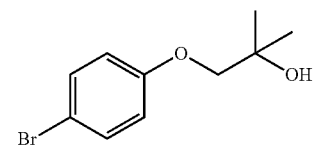

3-(4-chlorophenethoxy)-1-(4-(2-hydroxy-2-
methylpropoxy)phenyl)pyrazin-2(1H)-one

148

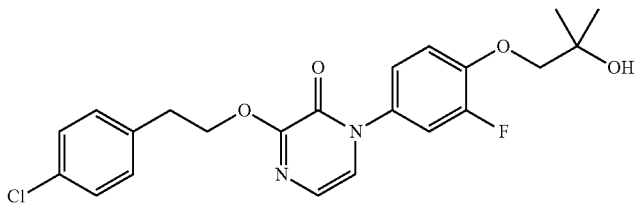 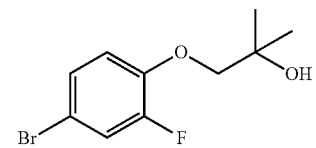

3-(4-chlorophenethoxy)-1-(3-fluoro-4-(2-hydroxy-
2-methylpropoxy)phenyl)pyrazin-2(1H)-one

149

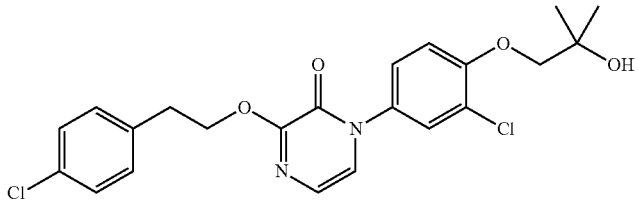 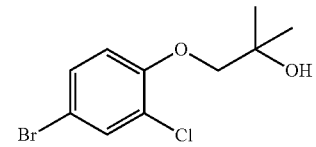

1-(3-chloro-4-(2-hydroxy-2-methylpropoxy)phenyl)-
3-(4-chlorophenethoxy)pyrazin-2(1H)-one

150

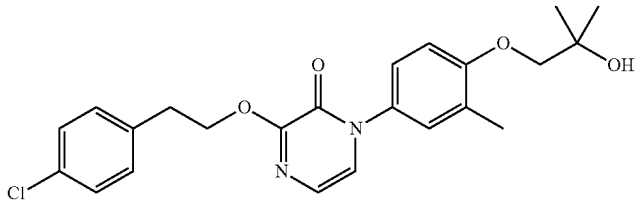 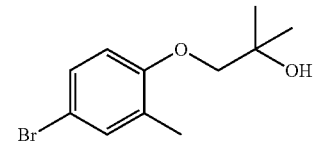

3-(4-chlorophenethoxy)-1-(4-(2-hydroxy)-2-methyl
propoxy)-3-methylphenyl)pyrazin-2(1H)-one TABLE 2-continued 3-Oxa substituted -1-arylpyrazin-2(1H)-ones 151 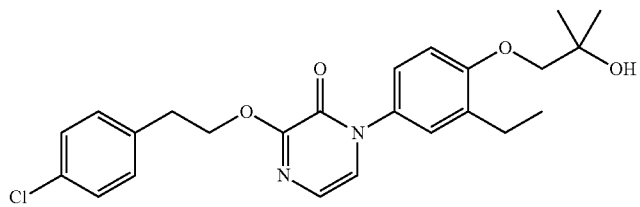 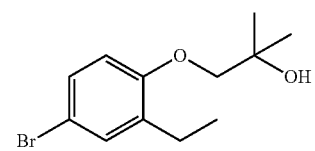

3-(4-chlorophenethoxy)-1-(3-ethyl-4-(2-hydroxy-
2-methylpropoxy)phenyl)pyrazin-2(1H)-one 152 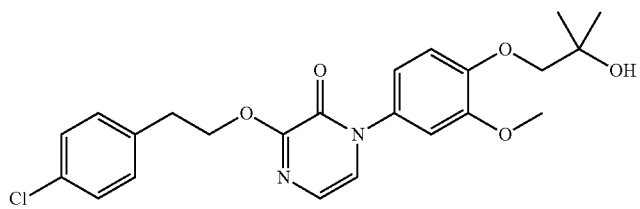 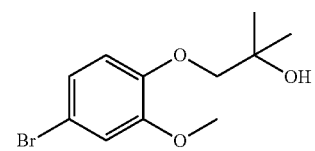

3-(4-chlorophenethoxy)-1-(4-(2-hydroxy)-2-methyl
propoxy)-3-methoxyphenyl)pyrazin-2(1H)-one 153 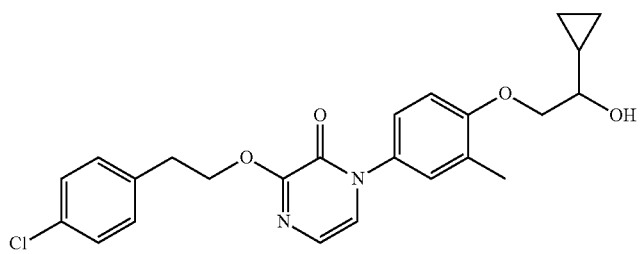 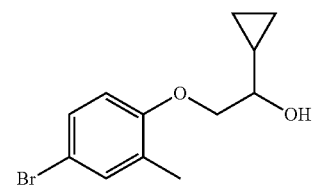

3-(4-chlorophenethoxy)-1-(4-(2-cyclopropyl-2-hydroxyethoxy)-
3-methylphenyl)pyrazin-2(1H)-one 154 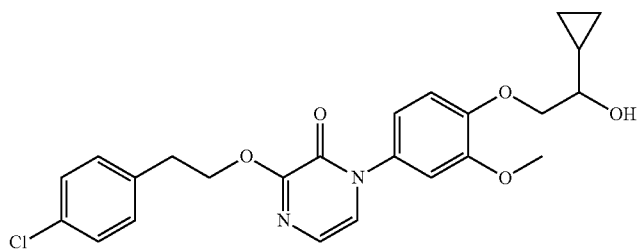 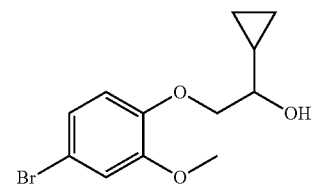

3-(4-chlorophenethoxy)-1-(4-(2-cyclopropyl-2-hydroxyethoxy)-
3-methoxy)phenyl)pyrazin-2(1H)-one 155 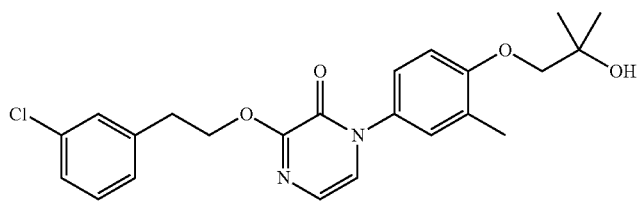 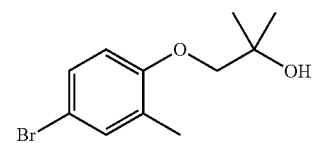

3-(3-chlorophenethoxy)-1-(4-(2-hydroxy-2-methyl
propoxy)-3-methylphenyl)pyrazin-2(1H)-one TABLE 2-continued 3-Oxa substituted -1-arylpyrazin-2(1H)-ones

156

3-(3-chlorophenethoxy)-1-(3-ethyl-4-(2-hydroxy-2-methylpropoxy)phenyl)pyrazin-2(1H)-one

| Ex. No. | Alcohol Component | Method | Yield (%) | HPLC | LC-MS | HNMR Data (CDCl$_3$) |
|---|---|---|---|---|---|---|
| 133 | phenethyl alcohol | 1 | 18 | 3.71 | 353 | 7.27(m, 5H), 6.93(m, 5H), 4.55(t, J = 7.5 Hz, 2H), 3.92(s, 3H), 3.89(s, 3H), 3.17(t, J = 7.5 Hz, 2H). |
| 134 | 4-chlorophenethyl alcohol | 1 | 26 | 3.96 | 387/389 | 7.25(m, 4H), 6.92(m, 5H), 4.52(t, J = 7.2 Hz, 2H), 3.92(s, 3H), 3.89(s, 3H), 3.12(t, J = 7.2 Hz, 2H). |
| 135 | 4-chlorobenzyl alcohol | 1 | 68 | 3.83 | 373/375 | 7.37(d, J = 8.4 Hz, 2H), 7.25(d, J = 8.4 Hz, 2H), 6.60(m, 5H), 5.32(s, 2H), 3.84(s, 3H), 3.80(s, 3H) |
| 136 | 3-chlorophenethyl alcohol | 7 | | | 445 | 1H NMR (500 MHz, chloroform-d) δ ppm 7.30(1 H, s), 7.22(3 H, d, J = 4.95 Hz), 6.94-7.00(2 H, m), 6.83-6.91(3 H, m), 4.54(2 H, t, J = 7.42 Hz), 3.85(5 H, s), 3.15(2 H, t, J = 7.42 Hz), 1.36(6 H, s) |
| 137 | 4-chlorophenol | 4 | | 3.59 | 403/405 | 7.42(d, J = 8.9 Hz, 2H), 7.18(d, J = 8.9 Hz, 2H), 7.02(m, 2H), 6.80(d, J = 4.6 Hz, 1H), 6.93(dd, J = 2.2 and 8.4 Hz, 1H), 6.81(d, J = 4.6 Hz, 1H), 4.25 (m, 1H), 4.05(dd, J = 3.0 and 9.6 Hz, 1H), 3.88(s, 3H), 3.86(dd, J = 1.0 and 9.6 Hz, 1H), 2.73(broad s, 1H), 1.27(d, J = 4.3 Hz, 3H). |
| 138 | phenethyl alcohol | 1 | 5 | 3.86 | 411 | 7.32(m, 5H), 7.23(m, 1H), 6.96(m, 2H), 6.87(m, 2H), 4.55(t, J = 2.0 Hz, 2H), 3.86(s, 5H), 3.18(t, J = 2.0 Hz, 2H), 1.35(s, 6H). |
| 139 | 4-fluorophenethyl alcohol | 7 | | | 399 | 1H NMR (500 MHz, chloroform-d) δ ppm 7.23-7.38(4 H, m), 6.95-7.05 (4 H, m), 6.84(2 H, s), 4.51(2 H, t, J = 7.29 Hz), 3.83(2 H, s), 3.14(2 H, s), 1.36(6 H, s) |
| 140 | 4-fluorophenethyl alcohol | 7 | | | 417 | 1H NMR (500 MHz, chloroform-d) δ ppm 7.25-7.30(2 H, m), 7.21(1 H, dd, J = 11.00, 2.47 Hz), 6.96-7.15(4 H, m), 6.75-6.90(2 H, m), 4.51(2 H, t, J = 7.29 Hz), 3.89(2 H, s), 3.13(2 H, t, J = 7.15 Hz), 1.38(6H, s) |
| 141 | 4-fluorophenethyl alcohol | 7 | | | 433 | 1H NMR (500 MHz, chloroform-d) δ ppm 7.45(1 H, d, J = 2.75 Hz), 7.22-7.35(3 H, m), 6.94-7.07(3 H, m), 6.75-6.88(2 H, m), 4.51(2 H, t, J = 7.15 Hz), 3.89(2 H, s), 3.13(2 H, t, J = 7.15 Hz), 1.40(6 H, s) |

TABLE 2-continued

3-Oxa substituted -1-arylpyrazin-2(1H)-ones

| | | | | |
|---|---|---|---|---|
| 142 | 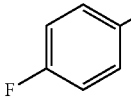 | 7 | 413 | 1H NMR (500 MHz, chloroform-d) δ ppm 7.24-7.31(2 H, m), 7.15-7.21 (2 H, m), 6.99(2 H, t, J = 8.66 Hz), 6.89(1 H, d, J = 7.97 Hz), 6.83(2 H, s), 4.50(2 H, t, J = 7.29 Hz), 3.84(2 H, s), 3.13(2H, t, J = 7.29 Hz), 2.29(3 H, s), 1.38(6 H, s) |
| 143 | 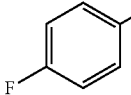 | 7 | 427 | 1H NMR (500 MHz, chloroform-d) δ ppm 7.24-7.31(2 H, m), 7.16-7.21 (2 H, m), 6.99(2 H, t, J = 8.66 Hz), 6.90(1 H, d, J = 9.35 Hz), 6.82-6.86 (2 H, m), 4.51(2 H, t, J = 7.29 Hz), 3.84(2 H, s), 3.14(2 H, t, J = 7.29 Hz), 2.71(2 H, q), 1.39(6 H, s), 1.24(3 H, t, J = 7.56 Hz) |
| 144 | 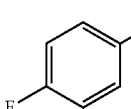 | 7 | 429 | 1H NMR (500 MHz, chloroform-d) δ ppm 7.23-7.32(2 H, m), 6.94-7.03 (4 H, m), 6.82-6.90(3 H, m), 4.51(2 H, t, J = 7.29 Hz), 5.85(5 H, s), 3.14(2 H, t, J = 7.29 Hz), 1.36(6 H, s) |
| 145 | 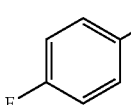 | 7 | 441 | 1H NMR (500 MHz, chloroform-d) δ ppm 7.24-7.32(2 H, m), 6.95-7.04 (4 H, m), 6.83-6.91(3 H, m), 4.51(2 H, t, J = 7.29 Hz), 4.20(1 H, dd, J = 9.76, 2.89 Hz), 4.03(1 H, dd, J = 9.90, 8.25 Hz), 3.31-3.43(1 H, m), 3.14(2 H, t, J = 7.29 Hz), 0.90-1.05(1 H, m), 0.52-0.68(2 H, m), 0.41-0.49(1 H, m), 0.26-0.35(1 H, m) |
| 146 | 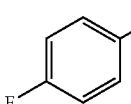 | 7 | 425 | 1H NMR (500 MHz, chloroform-d) δ ppm 7.25-7.31(2 H, m), 7.16-7.20 (2 H, m), 6.95-7.02(2 H, m), 6.90-6.94(1 H, m), 6.81-6.86(2 H, m), 4.50(2 H, t, J = 7.29 Hz), 4.14(1 H, dd, J = 9.35, 3.30 Hz), 4.04(1 H, dd, J = 9.35, 7.15 Hz), 3.36(1 H, dt, J = 8.45, 3.61 Hz), 3.13(2 H, t, J = 7.15 Hz), 2.27(3 H, s), 0.99-1.09(1 H, m), 0.55-0.70(2 H, m), 0.43-0.51 (1 H, m), 0.30-0.39(1 H, m) |
| 147 | 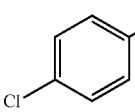 | 7 | 415 | 1H NMR (500 MHz, chloroform-d) δ ppm 7.32(2 H, d), 7.23-7.29(4 H, m), 7.02(2 H, d), 6.84(2 H, s), 4.51 (2H, t, J = 7.29 Hz), 3.83(2 H, s), 3.13 (2 H, t, J = 7.15 Hz), 1.36(6 H, s) |
| 148 | 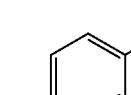 | 7 | 433 | 1H NMR (500 MHz, chloroform-d) δ ppm 7.18-7.31(5 H, m), 7.03-7.15 (2 H, m), 6.75-6.89(2 H, m), 4.51(2 H, t, J = 7.15 Hz), 3.89(2 H, s), 3.13(2 H, t, J = 7.15 Hz), 1.38(6 H, s) |
| 149 | 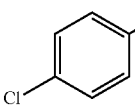 | 7 | 449 | 1H NMR (500 MHz, chloroform-d) δ ppm 7.45(1 H, d, J = 2.75 Hz), 7.22-7.32(5 H, m), 7.00(1 H, d, J = 8.80 Hz), 6.77-6.90(2 H, m), 4.51(2 H, t, J = 7.29 Hz), 3.89(2 H, s), 3.13(2 H, t, J = 7.15 Hz), 1.40(6 H, s) |

TABLE 2-continued

3-Oxa substituted -1-arylpyrazin-2(1H)-ones

| 150 | 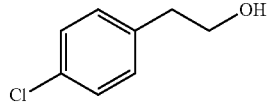 | 7 | 429 | 1H NMR (500 MH, chloroform-d) δ ppm 7.23-7.30(4 H, m), 7.14-7.20 (2 H, m), 6.88(1 H, d, J = 8.25 Hz), 6.83(2 H, s), 4.51(2 H, t, J = 7.15 Hz), 3.84(2 H, s), 3.13(2 H, t, J = 7.15 Hz), 2.29(3 H, s), 1.38(6 H, s) |
|---|---|---|---|---|
| 151 | 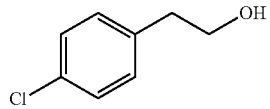 | 7 | 443 | 1H NMR (500 MHz, chloroform-d) δ ppm 7.23-7.29(4 H, m), 7.16-7.21 (2 H, m), 6.90(1 H, d, J = 9.35 Hz), 6.84(2 H, q, J = 4.49 Hz), 4.51(2 H, t, J = 7.29 Hz), 3.84(2 H, s), 3.13(2 H, t, J = 7.29 Hz), 2.71(2 H, q, J = 7.51 Hz), 1.39(6 H, s), 1.23(3 H, t, J = 7.56 Hz) |
| 152 | 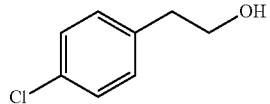 | 7 | 445 | 1H NMR (500 MHz, chloroform-d) δ ppm 7.18-7.33(4 H, m), 6.93-7.04 (2 H, m), 6.79-6.91(3 H, m), 4.51(2 H, t, J = 7.15 Hz), 3.85(5 H, s), 3.14(2 H, t, J = 7.29 Hz), 1.36(6 H, s) |
| 153 | 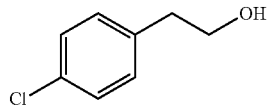 | 7 | 441 | 1H NMR (500 MHz, chloroform-d) δ ppm 7.23-7.29(4 H, m), 7.16-7.20 (2 H, m), 6.92(1 H, d), 6.80-6.85(2 H, m), 4.51(2 H, t, J = 7.29 Hz), 4.14 (1 H, dd, J = 9.35, 3.57 Hz), 4.04(1 H, dd, J = 9.35, 7.15 Hz), 3.31-3.42(1 H, m), 3.13(2 H, t, J = 7.29 Hz), 2.27 (3 H, s), 0.97-1.11(1 H, m), 0.55-0.70(2 H, m), 0.42-0.51(1 H, m), 0.30-0.40(1 H, m) |
| 154 | 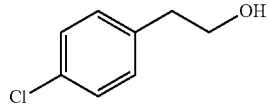 | 7 | 457 | 1H NMR (500 MHz, chloroform-d) δ ppm 7.23-7.29(4 H, m), 7.01(1 H, d, J = 8.30 Hz), 6.97(1 H, d, J = 2.47 Hz), 6.82-6.91(3 H, m), 4.51(2 H, t, J = 7.15 Hz), 4.20(1 H, dd, J = 9.76, 2.89 Hz), 4.03(1 H, dd, J = 9.62, 8.25 Hz), 3.86(3 H, s), 3.30-3.41(1 H, m), 3.14(2 H, t, J = 7.15 Hz), 0.89-1.04(1 H, m), 0.52-0.68(2 H, m), 0.42-0.50(1 H, m), 0.25-0.37(1 H, m) |
| 155 | 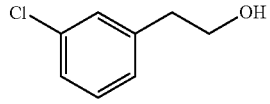 | 7 | 429 | 1H NMR (500 MHz, chloroform-d) δ ppm 7.30(1 H, s), 7.16-7.25(5 H, m), 6.89(1 H, d, J = 8.52 Hz), 6.83(2 H, s), 4.53(2 H, t, J = 7.42 Hz), 3.84(2 H, s), 3.14(2 H, t, J = 7.29 Hz), 2.29(3 H, s), 1.38(6 H, s) |
| 156 | 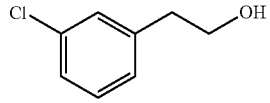 | 7 | 443 | 1H NMR (500 MHz, chloroform-d) δ ppm 7.30(1 H, s), 7.16-7.25(5 H, m), 6.90(1 H, d, J = 9.35 Hz), 6.82-6.87(2 H, m), 4.53(2 H, t, J = 7.42 Hz), 3.84(2 H, s), 3.15(2 H, t, J = 7.29 Hz), 2.65-2.76(2 H, m), 1.38(6 H, s), 1.24(3 H, t, J = 7.56 Hz) |

TABLE 3

3-Substituted-1-heteroarylpyrazin-2(1H)-ones

| Ex. No. | Structure | Aniline/Bromide Component |
|---|---|---|
| 157 | 1-(6-(2-hydroxy-2-methylpropoxy)pyridin-3-yl)-3-(4-(trifluoromethyl)phenylthio)pyrazin-2(1H)-one | |
| 158 | 1-(6-(2-hydroxy-2-methylpropoxy)pyridin-3-yl)-3-(4-(trifluoromethoxy)phenylthio)pyran-2(1H)-one | |
| 159 | 1-(6-(2-hydroxy-2-methylpropoxy)pyridin-3-yl)-3-(phenethylthio)pyrazin-2(1H)-one | |
| 160 | 3-(2-fluorophenethylthio)-1-(6-(2-hydroxy-2-methylpropoxy)pyridin-3-yl)pyrazin-2(1H)-one | |

TABLE 3-continued

3-Substituted-1-heteroarylpyrazin-2(1H)-ones

161 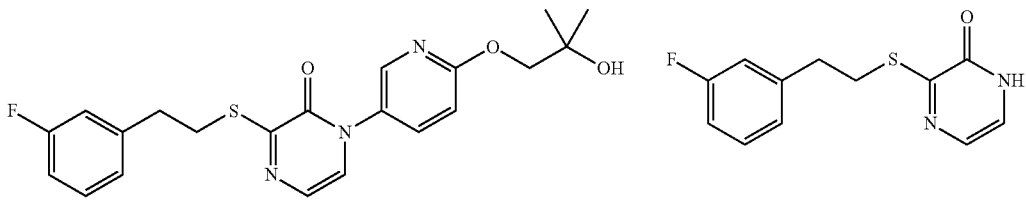

3-(3-fluorophenethylthio)-1-(6-(2-hydroxy-2-methyl
propoxy)pyridin-3-yl)pyrazin-2(1H)-one 162 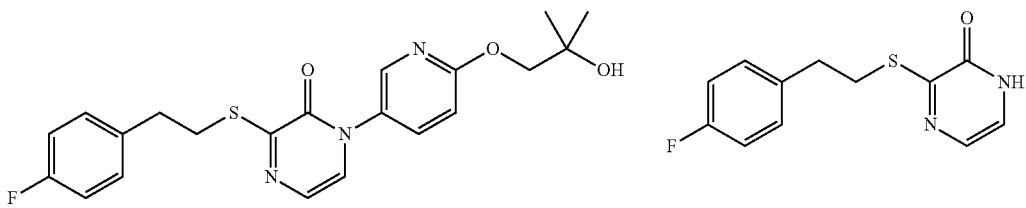

3-(4-fluorophenethylthio)-1-(6-(2-hydroxy-2-methyl
propoxy)pyridin-3-yl)pyrazin-2(1H)-one 163 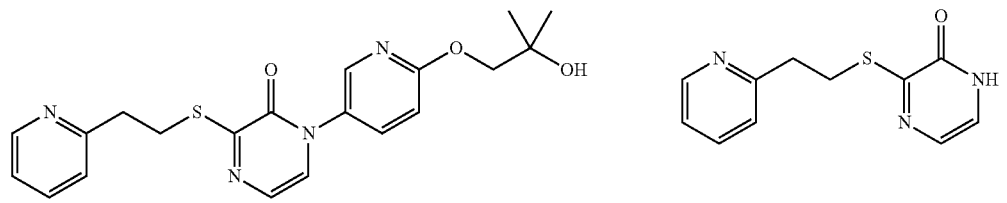

1-(6-(2-hydroxy-2-methylpropoxy)pyridin-3-yl)-
3-(2-(pyridin-2-yl)ethylthio)pyrazin-2(1H)-one 164 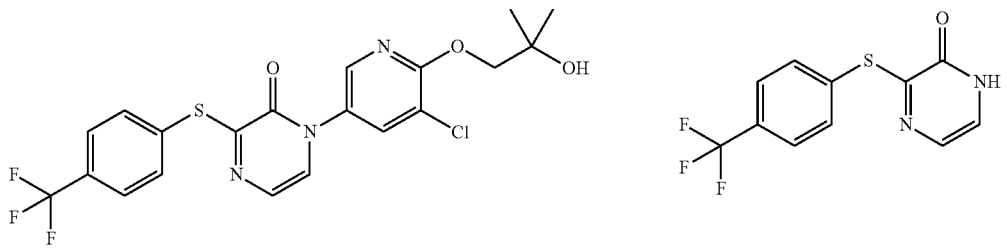

1-(5-chloro-6-(2-hydroxy-2-methylpropoxy)pyridin-
3-yl)-3-(4-(trifluoromethyl)phenylthio)pyrazin-2(1H)-one 165 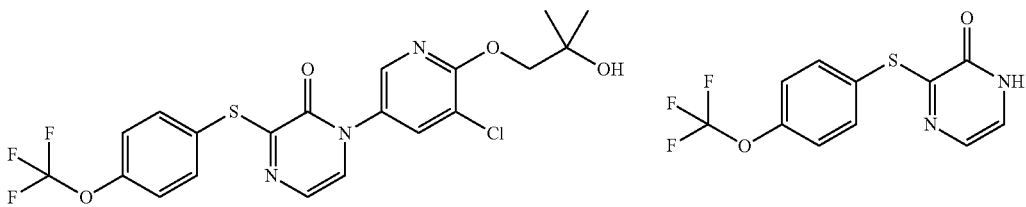

1-(5-chloro-6-(2-hydroxy-2-methylpropoxy)pyridin-3-yl)-
3-(4-(trifluoromethoxy)phenylthio)pyrazin-2(1H)-one TABLE 3-continued 3-Substituted-1-heteroarylpyrazin-2(1H)-ones 166 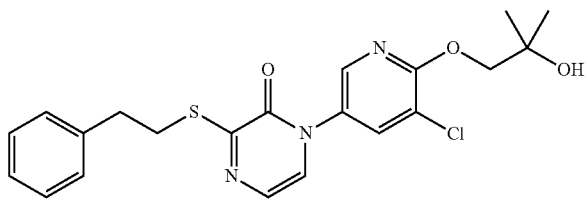 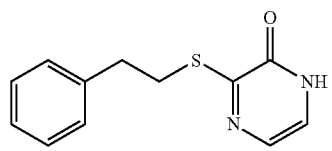

1-(5-chloro-6-(2-hydroxy-2-methylpropoxy)
pyridin-3-yl)-3-(phenethylthio)pyrazin-2(1H)-one 167 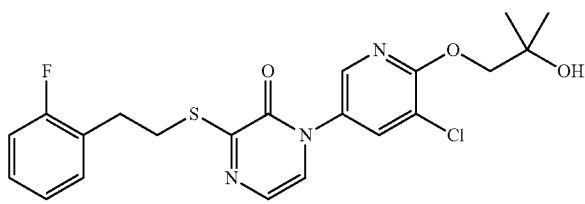 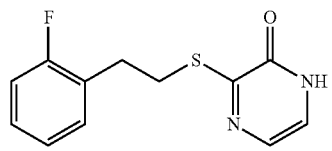

1-(5-chloro-6-(2-hydroxy-2-methylpropoxy)pyridin-
3-yl)-3-(2-fluorophenylthio)pyrazin-2(1H)-one 168 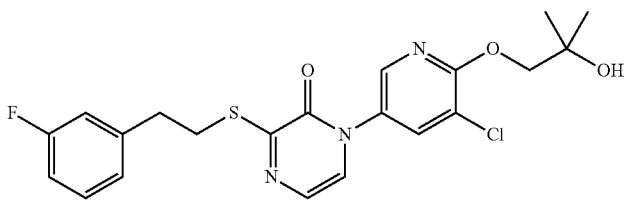 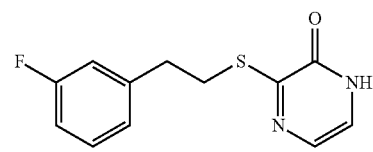

1-(5-choro-6-(2-hydroxy-2-methylpropoxy)
pyridin-3-yl)-3-(3-fluorophenethylthio)pyrazin-2(1H)-one 168 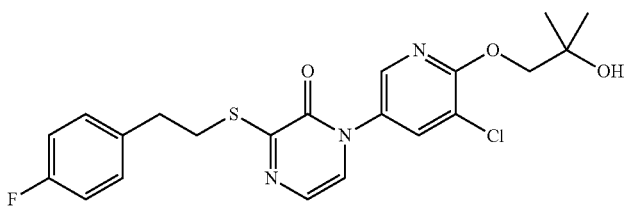 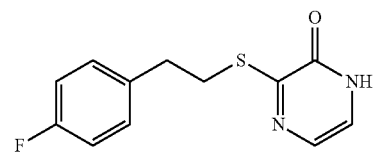

1-(5-chloro-6-(2-hydroxy-2-methylpropoxy)pyridin-3-yl)-
3-(4-fluorophenethylthio)pyrazin-2(1H)-one 169 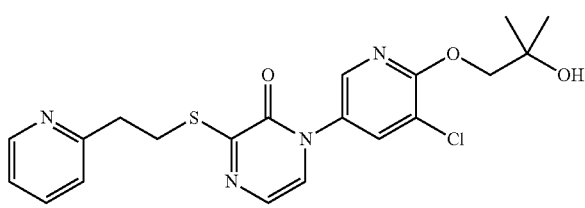 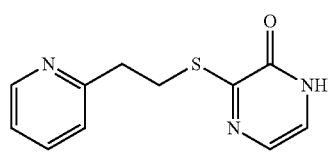

1-(5-chloro-6-(2-hydroxy-2-methylpropoxy)pyridin-
3-yl)-3-(2-(pyridin-2-yl)ethylthio)pyrazin-2(1H)-one TABLE 3-continued 3-Substituted-1-heteroarylpyrazin-2(1H)-ones 170 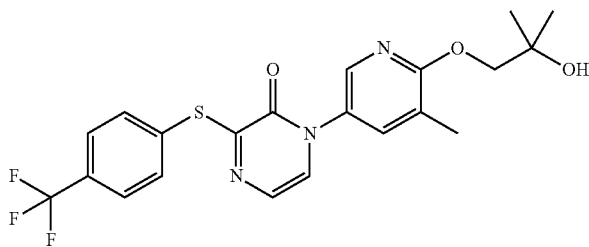 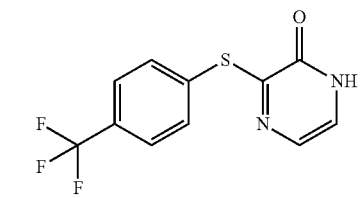

1-(6-(2-hydroxy-2-methylpropxy)-5-methylpyridin-3-
yl)-3-(4-(trifluoromethyl)phenylthio)pyrazin-2(1H)-one 171 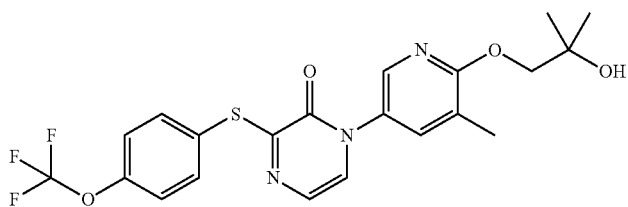 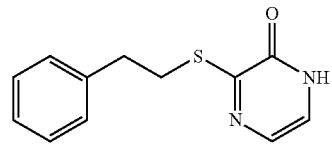

1-(6-(2-hydroxy-2-methylpropoxy)-5-methylpyridin-3-yl-
3-(4-(trifluoromethoxy)phenylthio)pyrazin-2(1H)-one 172 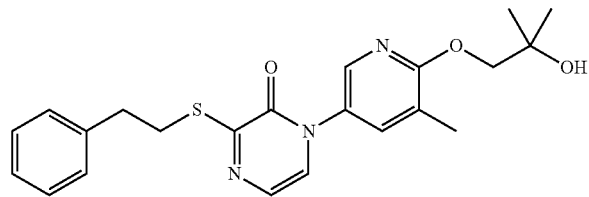 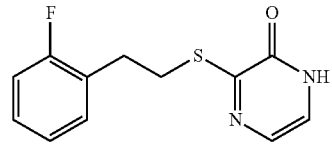

1-(6-(2-hydroxy-2-methylpropoxy)-5-methylpyridin-
3-yl)-3-(phenethylthio)pyrazin-2(1H)-one 173 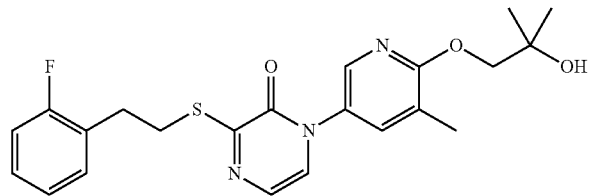 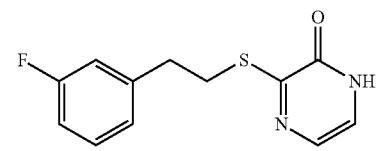

3-(2-fluorophenethylthio)-1-(6-(2-hydroxy-2-methyl
propoxy)-5-methylpyridin-3-yl)pyrazin-2(1H)-one 174 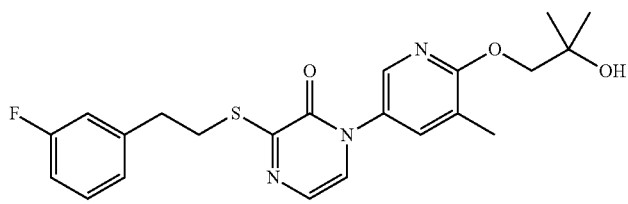

3-(3-fluorophenethylthio)-1-(6-(2-hydroxy-2-methyl
propoxy)-5-methylpyridin-3-yl)pyrazin-2(1H)-one TABLE 3-continued 3-Substituted-1-heteroarylpyrazin-2(1H)-ones 175 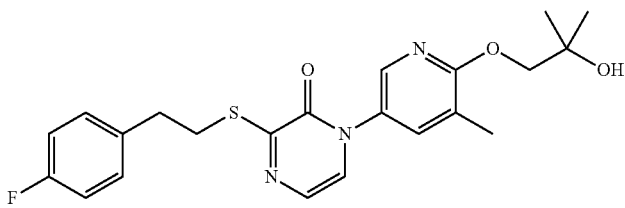 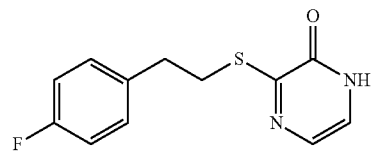

3-(4-fluorophenethylthio)-1-(6-(2-hydroxy-2-methyl
propoxy)-5-methylpyridin-3-yl)pyrazin-2(1H)-one 176 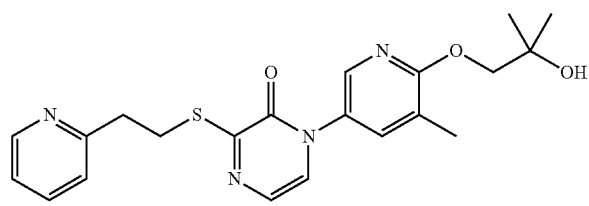 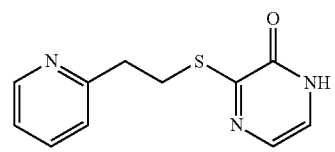

1-(6-(2-hydroxy-2-methylpropoxy)-5-methylpyridin-
3-yl)-3-(2-pyridin-2-yl)ethylthio)pyrazin-2(1H)-one 177 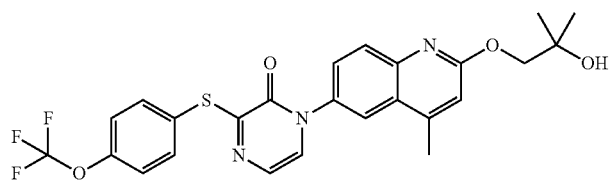 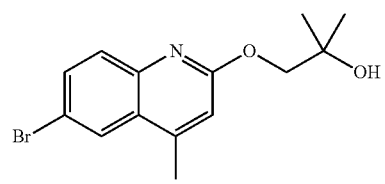

1-(2-(2-hydroxy-2-methylpropoxy)-4-methylquinolin-6-yl)-3-(4-
(trifluoromethoxy)phenylthio)pyridin-2(1H)-one 178 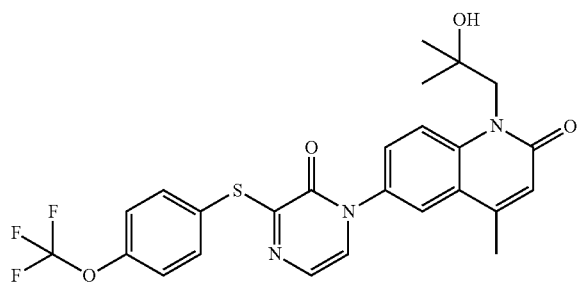 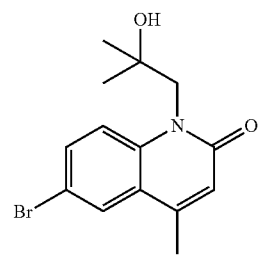

1-(2-hydroxy-2-methylpropyl)-4-methyl-6-(2-oxo-3-(4-
(trifluoromethoxy)phenylthio)pyrazin-1(2H)-yl)quinolin-2(1H)-one 179 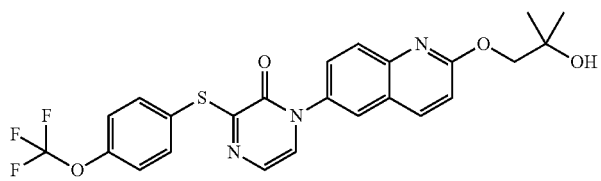 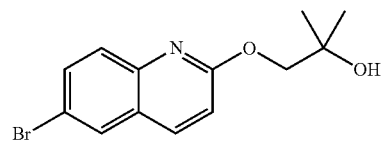

1-(2-(2-hydroxy-2-methylpropoxy)quinolin-6-yl)-3-
(4-(trifluoromethoxy)phenylthio)pyriazin-2(1H)-one TABLE 3-continued 3-Substituted-1-heteroarylpyrazin-2(1H)-ones

180

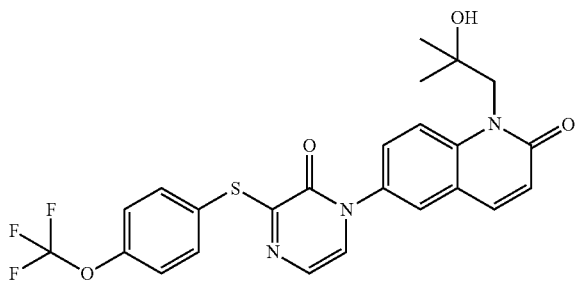 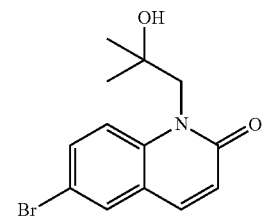

1-(2-hydroxy-2-methypropyl)-6-(2-oxo-3-(4-
(trifluoromethoxy)phenylthio)pyrazin-1(2H)-yl)quinolin-2(1H)-one

181

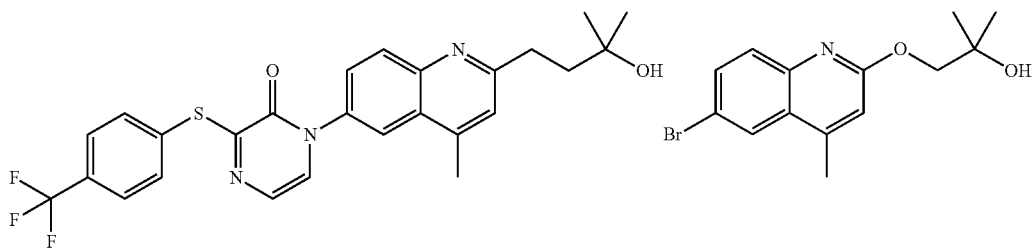

1-(2-(2-hydroxy)-2-methylpropoxy)-4-methylquinolin-6-yl)-
3-(4-(trifluoromethyl)phenylthio)pyrazin-2(1H)-one

182

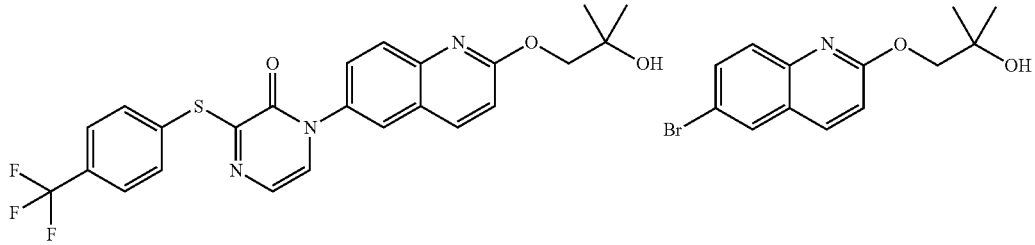

1-(2-(2-hydroxy-2-methylpropoxy)quinolin-6-yl)-
3-(4-(trifluoromethyl)phenylthio)pyrazine-2(1H)-one

183

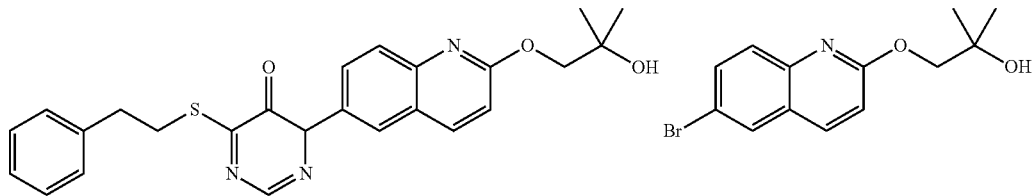

1-(2-(2-hydroxy-2-methylpropoxy)quinolin-6-yl)-
3-(phenethylthio)pyrazin-2(1H)-one TABLE 3-continued 3-Substituted-1-heteroarylpyrazin-2(1H)-ones 184 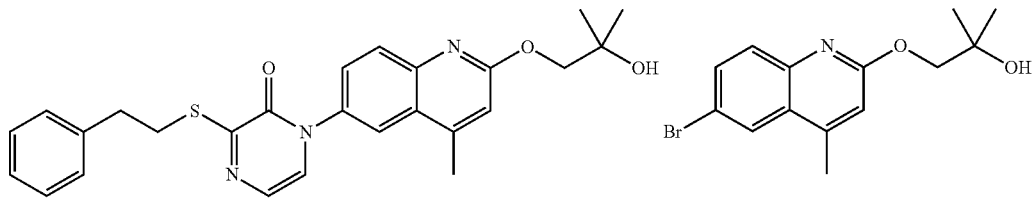

1-(2-(2-hydroxy-2-methylpropoxy)-4-methylquinolin-
6-yl)-3-(phenethylthio)pyrazin-2(1H)-one 185 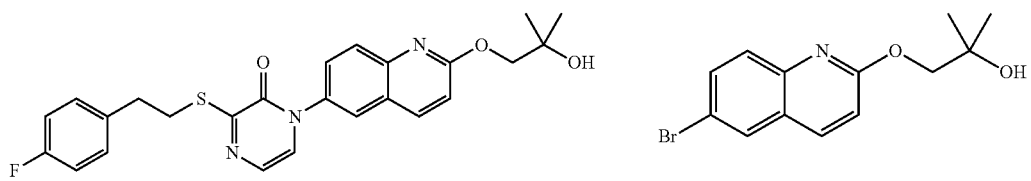

3-(4-fluorophenethylthio)-1-(2-(2-hydroxy-2-
methylpropoxy)quinolin-6-yl)pyrazin-2(1H)-one 186 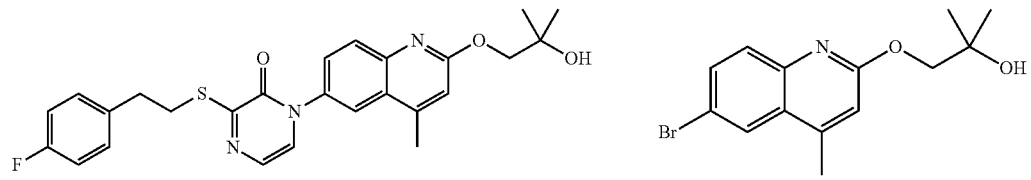

3-(4-fluorophenethylthio)-1-(2-(2-hydroxy-2-methyl
propoxy)-4-methylquinolin-6-yl)pyrazin-2(1H)-one 187 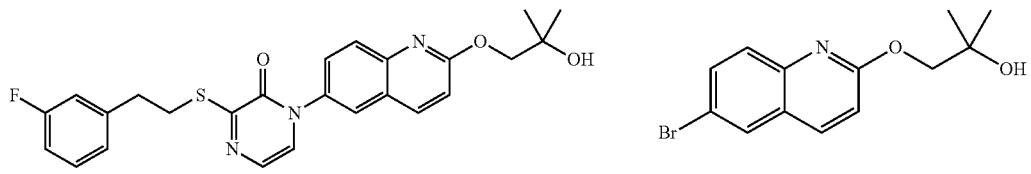

3-(3-fluorophenethylthio)-1-(2-(2-hydroxy-2-
methylpropoxy)quinolin-6-yl)pyrazin-2(1H)-one 188 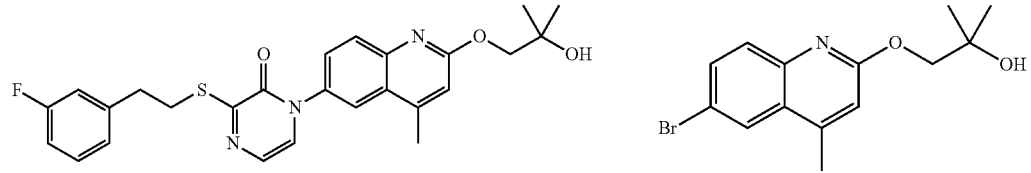

3-(3-fluorophenethylthio)-1-(2-(2-hydroxy-2-methyl
propoxy)-4-methylquinolin-6-yl)pyrazin-2(1H)-one

TABLE 3-continued

3-Substituted-1-heteroarylpyrazin-2(1H)-ones

189 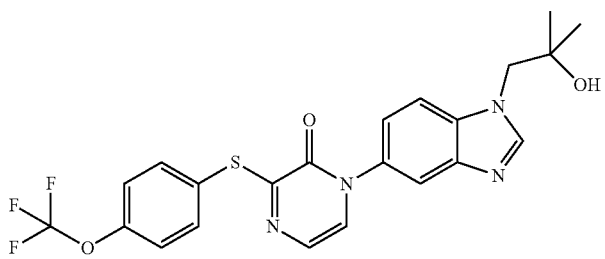

1-(1-(2-hydroxy-2-methylpropyl)-1H-benzo[d]imidazol-
5-yl)-3-(4-(trifluoromethoxy)phenylthio)pyrazin-2(1H)-one

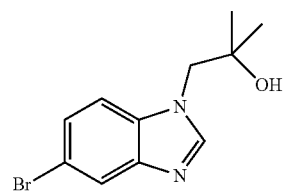

190 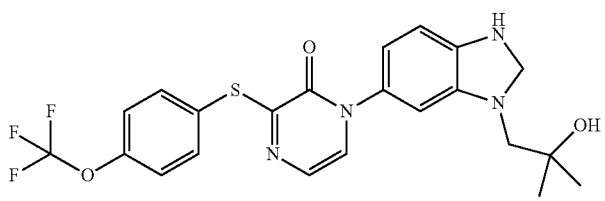

1-(3-(2-hydroxy-2-methylpropyl)-2,3-dihydro-1H-benzo[d]imi-
5-yl)-3-(4-(trifluoromethoxy)phenylthio)pyrazin-2(1H)-one

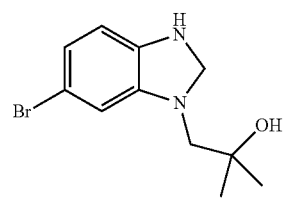

191 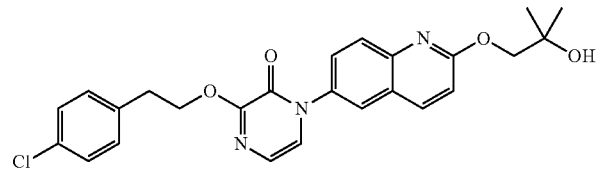

3-(4-chlorophenethoxy)-1-(2-(2-hydroxy-2-methyl
propoxy)quinolin-6-yl)pyrazin-2(1H)-one 192 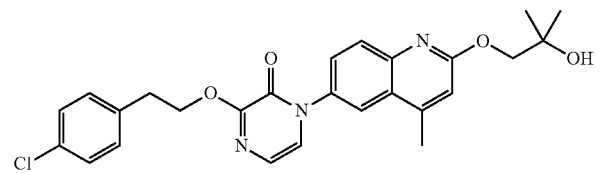

3-(4-chlorophenethoxy)-1-(2-(2-hydroxy-2-methyl
propoxy)-4-methylquinolin-6-yl)pyrazin-2(1H)-one

| Ex. No. | Alcohol Component | Method | Yield (%) | HPLC | LC-MS | HNMR Data (CDCl$_3$) |
|---|---|---|---|---|---|---|
| 157 | | 8 | | | 438 | 1H NMR (500 MHz, methanol-d$_3$) δ ppm 8.41(1 H, d, J = 2.47 Hz), 8.09 (1 H, dd, J = 9.07, 2.75 Hz), 7.72-7.79(4 H, m), 7.35(1 H, d, J = 4.40 Hz), 7.24(1 H, d, J = 9.07 Hz), 7.19 (1 H, d, J = 4.67 Hz), 4.25(2 H, s), 1.33(6 H, s). |
| 158 | | 8 | | | 454 | 1H NMR (500 MHz, methanol-d$_3$) δ ppm 8.25(1 H, d, J = 2.47 Hz), 7.84 (1 H, dd, J = 8.80, 2.75 Hz), 7.63-7.69(2 H, m), 7.37(2 H, d, J = 7.97 Hz), 7.31(1 H, d, J = 4.40 Hz), 7.17 (1 H, d, J = 4.67 Hz), 7.00(1H, d, J = 8.80 Hz), 4.19(2 H, s), 1.31(6 H, s) |

TABLE 3-continued

3-Substituted-1-heteroarylpyrazin-2(1H)-ones

| 159 | | 8 | 398 | 1H NMR (400 MHz, methanol-d₃) δ ppm 8.23(1 H, d, J = 2.64 Hz), 7.80 (1 H, dd, J = 8.90, 2.75 Hz), 7.39(1 H, d, J = 4.39 Hz) 7.15-7.33(6 H, m), 6.98(1 H, d, J = 8.79 Hz), 4.18(2 H, s), 3.30-3.38(2 H, m), 2.91-3.08(2 H, m), 1.31(6 H, s) |
|---|---|---|---|---|
| 160 | | 8 | 416 | 1H NMR (400 MHz, methanol-d₃) δ ppm 8.22(1 H, d, J = 2.64 Hz), 7.80 (1 H, dd, J = 8.90, 2.75 Hz), 7.37(1 H, d, J = 4.61 Hz), 7.28-7.35(1 H, m), 7.17-7.28(2 H, m), 6.88-7.16 (3 H, m), 4.18(1 H, s), 3.25-3.43(2 H, m), 3.04(2 H, t, J = 7.47 Hz), 1.30(6 H, s) |
| 161 | | 8 | 416 | 1H NMR (400 MHz, methanol-d₃) δ ppm 8.23(1 H, d, J = 2.64 Hz), 7.80 (1 H, dd, J = 8.90, 2.75 Hz), 7.40(1 H, d, J = 4.61 Hz), 7.23-7.34(2 H, m), 6.89-7.14(4 H, m), 4.18(1 H, s), 3.29-3.40(2 H, m), 2.95-3.06 (2 H, m), 1.30(6 H, s) |
| 162 | | 8 | 416 | 1H NMR (400 MHz, methanol-d₃) δ ppm 8.15(1 H, d, J = 2.42 Hz), 7.73 (1 H, dd, J = 8.90, 2.75 Hz), 7.31(1 H, d, J = 4.39 Hz), 7.15-7.26(3 H, m), 6.85-7.00(3 H, m), 4.10(2 H, s), 3.22-3.29(2 H, m), 2.89(2 H, t, J = 7.58 Hz), 1.23(6 H, s) |
| 163 | | 8 | 399 | 1H NMR (400 MHz, methanol-d₃) δ ppm 8.40-8.54(1 H, m), 8.22(1 H, d, J = 2.20 Hz), 7.72-7.86(2 H, m), 7.35-7.44(2 H, m), 7.23-7.32(2 H, m), 6.98(1 H, d, J = 9.01 Hz), 4.18(2 H, s), 3.47(2 H, t, J = 7.36 Hz), 3.19(2 H, t, J = 7.36 Hz), 1.30(6 H, s) |
| 164 | | 8 | 472 | 1H NMR (500 MHz, chloroform-d) δ ppm 8.11(1 H, d, J = 2.47 Hz), 7.89(1 H, d, J = 2.47 Hz), 7.71(4 H, s), 7.16(1 H, d, J = 4.40 Hz), 6.95(1 H, d, J = 4.40 Hz), 4.30(2 H, s), 1.38(6 H, s) |
| 165 | | 8 | 488 | 1H NMR (500 MHz, chloroform-d) δ ppm 8.10(1 H, d, J = 2.47 Hz), 7.88(1 H, d, J = 2.47 Hz), 7.61(2 H, d, J = 8.80 Hz), 7.30(2 H, d, J = 7.97 Hz), 7.16(1 H, d, J = 4.67 Hz), 6.94(1 H, d, J = 4.40 Hz), 4.30(2 H, s), 1.38(6 H, s) |
| 166 | | 8 | 432 | 1H NMR (400 MHz, chloroform-d) δ ppm 8.09(1 H, d, J = 2.42 Hz), 7.86(1 H, d, J = 2.64 Hz), 7.21-7.37(6 H, m), 6.91(1 H, d, J = 4.39 Hz), 4.29(2 H, s), 3.28-3.43(2 H, m), 2.94-3.09(2 H, m), 1.37(6 H, s) |
| 167 | | 8 | 450 | 1H NMR (400 MHz, chloroform-d) δ ppm 8.08(1 H, d, J = 2.42 Hz), 7.86 (1 H, d, J = 2.42 Hz), 7.16-7.33(3 H, m), 6.98-7.13(2 H, m), 6.90(1 H, d, J = 4.61 Hz), 4.29(2 H, s), 3.29-3.41(2 H, m), 3.07(2 H, t, J = 7.69 Hz), 1.37(6 H, s) |

TABLE 3-continued

3-Substituted-1-heteroarylpyrazin-2(1H)-ones

| # | Structure | | MW | NMR |
|---|---|---|---|---|
| 168 | (5-bromo-3-chloropyridin-2-yloxy / 2-methyl-2-hydroxypropyl) | 8 | 450 | 1H NMR (500 MHz, chloroform-d) δ ppm 8.09(1 H, d, J = 2.20 Hz), 7.86 (1 H, d, J = 2.47 Hz), 72.6-7.34(2 H, m), 7.06(1 H, d, J = 7.70 Hz), 6.98-7.03(1 H, m), 6.89-6.97(2 H, m), 4.29(2 H, s), 3.27-3.40(2 H, m), 2.94-3.10(2 H, m), 1.37(6 H, s) |
| 168 | (5-bromo-3-chloropyridin-2-yloxy / 2-methyl-2-hydroxypropyl) | 8 | 450 | 1H NMR (500 MHz, chloroform-d) δ ppm 8.08(1 H, d, J = 2.47 Hz), 7.86 (1 H, d, J = 2.47 Hz), 7.30(1 H, d, J = 4.40 Hz), 7.21-7.25(2 H, m), 7.00(2 H, t, J = 8.66 Hz), 6.91(1 H, d, J = 4.67 Hz), 4.29(2 H, s), 3.23-3.39(2 H, m), 2.91-3.05(2 H, m), 1.37(6 H, s) |
| 169 | (5-bromo-3-chloropyridin-2-yloxy / 2-methyl-2-hydroxypropyl) | 8 | 433 | 1H NMR (500 MHz, chloroform-d) δ ppm 8.57(1 H, d, J = 3.85 Hz), 8.08 (1 H, d, J = 2.47 Hz), 7.85(1 H, d, J = 2.47 Hz), 7.63(1 H, d, td, J = 7.63, 1.79 Hz), 7.31(1 H, d, J = 4.67 Hz), 7.24(1 H, d, J = 7.70 Hz), 7.11-7.18(1 H, m), 6.90(1 H, d, J = 4.40 Hz), 4.29(2 H, s), 3.45-3.59 (2 H, m), 3.22(2 H, t, J = 7.42 Hz), 1.37(6 H, s) |
| 170 | (5-bromo-3-methylpyridin-2-yloxy / 2-methyl-2-hydroxypropyl) | 8 | 452 | 1H NMR (500 MHz, chloroform-d) δ ppm 8.00(1 H, d, J = 2.75 Hz), 7.67-7.76(4 H, m), 7.60(1 H, d, J = 1.92 Hz), 7.14(1 H, d, J = 4.40 Hz), 6.96 (1 H, d, J = 4.40 Hz), 4.28(2 H, s), 2.30(3 H, s), 1.36(6 H, s) |
| 171 | (5-bromo-3-methylpyridin-2-yloxy / 2-methyl-2-hydroxypropyl) | 8 | 468 | 1H NMR (500 MHz, chloroform-d) δ ppm 8.00(1 H, d, J = 2.75 Hz), 7.57-7.65(3 H, m), 7.29(2 H, d, J = 7.97 Hz), 7.14(1 H, d, J = 4.40 Hz), 6.94 (1 H, d, J = 4.40 Hz), 4.28(2 H, s), 2.29(3 H, s), 1.35(6 H, s) |
| 172 | (5-bromo-3-methylpyridin-2-yloxy / 2-methyl-2-hydroxypropyl) | 8 | 412 | 1H NMR (500 MHz, chloroform-d) δ ppm 7.98(1 H, d, J = 2.20 Hz), 7.58 (1 H, d, J = 1.65 Hz), 7.27-7.36(5 H, m), 7.21-7.25(1 H, m), 6.91(1 H, d, J = 4.40 Hz), 4.27(2 H, s), 3.27-3.40(2 H, m), 2.95-3.11(2 H, m), 2.28(3 H, s), 1.35(6 H, s) |
| 173 | (5-bromo-3-methylpyridin-2-yloxy / 2-methyl-2-hydroxypropyl) | 8 | 430 | 1H NMR (500 MHz, chloroform-d) δ ppm 7.98(1 H, d, J = 2.75 Hz), 7.58 (1 H, d, J = 1.92 Hz), 7.27-7.33(2 H, m), 7.18-7.24(1 H, m), 7.00-7.12 (2 H, m), 6.91(1 H, d, J = 4.40 Hz), 4.27(2 H, s), 3.29-3.41(2 H, m), 3.07(2 H, t, J = 7.70 Hz), 2.28(3 H, s), 1.35(6 H, s) |
| 174 | (5-bromo-3-methylpyridin-2-yloxy / 2-methyl-2-hydroxypropyl) | 8 | 430 | 1H NMR (500 MHz, chloroform-d) δ ppm 7.98(1 H, d, J = 2.47 Hz), 7.58 (1 H, d, J = 1.92 Hz), 7.27-7.32(1 H, m), 7.26(1 H, d, J = 7.70 Hz), 7.06(1 H, d, J = 7.70 Hz), 6.98-7.04(1 H, m), 6.89-6.95(2 H, m), 4.27(2 H, s), 3.25-3.38(2 H, m), 2.94-3.08 (2 H, m), 2.28(3 H, s), 1.35(6 H, s) |

TABLE 3-continued

3-Substituted-1-heteroarylpyrazin-2(1H)-ones

| | | | |
|---|---|---|---|
| 175 | 5-bromo-3-methyl-2-(2-hydroxy-2-methylpropoxy)pyridine | 8 | 430 | 1H NMR (500 MHz, chloroform-d) δ ppm 7.98(1 H, d, J = 2.75 Hz), 7.58 (1 H, d, J = 1.92 Hz), 7.28(1 H, d, J = 4.67 Hz), 7.21-7.25(2 H, m), 7.00(2 H, t, J = 8.66 Hz), 6.91(1 H, d, J = 4.40 Hz), 4.27(2 H, s), 3.22-3.38(2 H, m), 2.92-3.07(2 H, m), 2.28(3 H, s), 1.35(6 H, s) |
| 176 | 5-bromo-3-methyl-2-(2-hydroxy-2-methylpropoxy)pyridine | 8 | 413 | 1H NMR (500 MHz, chloroform-d) δ ppm 8.57(1 H, d, J = 3.85 Hz), 7.97 (1 H, d, J = 2.20 Hz), 7.62(1 H, td, J = 7.63, 1.79 Hz), 7.57(1 H, d, J = 1.92 Hz), 7.29(1 H, d, J = 4.40 Hz), 7.24(1 H, d, J = 7.97 Hz), 7.15 (1 H, dd, J = 6.60, 4.95 Hz), 6.90(1 H, d, J = 4.67 Hz), 4.27(2 H, s), 3.51 (2 H, t, J = 7.42 Hz), 3.22(2 H, t, J = 7.42 Hz), 2.27(3 H, s), 1.35(6 H, s) |
| 177 | 4-(trifluoromethoxy)benzenethiol | 6 | 518 | 1H NMR (500 MHz, methanol-d₃) d ppm 8.08(1 H, d, J = 2.47 Hz), 7.93 (1 H, d, J = 8.80 Hz), 7.65-7.74(3 H, m), 7.43(1 H, d, J = 4.67 Hz), 7.38(2 H, d, J = 7.97 Hz), 7.22(1 H, d, J = 4.40 Hz), 6.98(1 H, d, J = 1.10 Hz), 4.31(2 H, s), 2.66(3 H, d, J = 1.10 Hz), 1.34(6 H, s) |
| 178 | 4-(trifluoromethoxy)benzenethiol | 6 | 518 | 1H NMR (500 MHz, methanol-d₃) δ ppm 8.09(1 H, d, J = 9.35 Hz), 7.96 (1 H, d, J = 2.47 Hz), 7.64-7.75(3 H, m), 7.29-7.49(3 H, m), 7.21(1 H, d, J = 4.40 Hz), 6.69(1 H, s), 4.38-4.58(2 H, m), 2.54(3 H, s), 1.28(6 H, s) |
| 179 | 4-(trifluoromethoxy)benzenethiol | 6 | 504 | 1H NMR (500 MHz, methanol-d₃) δ ppm 8.21(1 H, d, J = 8.80 Hz), 7.90-7.98(2 H, m), 7.73(1 H, dd, J = 8.80, 2.47 Hz), 7.67(2 H, d), 7.35-7.42 (3 H, m), 7.21(1 H, d, J = 4.40 Hz), 7.11(1 H, d, J = 9.07 Hz), 4.34(2 H, s), 1.35(6 H, s). |
| 180 | 4-(trifluoromethoxy)benzenethiol | 6 | 504 | 1H NMR (500 MHz, methanol-d₃) δ ppm 8.08(1 H, d, J = 9.35 Hz), 7.97 (1 H, d, J = 9.35 Hz), 7.84(1 H, d, J = 2.47 Hz), 7.63-7.73(3 H, m), 7.31-7.42(3 H, m), 7.20(1 H, d, J = 4.40 Hz), 6.78(1 H, d, J = 9.35 Hz), 4.50(2 H, br s), 1.29(6 H, s) |
| 181 | 4-(trifluoromethyl)benzenethiol | 6 | 502 | 1H NMR (400 MHz, chloroform-d) δ ppm 7.89-8.00(2 H, m), 7.68-7.79(4 H, m), 7.64(1 H, dd, J = 8.79, 2.42 Hz), 7.19(1 H, d, J = 4.39 Hz), 7.11 (1 H, d, J = 4.39 Hz), 6.92(1 H, d, J = 0.88 Hz), 4.41(2 H, s), 2.64(3 H, s), 1.36(6 H, s) |
| 182 | 4-(trifluoromethyl)benzenethiol | 6 | 488 | 1H NMR (400 MHz, chloroform-d) δ ppm 8.06(1 H, d, J = 8.79 Hz), 7.94 (1 H, d, J = 9.01 Hz), 7.85(1 H, d, J = 2.42 Hz), 7.64-7.78(5 H, m), 7.18(1 H, d, J = 4.61 Hz), 7.11(1 H, d, J = 4.39 Hz), 7.06(1 H, d, J = 9.01 Hz), 4.43(2 H, s), 1.38(6 H, s) |

TABLE 3-continued

3-Substituted-1-heteroarylpyrazin-2(1H)-ones

| | | | | |
|---|---|---|---|---|
| 183 | phenethyl-SH | 6 | 448 | 1H NMR (400 MHz, chloroform-d) δ ppm 8.04(1 H, d, J = 8.78 Hz), 7.92 (1 H, d, J = 9.04 Hz), 7.83(1 H, d, J = 2.51 Hz), 7.65(1 H, dd, J = 8.91, 2.38 Hz), 72.8-7.36(5 H, m), 7.20-7.28(1 H, m), 7.02-7.09(2 H, m), 4.42(2 H, s), 3.28-3.44(2 H, m), 2.93-3.12(2 H, m), 1.37(6 H, s) |
| 184 | phenethyl-SH | 6 | 462 | 1H NMR (400 MHz, chloroform-d) δ ppm 7.88-7.98(2 H, m), 7.62(1 H, dd, J = 8.91, 2.38 Hz), 7.20-7.37(6 H, m), 7.07(1 H, d, J = 4.27 Hz), 6.90 (1 H, s), 4.40(2 H, s), 3.30-3.39(2 H, m), 2.98-3.12(2 H, m), 2.63(3 H, s), 1.35(6 H, s) |
| 185 | 4-F-phenethyl-SH | 6 | 466 | 1H NMR (500 MHz, chloroform-d) δ ppm 8.04(1 H, d, J = 8.80 Hz), 7.92 (1 H, d, J = 9.07 Hz), 7.83(1 H, d, J = 2.20 Hz), 7.65(1 H, dd, J = 8.94, 2.34 Hz), 7.32(1 H, d, J = 4.40 Hz), 7.23-7.30(2 H, m), 6.92-7.12(4 H, m), 4.42(2 H, s), 3.43-3.57(2 H, m), 3.25-3.33(2 H, m), 2.91-3.08 (2 H, m), 1.37(6 H, s) |
| 186 | 4-F-phenethyl-SH | 6 | 480 | 1H NMR (500 MHz, chloroform-d) δ ppm 7.88-7.97(2 H, m), 7.62(1 H, dd, J = 8.80, 2.47 Hz), 7.33(1 H, d, J = 4.40 Hz), 7.23-7.29(2 H, m), 7.07(1 H, d, J = 4.40 Hz), 7.01(2 H, t, J = 8.66 Hz), 6.90(1 H, s), 4.40(2 H, s), 3.27-3.38(2 H, m), 2.95-3.08(2 H, m), 2.63(3 H, s), 1.35(6 H, s) |
| 187 | 3-F-phenethyl-SH | 6 | 466 | 1H NMR (500 MHz, chloroform-d) δ ppm 8.04(1 H, d, J = 8.80 Hz), 7.92 (1 H, d, J = 9.07 Hz), 7.83(1 H, d, J = 2.47 Hz), 7.65(1 H, dd, J = 8.80, 2.47 Hz), 7.34(1 H, d, J = 4.40 Hz), 7.27-7.31(1 H, m), 6.99-7.10(4 H, m), 6.89-6.97(1 H, m), 4.42(2 H, s), 3.30-3.38(2 H, m), 2.98-3.08(2 H, m), 1.37(6 H, s) |
| 188 | 3-F-phenethyl-SH | 6 | 480 | 1H NMR (500 MHz, chloroform-d) δ ppm 7.95(1 H, d, J = 2.20 Hz), 7.91 (1 H, d, J = 8.80 Hz), 7.62(1 H, dd, J = 8.94, 2.34 Hz), 7.34(1 H, d, J = 4.67 Hz), 7.28(1 H, dd, J = 7.97, 1.92 Hz), 7.00-7.10(3 H, m), 6.89-6.97(2 H, m), 4.40(2 H, s), 3.28-3.41(2 H, m), 2.97-3.10(2 H, m), 2.63(3 H, s), 1.35(6 H, s) |
| 189 | 4-(OCF3)-phenyl-SH | 6 | 477 | 1H NMR (500 MHz, methanol-d3) δ ppm 8.28(1 H, s), 7.70-7.80(2 H, m), 7.55-7.61(2 H, m), 7.25-7.32 (4 H, m), 7.11(1 H, d, J = 4.40 Hz), 4.19(2 H, s), 1.14(6 H, s) |
| 190 | 4-(OCF3)-phenyl-SH | 6 | 477 | 1H NMR (500 MHz, methanol-d3) δ ppm 8.30(1 H, s), 7.76-7.85(2 H, m), 7.65-7.71(2 H, m), 7.34-7.42 (3 H, m), 7.20(1 H, d, J = 4.40 Hz), 4.29(2 H, s), 1.24(6 H, s) |

TABLE 3-continued

3-Substituted-1-heteroarylpyrazin-2(1H)-ones

| 191 | ![4-chlorophenethyl thiol] | 7 | 466 | 1H NMR (500 MHz, chloroform-d₃) δ ppm 8.04(1 H, d, J = 8.80 Hz), 7.92 (1 H,d , J = 8.80 Hz), 7.80(1 H, d, J = 2.47 Hz), 7.64(1 H, dd, J = 8.94, 2.34 Hz), 7.23-7.30(4 H, m), 7.04 (1 H, d, J = 8.80 Hz), 6.95(1 H, d, J = 4.67 Hz), 6.90(1 H, d, J = 4.67 Hz), 4.54(2 H, t, J = 7.15 Hz), 4.42(2 H, s), 3.15(2 H, t, J = 7.29 Hz), 1.37(6 H, s) |
| --- | --- | --- | --- | --- |
| 192 | ![4-chlorophenethyl alcohol] | 7 | 480 | 1H NMR (500 MHz, chloroform-d) δ ppm 7.88-7.95(2 H, m), 7.61(1 H, dd, J = 8.80, 2.47 Hz), 7.27-7.30(4 H, m), 6.96(1 H, d, J = 4.67 Hz), 6.90(2 H, d, J = 4.67 Hz), 4.54(2 H, t, J = 7.15 Hz), 4.40(2 H, s), 3.15(2 H, t, J = 7.15 Hz), 2.62(3 H, s), 1.35(6 H, s) |

Part A. 1-(2-Methoxy-4-(2-oxo-3-(4-(trifluoromethyl)phenylthio)pyrazin-1(2H)-yl)phenoxy)-2-methylpropan-2-yl 2-(tert-butoxycarbonylamino)acetate

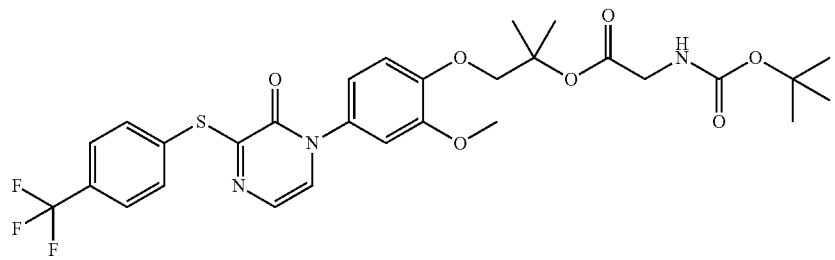

Prodrugs were prepared of selected secondary and tertiary alcohols to improve solubility and exposure. Standard conditions, employed to generate amino acid esters of all but the glycine ester of the tertiary alcohols, are exemplified in Example 193. Preparation of the glycine ester of the tertiary alcohols is exemplified in Example 202. Preparation of a phosphate ester prodrug is exemplified by Example 204.

Example 193

1-(2-Methoxy-4-(2-oxo-3-(4-(trifluoromethyl)phenylthio)pyrazin-1(2H)-yl)phenoxy)-2-methylpropan-2-yl 2-aminoacetate

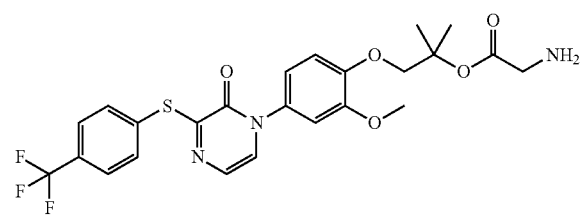

To a stirred suspension of the alcohol prepared in Example 36 (3.0 g, 6.4 mmol), 4-pyrrolidinopyridine (0.95 g, 6.4 mmol) and BOC-glycine (3.4 g, 19 mmol) in CH₂Cl₂ (60 mL) at 42° C. was added N,N'-diisopropylcarbodiimide 3.0 mL, 19 mmol) over 3.5 h. After stirring at reflux for 2.5 h, HPLC analysis showed 25% alcohol still remained. More BOC-glycine (3.4 g, 19 mmol) was added followed by additional N,N'-diisopropylcarbodiimide (3.0 mL, 19 mmol) which was slowly added over 3.5 h; whereupon, HPLC analysis showed <5% alcohol remained. The reaction was allowed to cool to RT prior to addition of hydrazine monohydrate (18 mL, 370 mmol). After stirring for 5 minutes, the reaction mixture was cooled to 0° C. and filtered. The filtrates were sequentially washed with cold 1M HCl (3×20 mL) and cold 2% NaHCO₃ (3×20 mL) prior to drying over MgSO₄ and concentrating under vacuum to afford 5.6 g of crude product. Chromatography (silica gel 230-400 mesh, gradient elution: 0 to 60% EtOAc/hexane over 47 min) of the residue afforded the desired ester (3.9 g, 88% yield). HPLC 4.42 min. LC MS (M+1=624), H-NMR (CDCl₃) 7.72 (m, 4H), 7.12 (d, J=4.4 Hz, 1H), 7.02 (d, J=4.4 Hz, 1H), 7.00 (d, J=8.3 Hz, 1H), 6.99 (d, J=2.5 Hz, 1H), 6.90 (dd, J=2.5 and 8.3 Hz, 1H), 4.21 (s, 2H), 3.87 (s, 3H), 3.78 (m, 2H), 1.61 (s, 6H), 1.45 (s, 9H).

Part B. 1-(2-Methoxy-4-(2-oxo-3-(4-(trifluoromethyl)phenylthio)pyrazin-1(2H)-yl)phenoxy)-2-methylpropan-2-yl 2-aminoacetate

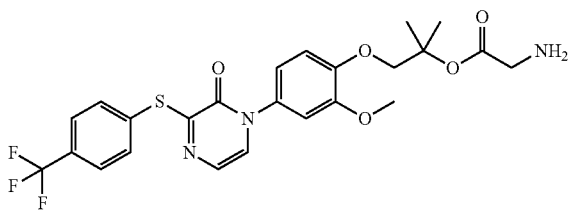

The BOC'd glycinate ester described in Part A (3.9 g, 6.2 mmol) was treated with 1:2 TFA/CH$_2$Cl$_2$ (145 mL) at RT for 25 min. After removal of the volatiles under vacuum, the residual TFA was removed by co-evaporation with CH$_2$Cl$_2$ (3×8 mL) and drying under vacuum for 20 min. Following dissolution in CH$_2$Cl$_2$ (70 mL), the solution was washed with cold 5% NaHCO$_3$ (3×30 mL) dried over MgSO$_4$ and concentrated to yield 3.3 g of crude product. Purification by flash chromatography (120 g silica gel, 0 to 5% MeOH/CH$_2$Cl$_2$ over 24 min) afforded the desired free amine (2.5 g, 77% yield).). HPLC 3.72 min. LC MS 2.18 min (M+1=524), H-NMR (CDCl$_3$) 7.75 (d, J=8.7 Hz, 2H), 7.72 (d, J=8.7 Hz, 2H), 7.14 (d, J=4.4 Hz, 1H), 7.02 (d, J=4.4 Hz, 1H), 7.00 (d, J=8.5 Hz, 1H), 6.99 (d, J=2.4 Hz, 1H), 6.92 (dd, J=2.4 and 8.5 Hz, 1H), 4.24 (s, 2H), 3.89 (s, 3H), 3.36 (m, 2H), 1.63 (s, 6H), 1.54 (broad s, 2H).

Examples 194 to 201

Examples 194 to 201 were prepared in a similar manner to Example 193 using the appropriate alcohol and BOC glycine followed by TFA removal of the BOC group.

TABLE 4

| | Glycine Prodrug Esters | | | |
|---|---|---|---|---|
| Example No. | Glycine ester of Example No. | HPLC (Met1) | LC MS | $^1$H-NMR (CDCl$_3$) |
| 194 | 38 | 3.86 | 540 | 7.55 (d, J = 9.3 Hz, 2H), 7.27 (d, J = 9.3 Hz, 2H), 7.18 (d, J = 4.4 Hz, 1H), 7.06 (d, J = 4.4 Hz, 1H), 7.01 (d, J = 2.2 Hz, 1H), 6.99 (d, J = 8.2 Hz, 1H), 6.86 (dd, J = 2.2 and 8.2 Hz, 1H), 4.15 (s, 2H), 3.76 (s, 3H), 3.17 (s, 2H), 1.50 (s, 6H). |
| 195 | 32 | 3.59 | 470 | 7.47 (d, J = 8.7 Hz, 2H), 7.27 (d, J = 8.7 Hz, 2H), 7.11 (d, J = 4.4 Hz, 1H), 6.98 (d, J = 2.3 Hz, 1H), 6.97 (d, J = 8.5 Hz, 1H), 6.95 (d, J = 4.4 Hz, 1H), 6.88 (dd, J = 2.3 and 8.5 Hz, 1H), 4.20 (s, 2H), 3.86 (s, 3H), 3.33 (s, 2H), 2.40 (s, 3H), 1.50 (s, 6H). |
| 196 | 50 | 3.78 | 484 | 7.34 (d, J = 8.3 Hz, 2H), 7.22 (d, J = 8.3 Hz, 2H), 7.05 (d, J = 4.4 Hz, 1H), 6.92 (d, J = 2.2 Hz, 1H), 6.90 (d, J = 8.2 Hz, 1H), 6.87 (d, J = 4.4 Hz, 1H), 6.83 (dd, J = 2.2 and 8.2 Hz, 1H), 4.14 (s, 2H), 3.79 (s, 3H), 3.27 (s, 2H), 2.63 (q, H = 7.7 Hz, 2H), 1.54 (s, 6H), 1.19 (t, J = 7.7 Hz, 3H). |
| 197 | 65 | | 482 | 7.25-7.09 (m, 8H), 6.87 (d, J = 4.4 Hz, 1H), 6.80 (d, J = 9.4 Hz, 1H), 4.09 (s, 2H), 3.30 (2, 2H), 3.23 (dd, J = 7.2, 9.8 Hz, 2H), 2.94 (dd, J = 7.2 and 8.2 Hz, 2H), 2.58 (q, J = 7.6 Hz, 2H), 1.55 (s, 6H), 1.13 (t, J = 7.6 Hz, 3H). |
| 198 | 87 | | 524 | 1H NMR (400 MHz, chloroform-d) δ ppm 8.40 (2H, br. s.), 7.59 (2H, d, J = 8.78 Hz), 7.28 (2H, d, J = 8.03 Hz), 7.09-7.23 (3H, m), 6.97 (2H, d, J = 4.27 Hz), 4.22 (2H, br. s.), 3.79 (2H, br. s.), 2.27 (3H, s), 1.62 (6H, s) |
| 199 | 88 | | 544 | 1H NMR (500 MHz, methanol-d$_3$) δ ppm 7.65 (2H, d, J = 9.07 Hz), 7.61 (1H, d, J = 2.47 Hz), 7.34-7.43 (3H, m), 7.23-7.29 (2H, m), 7.16 (1H, d, J = 4.40 Hz), 4.38 (2H, s), 3.75 (2H, s), 1.68 (6H, s) |
| 200 | 123 | | 486 | 1H NMR (500 MHz, methanol-d$_3$) δ ppm 7.38 (1H, d, J = 4.40 Hz), 7.29 (2H, dd, J = 8.52, 5.50 Hz), 7.19-7.25 (3H, m), 6.98-7.05 (3H, m), 4.29 (2H, s), 3.74 (2H, s), 3.31-3.35 (2H, m), 2.98 (2H, t, J = 7.56 Hz), 2.28 (3H, s), 1.67 (6H, s) |
| 201 | 113 | | 468 | 1H NMR (500 MHz, methanol-d$_3$) δ ppm 7.39 (1H, d, J = 4.40 Hz), 7.25-7.31 (4H, m), 7.17-7.25 (4H, m), 7.03 (1H, d, J = 8.25 Hz), 4.28 (2H, s), 3.74 (2H, s), 3.24-3.39 (2H, m), 2.91-3.04 (2H, m), 2.28 (3H, s), 1.67 (6H, s) |

If desired the amino acid prodrug esters may be converted to the corresponding HCl salt. For example, the HCl salt of Example 197 was prepared by dissolving the compound (0.655 mg, 1.36 mmoles) in $CH_2Cl_2$ (10 mL) and MeOH (1 mL) and cooling to −30° C. 1N HCl in ether (2.3 mL, 1.7 eq) was added with stirring. Evaporation in vacuo afforded the desired salt. (0.71 g). LC MS was identical to the free base. H-NMR ($CD_3OD$) 7.30 (d, J=4.4 Hz, 1H), 7.20 (m, 4H), 7.13 (m, 4H), 6.93 (d, J=8.5 Hz, 1H), 4.19 (s, 2H), 3.64 (s, 2H), 3.23 (dd, J=7.4, 15.4 Hz, 2H), 2.90 (dd, J=8.0 and 15.4 Hz, 2H), 2.62 (q, J=7.5 Hz, 2H), 1.59 (s, 6H), 1.14 (t, J=7.5 Hz, 3H).

Example 202

1-(2-Methoxy-4-(2-oxo-3-(4-(trifluoromethyl)phenylthio)pyrazin-1(2H)-yl)phenoxy)propan-2-yl 2-amino-3-methylbutanoate

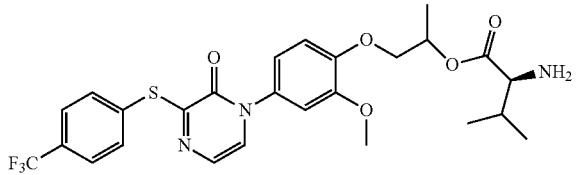

To a stirred mixture of the alcohol described in Example 71 (0.882 g, 1.949 mmol), 4-dimethylaminopyridine (0.714 g, 5.85 mmol) and N-(t-butoxycarbonyl)-L-valine (1.271 g, 5.85 mmol) in 18 mL of $CH_2Cl_2$ at rt was added WSC (1.121 g, 5.85 mmol). After stirring at ambient temperature for 30 min, the reaction mixture was transferred to a separatory funnel, washed with cold 5% $H_2SO_4$ (3×), 5% $Na_2CO_3$ (2×), and water and dried over $MgSO_4$. Evaporation of the solvent afforded 1.03 g of crude product as the BOC amine. The crude product was dissolved in a 1:2 mixture of $TFA/CH_2Cl_2$ (18 mL). After stirring for 15 min the solvent was evaporated in vacuo. The residue was transferred to a separatory funnel with $CH_2Cl_2$, washed with cold 5% $Na_2CO_3$ (2×), and dried over $MgSO_4$ to afford crude 790 mg of product after evaporation of the solvent. The product was purified by flash chromatography (80 g silica gel, gradient elution: 1 to 8% $MeOH/CH_2Cl_2$ over 24 min) to afforded the desired valine ester as a free base (0.69 g, 64% yield).

HPLC (Method 1) 3.84 min. LC MS 2.26 min (M+1=552), H-NMR ($CDCl_3$) 7.74 (d, J=8.7 Hz, 2H), 7.72 (d, J=8.7 Hz, 2H), 7.13 (d, J=4.4 Hz, 1H), 7.02 (d, J=4.4 Hz, 1H), 7.00 (d, J=8.5 Hz, 1H), 6.99 (d, J=2.4 Hz, 1H), 6.91 (dd, J=2.4 and 8.5 Hz, 1H), 5.34 (m, 1H), 4.12 (m, 2H), 3.86 (d, 3H), 3.30 (t, J=5.2 Hz, 1H), 2.05 (m, 1H), 1.40 (d, J=6.4 Hz), 0.98 (m, 3H), 0.92 (m, 3H).

The HCl salt of Example 176 was prepared by dissolving the compound in $CH_2Cl_2$ (9 mL). After cooling the solution to −30° C., 1N HCl in ether (2.85 mL, 1.7 eq) was added with stirring. The yellow precipitate was collected and dried to afford the HCl salt (0.74 g).

LC MS was identical to the free base. H-NMR ($CDCl_3$) 7.74 (d, J=8.7 Hz, 2H), 7.79 (m, 4H), 7.33 (d, J=4.4 Hz, 1H), 7.18 (d, J=8.5 Hz, 1H), 7.15 (d, J=2.4 Hz, 1H), 7.02 (dd, J=2.4 and 8.5 Hz, 1H), 5.51 (m, 1H), 4.24 (m, 2H), 3.86 (d, 3H), 3.33 (s, 1H), 2.30 (m, 1H), 1.41 (d, J=6.4 Hz), 1.12 (m, 6H).

Example 203

(2S)-1,1,1-Trifluoro-3-(2-methoxy-4-(2-oxo-3-(4-(trifluoromethyl)phenylthio)pyrazin-1(2H)-yl)phenoxy)propan-2-yl 2-amino-3-methylbutanoate

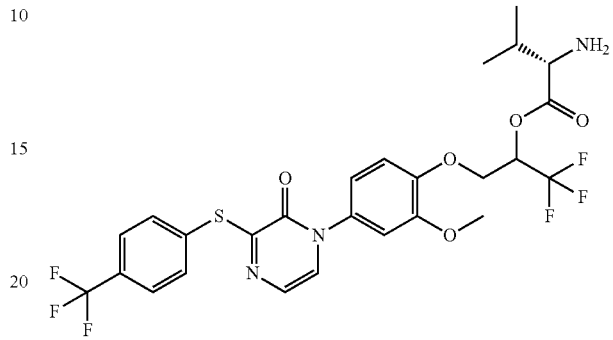

In an analogous fashion to that described in Example 202, the valine ester of the alcohol described in Example 74 was prepared.

LC MS at t=2.35 min. (m+1=606) Phenomenex S5 C18 4.6×30 mm column/water-MeOH-TFA 90:10:0.1 to 10:90:0.1 gradient over 2 min at 5 mL/min with 1 min hold at the end of the gradient.

$^1$H NMR (500 MHz, $CDCl_3$) δ ppm 0.97 (dd, J=35.13, 6.92 Hz, 6H), 1.97-2.20 (m, 1H), 3.42 (d, J=4.78 Hz, 1H), 3.86 (s, 4H), 4.26-4.36 (m, 1H), 4.44 (dd, J=11.08, 3.53 Hz, 1H), 5.73-5.87 (m, 1H), 6.91 (dd, J=8.56, 2.27 Hz, 1H), 6.97-7.06 (m, 2H), 7.13 (d, J=4.53 Hz, 1H), 7.58 (s, 1H), 7.66-7.77 (m, 4H).

Example 204

Sodium 3,3-difluoro-1-((2-methoxy-4-(2-oxo-3-(4-(trifluoromethoxy)-phenylthio)pyrazin-1(2H)-yl)phenoxy)methyl)cyclobutyl phosphate

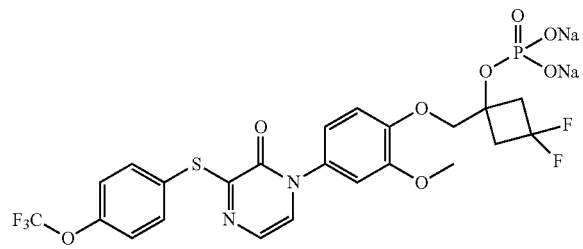

Part A. Dibenzyl 3,3-difluoro-1-((2-methoxy-4-(2-oxo-3-(4-(trifluoromethoxy)phenylthio)pyrazin-1(2H)-yl)phenoxy)methyl)cyclobutyl phosphate

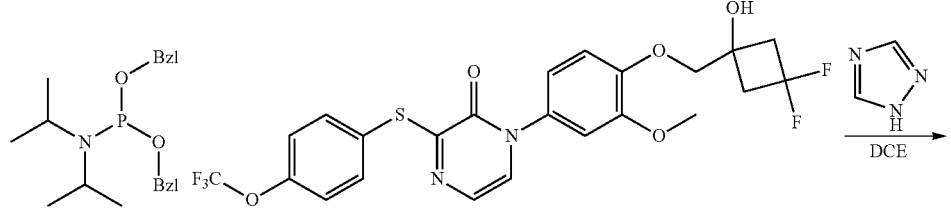

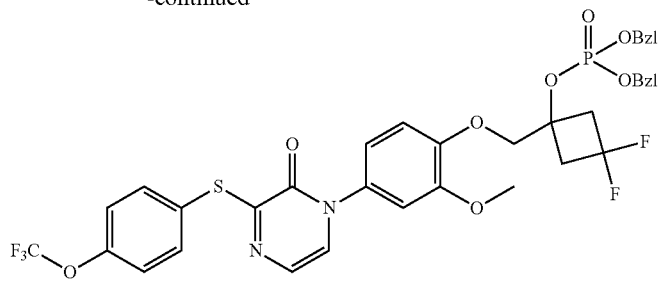

To a mixture of dibenzyl diisopropylphosphoramidite (135 mg, 0.390 mmol), 1-(4-((3,3-difluoro-1-hydroxycyclobutyl)methoxy)-3-methoxyphenyl)-3-(4-(trifluoromethoxy)phenylthio)pyrazin-2(1H)-one (Example 75) (69 mg, 0.130 mmol) and 1H-1,2,4-triazole (27.0 mg, 0.390 mmol) in DCE (20 mL) was stirred at reflux for 6 hours. The mixture was cooled to RT. 30% hydrogen peroxide in water (10 ml) was slowly added and the mixture was stirred at RT for 30 min. The mixture was diluted with a solution of aqueous 10% sodium thiosulfate (40 ml) and was extracted with DCM (50 ml). The DCM layer was dried over sodium sulfate and concentrated.

The crude product was purified by ISCO silica gel Column (40 g) and the product was eluted with hexane to 100% ethyl acetate in 10 min. Yield dibenzyl 3,3-difluoro-1-((2-methoxy-4-(2-oxo-3-(4-(trifluoromethoxy)phenylthio)pyrazin-1(2H)-yl)phenoxy)methyl)cyclobutyl phosphate (79 mg, 0.100 mmol, 77% yield) as off-white solid. 1H NMR (400 MHz, chloroform-d) δ ppm 7.57-7.66 (2H, m), 7.27-7.39 (12 H, m), 7.13 (1H, d, J=4.53 Hz), 6.81-7.00 (4H, m), 4.97-5.14 (4H, m), 4.29 (2H, s), 3.75 (3H, s), 2.93-3.20 (4H, m).

Part B. Sodium 3,3-difluoro-1-((2-methoxy-4-(2-oxo-3-(4-(trifluoromethoxy)phenylthio)pyrazin-1(2H)-yl)phenoxy)methyl)cyclobutyl phosphate To a solution of dibenzyl 3,3-difluoro-1-((2-methoxy-4-(2-oxo-3-(4-(trifluoromethoxy)phenylthio)pyrazin-1(2H)-yl)phenoxy)methyl)cyclobutyl phosphate (79 mg, 0.100 mmol) in TFA (2 mL) was stirred at RT for 3.5 hours. The mixture was concentrated. The crude product was purified by prep-HPLC (Phenomenex, Luna 5 micron 25×250 mm, flow rate=30 ml/min., gradient=20% A to 100% B in 10 min., A=90% H$_2$O/10% MeOH/0.1% TFA, B=10% H$_2$O/90% MeOH/0.1% TFA). Yield 46 mg, 0.075 mmol as yellow gum. The yellow gum in ACN (2 ml) was added 0.5 N aqueous sodium bicarbonate (302 μl, 0.151 mmol), the mixture was diluted with water (5 ml). The solution was then lyophilized. Yield sodium 3,3-difluoro-1-((2-methoxy-4-(2-oxo-3-(4-(trifluoromethoxy)phenylthio)pyrazin-1(2H)-yl)phenoxy)methyl)cyclobutyl phosphate (51.08 mg, 0.078 mmol, 78% yield) as off-white powder. MS (M+H=611). 1H NMR (400 MHz, MeOD) δ ppm 7.54-7.63 (2H, m), 7.19-7.33 (3 H, m), 7.02-7.17 (3H, m), 6.91 (1H, dd, J=8.44, 2.39 Hz), 4.28 (2H, s), 3.80 (3H, s), 3.13-3.32 (2H, m), 2.75-2.90 (2H, m).

Example 205

Sodium 1-(2-methoxy-4-(2-oxo-3-(4-(trifluoromethoxy)phenylthio)pyrazin-1(2H)-yl)phenoxy)-2-methylpropan-2-yl phosphate

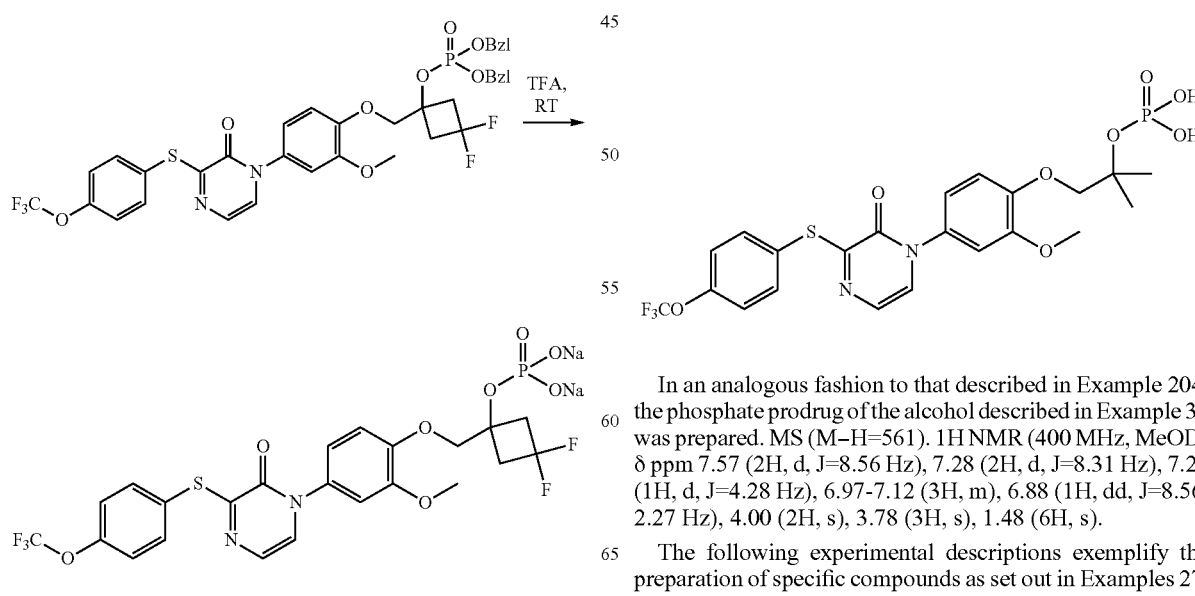

In an analogous fashion to that described in Example 204, the phosphate prodrug of the alcohol described in Example 38 was prepared. MS (M−H=561). 1H NMR (400 MHz, MeOD) δ ppm 7.57 (2H, d, J=8.56 Hz), 7.28 (2H, d, J=8.31 Hz), 7.20 (1H, d, J=4.28 Hz), 6.97-7.12 (3H, m), 6.88 (1H, dd, J=8.56, 2.27 Hz), 4.00 (2H, s), 3.78 (3H, s), 1.48 (6H, s).

The following experimental descriptions exemplify the preparation of specific compounds as set out in Examples 27, 95, 110, 113, and 124.

Example 27

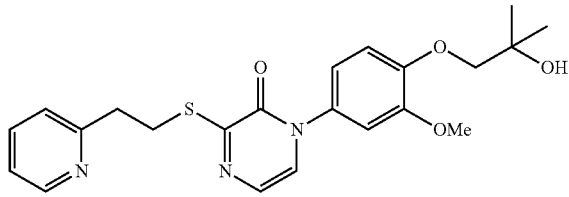

1-(4-(2-Hydroxy-2-methylpropoxy)-3-methoxyphenyl)-3-(2-(pyridin-2-yl)-ethylthio)pyrazin-2(1H)-one Following the procedures described in parts A-D of example 134, 2-methoxy-4-nitrophenol was converted to 1-(4-(2-hydroxy-2-methylpropoxy)-3-methoxyphenyl)pyrazine-2,3(1H,4H)-dione. A solution of 1-(4-(2-hydroxy-2-methylpropoxy)-3-methoxyphenyl)pyrazine-2,3(1H,4H)-dione prepared in Part ? (2.28 g, 7.44 mmol), EtN(iPr)$_2$ (3.9 mL, 22.3 mmol), PyBOP (6.78 g, 13.0 mmol) in DMF (35 mL) was stirred at ambient temperature for 1.5 h. After addition of 2-pyridylethyl mercaptan (1.24 g, 8.93 mmol), the reaction was stirred at ambient temperature. After stirring overnight the reaction mixture was partially concentrated under reduced pressure, quenching by addition of aq. NaHCO$_3$ and extracted with EtOAc. The EtOAc extracts were washed with brine, dried over MgSO$_4$ and concentrated. Chromatography on silica employing a gradient elution with 2.5-10% methanol/methylene chloride, followed by chromatography on silica eluting with EtOAc, and trituration with EtOAc/Hexanes afforded the desired product 1-(4-(2-hydroxy-2-methylpropoxy)-3-methoxyphenyl)-3-(2-(pyridin-2-yl)ethylthio)pyrazin-2(1H)-one (2.15 g, 68% yield).

Example 95

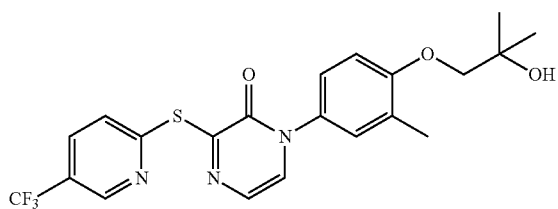

1-(4-(2-Hydroxy-2-methylpropoxy)-3-methylphenyl)-3-(5-(trifluoromethyl)pyridin-2-ylthio)pyrazin-2(1H)-one

Part A.
2-Methyl-1-(2-methyl-4-nitrophenoxy)propan-2-ol

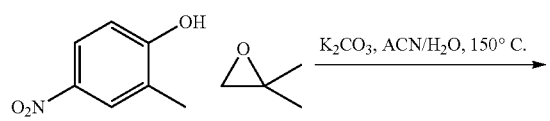

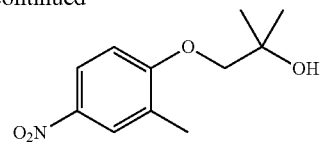

A mixture of 2-methyl-4-nitrophenol (5.50 g, 35.9 mmol), 2,2-dimethyloxirane (7.77 g, 108 mmol), K$_2$CO$_3$ (4.96 g, 35.9 mmol) and NaH$_2$PO$_4$ (4.31 g, 35.9 mmol) in MeCN (50 mL) and H$_2$O (8.82 mL) was stirred at 140° C. in a steel bomb for 6 hours. After cooling to RT, the reaction was diluted with aq. saturated NaHCO$_3$ (80 ml) prior to extraction with EtOAc (100 ml). The EtOAc layer was dried over Na$_2$SO$_4$ and concentrated. The crude product was purified by silica gel chromatography employing a solvent gradient (hexane to 60% ethyl acetate) to elute 2-methyl-1-(2-methyl-4-nitrophenoxy)propan-2-ol (7.3 g, 32.4 mmol, 90% yield) as yellow oil. MS (M+1=226). 1H NMR (500 MHz, chloroform-d) δ ppm 8.00-8.15 (2H, m), 6.86 (1H, d, J=8.80 Hz), 3.90 (2H, s), 2.33 (3H, s), 1.40 (6H, s).

Part B.
1-(4-Amino-2-methylphenoxy)-2-methylpropan-2-ol

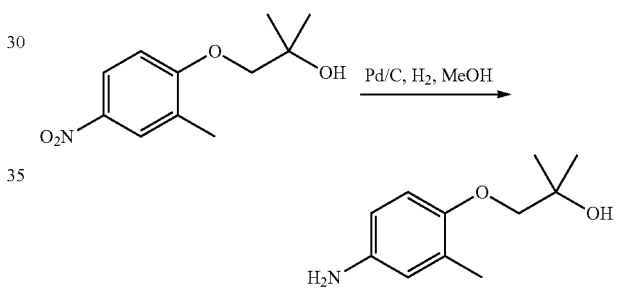

A mixture of 2-methyl-1-(2-methyl-4-nitrophenoxy)propan-2-ol (7.30 g, 32.4 mmol) and 10% Pd/C (0.345 g, 3.24 mmol) in MeOH (150 mL) was hydrogenated at 1 atm of H$_2$ for 18 hours. After removal of the Pd/C by filtration, the solution was concentrated to yield 1-(4-amino-2-methylphenoxy)-2-methylpropan-2-ol (6.10 g, 29.7 mmol, 92% yield) as clear gum which was carried forward without further purification.

Part C. N1-(2,2-Dimethoxyethyl)-N2-(4-(2-hydroxy-2-methylpropoxy)-3-methylphenyl)oxalamide

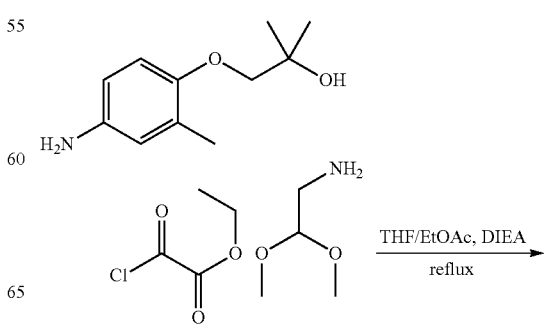

-continued

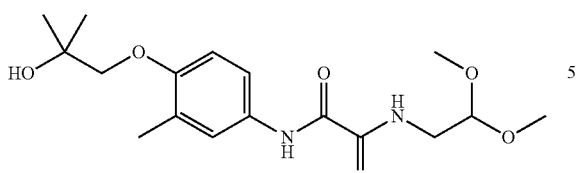

Slow addition of a solution of ethyl 2-chloro-2-oxoacetate (4.69 g, 34.4 mmol) in THF (30 ml) to a solution of 1-(4-amino-2-methylphenoxy)-2-methylpropan-2-ol (6.10 g, 31.2 mmol) in THF (100 mL) resulted in formation of a precipitate as the reaction stirred at RT for 30 min. At which time a solution of Et₃N (13.06 mL, 94 mmol) and 2,2-dimethoxyethanamine (3.94 g, 37.5 mmol) in EtOAc (100 mL) was added prior to heating the mixture at reflux for 25 hours. After cooling and concentration under vacuum, the residue, following dilution with CH₂Cl₂, was extracted with aqueous 0.5 N HCl (2×150 ml). The CH₂Cl₂ layer was dried over sodium sulfate and concentrated to yield N1-(2,2-dimethoxyethyl)-N2-(4-(2-hydroxy-2-methylpropoxy)-3-methylphenyl)-oxalamide (11.40 g, 30.6 mmol, 98% yield) as white solid which was carried forward without further purification.

Part D. 3-Hydroxy-1-(4-(2-hydroxy-2-methylpropoxy)-3-methylphenyl)pyrazin-2(1H)-one

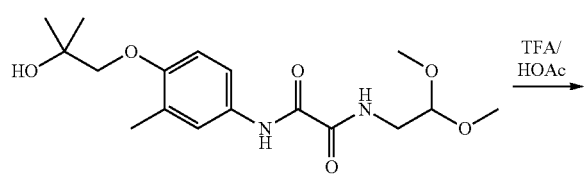

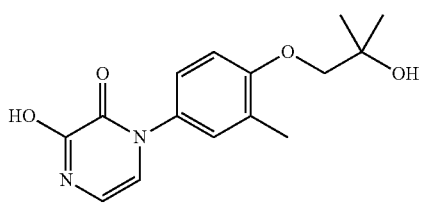

A solution of N1-(2,2-dimethoxyethyl)-N2-(4-(2-hydroxy-2-methylpropoxy)-3-methylphenyl)oxalamide (11.4 g, 32.2 mmol) and TFA (2.97 mL, 38.6 mmol) in AcOH (120 mL) was stirred at 135° C. in a seal tube for 60 min. After cooling and concentration under vacuum, addition of CH₂Cl₂ (300 ml) produced a precipitate which was collected by filtration and was washed with CH₂Cl₂ (150 ml) to yield 3-hydroxy-1-(4-(2-hydroxy-2-methylpropoxy)-3-methylphenyl)pyrazin-2(1H)-one (7.19 g, 23.53 mmol, 73.1% yield) as brown solid. MS (M+1=226). 1H NMR (500 MHz, methanol-d₃) δ ppm 7.13-7.26 (2H, m), 6.98 (1H, d, J=8.52 Hz), 6.50 (1H, d, J=5.77 Hz), 6.41 (1H, d, J=6.05 Hz), 3.82 (2H, s), 2.29 (3H, s), 1.35 (6H, s).

Part E. 1-(4-(2-Hydroxy-2-methylpropoxy)-3-methylphenyl)-3-(5-(trifluoromethyl)-pyridin-2-ylthio)pyrazin-2(1H)-one

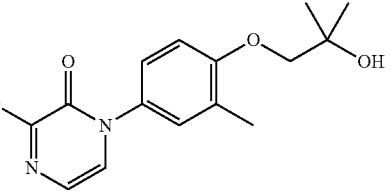

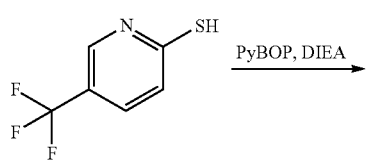

A mixture of 3-hydroxy-1-(4-(2-hydroxy-2-methylpropoxy)-3-methylphenyl)pyrazin-2(1H)-one (100 mg, 0.344 mmol), PyBOP (314 mg, 0.603 mmol) and EtN(iPr)₂ (0.180 mL, 1.033 mmol) in DMF (6 mL) was stirred at RT for 3 hours prior to addition of 5-(trifluoromethyl)pyridine-2-thiol (74.1 mg, 0.413 mmol). After stirring for 3 days, The reaction was diluted with aq. saturated NaHCO₃ (15 ml) prior to extraction with EtOAc (20 ml). The EtOAc layer was dried over Na₂SO₄ and concentrated. The crude product was purified by prep-HPLC (Phenomenex, Luna 5 micron 30×250 mm, flow rate=30 ml/min., gradient=20% A to 100% B in 30 min., A=90% H₂O/10% MeOH/0.1% TFA, B=10% H₂O/90% MeOH/0.1% TFA). After concentration, the residue in EtOAc (30 ml) was converted to the free base by washing with aq. saturated NaHCO₃ (30 ml). The EtOAc layer was dried over Na₂SO₄ and concentrated. To yield 1-(4-(2-hydroxy-2-methylpropoxy)-3-methylphenyl)-3-(5-(trifluoromethyl)pyridin-2-ylthio)pyrazin-2(1H)-one (22.76 mg, 14%) as off-white solid. MS (M+1=452). 1H NMR (500 MHz, chloroform-d) δ ppm 8.88 (1H, s), 7.89-7.99 (2H, m), 7.16-7.24 (3H, m), 7.07 (1H, d, J=4.40 Hz), 6.90 (1H, d, J=8.52 Hz), 3.84 (2H, s), 2.30 (3H, s), 1.39 (6H, s).

Example 110

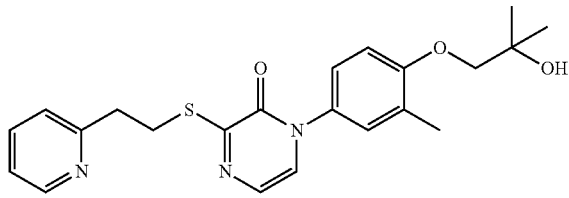

1-(4-(2-Hydroxy-2-methylpropoxy)-3-methylphenyl)-3-(2-(pyridin-2-yl)ethylthio)pyrazin-2(1H)-one

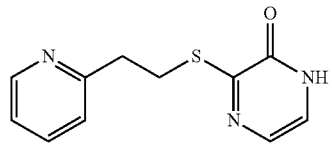

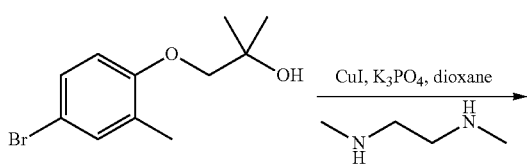

A mixture of 3-(2-(pyridin-2-yl)ethylthio)pyrazin-2(1H)-one (100 mg, 0.429 mmol), which was prepared by the procedure described in Method 7 except for substitution of 2-(2-pyridylethylthiol) for 2-(4-chlorophenethanol), 1-(4-bromo-2-methylphenoxy)-2-methylpropan-2-ol (133 mg, 0.514 mmol), N1,N2-dimethylethane-1,2-diamine (113 mg, 1.286 mmol), K$_3$PO$_4$ (0.106 mL, 1.286 mmol) and copper(1) iodide (82 mg, 0.429 mmol) in dioxane (1.0 mL) was stirred at 115° C. for 90 min. The reaction mixture, after cooling to RT, was filtered and the filtrate was concentrated. The crude product was purified by silica gel chromatography employing a solvent gradient (hexane to 100% ethyl acetate) to yield 1-(4-(2-hydroxy-2-methylpropoxy)-3-methylphenyl)-3-(2-(pyridin-2-yl)ethylthio)pyrazin-2(1H)-one (140 mg, 0.340 mmol, 79% yield) as white solid. MS (M+H 412). 1H NMR (400 MHz, MeOD) δ ppm 8.67 (1H, d), 8.48 (1H, td, J=7.91, 1.51 Hz), 8.02 (1H, d, J=8.28 Hz), 7.81-7.95 (1H, m), 7.07-7.29 (4H, m), 6.93 (1H, d, J=8.78 Hz), 3.76 (2H, s), 3.35-3.57 (4H, m), 2.22 (3H, s), 1.27 (6H, s).

Example 113

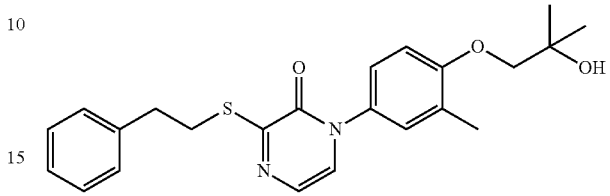

1-(4-(2-Hydroxy-2-methylpropoxy)-3-methylphenyl)-3-(phenethylthio)pyrazin-2(1H)-one

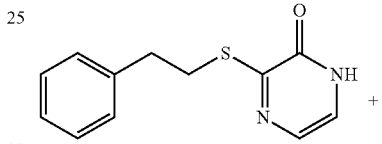

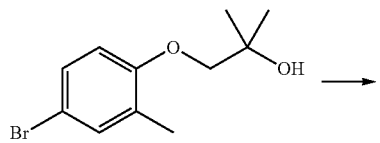

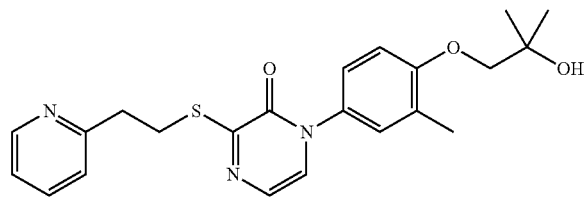

A mixture of 3-(phenethylthio)pyrazin-2(1H)-one (25 mg, 0.108 mmol), which was prepared by the procedure described in Method 7 except for substitution of 2-phenethylthiol for 2-(4-chlorophenethanol), 1-(4-bromo-2-methylphenoxy)-2-methylpropan-2-ol (33.5 mg, 0.129 mmol), copper iodide (20.50 mg, 0.108 mmol), K$_3$PO$_4$ (70 mg, 0.323 mmol) and N,N'-dimethylethylenediamine (28.5 mg, 0.323 mmol) in dioxane (1.0 ml) was stirred at 115° C. for 2 hours. The reaction mixture, after cooling to RT, was filtered and the filtrate was concentrated. The crude product was purified by silica gel chromatography employing a solvent gradient (hexane to 100% ethyl acetate) to elute to yield 1-(4-(2-hydroxy-2-methylpropoxy)-3-methylphenyl)-3-(phenethylthio)-pyrazin-2(1H)-one (26.74 mg, 0.062 mmol, 57.5% yield) as off-white solid. MS (M+1=411). 1H NMR (500 MHz, methanol-d$_3$) δ ppm 7.38 (1H, d, J=4.40 Hz), 7.25-7.32 (4H, m), 7.16-7.24 (4H, m), 7.00 (1H, d, J=8.25 Hz), 3.83 (1H, s), 3.24-3.39 (2H, m), 2.90-3.05 (2H, m), 2.29 (3H, s), 1.35 (6H, s).

Radioligand Binding Assay for Assessment of MCHR1 Activity

Assay and Biological Evaluation

Compounds of Formula I were initially characterized in an in vitro binding assay to determine their Ki or ability to antagonize binding of a peptide agonist to the human melanin concentrating hormone receptor (MCHR1).

Radioligand Binding Assay for Assessment of MCHR1 Activity

Membranes from stably transfected HEK-293 cells expressing a mutated (E4Q, AST) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM $MgCl_2$, 2 mM EGTA, and 0.1% BSA (Binding Buffer) for 90 min. For competition binding assays, reactions were carried out in the presence of with 0.06-0.1 nM [$Phe^n$, [$^{125}I$]$Tyr^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phospho-buffered Saline (pH 7.4) containing 0.01% TX-100. Filters were dried; 0.05 ml microscint 20 was added to each well and radioactivity was subsequently quantified by scintillation counting on a TopCount™ microplate scintillation counter (Packard). Inhibitory constants were determined by nonlinear least squares analysis using a four parameter logistic equation.

Biological Data

The following representative in vitro biological data was measured in a binding assay for the compounds from the Examples herein above:

| Example | Ki (nM) |
| --- | --- |
| 113 | 8 |
| 124 | 9 |
| 65 | 10 |
| 110 | 17 |
| 125 | 17 |
| 131 | 18 |
| 38 | 20 |
| 181 | 21 |
| 67 | 28 |
| 36 | 33 |
| 95 | 41 |
| 155 | 45 |
| 69 | 49 |
| 71 | 62 |
| 27 | 63 |
| 151 | 64 |
| 141 | 78 |
| 172 | 85 |
| 59 | 125 |
| 170 | 132 |
| 10 | 141 |
| 46 | 232 |
| 178 | 290 |
| 3 | 576 |
| 169 | 1294 |
| 39 | 1580 |
| 157 | 1730 |
| 49 | 3043 |
| 19 | 3127 |
| 28 | 3153 |
| 40 | 3218 |
| 50 | 4664 |

Evaluation Of Prodrugs

The relative ability of the prodrug to enhance exposure (bioavailability) was assessed in an eight hour PK study using cannulated Sprague Dawley (CD, Charles River Breeding Laboratory) rats. The compounds (parent and prodrug esters) were administered p.o. at 2.0 ml/kg as a suspension in 0.5% methyl cellulose, 0.1% Tween 80 in water at 10 mg/kg p.o. Blood samples were taken at 1, 2, 4 and 8 hr. After determination of parent concentration, an AUC was calculated for the eight hour study.

Assessment of In Vivo MCHR1 Activity

Male Sprague Dawley (CD, Charles River Breeding Laboratory) rats weighing approximately 240 grams were placed in individual plastic cages with AlphaDri bedding. The room was maintained at 72° F. and 50% humidity, and a 12/12 light dark cycle with lights out at 1600 hours. The rats were conditioned for 5 days prior to the start of the study to having a choice of foods. A normal chow (Harlan Teklad, 2018) that contains 18% protein, 5% fat and 73% carbohydrate and a high fat high sugar diet (Research Diets (D2327) that contains 20% protein, 40% fat and 40% carbohydrate where the carbohydrate is entirely sucrose and the fat is soybean and coconut oil. Studies have revealed that rats exhibit a high preference for the high fat/high sucrose diet (80% preference). Body weight and consumption of both kinds of food as well as water intake were measured daily. Water was available ad lib throughout the study. Food consumption is presented as daily caloric consumption which is the sum of grams of chow multiplied by the Kcal per gram (3.5) plus grams of high fat high sugar multiplied by Kcal per gram (4.59).

Baseline body weight was measured prior to drug treatment on day 0 of the study. Baseline food consumption was the average of the 3 days prior to the first drug treatment. Drug was administered daily p.o. at 2.0 ml/kg at 1500 hours beginning on day 0 and continuing daily through day 4 as a suspension in 0.5% methyl cellulose, 0.1% Tween 80 in water at 3.0, 10 and 30 mg/kg p.o. All data were evaluated using ANOVA and Fishers PLSD statistics.

Biological Data

| Example | Dose (mg/kg) | Weight Reduction versus Vehicle |
| --- | --- | --- |
| 193 | 3 | 0.7% |
|  | 10 | 2.1% |
|  | 30 | 3.4% |
| 194 | 3 | 0.9% |
|  | 10 | 2.7% |
|  | 30 | 7.4% |
| 202 | 30 | 2.2% |
| 27 | 45 | 4.1% |
| 113 | 45 | 4.2% |

While the invention has been described according to several embodiments, various modifications thereto, in addition to those described herein, may become apparent to those skilled in the art from the foregoing description. Such modifications are also intended to fall within the scope of the appended claims.

What is claimed is:

1. A compound of Formula I or a pharmaceutically acceptable salt thereof

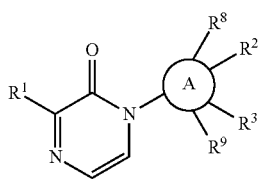

wherein

A

is a phenylene ring;
R¹ is Z—Y—X—, wherein
X is S, —SO— or —SO₂—;
Y is a bond, a 3- to 6-membered cycloalkyl, or an alkylene chain of 2 to 3 carbon atoms optionally substituted with a lower alkyl moiety;
Z is aryl or heteroaryl, wherein Z may be substituted with 1, 2 or 3 of halo, $C_{1-6}$ alkyl, $C_{1-3}$ alkoxy, $C_{1-3}$ thioalkyl, $C_{1-3}$ trifluoroalkoxy, trifluoromethyl, cycloalkyl, cycloalkoxy, or heteroaryl;
R² is -E-G-(J)$_m$, with m being an integer from 1 to 3;
E is O or S;
G is lower alkyl, phenylalkyl, cycloalkyl, cycloalkylalkyl, alkylcycloalkyl, cycloalkoxy, alkylcycloalkoxy, or cycloalkoxyalkyl;
each J is independently hydrogen, OH, CN, —SO₂R⁷, —SR⁷, —SOR⁷, lower alkyl, lower alkoxy, CF₃, —OCF₃, or —COOR⁵;
R⁵ is H, $C_{1-6}$ alkyl, or cycloalkyl;
R⁷ is lower alkyl;
R³ is $C_{1-6}$ alkyl, lower cycloalkyl, $C_{1-6}$ alkoxy, halogen, hydrogen, or —S—$C_{1-6}$ alkyl;
R⁸ and R⁹ are each independently hydrogen, halogen, or lower alkyl;
with the proviso that E-G and R³ are not identical unsubstituted lower alkoxy groups; and
when G is lower alkyl and J is H, R³ is not hydrogen; and
prodrugs thereof selected from the group consisting of acetates, pivalates, methylcarbonates, benzoates, amino acid esters, phosphates, malonates, succinates and glutarates; and all stereoisomers thereof.

2. The compound as defined in claim 1 wherein
X is S;
Y is a bond or an alkylene chain of 2 to 3 carbon atoms;
Z is aryl or heteroaryl, wherein Z may be substituted with 1, 2 or 3 of halo, $C_{1-6}$ alkyl, $C_{1-3}$ alkoxy, $C_{1-3}$ thioalkyl, $C_{1-3}$ trifluoroalkoxy, trifluoromethyl, cycloalkyl, cycloalkoxy, or heteroaryl;
R² is -E-G-J;
E is O or S;
G is lower alkyl or alkylcycloalkyl;
J is H, OH, SO₂R⁷, lower alkyl, lower alkoxy, or CF₃;
R³ is $C_{1-6}$ alkyl, $C_{1-6}$ alkoxy, H, or halo;
R⁸ is H or lower alkyl; and
R⁹ is H.

3. The compound as defined in claim 1 wherein
Z is
(1) aryl, which is optionally substituted with:
  a) halo,
  b) $C_{1-6}$ alkyl,
  c) $C_{1-3}$ alkoxy,
  d) trifluoromethyl,
  e) $C_{1-3}$ trifluoroalkoxy, or
  g) $C_{1-3}$ alkylthio,
(2) heteroaryl which is:
  a) pyridinyl,
  b) pyrazinyl, or
  c) pyrimidinyl,
each of a), b) or c) being optionally substituted with $C_{1-6}$ alkyl, trifluoromethyl, $C_{1-3}$ alkoxy, or halogen,
(3) benzothiazole optionally substituted with halo or $C_{1-3}$ alkoxy,
(4) benzoxazole optionally substituted with halo,
(5) benzimidazole,
(6) thiazole optionally substituted with $C_{1-6}$ alkyl,
(7) indanyl, or
(8) quinolinyl optionally substituted with trifluoromethyl;
Y is a bond or alkylene chain of 2 to 3 carbon atoms;
X is S, SO, or SO₂;
J is
(1) H,
(3) OH,
(4) COOH,
(5) COO($C_{1-6}$ alkyl),
(6) SO₂R⁷, or
(7) prodrug esters which are selected from glycine

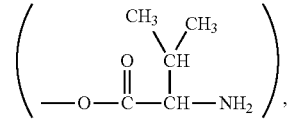

valine

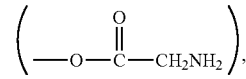

and phosphate

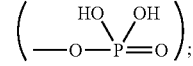

m is 1 or 2;
G is CH₂, (CH₂)₂, (CH₂)₃,

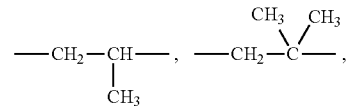

cycloalkyl which is

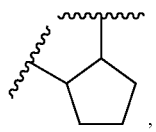, or cycloalkoxy which is

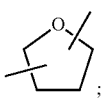;

E is O;
$R^3$ is H, $C_{1-6}$ alkoxy, $C_{1-6}$ alkyl, or halo;
$R^8$ is H, halo or lower alkyl; and
$R^9$ is H.

4. The compound of claim 1 in a prodrug ester form, wherein $R^2$ is

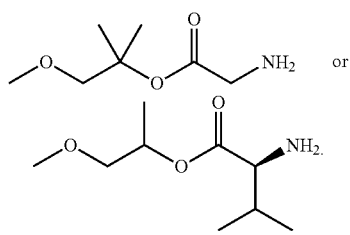

5. The compound as defined in claim 1, wherein the compound is of Formula IA or a pharmaceutically acceptable salt thereof

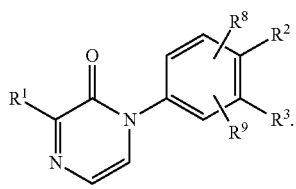

IA

6. The compound of claim 5 wherein:
X is S;
Y is a bond or alkylene chain of 2 to 3 carbon atoms;
Z is phenyl or pyridyl;
E is O;
G is lower alkyl or alkylcycloalkyl;
J is H or OH;
$R^3$ is H, $C_{1-6}$ alkoxy, $C_{1-6}$ alkyl, or halo;
$R^8$ is H or $CH_3$; and
$R^9$ is H.

7. The compound of claim 5, wherein Z is selected from the group consisting of phenyl, naphthyl, pyridinyl, pyrimidinyl, pyrazinyl, benzimidazolyl, and benzoxazolyl.

8. The compound of claim 5, wherein $R^3$ is $C_{1-6}$ alkoxy or $C_{1-6}$ alkyl.

9. The compound of claim 5, wherein $R^1$ is selected from the group consisting of:

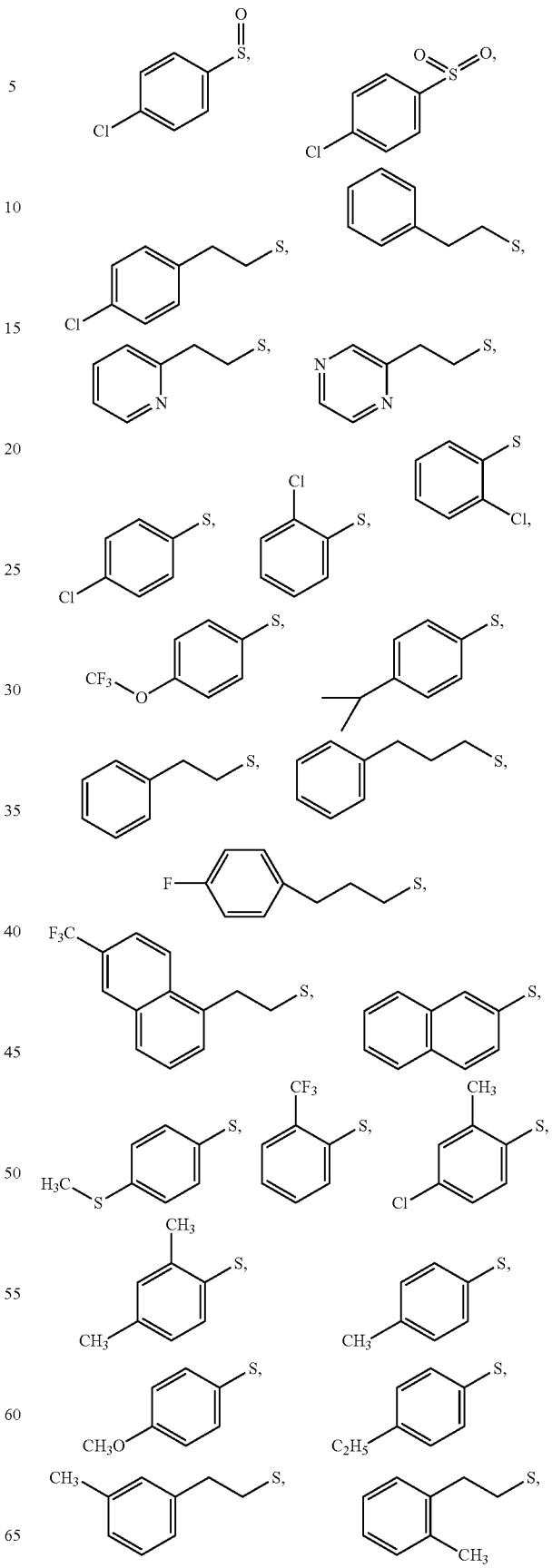

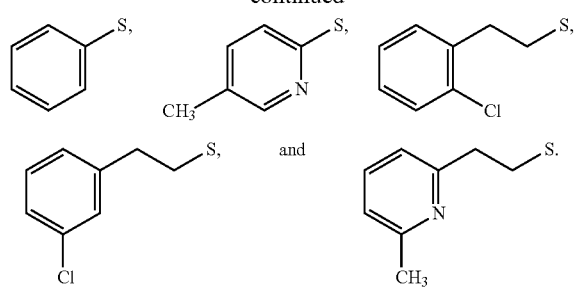
10. The compound of claim 5 wherein
$R^2$ is
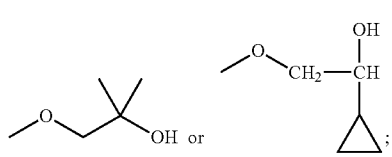
$R^3$ is methoxy or methyl; and
$R^1$ is selected from the group consisting of:
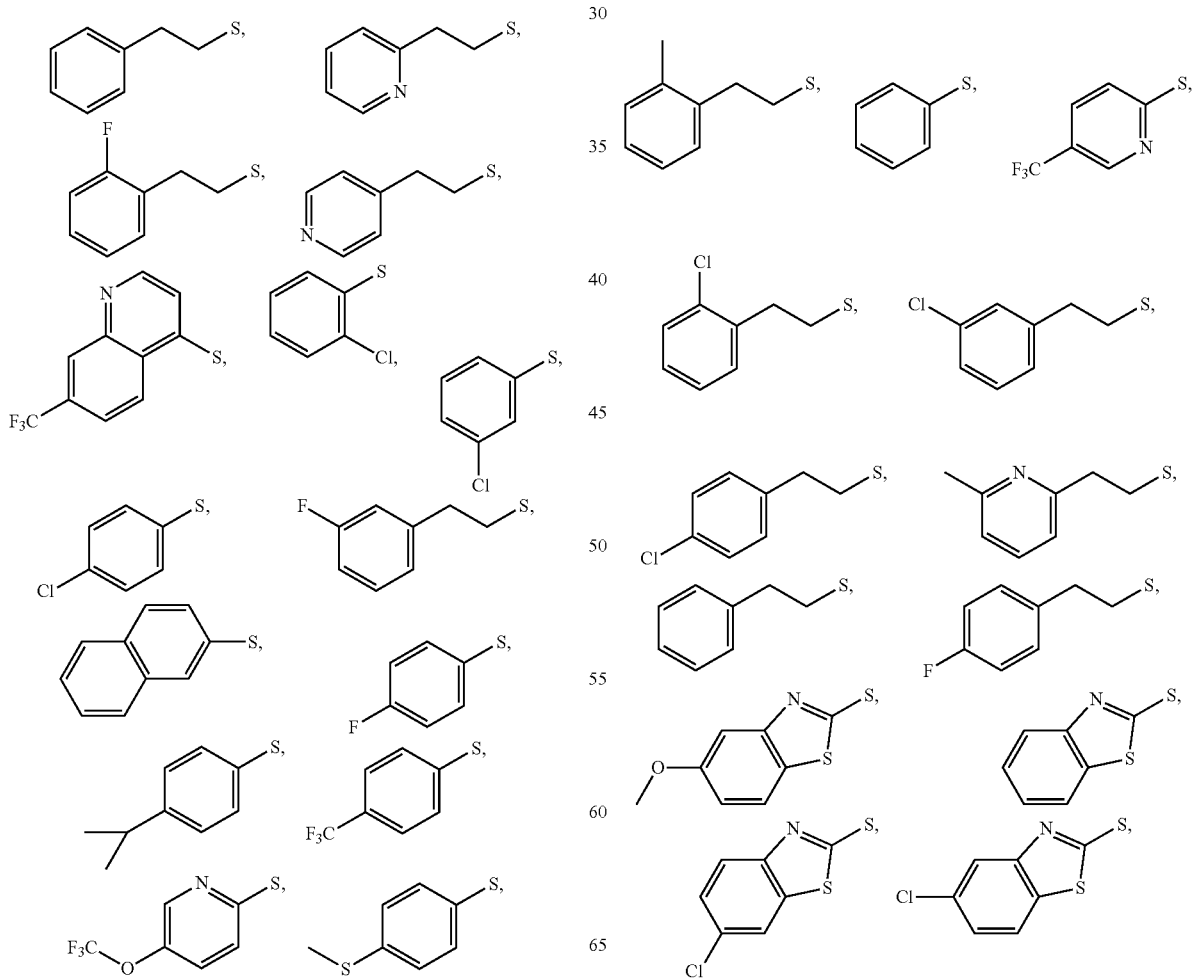
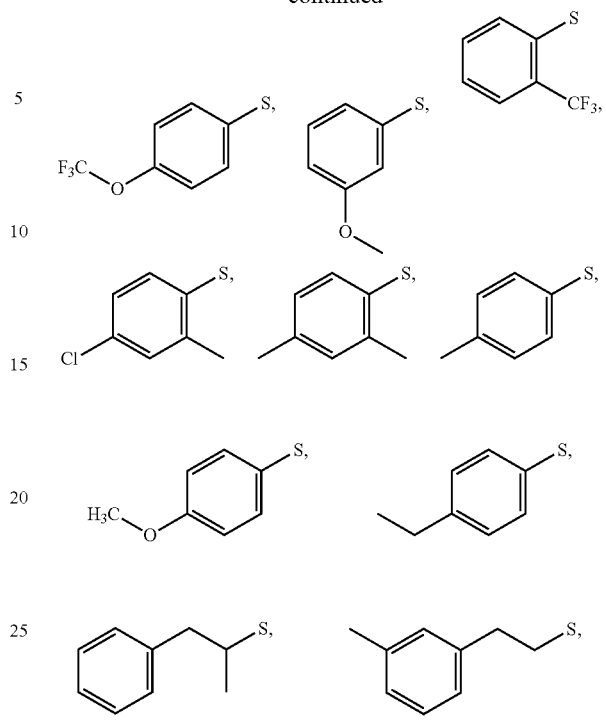

-continued

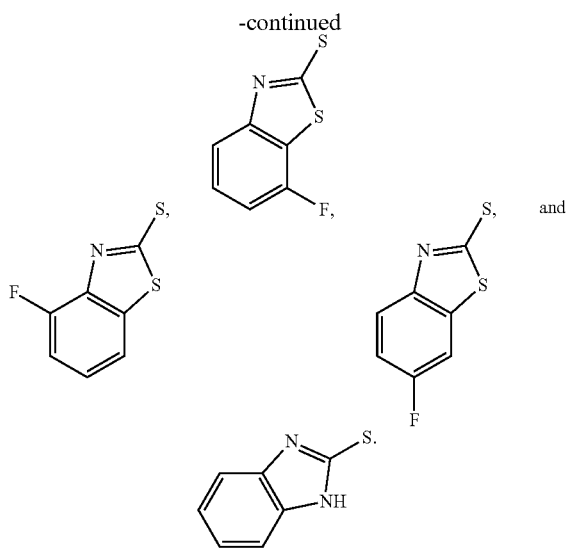

11. The compound as defined in claim 5 wherein
X is S;
Y is a bond or (CH$_2$)$_2$;

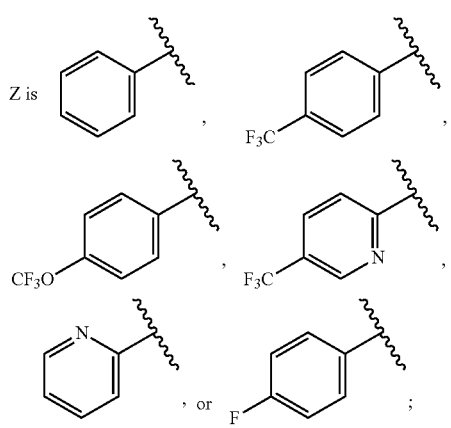

E-G-J is

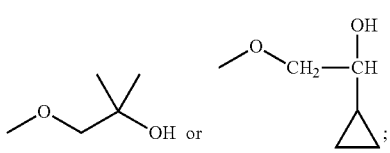

R$^3$ is CH$_3$O or CH$_3$;
R$^8$ is H; and
R$^9$ is H.

12. A pharmaceutical composition comprising a therapeutically effective amount of a compound as defined in claim 1, in association with a pharmaceutically acceptable carrier or diluent.

13. A pharmaceutical composition comprising a therapeutically effective amount of a compound as defined in claim 2, in association with a pharmaceutically acceptable carrier or diluent.

14. A pharmaceutical composition comprising a therapeutically effective amount of a compound as defined in claim 3, in association with a pharmaceutically acceptable carrier or diluent.

15. A pharmaceutical composition comprising a therapeutically effective amount of a compound as defined in claim 4, in association with a pharmaceutically acceptable carrier or diluent.

16. A pharmaceutical composition comprising a therapeutically effective amount of a compound as defined in claim 5, in association with a pharmaceutically acceptable carrier or diluent.

17. A pharmaceutical composition comprising a therapeutically effective amount of a compound as defined in claim 6, in association with a pharmaceutically acceptable carrier or diluent.

18. A pharmaceutical composition comprising a therapeutically effective amount of a compound as defined in claim 7, in association with a pharmaceutically acceptable carrier or diluent.

19. A pharmaceutical composition comprising a therapeutically effective amount of a compound as defined in claim 8, in association with a pharmaceutically acceptable carrier or diluent.

20. A pharmaceutical composition comprising a therapeutically effective amount of a compound as defined in claim 9, in association with a pharmaceutically acceptable carrier or diluent.

21. A pharmaceutical composition comprising a therapeutically effective amount of a compound as defined in claim 10, in association with a pharmaceutically acceptable carrier or diluent.

22. A pharmaceutical composition comprising a therapeutically effective amount of a compound as defined in claim 11, in association with a pharmaceutically acceptable carrier or diluent.

23. A compound selected from the group consisting of the following structures or pharmaceutically acceptable salts thereof:

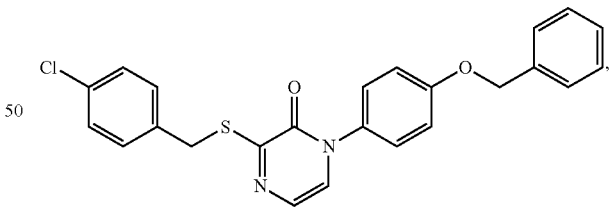

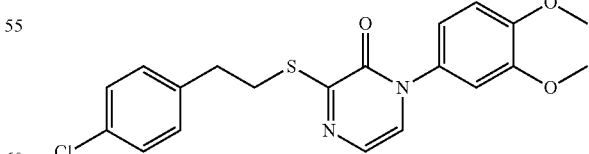

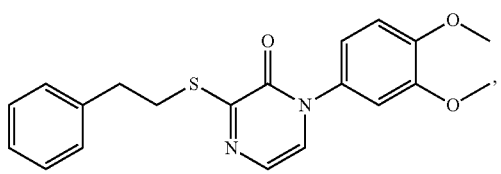

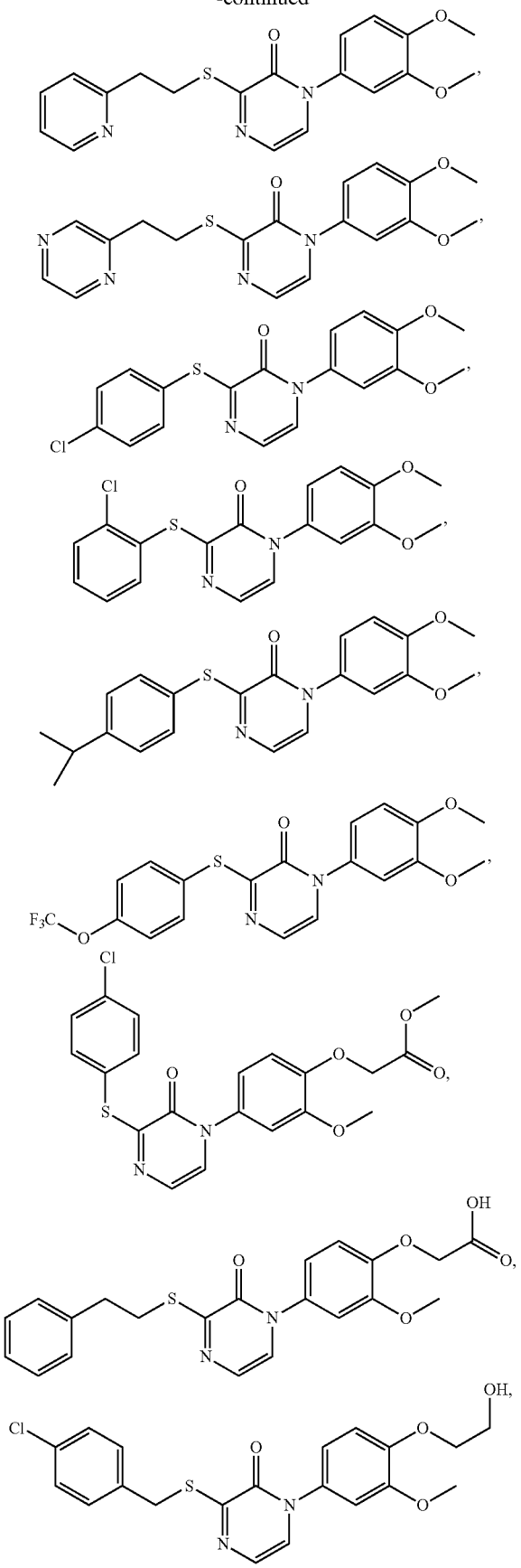
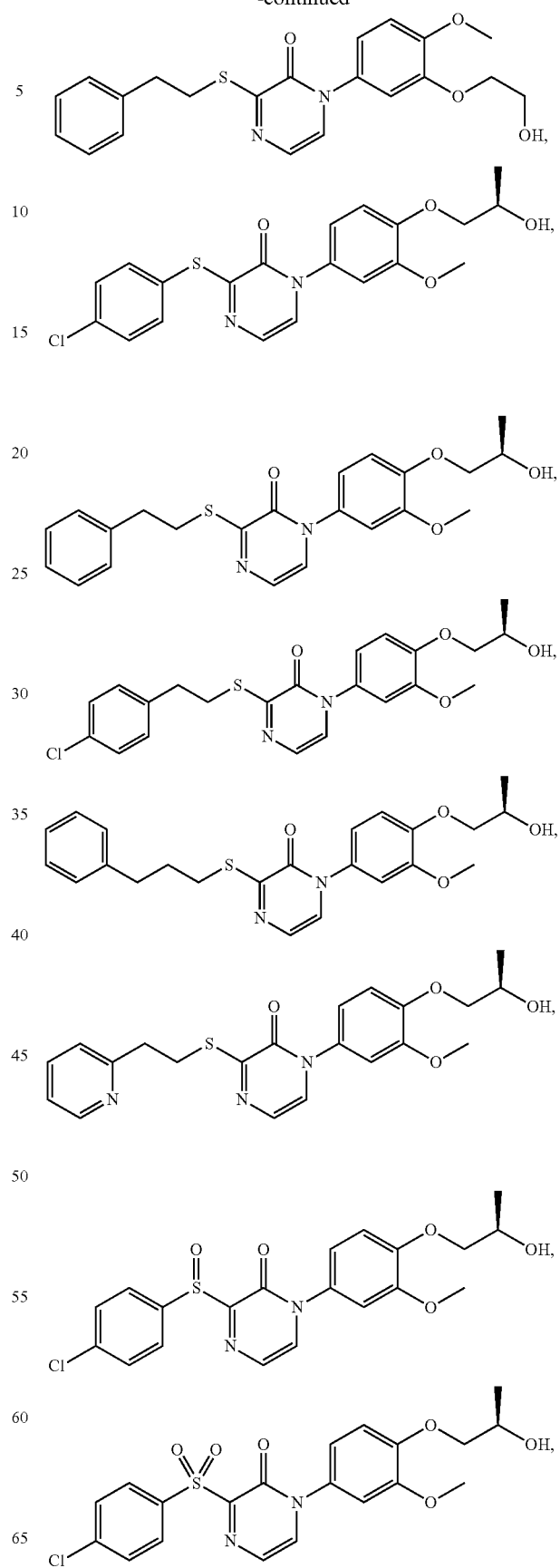

199
-continued
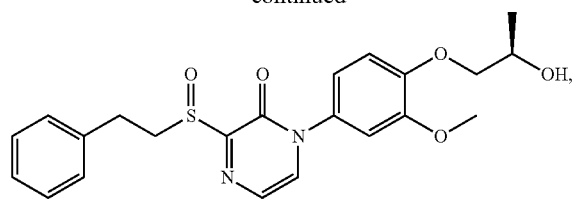
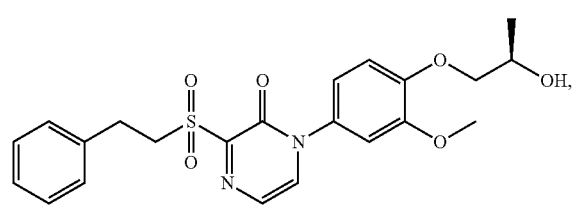
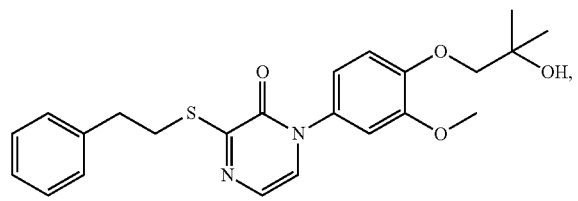
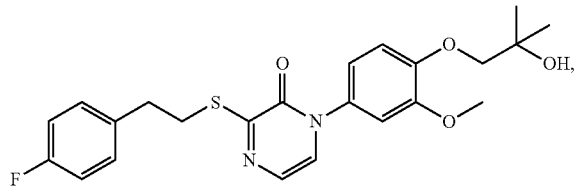
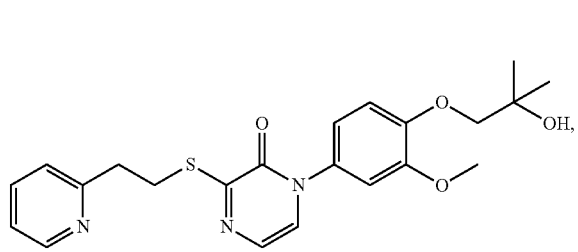
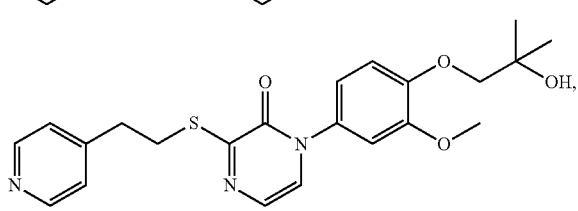
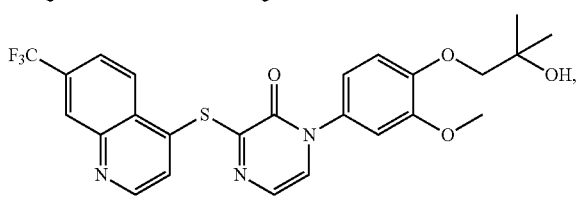
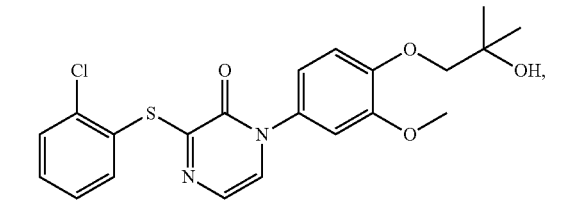
200
-continued
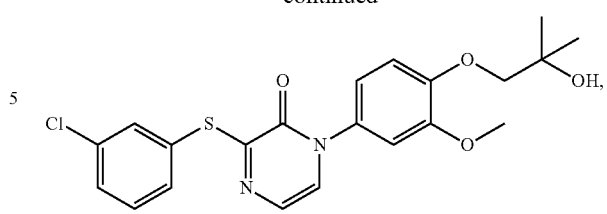
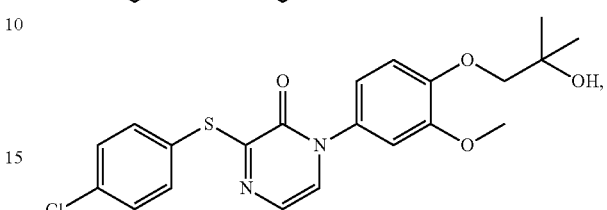
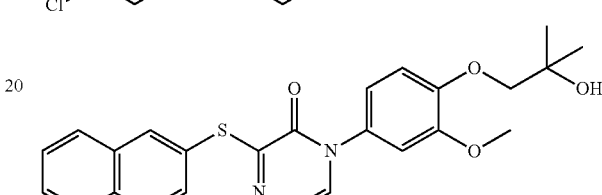
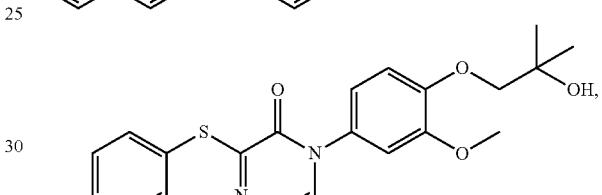
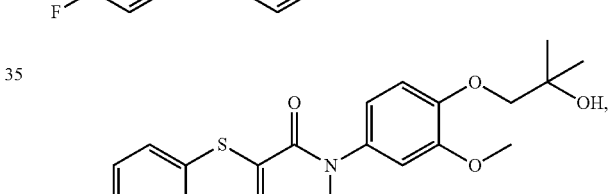
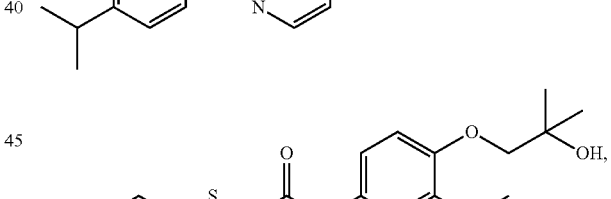
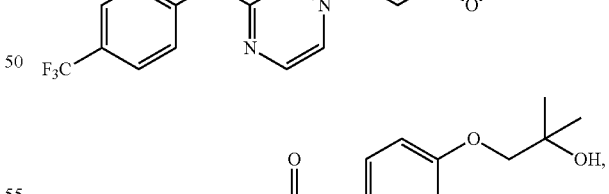
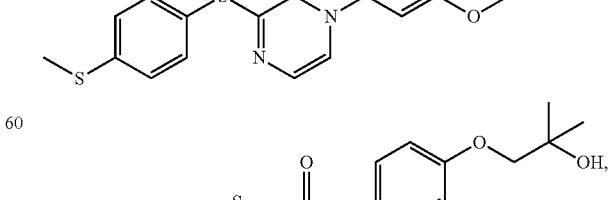
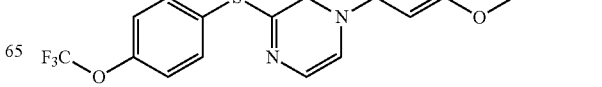

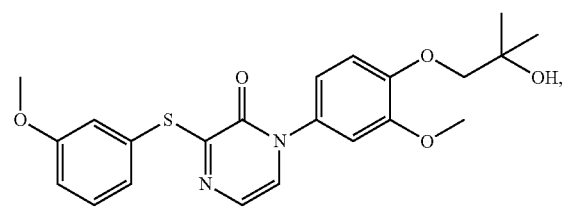
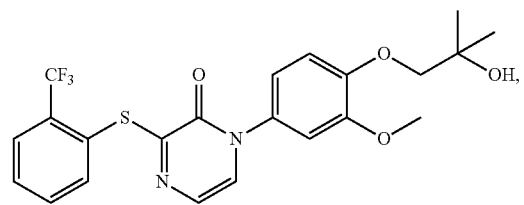
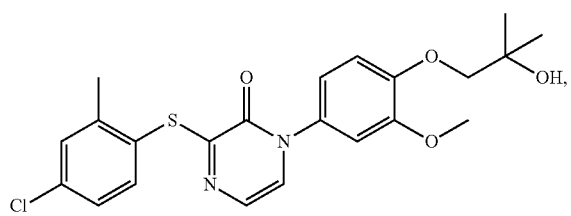
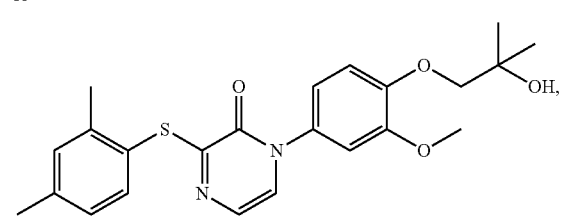
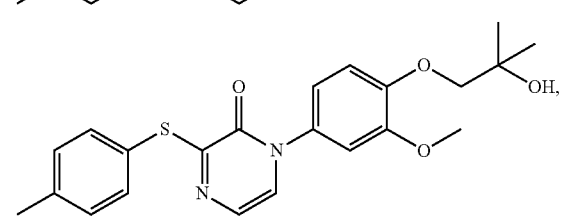
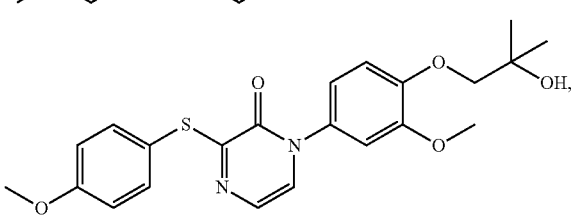
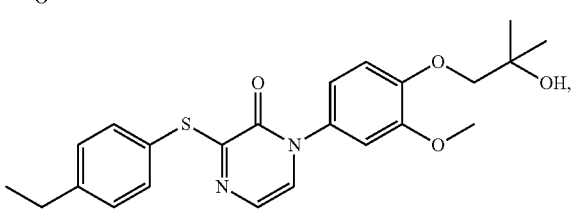
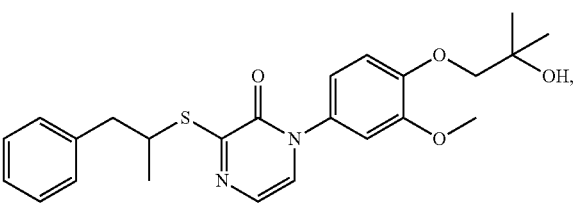
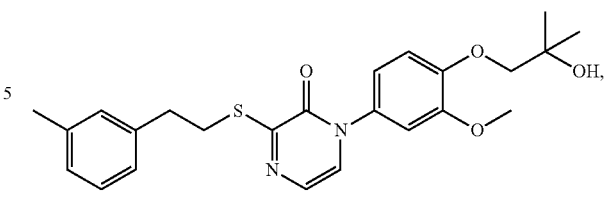
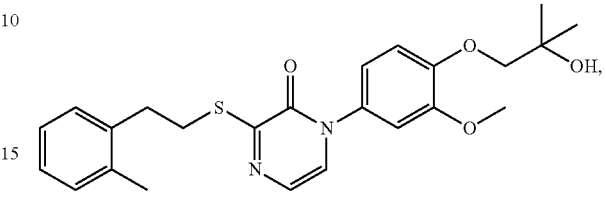
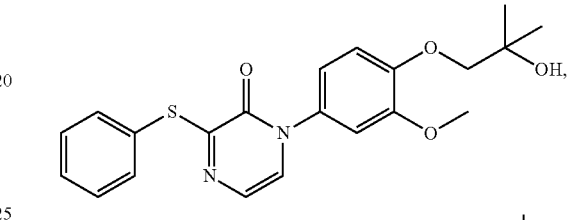
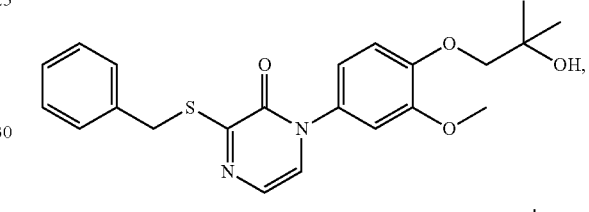
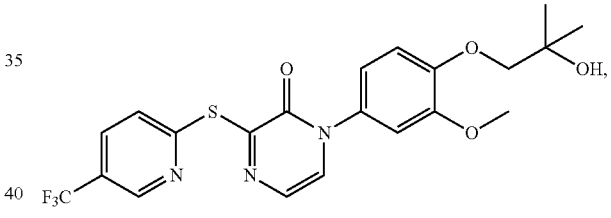
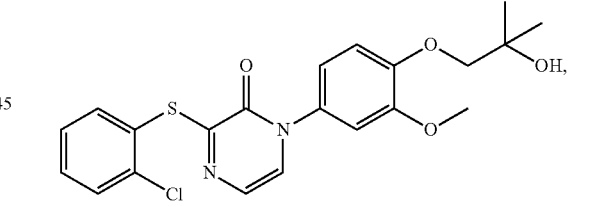
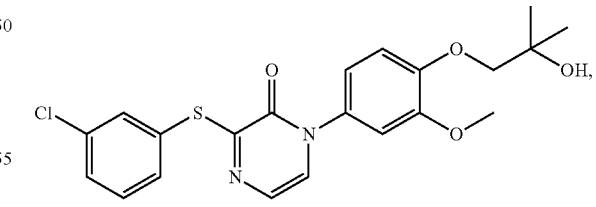
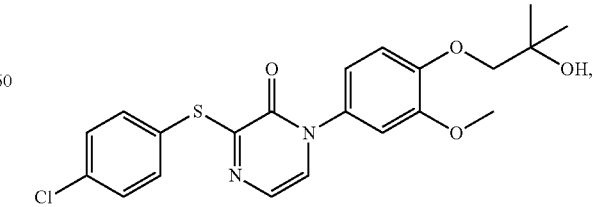

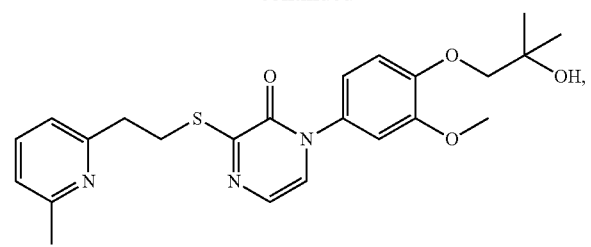
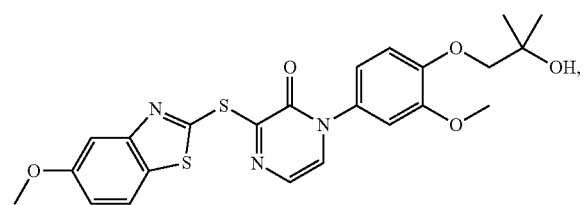
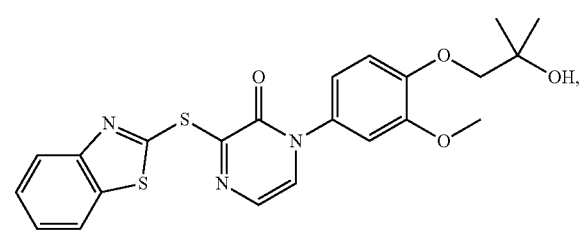
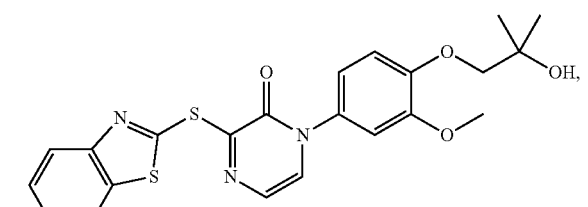
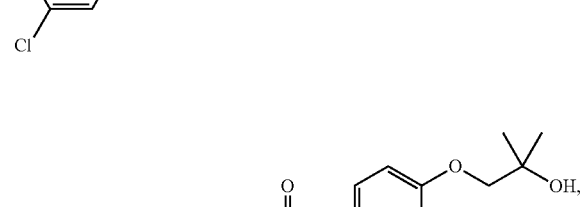
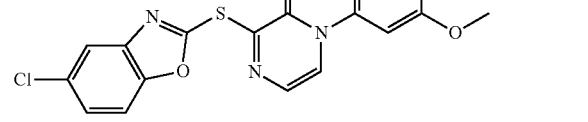
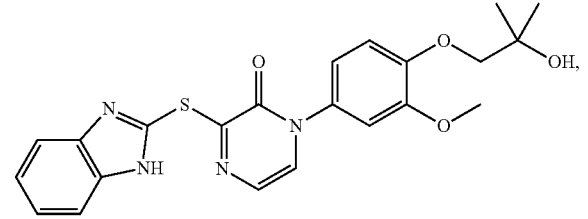
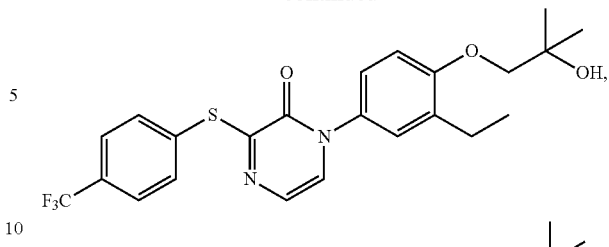
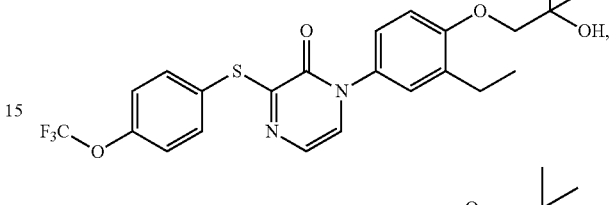
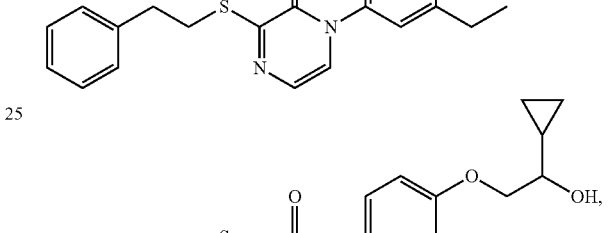
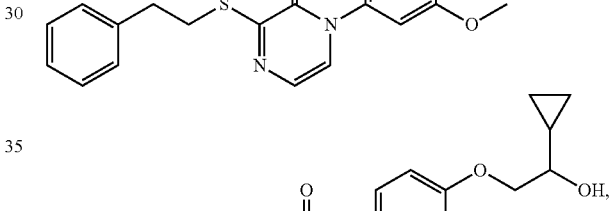
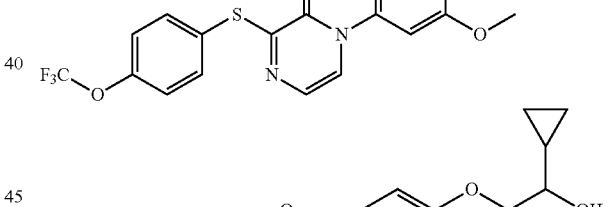
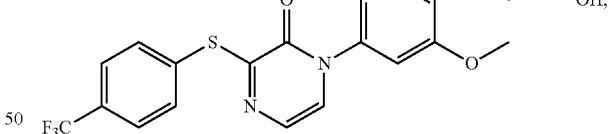
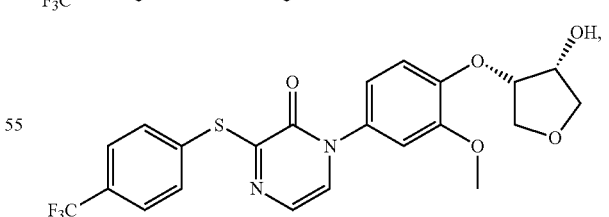
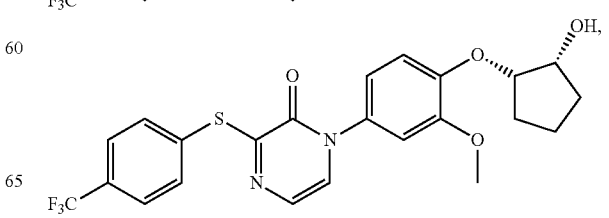

-continued
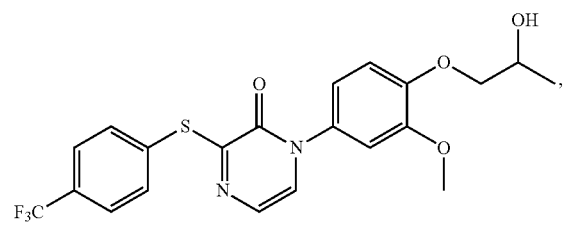
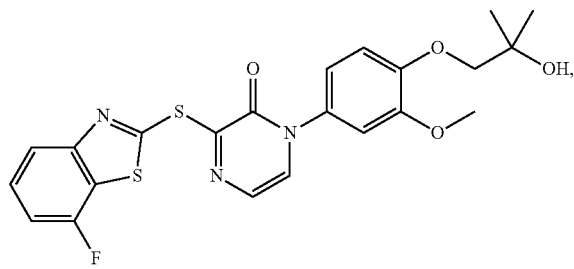
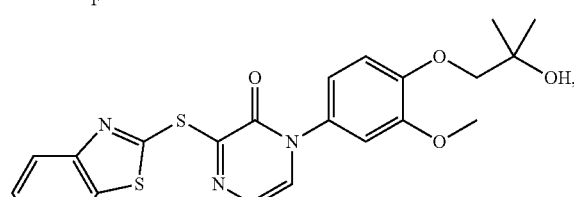
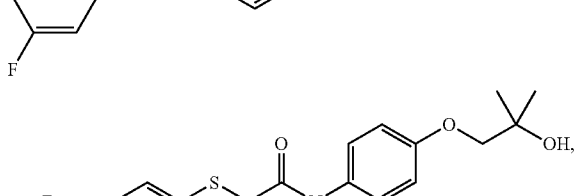
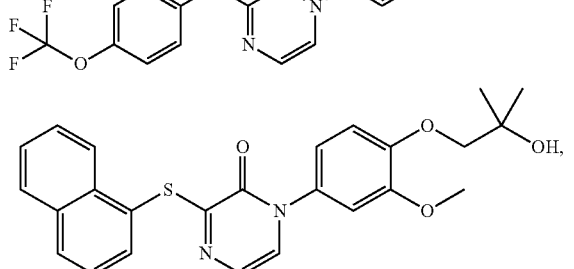
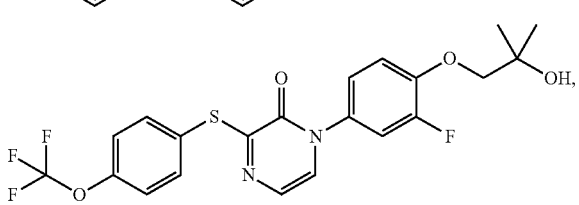
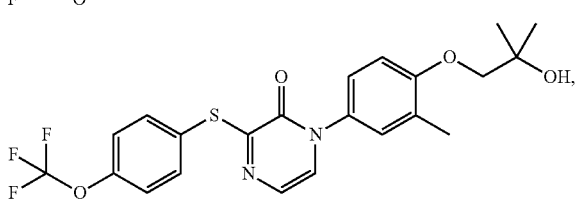
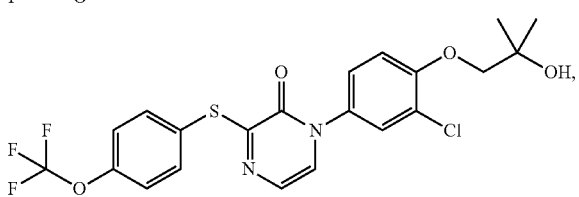
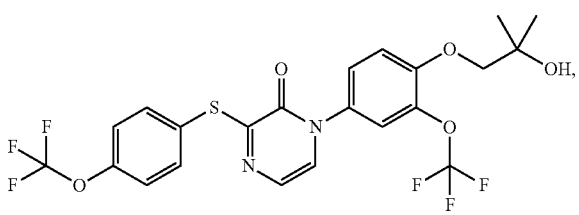

207
-continued

208
-continued

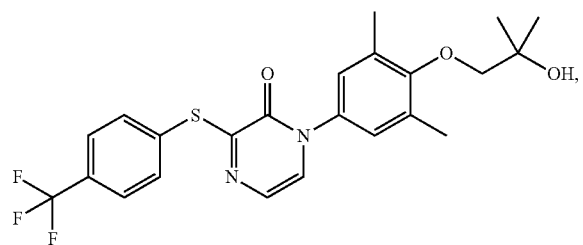
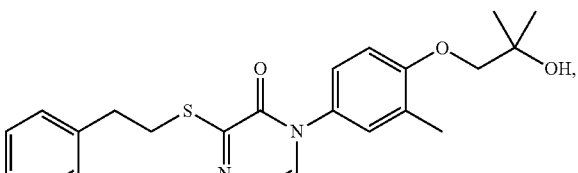
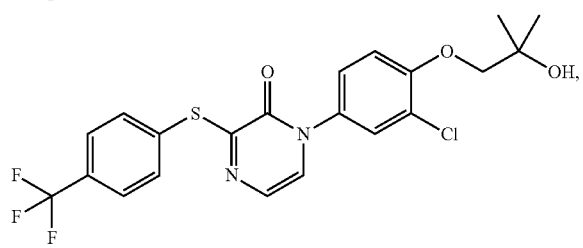
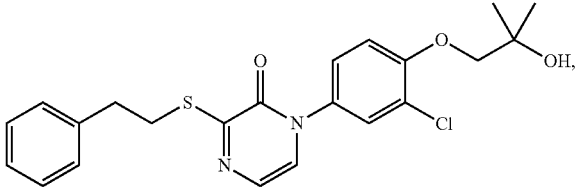
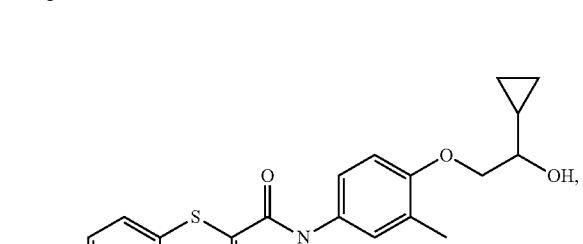
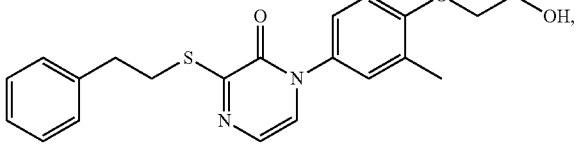
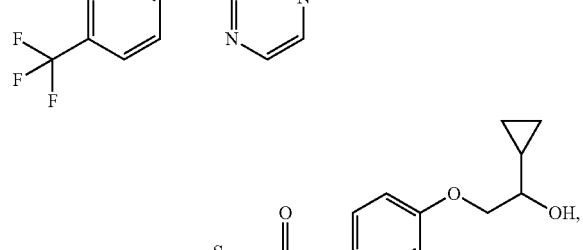
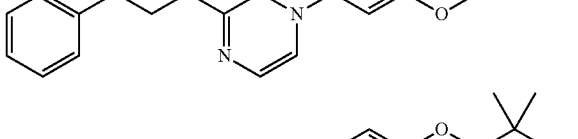
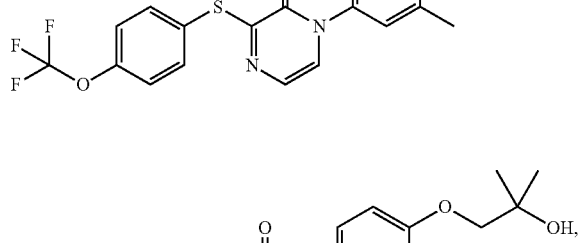
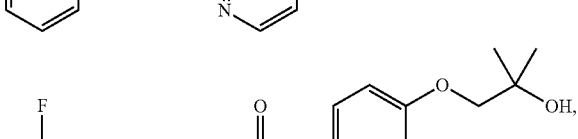
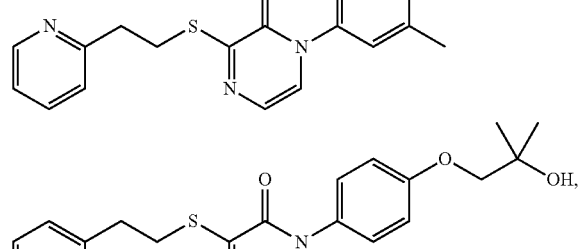
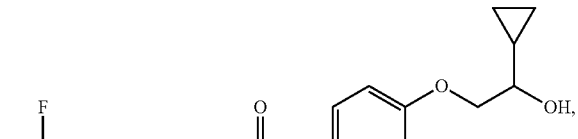
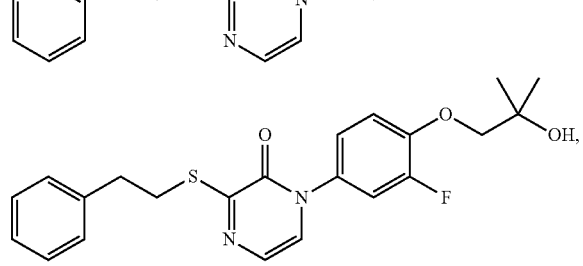
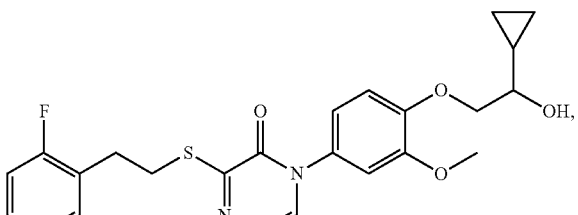

211
-continued
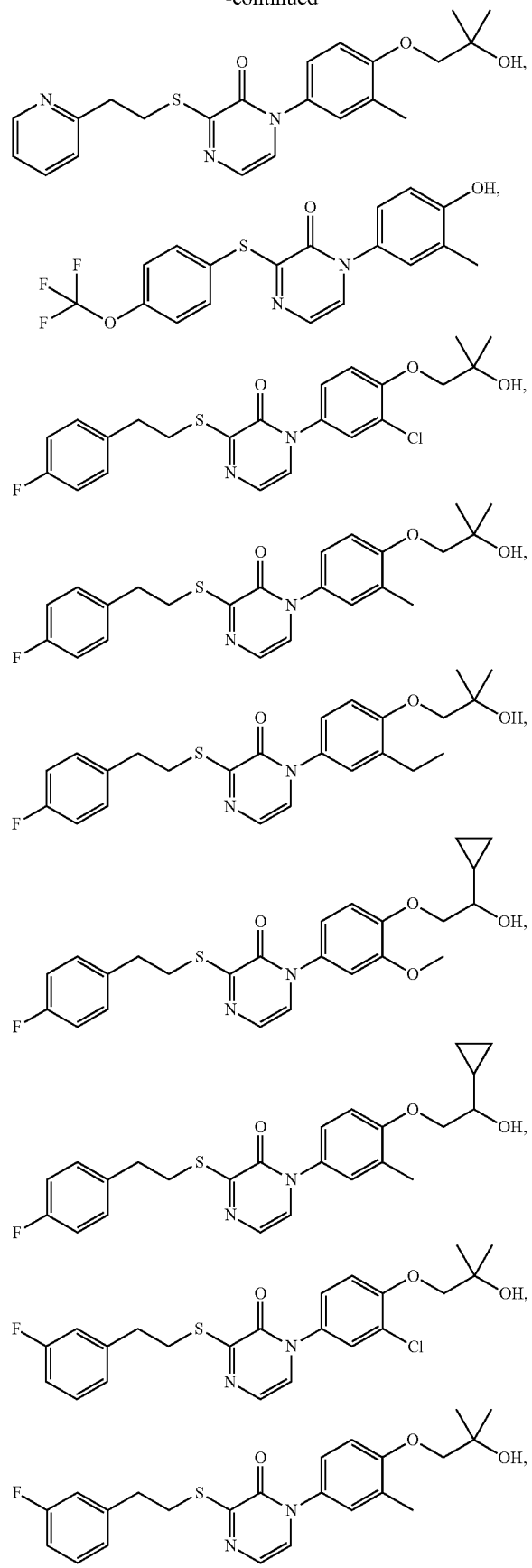
212
-continued
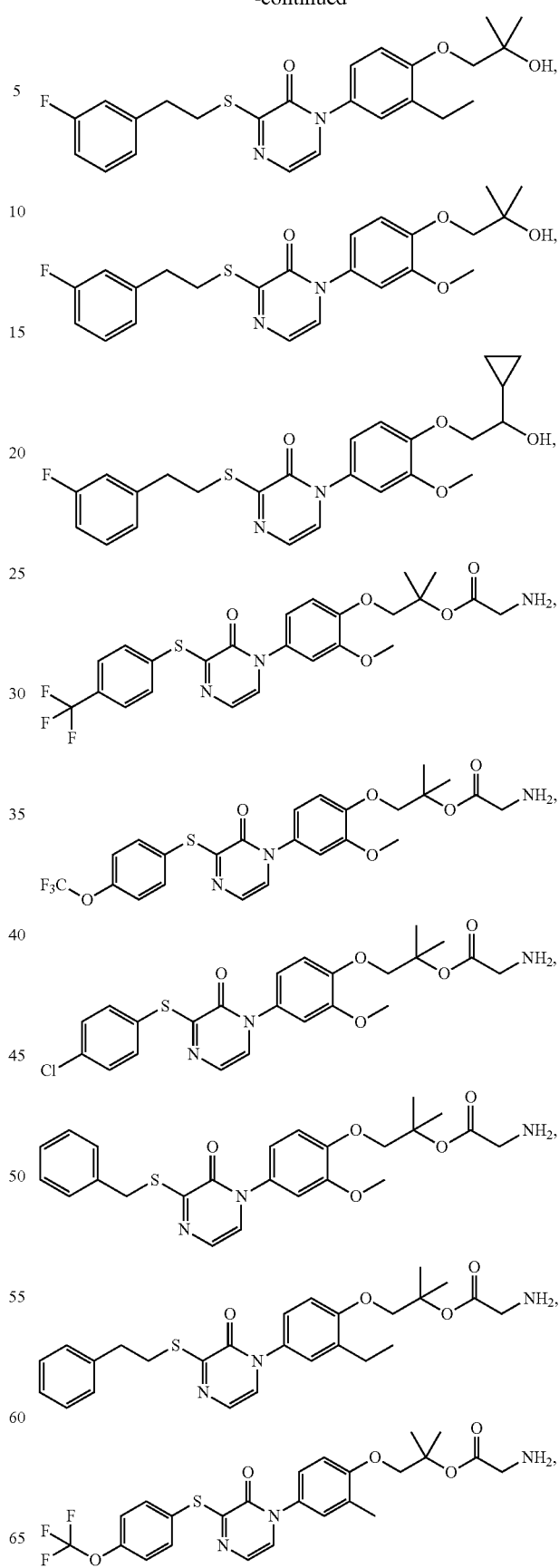

213
-continued
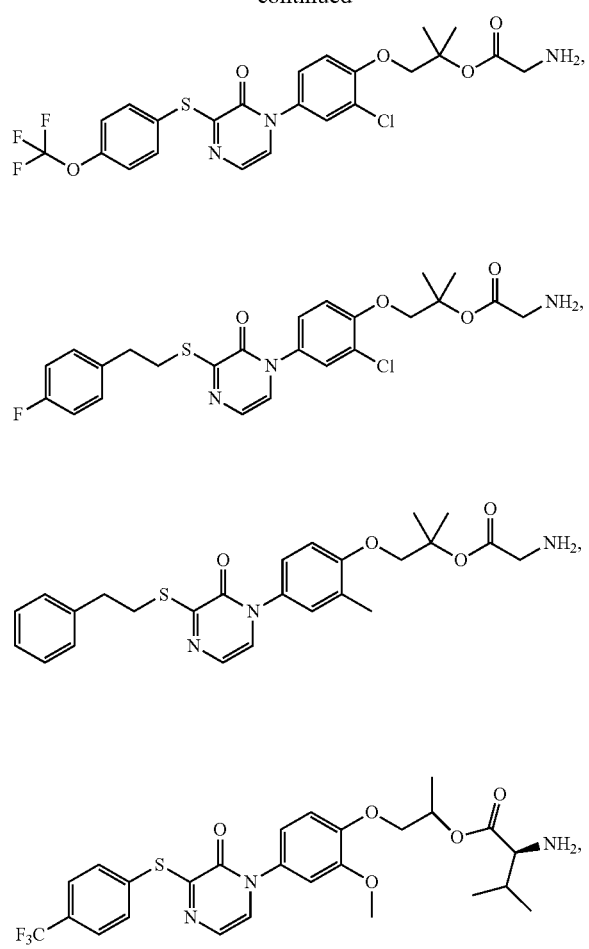
214
-continued
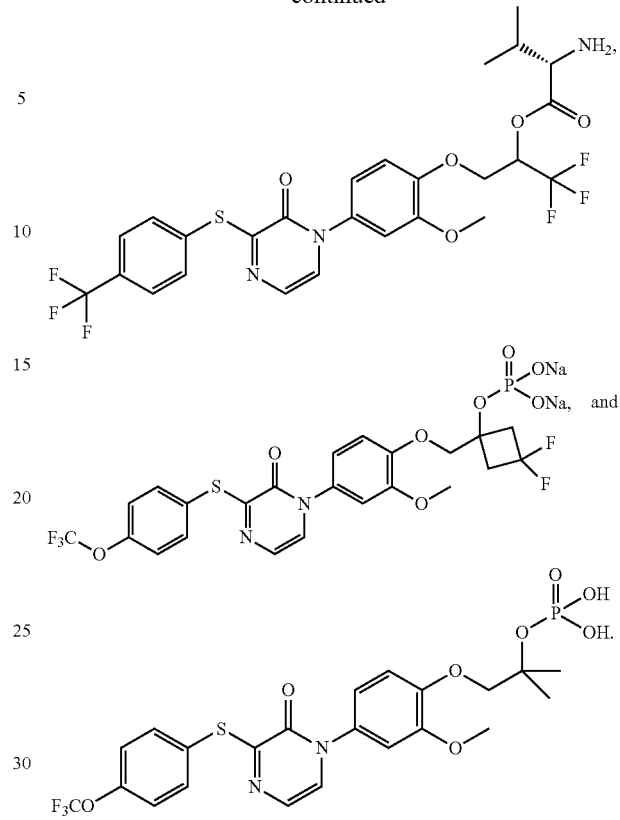
24. A pharmaceutical composition comprising a therapeutically effective amount of a compound as defined in claim 23, in association with a pharmaceutically acceptable carrier or diluent.
* * * * *

UNITED STATES PATENT AND TRADEMARK OFFICE
CERTIFICATE OF CORRECTION

| | | |
|---|---|---|
| PATENT NO. | : 8,012,984 B2 | Page 1 of 1 |
| APPLICATION NO. | : 12/881234 | |
| DATED | : September 6, 2011 | |
| INVENTOR(S) | : Philip Stein et al. | |

It is certified that error appears in the above-identified patent and that said Letters Patent is hereby corrected as shown below:

Column 190

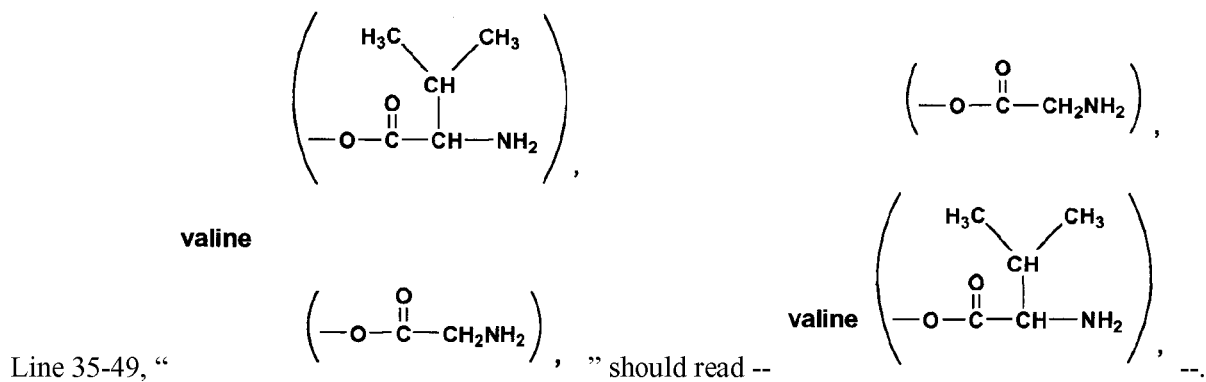

Line 35-49, " " should read -- --.

Column 194

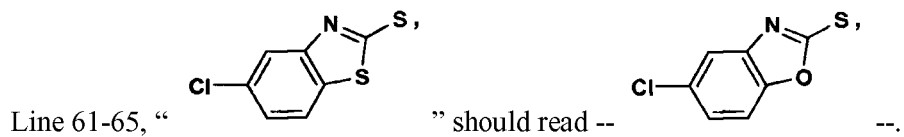

Line 61-65, " " should read -- --.

Signed and Sealed this
Third Day of January, 2012

David J. Kappos
*Director of the United States Patent and Trademark Office*